US008007798B2

(12) United States Patent
Ashkenazi et al.

(10) Patent No.: US 8,007,798 B2
(45) Date of Patent: *Aug. 30, 2011

(54) TREATMENT OF COMPLEMENT-ASSOCIATED DISORDERS

(75) Inventors: Avi Ashkenazi, San Mateo, CA (US); Karim Yussef Helmy, San Francisco, CA (US); Sherman Fong, Alameda, CA (US); Audrey Goddard, San Francisco, CA (US); Austin L. Gurney, San Francisco, CA (US); Kenneth James Katschke, Jr., Millbrae, CA (US); Menno Van Lookeren, San Francisco, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 808 days.

This patent is subject to a terminal disclaimer.

(21) Appl. No.: 11/249,825

(22) Filed: Oct. 12, 2005

(65) Prior Publication Data

US 2007/0190054 A1 Aug. 16, 2007

Related U.S. Application Data

(60) Continuation-in-part of application No. 11/159,919, filed on Jun. 22, 2005, which is a continuation-in-part of application No. 10/964,263, filed on Oct. 12, 2004, now Pat. No. 7,419,663, which is a continuation-in-part of application No. 10/767,374, filed on Jan. 29, 2004, now Pat. No. 7,282,565, and a continuation-in-part of application No. 10/767,904, filed on Jan. 29, 2004, now Pat. No. 7,211,400, which is a division of application No. 09/953,499, filed on Sep. 14, 2001, now Pat. No. 6,838,554, application No. 11/249,825, which is a continuation-in-part of application No. PCT/US03/31207, filed on Oct. 1, 2003, which is a continuation-in-part of application No. 10/633,008, filed on Jul. 31, 2003, now Pat. No. 7,192,589, which is a continuation-in-part of application No. 10/265,542, filed on Oct. 3, 2002, now abandoned, which is a continuation-in-part of application No. 09/953,499, filed on Sep. 14, 2001, now Pat. No. 6,838,554, which is a continuation of application No. 09/254,465, filed on Mar. 5, 1999, now Pat. No. 6,410,708, and a continuation-in-part of application No. 09/380,138, filed as application No. PCT/US99/05028 on Mar. 8, 1999, now abandoned, which is a continuation-in-part of application No. 09/254,465, filed as application No. PCT/US98/24855 on Nov. 20, 1998, now Pat. No. 6,410,708.

(60) Provisional application No. 60/078,936, filed on Mar. 20, 1998.

(51) Int. Cl.
*A61K 39/395* (2006.01)

(52) U.S. Cl. .................................. 424/145.1; 424/130.1
(58) Field of Classification Search .................. None
See application file for complete search history.

(56) References Cited

U.S. PATENT DOCUMENTS

| | | | |
|---|---|---|---|
| 4,579,827 A | 4/1986 | Sakamoto et al. | |
| 5,650,295 A | 7/1997 | Li et al. | |
| 6,022,708 A | 2/2000 | de Sauvage et al. | |
| 6,410,708 B1 | 6/2002 | Ashkenazi et al. | |
| 6,472,520 B2 | 10/2002 | Fisher | |
| 6,569,992 B1 | 5/2003 | LaFleur et al. | |
| 6,642,353 B1 | 11/2003 | McConnell et al. | |
| 6,838,554 B2 | 1/2005 | Ashkenazi et al. | |
| 7,192,589 B2 | 3/2007 | Ashkenazi et al. | |
| 7,211,400 B2 | 5/2007 | Ashkenazi et al. | |
| 7,282,565 B2 | 10/2007 | Goddard et al. | |
| 7,419,663 B2 | 9/2008 | Ashkenazi et al. | |
| 2004/0152105 A1 | 8/2004 | Vogt et al. | |
| 2005/0197285 A1 | 9/2005 | Rosen et al. | |
| 2006/0233803 A1 | 10/2006 | Ashkenazi et al. | |
| 2007/0190054 A1 | 8/2007 | Ashkenazi et al. | |

FOREIGN PATENT DOCUMENTS

| | | |
|---|---|---|
| EP | 0 199 141 | 10/1986 |
| EP | 317 050 | 5/1989 |
| EP | 0 616 812 A1 | 9/1994 |
| EP | 0 616 812 B1 | 9/1994 |
| WO | WO 90/05537 | 5/1990 |
| WO | WO 96/34943 | 11/1996 |
| WO | WO 98/24897 | 6/1998 |
| WO | WO 98/40483 | 9/1998 |
| WO | WO 98/42739 | 10/1998 |

(Continued)

OTHER PUBLICATIONS

The Merck Manuals Online Medical Library, [online]. Whitehouse Station, NJ: Merck Research Laboratories, 2006-2007. [retrieved on Sep. 7, 2010]. Retrieved from the Internet: < URL: http://www.merck.com/mmpe/print/sec09/ch106/ch106b.html >. Age-Related Macular Degeneration (AMD or ARMD); pp. 1-4.*

Arrate, et al., "Cloning of human junctional adhesion molecule 3 (JAM3) and its identification as the JAM2 counter-receptor", The Journal of Biological Chemistry, vol. 276, No. 49, pp. 45826-45832, (2001).

Atwood, et al., "The babel of bioinformatics", Science, vol. 290, pp. 471-473, (2000).

Casset, et al., "A peptide mimetic of an anti-CD4 monoclonal antibody by rational design", BBRC, 307: 198-205, (2003).

(Continued)

*Primary Examiner* — Sharon Wen
(74) *Attorney, Agent, or Firm* — Arnold & Porter LLP; Bonny Yeung; Ginger R. Dreger

(57) ABSTRACT

The present invention concerns a recently discovered macrophage specific receptor, CRIg, and its use in the prevention and treatment of complement-associated disorders, including complement-associated eye conditions, such as age-related macular degeneration (AMD) and choroidal neovascularization (CNV).

47 Claims, 90 Drawing Sheets

FOREIGN PATENT DOCUMENTS

| WO | WO 99/02561 | 1/1999 |
|---|---|---|
| WO | WO 99/27098 | 6/1999 |
| WO | WO 99/40100 A1 | 8/1999 |
| WO | WO 99/46281 | 9/1999 |
| WO | WO 00/12703 A2 | 3/2000 |
| WO | WO 00/29583 A2 | 5/2000 |
| WO | WO 00/36102 | 6/2000 |
| WO | WO 00/37638 A2 | 6/2000 |
| WO | WO 00/53749 A2 | 9/2000 |
| WO | WO 00/53758 | 9/2000 |
| WO | WO 01/04311 | 1/2001 |
| WO | WO 01/36432 A2 | 5/2001 |
| WO | WO 01/40466 A2 | 6/2001 |
| WO | WO 02/00690 A2 | 1/2002 |
| WO | WO 02/08284 | 1/2002 |
| WO | WO 02/08284 A2 | 1/2002 |
| WO | WO 2004/022594 A2 | 3/2004 |

OTHER PUBLICATIONS

GenBank Accession No. Q80WA3, V-set and immunoglobulin domain containg 4, VSIG4, Mar. 1, 2004, pp. 1-2.
Kahan., "Immunosuppressive therapy", Current Opinion in Immunology, 4: 553-560, (1992).
Katschke, et al., "A novel inhibitor of the alternative pathway of complement reverses inflammation and bone destruction in experimental arthritis", Brief Definitive Report, vol. 204, No. 6, pp. 1319-1325, (2007).
Kim, et al., "Characterization of monoclonal antibody specific to the Z39Ig protein, a member of immunoglobulin superfamily", Immunology Letters, 99: 153-161, (2005).
Lee, et al., "Z39Ig is expressed on macrophages and may mediate inflammatory reactions in arthritis and atherosclerosis", Journal of Leukocyte biology, vol. 80, pp. 922-928, (2006).
MacCallum, et al., "Antibody-antigen interactions: Contact analysis and binding site topography", J. Mol. Biol., 262: 732-745, (1996).
Rudikoff, et al., "Single amino acid substitution altering antigen-binding specificity", PNAS, vol. 79, pp. 1979-1983, (1982).
Skolnick, et al., "From genes to protein structure and function: novel applications of computational approaches in the genomic era", Trends in Biotech, 18: 34-39, (2000).
Strausberg, et al., "Generation and initial analysis of more than 15,000 full-length human and mouse cDNA sqeuences", PNAS, vol. 99, No. 26, pp. 16899-16903, (2002).
Tsukita, et al., "Multifunctional strands in tight junctions", Nature Reviews, vol. 2, pp. 285-293, (2001).
Walker, et al., "Z39Ig is co-expressed with activation macrophage genes", Biochimica et Biophysica Acta, 1574: 387-390, (2002).
Wu, et al., "Humanization of a murine monoclonal antibody by simultaneous optimization of framework and CRD residues", JMB, 294: 151-162, (1999).
Alderson, et al., "Molecular and biological characterization of human 4-1BB and its ligand", European Journal of Immunology, 24(9): 2219-2227, (1994).
Altchul, et al., "Local alignment statistics", Methods in Enzymology, 266: 460-480, (1996).
Auffray, et al., "*H. sapiens* partial cDNA sequence; clone c-Oxd10 partial cDNA sequence; transcribed sequence fragment", (Database EMBL-EMEST16 Accession No. F02373) (1995).
Barsoum, et al., "Effect of microencapsulated ampicillin on cell mediated immune responses in mice", J. Antimicrob. Chemother., , 40(5): 721-724, (1997).
Bork, et al., Trends in Genetics, 12: 425-427, (1996).
Bork, Genome Research, 10: 398-400, (2000).
Bowie, et al., Science, 247: 1306-1310, (1990).
Boyum, et al., "A one stage procedure for isolation of granulocytes and lympocytes form human blood", Norweigan defense establishment, Div. of toxicology, pp. 51-76.
Brenner, Trends in Genetics, 15: 132-133, (1999).
Campo, et al., "Zinc inhibits the mixed lymphocyte culture", Biology Trace elementary Res., 79(1): 15-22, (2001).
Chambers, et al., "Co-stimulation in T cell responses", Current Opinion in Immunology, 9(3): 396-404, (1997).
Coligan, et al., "Isolation of mouse mononuclear cells", Current Protocols in Immunology, vol. 1, unit 3.1.2, (1993).
De Smet, et al., "The activation of human gene MAGE-1 in tumor cells is correlated with genome-wide demethylation", PNAS, 93(14): 7149-7153, (1996).
Doerks, et al., Trends in Genetics, 14: 248-250, (1998).
Finn, et al., "Introduction: Third keystone symposium on cellular immunology and the immunotherapy of cancer", Journal of Immunotherapy, 21(2): 114-118, (1998).
GBTRANS Database Accession No. AJ132502, "HSA132502_1Z39Ig protein—*Homo sapiens*" (blast results) (Direct Submission Jan. 25, 1999).
GBTRANS Database Accession No. AL034397, "HS159A1_1 dA159A1.1 (novel protein)—*Homo sapiens*" (blast results) (Direct Submission Dec. 4, 1998).
GBTRANS Database Accession No. AL136649, "HSM801619_1 hypothetical protein" (blast results) (Direct Submission Jan. 18, 2000).
GBTRANS Database Accession No. AY016009, (blast results) (Direct Submission Dec. 4, 2000).
GBTRANS Database, Accession No. AF172398 (blast results) (Direct Submission Feb. 26, 2001).
GBTRANS Database, Accession No. AF191495 (blast results) (Direct Submission Oct. 1, 1999).
GenBank Accession No. G15647, human STS SHGC-11352, available Jan. 4, 1996.
GENESEQ Patent Database Accession No. P_B19396, (blast results) (Direct Submission Oct. 19, 2000).
GENESEQ Patent Database Accession No. P_B24047, (blast results) (Direct Submission Sep. 14, 2000).
GENESEQ Patent Database Accession No. P_B24401, (blast results) (Direct Submission Jun. 8, 2000).
GENESEQ Patent Database Accession No. P_B24405, (blast results) (Direct Submission Jun. 8, 2000).
GENESEQ Patent Database Accession No. P_B33421, (blast results) (Direct Submission Sep. 14, 2000).
GENESEQ Patent Database Accession No. P_B33429, (blast results) (Direct Submission Sep. 14, 2000).
GENESEQ Patent Database Accession No. P_B44247, (blast results) (Direct Submission Sep. 14, 2000).
GENESEQ Patent Database Accession No. P_B53081, (blast results) (Direct Submission Sep. 14, 2000).
GENESEQ Patent Database Accession No. P_B53086, (blast results) (Direct Submission Sep. 14, 2000).
GENESEQ Patent Database Accession No. P_B55950, (blast results) (Direct Submission Nov. 23, 2000).
GENESEQ Patent Database Accession No. P_B56015, (blast results) (Direct Submission Nov. 23, 2000).
GENESEQ Patent Database Accession No. P_W61379, (blast results) (Direct Submission Jun. 11, 1998).
GENESEQ Patent Database Accession No. P_W74465, (blast results) (Direct Submission Jan. 21, 1999).
GENESEQ Patent Database Accession No. P_W75220, (blast results) (Direct Submission Sep. 17, 1998).
GENESEQ Patent Database Accession No. P_W85457, (blast results) (Direct Submission Oct. 1, 1998).
GENESEQ Patent Database Accession No. P_Y08060, (blast results) (Direct Submission Mar. 25, 1999).
GENESEQ Patent Database Accession No. P_Y08071, (blast results) (Direct Submission Mar. 25, 1999).
Jenkins, "The ups and downs of T cell costimulation", Immunity, 1(6): 443-446, (1994).
June, et al., "The B7 and CD28 receptor families", Immunology Today, 15(7): 321-331, (1994).
Kwon, et al., "Manipulation of T cell costimulatory and inhibitory signals for immunotherapy of prostate cancer", PNAS, 94(15): 8099-8103, (1997).
Linsley, et al., "The role of the CD28 receptor during T cell responses to antigen", Annual Review of Immunology, 11: 191-212, (1993).
Martin-Padura, et al., "Junctional adhesion molecule, a novel member of the immunoglobulin superfamily that distributes at intercellular junctions and modulates monocyte transmigration", J. Cell Biology, vol. 142, No. 1, pp. 117-127, (1998).

Monks, et al., "Feasibility of high-flux anticancer drug screen using a diverse panel of cultured human tumor cell lines", National cancer institute, 83: 757-766, (1991).

Ozaki, et al., "Cutting edge: Combined treatment of the TNF-alpha and IFN-gamma causes redistribution of junctional adhesion molecule in human endothelial cells", J. Immunol., vol. 163, No. 2, (1999).

Piccotti, et al., "Interleukin-12 (IL-12) driven alloimmune", Transplantation, 67(11): 1453-1460, (1999).

Reinsmoen, et al., Evaluation of the cellular immune response in transplantation. In manual of clinical laboratory immunology, 6$^{th}$ edition, pp. 1164-1175, (1994).

Sites, et al., Basic and clinical immunology, pp. 30-31, 208-209 and 246-247, (1997).

Smith, et al., Nature Biotechnology, 15: 1222-1223, (1997).

Szalai, et al., "The Arthus reaction in rodents: species-specific requirement of complement", J. Immunol., 164(1): 463-468, (2000).

Aggarwal, et al., "Evidence for activation of the alternate complement pathway in patients with juvenile rheumatoid arthritis", Rheumatology, 39: 189-192, (2000).

Atkinson, "Complement system on the attack in autoimmunity", The Journal of Clinical Investigation, vol. 112, No. 11, pp. 1639-1641, (2003).

Carpentier, et al., "Internalization pathway of C3b receptors in human neutrophils and its transmodulation by chemoattractant receptors stimulation", Cell Regulation, vol. 2, pp. 41-55, (1991).

Fang, et al., "Expression of complement receptors 1 and 2 on follicular dendritic cells is necessary for the generation of a strong antigen-specific IgG response", The Journal of Immunology, 160: 5273-5279, (1998).

Finch, et al., "Low-molecule-weight peptide and cyclic antagonists of the receptor for the complement factor C5a", J. Med. Chem., 42: 1965-1974, (1999).

Fujita, et al., "The lectin-complement pathway—its role in innate immunity and evolution", Immunological Reviews, vol. 198: 185-202, (2004).

Fung, et al., "Inhibition of complement, neutrophil, and platelet activation by an anti-factor D monoclonal antibody in simulated cardiopulmonary bypass circuits", The Journal of Thoracic and Cardiovascular Surgery, vol. 122, No. 1, pp. 113-122, (2001).

Kennedy, et al., "An anti-C3b(i) mAb enhances complement activation, C3b(i) deposition, and killing of CD20$^+$ cells by rituximab", Blood, vol. 101, No. 3, pp. 1071-1079, (2003).

Kissel, et al., "Microvascular deposition of complement membrane attack complex in dermatomyositis", The New England Journal of Medicine, vol. 314, No. 6, pp. 329-334, (1986).

Mollnes, et al., "Complement in inflammatory tissue damage and disease", Trends in Immnuology, vol. 23, No. 2, pp. 61-64, (2002).

Neumann, et al., "Local production of complement proteins in rhematoid arthritis synovium", Arthritis & Rheumatism, vol. 46, No. 4, pp. 934-945, (2002).

Schein, et al., "Complement activation and corticosteroid therapy in the development of the adult respiratory distress syndrome", CHEST, 91: 850-854, (1987).

Sengelov, "Complement receptors in neutrophils", Critical Reviews in Immunology, 15(2): 107-131, (1995).

Sengelov, et al., "Secretory vesicles are the intracellular reservoir of complement receptor 1 in human neutrophils", The Journal of Immunology, 153: 804-810, (1994).

Short, et al., "Effects of a new C5a receptor antagonist on C5a- and endotoxin-induced neutropenia in the rat", British Journal of Pharmacology, 126: 551-554, (1999).

Stahl, et al., "Role for the alternative complement pathway in ischemia/reperfusion injury", American Journal of Pathology, vol. 162, No. 2, pp. 449-455, (2003).

Tofukuji, et al., "Anti-C5A monoclonal antibody reduces cardiopulmonary bypass and cardioplegia-induced coronary endothelial dysfunction", Journal of Thoracic Cardiovascular Surgery, 116: 1060-1068, (1998).

Wang, et al., "Anti-C5 monoclonal antibody therapy prevents collagen-induced arthritis and ameliorates established disease", PNAS, vol. 92, pp. 8955-8959, (1995).

Watanabe, et al., "Modulation of renal disease in MRL/*lpr* mice genetically deficient in the alternative complement pathway factor B$^1$", The Journal of Immunology, 164: 786-794, (2000).

Woodruff, et al., "Antiarthritic activity of an orally active C5a receptor antagonist against antigen-induced monarticular arthritis in the Rat", Arthritis & Rheumatism, vol. 46, No. 9, pp. 2476-2485, (2002).

Database Genebank (Apr. 24, 2001), Ashkenazi et al., "Human Pro 1868 Protein" Database Accession No. AAB80272, XP002448361.

Langnaese, et al., "Cloning of Z39Ig, a novel gene with immunoglobulin-like domains on human chromosome X1", BBA, pp. 522-525, (2000).

Blast Report, http://expasy.org/cgi-bin/niceprot.pl/printable?ac=Q80WA3.

\* cited by examiner

```
  1  CCCACGCGTC CGCCACGCG TCCGCCACGCG GGTCCGCCCA CGGGTCCGCG CCGGTCCGGA AGAAAGGACA
     GGGTGCGCAG GCGGGTGCGC AGCGCGGGTG CCAGGCGCCC GGTGGTCTTC AAACCATCGT CCTCCGACCT TCTTTCCTGT

101  GAAGTAGCTC TGGCTGTGAT GGGGATCTTA CTGGGCCTGC TACTCCTGGG GCACCTAACA GTGGACACTT ATGGCGGTCC CATCCTGGAA GTGCCAGAGA
     CTTCATCGAG ACCGACACTA CCCCTAGAAT GACCCGGACG ATGAGGACCC CGTGGATTGT CACCTGTGAA TACCGGCAGG GTAGGACCTT CACGGTCTCT
  1                      M   G   I   L   L   G   L   L   L   L   G   H   L   T   V   D   T   Y   G   R   P   I   L   E   V   P   E   S
       SEQ ID NO:2  ^MET

201  GTGTAACAGG ACCTTGGAAA GGGGATGTGA ATCTTCCCTG CACCTATGAC CCCCTGCAAG GCTACACCCA AGTCTTGGTG AAGTGGCTGG TACAACGTGG
     CACATTGTCC TGGAACGTTT CCCCTACACT TAGAAGGGAC GTGGATACTG GGGGACGTTC CGATGTGGGT TCAGAACCAC TTCACCGACC ATGTTGCACC
 29   V   T   G   P   W   K   G   D   V   N   L   P   C   T   Y   D   P   L   Q   G   Y   T   Q   V   L   V   K   W   L   V   Q   R   G

301  CTCAGACCCT GTCACCATCT TTCTACGTGA CTCTTCTGGA GACCATATCC AGCAGGCAAA GTACACAGGC CGCCTGCATG TGAGCACAA GGTTCCAGGA
     GAGTCTGGGA CAGTGGTAGA AAGATGCACT GAGAAGACCT CTGGTATAGG TCGTCCGTTT CATGTGTCCG GCGGACGTAC ACTCGGTGTT CCAAGGTCCT
 62   S   D   P   V   T   I   F   L   R   D   S   S   G   D   H   I   Q   Q   A   K   Y   Q   G   R   L   H   V   S   H   K   V   P   G

401  GATGTATCCC TCCAATTGAG CACCCTGGAG ATGGATGACC GGAGCCACTA GGAGCCACTA CACGTGTGAA GTCACCTGAC AGACTCCTGA TGGCAACCAA GTCGAGAAG
     CTACATAGGG AGGTTAACTC GTGGGACCTC TACCTACTGG CCTCGGTGAT TACCTACTGG GTGCACACTT CAGTGGACCG TCTGAGGACT ACCGTTGGTT CAGCACTCTC
 95   D   V   S   L   Q   L   S   T   L   E   M   D   D   R   S   H   Y   T   C   E   V   T   W   Q   T   P   D   G   N   Q   V   V   R   D

501  ATAAGATTAC TGAGCTCGCT GTCCAGAGAAC TCTCTGTCTC CAAGCCCACA GTGACAACTG GCAGCGGGTTA TGGCTTCACG GTGCCCCAGG GAATGAGGAT
     TATTCTAATG ACTCGAGGCA CAGGTCTTTG AGAGACAGAG GTTCGGGTGT CACTGTTGAC CGTCGCCAAT ACCGAAGTGC CACGGGGTCC CTTACTCCTA
129   K   I   T   E   L   R   V   Q   K   L   S   V   S   K   P   T   V   T   T   G   S   G   Y   G   F   T   V   P   Q   G   M   R   I

601  TAGCCTTCAA TGCCAGGCTC GGGGTTCTCC TCCCATCAGT TATATTTGGT ATAAGCAACA GACTAATAAC CAGGAACCCA TCAAAGTAGC AACCCTAAGT
     ATCGGAAGTT ACGGTCCGAG CCCCAAGAGG AGGGTAGTCA ATATAAACCA TATTCGTTGT CTGATTATTG GTCCTTGGGT AGTTTCATCG TTGGATTCA
162   S   L   Q   C   Q   A   R   G   S   P   P   I   S   Y   I   W   Y   K   Q   Q   T   N   N   Q   E   P   I   K   V   A   T   L   S

701  ACCTTACTCT TCAAGCCTGC GGTGATAGCC GACTCAGGCT CCTATTCTG CACTGCCAAG GGCCAGGTTG GCTCTGAGCA GCACAGCGAC AATGTGAAGT
     TGGAATGAGA AGTTCGGACG CCACTAGCGG CTGAGTCCGA GGATAAAGAC GTGACGGTTC CCGGTCCAAC CGAGACTCGT CGTGTCGCTG TAACACTTCA
195   T   L   L   F   K   P   A   V   I   A   D   S   G   S   Y   F   C   T   A   K   G   Q   V   G   S   E   Q   H   S   D   I   V   K   F

801  TTGTGGTCAA AGACTCCTCA AAGCTACTCA AAGACCAAGAC TGAGGCACCT ACAACCTGGA TGTTGGTACT GTATGGGGAA CTTTCGTTGT GAAAGCAACA TCTACAGTGA AGCAGTCCTG
     AACACCAGTT TCTGAGGAGT TTCGATGAGT TCTGGTTCTG ACTCCGTGGA TGTTGGACCT ACAACCATGA CATACCCCTT GAAAGCAACA CATTCGTTGT GTATGGGGAA CTTTCGTTGT AGATGTCACT TCGTCAGGAC
229   V   V   K   D   S   S   K   L   L   K   T   K   T   E   A   P   T   T   M   T   Y   P   L   K   A   T   S   T   V   K   Q   S   W
```

Figure 1A (SEQ ID: 1,2)

```
 901  GGACTGGACC ACTGACATGG ATGGCTACCT TGGAGAGACC AGTGCTGGGC CAGGAAAGAG CCTGCCTGTC TTTGCCATCA TCCTCATCAT CTCCTTGTGC
      CCTGACCTGG TGACTGTACC TACCGATGGA ACCTCTCTGG TCACGACCCG GTCCTTTCTC GGACGGACAG AAACGGTAGT AGGAGTAGTA GAGGAACACG
 262   D   W   T   T   D   M   D   G   Y   L   G   E   T   S   A   G   P   G   K   S   L   P   V   F   A   I   I   L   I   I   S   L   C

1001  TGTATGGTGG TTTTTACCAT GGCCTATATC ATGCTCTGTC GGAAGACATC CCAACAGAG GGAAGCAGCC ATGTCTACG AAGCAGCCAG GTAAGAAAGT CTCTCCTCTT
      ACATACCACC AAAAATGGTA CCGGATATAG TACGAGACAG CCTTCTGTAG GGTTGTTCTC GTACAGATGC TTCGTCGGTC CATTCTTTCA GAGAGGAGAA
 295   C   M   V   V   F   T   M   A   Y   I   M   L   C   R   K   T   S   Q   Q   E   H   V   Y   E   A   A   R   Q

1101  CCATTTTGA CCCCGTCCCT GCCCTCAATT TTGATTACTG GCAGGAAATG TGGAGGAAGG GGGGTGTGGC ACAGACCCAA TCCTAAGGCC GGAGGCCTTC
      GGTAAAAACT GGGGCAGGGA CGGGAGTTAA AACTAATGAC CGTCCTTTAC ACCTCCTTCC CCCCACACCG TGTCTGGGTT AGGATTCCGG CCTCCGGAAG

1201  AGGGTCAGGA CATAGCTGCC TTCCCTCTCT CAGGCACCTT CTGAGGTTGT TTTTGGCCCTC TGAACACAAA GGATAATTTA GATCCATCTG CCTTCTGCTT
      TCCCAGTGCT GTATCGACGG AAGGGAGAGA GTCCGTGGAA GACTCCAACA AAACCGGGAG ACTTGTGTTT CCTATTAAAT CTAGGTAGAC GGAAGACGAA

1301  CCAGAATCCC TGGGTGGTAG GATCCTGATA ATTAATTGAG AAGAATTGAG GCAGAAGGGT GGGAAACCAG GACCACAGCC CCAAGTCCCT TCTTATCGGT
      GGTCTTAGGG ACCCACCATC CTAGGACTAT TAATTAACTC TTCTTAACTC CGTCTTCCCA CCCTTTGGTC CTGGTGTCGG AGAATACCCA

1401  GGTGGCTCT TGGGCCATAG GGCACATGCC AGAGAGGCCA AGAGAAACATG TCTTCCAAG AGGGTGGCCA TCTTCGAAG TGGCTGCTCC AGTGATGAGC
      CCACCCGAGA ACCCGGTATC CCGTGTACGG TCTCTCCGGT TGCTGAGACC TCTTTGGTAC TCCCACCGGT AGAAGGGTTC ACCGAGAGGG TCACTACTCG

1501  CAACTTCCCA GAATCTGGGC AACAACTACT AAGTAAGCCA GATGCATCTC CTGATGAGCC AGATCATGCC CCAGATACC GGCAACTACG CCCGCCTGCT
      GTTGAAGGGT CTTAGACCCG TTGTTGATGA TTCATTCGGT CTACGTAGAG GACTACTCGG GTCTAGTTA CGGTTGATGC GGGCGGACGA

1601  GGACACAGTT CCTCTGGATT ATGAGTTCTT GGCCACTGAG GGCAAAAGTG TCTGTTAAA ATGCCCCATT AGGCCAGGAT CTGCTGACAT AATTGCCTAG
      CCTGTGTCAA GGAGACCTAA TACTCAAGA CCGGTGACTC CCGTTGTCAC AGACAATTTT TACGGGGTAA TCCGGTCCTA GACGACTGTA TTAACGGATC

1701  TCAGTCCTTG CCTTCTCTTC CCTGCTGCAT GGCCTTCTTC CCTGCTACCT ATAGCCCAAA GTGTCCGCCT ACCAACACTG GAGCGCTGG GAGTCACTGG
      AGTCAGGAAC GGAAGAGAAG GGACGACGTA CCGGAAGAAG GGACGATGGA TATCGGGTTT CACAGGCCGA TGGTTGTGAC CTCGGCGACC CTCAGTGACC

1801  CTTTGCCCTG GAATTTGCCA GATGCATCTC AAGTAAGCCA ATGCATCTGG TTGGCTCTGG GCCCTTCTAG TATCTCTGCC GGGGGCTTCT GGTACTCCTC
      GAAACGGGAC CTTAAACGGT CTACGTAGAG TTCATTCGGT TACGTAGACC GGACGGT AACCGAGACC CGGGAAGATC ATAGAGACGG CCCCCGAAGA CCATGAGGAG

1901  TCTAAATACC AGAGGGAAGA TGCCCATAGC ACTAGGACTT GGTCATCATG CCTACAGCA GATCATTTCT CTTTCTTCAG TTGGCATCTT GCCACCAGAA GACCCGAGGG
      AGATTTATGG TCTCCCTTCT ACGGGTATCG TGATCCTGAA CCAGTAGTAC GGATGTCGTT GAAGAAGTC GAAATTTGAA ACCGTAGAA CGGTGGTCTT CTGGGCTCCC

2001  AGGCTCAGCT CTGCCAGCTC AGAGGACCAG CTATATCCAG GGCCAGACAG CTTTTAATTG AATTGTTAT TTCACAGGCC
      TCCGAGTCGA GACGGTCGAA TCTCCTGGTC GATATAGGTC CCGGTCTGTC GAAATTAAC TTTAACAATA AAGTGTCCGG

2101  AGGGTTCAGT TCTGCTCCTC CACTATAAGT GACTCTCTCA TAAATATCTA ATCATAACAG C
      TCCCAAGTCA AGACGAGGAG GTGATATTCA CTGAGAGAGT ATTTATGAT TAGTATTGTC G
```

Figure 1B
(SEQ ID: 1,2)

```
  1  CCAACTGCAC CTCGGTTCTA TCGATAGGAG AGGACAGAAG TAGCTCTGGC TGTGATGGGG ATCTTACTGG GCTGCTACT CCTGGGGCAC
     GGTTGACGTG GAGCCAAGAT AGCTATCCTC TCCTGTCTTC ATCGAGACCG ACACTACCCC TAGAATGACC CGGACGATGA GGACCCCGTC
  1                                                                   M   G       I   L   L   L       L   L   G   H
                                                                      ^MET

101  CTAACAGTGG ACACTTATGG CCGTCCCATC CTGGAAGTGC CAGAGAGTGT AACAGGACCT TGGAAAGGGG ATGTGAATCT TCCCTGCACC TATGACCCCC
     GATTGTCACC TGTGAATACC GGCAGGGTAG GACCTTCACG GTCTCTCACA TTGTCCTGGA ACCTTTCCCC TACACTTAGA AGGGACGTGG ATACTGGGGG
 13   L   T   V   D   T   Y   G   R   P   I   L   E   V   P   E   S   V   T   G   P   W   K   G   D   V   N   L   P   C   T   Y   D   P   L

201  TGCAAGGCTA CACCCAAGTC TTGGTGAAGT GGCTGGTACA ACGTGGCTCA GACCCTGTCA ACATCTTTCT ACGTGACTCT TCTGGAGACC ATATCCAGCA
     ACGTTCCGAT GTGGGTTCAG AACCACTTCA CCGACCATGT TGCACCGAGT CTGGGACAGT TGTAGAAAGA TGCACTGAGA AGACCTCTGG TATAGGTCGT
 47   Q   G   Y   T   Q   V   L   V   K   W   L   V   Q   R   G   S   D   P   V   T   I   F   L   R   D   S   G   D   H   I   Q   Q

301  GGCAAAGTAC CAGGGCCGCC TGCATGTGAG CCACAAGGTT CCAGGAGATG TATCCCTCCA ATTGAGCACC CTGGAGATGG ATGACCGGAG CCACTACACG
     CCGTTTCATG GTCCCGGCGG ACGTACACTC GGTGTTCCAA GGTCCTCTAC ATAGGGAGGT TAACTCGTGG GACCTCTACC TACTGGCCTC GGTGATGTGC
 80   A   K   Y   Q   G   R   L   H   V   S   H   K   V   P   G   D   V   S   L   Q   L   S   T   L   E   M   D   D   R   S   H   Y   T

401  TGTGAAGTCA CCTGGCAGAC CCCTGATGGC AACCAAGTCG TGGAGAGATAA GATTACTGAG ACTCTCTATT CTAATGACTC GAGGCACAGG TCTTTGAGAG ACAGAGGTTC GGGTGTCACT CCCACAGTGA
     ACACTTCAGT GGACCGTCTG GGGACTACCG TTGGTTCAGC ACCTCTCTATT CTAATGACTC GAGGCACAGG TCTTTGAGAG ACAGAGGTTC GGGTGTCACT CCCACAGTGA
113   C   E   V   T   W   Q   T   P   D   G   N   Q   V   V   R   D   K   I   T   E   L   R   V   Q   K   L   S   V   S   K   P   T   V   T

501  CAACTGGCAG CGGTTATGGC TTCACGGTGC CCCAGGGAAT GAGGATTAGC CTTCAATGCC AAGCTCGGGG TTCTCCTCCC ATCAGTTATA TTTGTATAA
     GTTGACCGTC GCCAATACCG AAGTGCCACG GGGTCCCTTA CTCCTAATCG GAAGTTACGG TTCGAGCCCC AAGAGGAGGG TAGTCAATAT AAACCATATT
147   T   G   S   G   Y   G   F   T   V   P   Q   G   M   R   I   S   L   Q   C   Q   A   R   G   S   P   P   I   S   Y   I   W   Y   K
```

Figure 2A

```
601   GCAACAGACT AATAACCAGG AACCCATCAA AGTAGCAACC CTAAGTACCT TACTCTTCAA GCCTGCGGTG ATAGCCGACT CAGGCTCCTA TATCTGCACT
      CGTTGTCTGA TTATTGGTCC TTGGGTAGTT TCATCGTTGG GATTCATGGA ATGAGAAGTT CGGACGCCAC TATCGGCTGA GTCCGAGGAT AAAGACGTGA
180    Q  Q  T   N  N  Q  E   P  I  K   V  A  T    L  S  T  L   F  K  P   A  V  I   A  D  S   G  S  Y    F  C  T

701   GCCAAGGGCC AGGTTGCCTC TGAGCAGCAC AGCGACATTG TGAAGTTTGT GGTCAAAGAC TACTCAAGAC TCCTCAAAGC CAACTACAGA GCACCTACAA
      CGGTTCCCGG TCCAACCGAG ACTCGTCGTG TCGCTGTAAC ACTTCAAACA CCAGTTTCTG ATGAGTTCTG AGGAGTTTCG GTTGATGTCT CGTGGATGTT
213    A  K  G  Q   V  G  S   E  Q  H    S  D  I  V   K  F  V    V  K  D    S  S  K  L   L  K  T    K  T  E   A  P  T  T

801   CCATGACATA CCCCTTGAAA GCAACATCTA CAGTGAAGCA GTCCTGGGAC TGACCACTGA CTACCTTGGA GAGACCAGTG CTGGGCCAGG
      GGTACTGTAT GGGGAACTTT CGTTGTAGAT GTCACTTCGT CAGGACCCTG ACTGGTGACT GATGGAACCT CTCTGGTCAC GACCCGGTCC
247    M  T  Y   P  L  K    A  T  S  T    V  K  Q   S  W  D    W  T  T  D   M  D  G    Y  L  G   E  T  S  A   G  P  G

901   AAAGAGCCTG CCTGTCTTTG CCATCATCCT CATCATCTCC TTGTGCTGTA TGGTGGTTTT ACCACCAAAA TACATAGTAC GATATCCAA
      TTTCTCGGAC GGACAGAAAC GGTAGTAGGA GTAGTAGAGG AACACGACAT ACCACCAAAA TGGTGGTTTT ATGTATCATG CTATAGGGTT
280    K  S  L   P  V  F  A    I  I  L    I  I  S    L  C  C  M   V  V  F    T  M  A   Y  I  M  L    C  R  K    T  S  Q

1001  CAAGAGCATG TCTACGAAGC AGCCAGGGCA CATGCCAGAG TGAGCCTGC ATAGGACAGG AGTACCAGAT CATCGCCCAG ACTACGCCG
      GTTCTCGTAC AGATGCTTCG TCGGTCCCGT GTACGGTCTC ACTCGGACG TATCCTGTCC TCATGGTCTA GTAGCGGGTC TGATGCGGGC
313    Q  E  H  V   Y  E  A    A  R  A    H  A  R  E   A  N  D    S  G  E   T  M  R  V   A  I  F    A  S  G   C  S  S  D

1101  ATGAGCCAAC TTCCCAGAAT CTGGGCAACA ACTACTCTGA TGAGCCCTGC ACTGAGGGCA AAGTGTCTG TTAAAAATGC CCCATTAGCC CAGGATCTGC TGACATAATC ACTACGCCCG
      TACTCGGTTG AAGGGTCTTA GACCCGTTGT TGATGAGACT ACTCGGGACG TGACTCCCGT TTCACGAGAC AATTTTTACG GGGTAATCCG GTCCTAGACG ACTGTATTAG
347    E  P  T   S  Q  N    L  G  N  N   Y  S  D    E  P  C    I  G  Q  E   Y  Q  I   I  A  Q    I  N  G  N   Y  A  R

1201  CCTGCTGGAC ACAGTTCCTC TGGATTATGA GTTTCTGGCC ACTGAGGGCA AAAGTGTCTG ACTGAGGGCA TGACTCCCGT TTCACGAGAC
      GGACGACCTG TGTCAAGGAG ACCTAACTACT CAAAGACCGG TGACTCCCGT TTCACGAGAC ACAAATAACG TCGAATATTA CCAATGTTTA
380    L  L  D    T  V  P  L    D  Y  E   F  L  A    T  E  G  K   S  V  C   Q

1301  TAGAGTCGAC CTGCAGCTG TTGCCCAACT TGTTTATTGC AGCTTATAAT GGTTACAAAT AA
      ATCTCAGCTG GACGTCGAC AACGGGTTGA ACAAATAACG TCGAATATTA CCAATGTTTA TT
```

Figure 2B

```
  1 GTCCAACTGC ACCTCGGTTC TATCGATAGG AGGCTGAAG AAAGGACAGA AGTAGCTCTG GCTGTGATGG GGATCTTACT GGGCCTGCTA CTCCTGGGC
    CAGGTTGACG TGGAGCCAAG ATAGCTATCC TCCGACCTTC TTTCCTGTCT TCATCGAGAC CGACACTACC CTAGAATGA CCCGGACGAT GAGGACCCG
                                                    ^insert begins here     M  G  I  L  L   G  L  L   L  L  G  H 101 ACCTAACAGT GGACACTTAT GGCCGTCCCA TCCTGGAAGT GCCAGAGAGT GTAACAGGAC CTTGGAAAGG GGATGTGAAT CTTCCCTGCA CCTATGACCC
 13 TGGATTGTCA CCTGTGAATA CCGGCAGGGT AGGACCTTCA CGGTCTCTCA CATTGTCCTG CCTACACTTA GAACCTTTCC CCTACACTTT GGATACTGGG
     L  T  V   D  T  Y   G  R  P  I   L  E  V   P  E  S    V  T  G   P  W  K  G   D  V  N   L  P  C  T   Y  D  P 201 CCTGCAAGGC TACACCCAAG TCTTGGTGAA GTGGCTGGTA CAACGTGGCT CAGACCCTGT CACCATCTTT CTACGTGACT CTTCTGGAGA CCATATCCAG
 46 GGACGTTCCG ATGTGGGTTC AGAACCACTT GTTGCACCGA GTCTGGGACA GATGCACTGA GAAGACCTCT GGTATAGGTC
     L  Q  G   Y  T  Q  V   L  V  K   W  L  V   Q  R  G  S   D  P  V   T  I  F   L  R  D  S   S  G  D   H  I  Q 301 CAGGCAAAGT ACCAGGGCCG CCTGGATGTG AGCCACAAGT TCCAGGAGAT CGTGAGAGAT AAGATTACTG AGCTCCGTGT CCAGAAACAC TCCTCAAAGC TACTCAAGAC
 79 GTCCGTTTCA TGGTCCCGGC GGACCTACAC TCGGTGTTCA AGGTCCTCTA ACATAGGGAG TTCTAATGAC TCGAGGCACA GGTCTTTGTG AGGAGTTTCG ATGAGTTCTG
     Q  A  K  Y   Q  G  R   L  D  V   S  H  K  V   P  G  D   V  S  L   Q  L  S  T   L  E  M   D  D  R   S  H  Y  T 401 CGTGTGAAGT CACCTGGCAG ACTCCTGATG GCAACCAAGT CGTTGGTTCA GCAACATCTA CCCCTTGAAA GCAACTTTT CGTTGTAGAT GTCACTTCGT CAGGACCCTG
113 GCACACTTCA GTGGACCGTC TGAGGACTAC CGTTGGTTCA GCAACCAAGT CGTTGTAGAT GGGAACTTT CGTTGTAGAT GTCACTTCGT CAGGACCCTG
     C  E  V   T  W  Q   T  P  D  G   N  Q  V   V  R  D   K  I  T  E   L  R  V   Q  K  H   S  S  K  L   L  K  T 501 CAAGACTGAG GCAACCACAA CCATGACATA CCCCCTTGAAA GCAACTTTT CGTGTAGAT GGGAACTTT CGTTGTAGAT GTCACTTCGT CAGGACCCTG ACCTGGTGAC TGTACCTACC GATGAACCT
146 GTTCTGACTC CGTGGTGTT GGTACTGTAT GGTACTGTGT GTACTGTAT CAGAACTTTG GTTCTGACTC CGTGGTGTT GGTACTGTAT
     K  T  E   A  P  T  T   M  T  Y   P  L  K   A  T  S  T   V  K  Q   S  W  D   W  T  T  D   M  D  G   Y  L  G
```

Figure 3A

601  GAGACCAGTG CTGGGCCAGG AAAGAGCCTG CCTGTCTTTG CCATCATCCT CATCATCTCC TTGTGCTGTA TGGTGGTTTT TACCATGGCC TATATCATGC
     CTCTGGTCAC GACCCGGTCC TTTCTCGGAC GGACAGAAAC GGTAGTAGGA GTAGTAGAGG AACACGACAT ACCACCAAAA ATGGTACCGG ATATAGTACG
179   E  T  S  A  G  P  G  K  S  L  P  V  F  A  I  I  L  I  I  S  L  C  C  M  V  V  F  T  M  A  Y  I  M  L

701  TCTGTCGGAA GACATCCCAA CAAGAGCCAT CTACGAAAGC GTTCTCGTAC AGATGCTTCG TCGGTCCCGT GTACGGTCTC TCCGGTTGCT GAGACCTCTT TGGTACTCCC ACCGGTAGAA
     AGACAGCCTT CTGTAGGGTT GTTCTCGGTA CAGATGCTTCG TCGGTCCCGT GTACGGTCTC TCCGGTTGCT GAGACCTCTT TGGTACTCCC ACCGGTAGAA
213   C  R  K  T  S  Q  Q  E  H  V  Y  E  A  A  R  A  H  A  R  E  A  N  D  S  G  E  T  M  R  V  A  I  F

801  CGCAAGTGGC TGCTCCAGTG CTGGGCAACA TTCCCAGAAT CTGGGCAACA CTACTCTGA TGAGCCCTGC ATAGGACAGG AGTACCAGAT CATCGCCCAG
     GCGTTCACCG ACGAGGTCAC GACGAGGTCAC GACCCGTTGT AAGGGTCTTA GACGAGGTCAC ACTCGGGACG TATCCTGTCC TCATGGTCTA GTAGCGGGTC
246   A  S  G  C  S  S  D  E  P  T  S  Q  N  L  G  N  N  Y  S  D  E  P  C  I  G  Q  E  Y  Q  I  I  A  Q

901  ACTGAGGGCA AAGTGTCTG TTAAAAATGC CCCATTAGGC
     ATCAATGGCA ACTACGCCCG CCTGCTGGAC ACAGTTCCTC TGGATTATGA GTTCTGGCC ACTGAGGGCA AAGTGTCTG TTAAAAATGC CCCATTAGGC
     TAGTTACCGT TGATGCGGGC GGACGACCTG TGTCAAGGAG ACCTAATACT CAAGACCGG TGACTCCCGT TTTCACAGAC AATTTTTACG GGGTAATCCG
279   I  N  G  N  Y  A  R  L  L  D  T  V  P  L  D  Y  E  F  L  A  T  E  G  K  S  V  C  Q

1001 CAGGATCTGC TGACATAATC TAGAGTCGAC CTGCAGAAGC TTGGCCCGCCA TGGCCCAACT TGTTTATTGC AGCTTATAAT GGTTACAATA
     GTCCTAGACG ACTGTATTAG ATCTCAGCTG GACGTCTTCG AACCGGGCGGT ACCGGGTTGA ACAAATAACG TCGAATATTA CCAATGTTAT

^insert ends here

Figure 3B

```
  1 GTCCAACTGC ACCTCGGTTC TATCGATTCG AATTCGGCCA CACTGGCCGG ATCCTCTAGA GATCCCTCGA CCTCGACCCA CCGGTCCGAG CAGCAAGAGG
    CAGGTTGACG TGGAGCCAAG ATAGCTAAGC TTAAGCCGGT GTGACCGGCC TAGGAGATCT CTAGGGAGCT GGAGCTGGGT GCCAGGCTC GTCGTTCTCC

101 ATGGAAGGAT GAATAGAAGT AGCTTCAAAT AGGATGGAGA TCTCATCAGG CTTGCTGTTC CTGGGCCACC TAATAGTGCT CACCTATGGC CACCCCACCG
    TACCTTCCTA CTTATCTTCA TCGAAGTTTA TCCTACCTCT AGAGTAGTCC GAACGACAAG GACCCGGTGG ATTATCACGA GTGGATACCG GTGGGGTGGG
                   M  E  I     S  S  G     L  L  F     L  G  H  L     I  V  L     T  Y  G     H  P  T  L
  1            ^MET

201 TAAAAACACC TGAGAGTGTG ACAGGACCT GGAAAGGAGA TGTGAAGATT CAGTGCATCT ATGATCCCCT GAGAGGCTAC AGGCAAGTTT TGGTGAAATG
    ATTTTGTGG ACTCTCACAC TGTCCCTGGA CCTTTCCTCT ACACTTCTAA GTCACGTAGA TACTAGGGGA CTCTCCGATG TCCGTTCAAA ACCACTTTAC
 24    K  T  P    E  S  V     T  G  T  W     K  G  D     V  K  I     Q  C  I  Y     D  P  L     R  G  Y     R  Q  V  L     V  K  W

301 GCTGGTAAGA CACGGCTCTG ACTCCGTCAC CATCTTCCTA CGTGACTCCA CTGGAGACCA TATCCAGCAG GCAAAGTACA GAGGCCGCCT GAAAGTGAGC
    CGACCATTCT GTGCCGAGAC TGAGGCAGTG GTAGAAGGAT GCACTGAGGT GACCTCTGGT ATAGGTCGTC CGTTTCATGT CTCCGGCGGA CTTTCACTCG
 57    L  V  R    H  G  S  D     S  V  T     I  F  L     R  D  S  T     G  D  H     I  Q  Q     A  K  Y  R     G  R  L     K  V  S

401 CACAAAGTTC CAGGAGATGT GTCCCTCCAA ATAAATACCC TGCAGATGGA TGACAGGAAT CACTATACAT GTGAGGTCAC CTGGCAGACT CCTGATGGAA
    GTGTTTCAAG GTCCTCTACA CAGGGAGGTT TATTTATGGG ACGTCTACCT ACTGTCCTTA GTGATATGTA CACTCCAGTG GACCGTCTGA GGACTACCTT
 90    H  K  V  P     G  D  V     S  L  Q     I  N  T  L     Q  M  D     D  R  N     H  Y  T  C     E  V  T     W  Q  T     P  D  G  N
```

Figure 4A

```
501  ACCAAGTAAT AAGAGATAAG ATCATTGAGC TCCGTGTTCG GAAATATAAT CCACCTAGAA AGCACCTACA ACCCTGCACT CCTCTTTGGA
     TGGTTCATTA TTCTCTATTC TAGTAACTCG AGGCACAAGC CTTTATATTA GGTGGATCTT AGTTATGACT TCGTGGACGTGT GGAGAAACCT
124  Q  V  I  R  D  K     I  I  E  L  R  V  R     K  Y  N  P  P  R     I  N  T  E  A  P  T     T  L  H  S  S  L  E

601  AGCAACAACT ATAATGAGTT CAACCTCTGA CTTGACCACT AATGGGACTG GAAAACTTGA GGAGACCATT GCTGGTTCAG GGAGGAACCT GCCAATCTTT
     TCGTTGTTGA TATTACTCAA GTTGGAGACT GAACTGGTGA TTACCCTGAC CTTTTGAACT CCTCTGGTAA CGACCAAGTC CCTCCTTGGA CGGTTAGAAA
157  A  T  T     I  M  S  S  T  S  D     L  T  T     N  G  T  G  K  L  E  E  T  I     A  G  S  G     R  N  L     P  I  F

701  GCCATAATCT TCATCATCTC CCTTTGCTGC ATAGTAGCTG TCACCATACC TTATATCTTG TTCCGCTGCA GGACATTCCA ACAAGAGTAT GTCTATGGAG
     CGGTATTAGA AGTAGTAGAG GGAAACGACG TATCATCGAC AGTGGTATGG AATATAGAAC AAGGCGACGT CCTGTAAGGT TGTTCTCATA CAGATACCTC
190  A  I  I  F     I  I  S     L  C  C     I  V  A  V  T  I  P     Y  I  L     F  R  C  R     T  F  Q     Q  E  Y  V  Y  G  V

801  TGAGCAGGGT GTTTGCCAGG AAGACAAGCA ACTCTGAAGA AACCACAAGG GTGACTACCA TCGCAACTGA TGAACCAGAT TCCCAGGCTC TGATTAGTGA
     ACTCGTCCCA CAAACGGTCC TTCTGTTCGT TGAGACTTCT TTGGTGTTCC CACTGATGGT AGCGTTGACT ACTTGGTCTA AGGGTCCGAG ACTAATCACT
224  S  R  V     F  A  R     K  T  S  N     S  E  E     T  T  R  V  T  T  I     A  T  D     E  P  D     S  Q  A  L     I  S  D

901  CTACTCTGAT GATCCTTGCC TCAGCCAGGA GTACCAAATA ACCATCAGAT CAACAATGTC TATTCCTGCC TGCTGAACAC AGTTTCCAGA AACTAAGAAG
     GATGAGACTA CTAGGAACGG AGTCGGTCCT CATGGTTTAT TGGTAGTCTA GTTGTTACAG ATAAGGACGG ACGACTTGTG TCAAAGGTCT TTGATTCTTC
257  Y  S  D     D  P  C  L     S  Q  E     Y  Q  I     T  I  R  S     T  M  S     I  P  A  C  Q

1001 TTCTTGCTAC TGAAGAAAAT AACATCTGCT AAAATGCCCC TACTAAGTCA AGTCTACTG TTTTACGGGG ATGATTCAGT GCCTTCAACA
     AAGAACGATG ACTTCTTTTA TTGTAGACGA TTTTACGGGG ATGATTCAGT TCCAGATGAC CGCATTAATG GACAATGAAT AAATGATGAA CGGAAGTTGT
```

Figure 4B

```
1101  TAGCTTTCTC CCTGGCTTCC TTTCTTCTTA GACAACCTAA AGTATCTATC TAGTCTGCCA ATTCTGGGGC CATTGAGAAA TCCTGGGTTT GGCTAAGAAT
      ATCGAAAGAG GGACCGAAGG AAAGAAGAAT CTGTTGGATT TCATAGATAG ATCAGACGGT TAAGACCCCG GTAACTCTTT AGGACCCAAA CCGATTCTTA

1201  ATACTACATG CACCTCAAGA AATCTAGCTT CTGGGCCTTCA CCCAGAACAA TTTTCTTCCT AGGGCCTTCA CAACTCTTCT CCAAACAGCA GAGAAATTCC
      TATGATGTAC GTGGAGTTCT TTAGATCGAA GACCCGAAGT GGGTCTTGTT AAAAGAAGGA TCCCGGAAGT GTTGAGAAGA GGTTTGTCGT CTCTTTAAGG

1301  ATAGCAGTAG AGTTCTTTA TCATGCCTCC AGACAGCGTG AGTCTCAGTC CTACAAACTC AGACAAGCAC ATGGGTCTAG GATTACTCCT CTTTCTCTAG
      TATCGTCATC TCCAAGAAAT AGTACGGAGG TCTGTCGCAC TCAGAGTCAG GATGTTTGAG TCTGTTCGTG TACCCAGATC CTAATGAGGA GAAAGAGATC

1401  GGCCAGATGA CTTTTAATTG ATATTACTAT TGAATCTAAT GCACATGTAT TCTTTTGTTG TTAATAAATG TTTAATCATG ACATCAAAAA
      CCGGTCTACT GAAAATTAAC TATAATGATA ACGATGTAAT ACTTAGATTA CGTGTACATA AGAAAACAAC AATTATTTAC AAATTAGTAC TGTAGTTTTT

1501  AAAAAAAAAA AAGGGCGGCC GGGACTCTAG AGTCGACCTG CAGTAGGGAT AACAGGGTAA TAAGCTTGGC CGCCATGGCC CAACTTGTTT
      TTTTTTTTTT TTCCCGCCGG CGCTGAGATC TCAGCTGGAC GTCATCCCTA TTGTCCCATT ATTCGAACCG GCGGTACCGG GTTGAACAAA

^pRK5 continues here
```

Aveolar Macs

Liver Kupffer cells

Liver Kupffer cells
 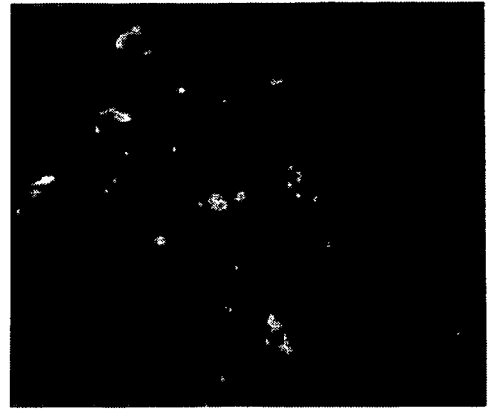
Liver-STIgMA  Liver-CD68
Figure 14

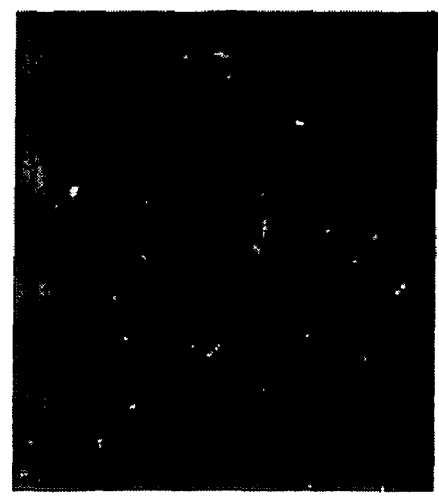
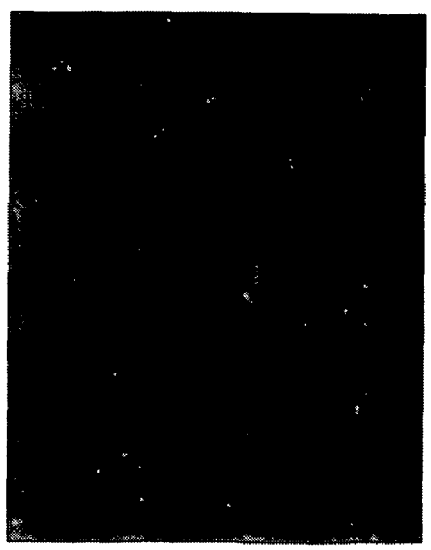
Brain Microglial cells
Figure 15

Placental Hofbauer cells
Placenta-STIgMA/CD68
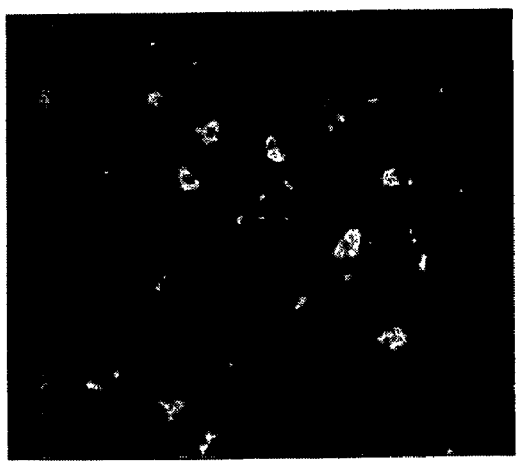
Placenta-CD68
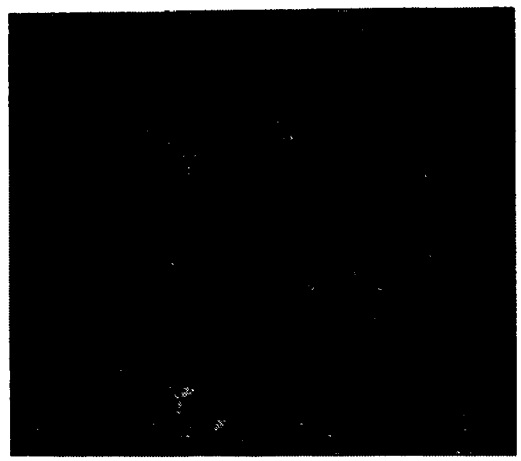
Placenta-STIgMA
Figure 16

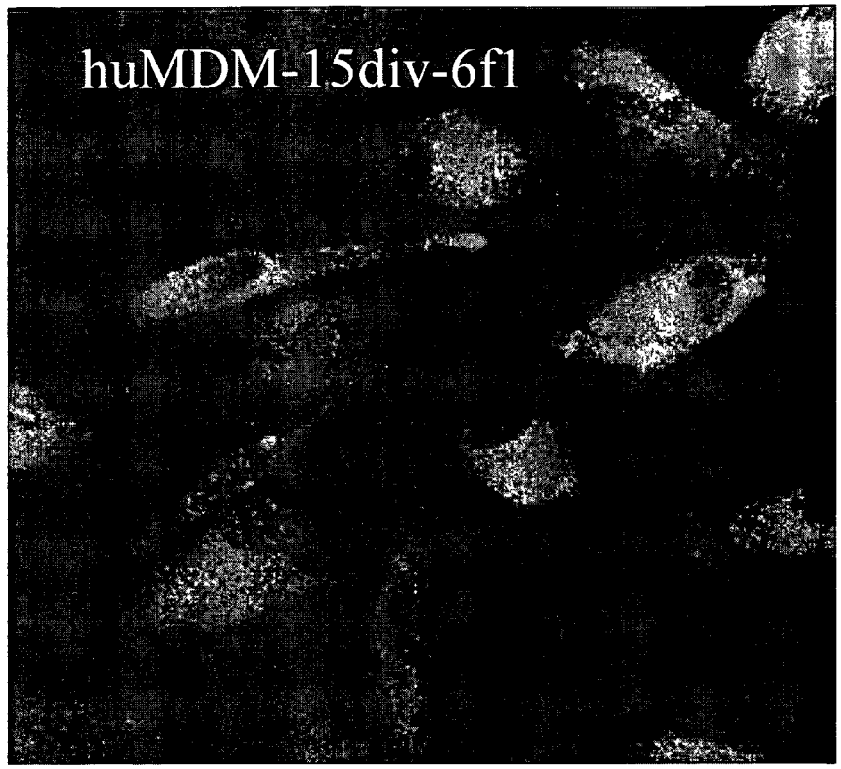
Figure 22

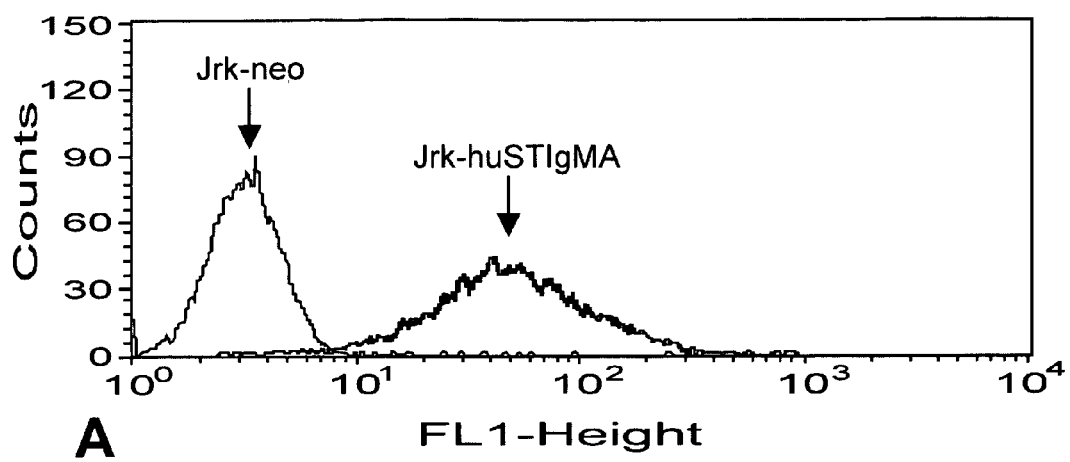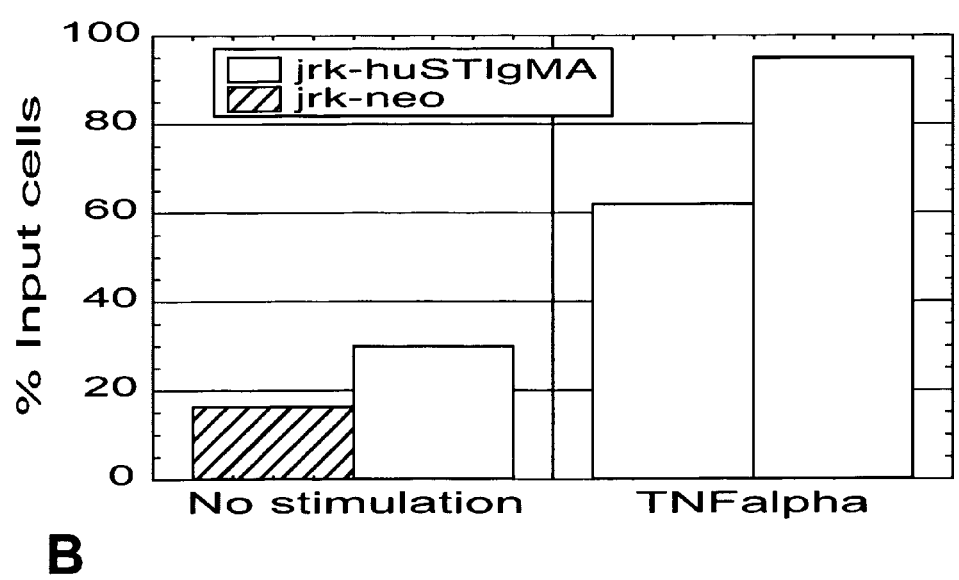
Figure 30 consen02 (SEQ ID NO:9)

```
GCAGGCAAAG TACCAGGGCC GCCTGCATGT GAGCCACAAG GTTCCAGGAG 50
ATGTATCCCT CCAATTGAGC ACCCTGGAGA TGGATGACCG GAGCCACTAC 100
ACGTGTGAAG TCACCTGGCA GACTCCTGAT GGCAACCAAG TCGTGAGAGA 150
TAAGATTACT GAGCTCCGTG TCCAGAAACT CTCTGACTCC AAGCCCACAG 200
TGACAACTGG CAGCGGTTAT GGCTTCACGG TGCCCCAGGG AATGAGGATT 250
AGCCTTCAAT GCCAGGGTTC GGGGTTCTCC TCCCATCAGT TATATTTGGT 300
ATAAGCAACA GACTAATAAC GAGGGAACCC ATCAAAGTAG CAACCCTAAG 350
TACCTTACTC TTCAAGCCTG CGGTGATAGC CGACTCAGGC TCCTATTTCT 400
GCACTGCCAA GGGCCAGGTT GGCTCTGAGC AGCACAGCGA CATTGTGAAG 450
TTTGTGGTCA AAGACTCCTC AAAGCTACTC AAGACCAAGA CTGAGGCACC 500
TACAACCATG ACATACCCCT TGAAAGAAAC ATCTACAGTG AAGCAGTCCT 550
GGGACTGGAC CACTGACATG GATGGCTACC TTGGAGAGAC CAGTGCTGGG 600
CCAGGAAAGA GCCTGCCTGT CTTTGCCATC ATCCTCATCA TCTCCTTGTG 650
CTGTATGGTG GTTTTACCC TGGCCTATAT CATGCTCTGT CGGAAGACAT 700
CCCAACAAGA GCATGTCTAC GAAGCAGCCA GGGCACATGC CAGAGAGGCC 750
AACGACTCTG AGAAACCAT GAGGGTGGCC ATCTTCGCAA GTGGCTGCTC 800
CAGTGATGAG CCAACTTCCC AGAATCTGGG GCAACAACTA CTCTGATGAG 850
CCCTGCATAG GACAGGAGTA CCAGATCATC GCCCAGATCA ATGGCAACTA 900
CGCCCGCCTG CTGGACACAG TTCCTCTGGA TTATGAGTTT CTGGCCACTG 950
AGGGCAAAAG TGTCTGTTAA AAATGCCCCA GAGCCACAAG ATCTGCTGAC 1000
ATAATTGCCT AGTCAGTCCT TGCCTTCTGC ATGTCCTTCT TCCCTACTAC 1050
CTCTCTTCCT GGATAGCCCA AAGTGTCCGC CTACCAACAC TGGAGCCGCT 1100
GGGAGTCACT GGCTTTGCCC TGGAATTTGC CAGATGCATC TCAAGTAAGC 1150
GAGCTGCTGG ATTTGGCTCT GGGCCCTTCT AGTATCTCTG CCGGGGGCTT 1200
CTGGTACTCC TCTCTAAATA CCAGAGGGAA GATGCCCATA GCACTAGGAC 1250
TTGGTCATCA TGCCTACAGA CACTATTCAA CTTTGGCATC TTGCCACCAG 1300
AAGACCCGAG GGGATTCTCA GCTCTGCCAG CTCAGAGGAC CAGCTATATC 1350
TATTTCACAG TCTCTTTCTT CAGGGCCAGA CAGCTTTTAA TTGAAATTGT 1400
TATTTCACAG GCCAGGGTTC AGTTCTGCTC CTCCACTATA AGTCTAATGT 1450
TCTGACTCTC TCCTGGTGCT CAATAAATAT CTAATCATAA CAGCAAAAAA 1500
AAA 1503
```

Figure 32

Figure 34

STIgMA-Fc treatment does not alter the number nor morphology of tissue resident macrophages
STIgMA-Fc
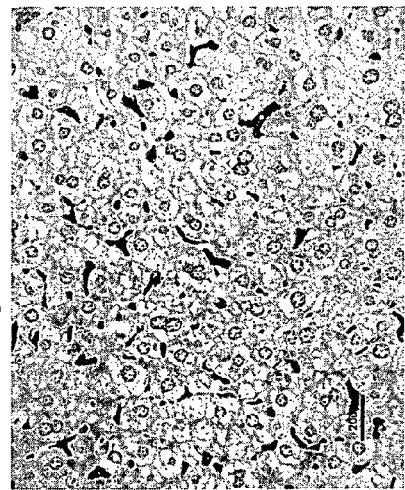
IgG1
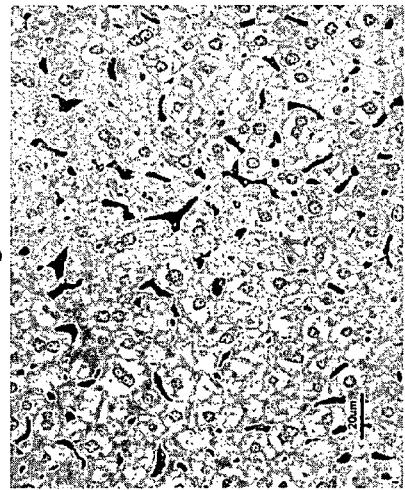
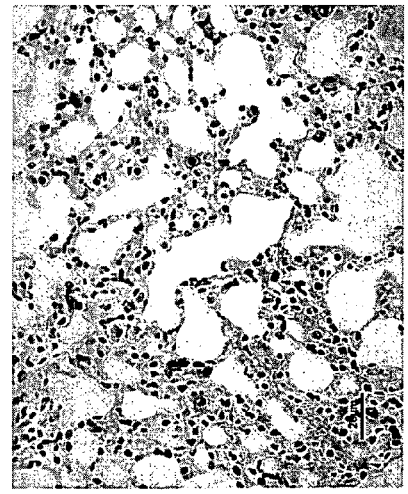
liver
lung
Collagen-induced arthritis day 70
Figure 36

MuSTIgMA-Fc inhibits joint inflammation in antibody-induced arthritis
muSTIgMA-Fc
mulgG1
- Control treated mice (mulgG1) have moderate to severe arthritis (left)
- MuSTIgMA-Fc treated mice have minimal to no arthitis (right)
H&E staining
Figure 41

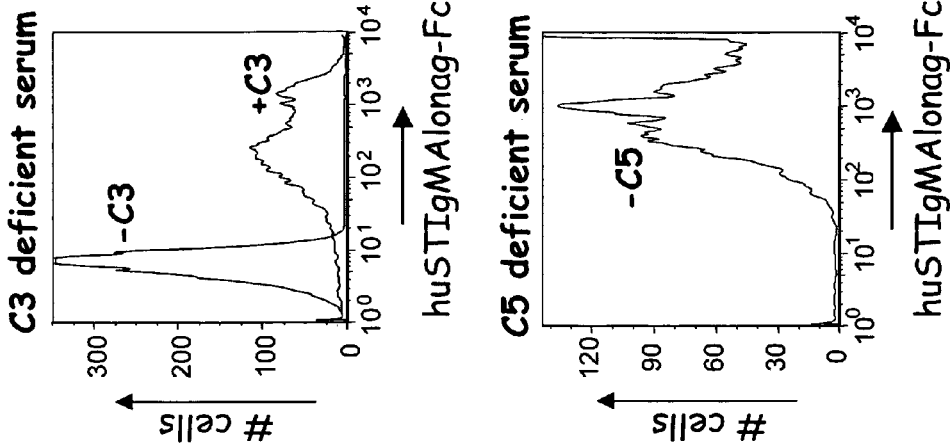
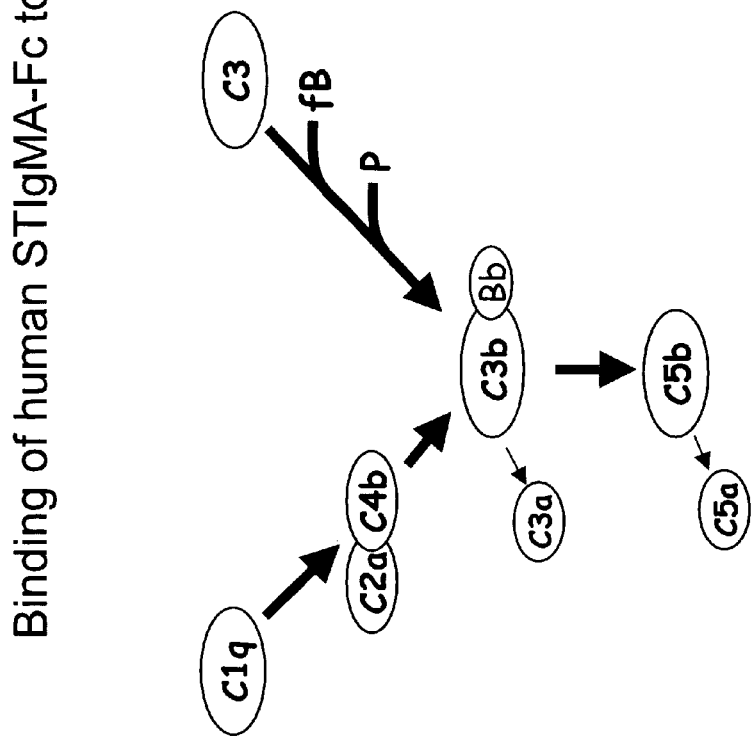
Figure 44

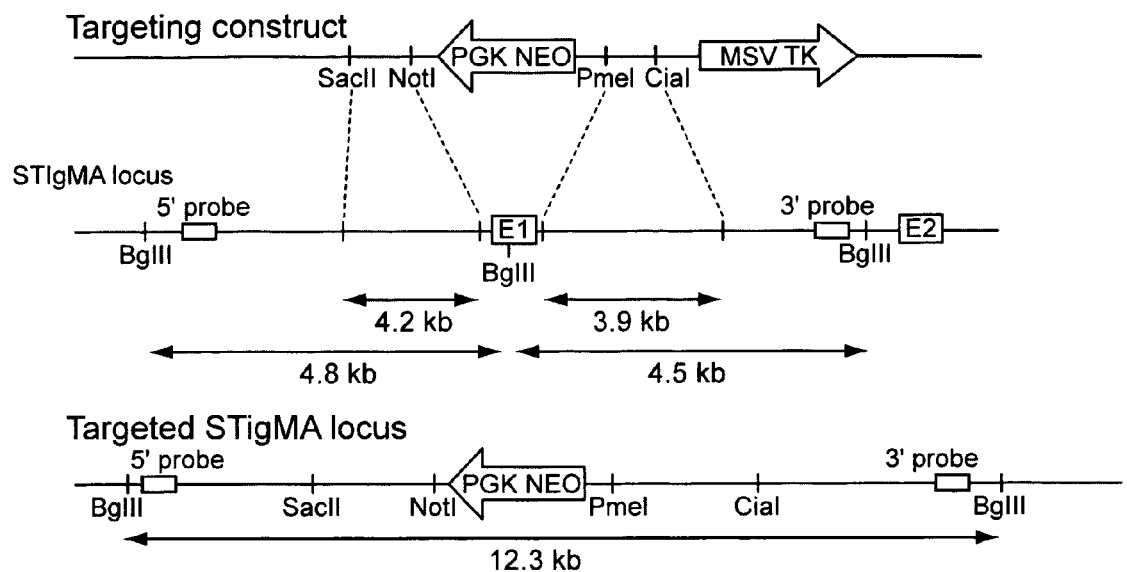
Figure 53A
Figure 53B
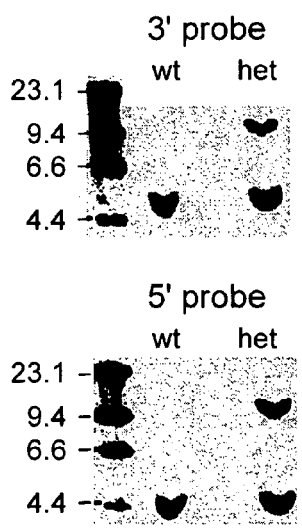

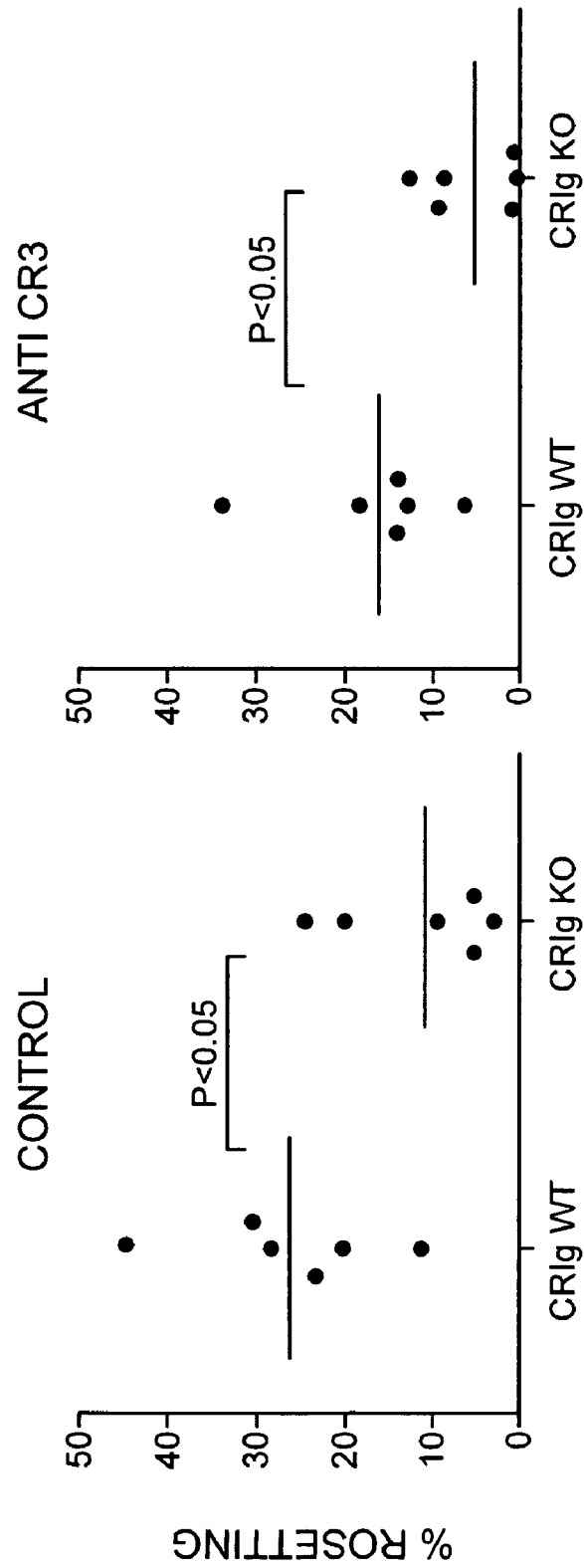
Figure 54D

A
><cloning linker>
CCTCGGTTCT
><Cla {underline=1-6, dir=f, 5tag=}>
ATCGATGCTCTCAATAAACCACC
><MET>
><DNA185041_ClaI_F 5'tag:ttttttttatcgattaaaccacc {underline=1-24, dir=f, 5tag=}>
<Comment {trans=1-8, dir=f, res=1}>
ATGGGGATCTTACTGGGCTGCTACTCCTGGGCACTCAACAGTGGACACTTATGGCCGTCCCATCCTGAAGTGCCAGA
GAGTGTAACAGGACCTTGGAAAGGGATGTGAATCTTCCCTGCACCTATGACCCCCTGCAAGGCTACACCCAAGTCTTGG
TGAAGTGGCTGGTACAACGTGGCTCAGACCCTGTCAGAGGTTCTCACCATCTTTCTACGTGACTCTTCTGGAGACCATATCCAGCAGCA
AGTACCAGGGCCGCCTGCATGTGAAGTCACTGGCAGACTCCTGATGGCAACCAAGTCGTGAGAGATAAGATTACTGAGCTCC
CCGGAGCCACTACACGTGTGAAGTCACTGGCAGACTCCTGATGGCAACCAAGTCGTGAGAGATAAGATTACTGAGCTCC
GTGTCCAGAAACACTCCTCAAAGCTACTCAAGACCAAGACTGAGGCACCTACAACCATGACCATACCCCTTGAAAGCAACA
TCTACAGTGAAGCAGTCCTGGGACTGGACCACTGACATG
><begin hIgG1 - linker region (DKTHT) {underline=1-15, dir=f, 5tag=}>
GACAAAACTCACACACATGCCCACCGTGCCCAGCACCTCCTGGGGGACCGTCAGTCTTCCTCTTCCCCCCAAAACC
CAAGGACACCCTCATGATCTCCCGGACCCCTGAGGTCACATGCGTGGTGGTGGACGTGAGCCACGAAGACCCTGAGGTCA
AGTTCAACTGGTACGTGGACGGCGTGGAAGTGC
><Fc 3-1 {underline=1-29, dir=b, 5tag=}>
ATAATGCCAAGACAAAGCCGCGGGAGGAGCAGTACAACAGCACGTACCGTGTGGTCAGCGTCCTCACCGTCCTGCACCAG
GACTGGCTGAATGCAAGGACAAGTGCAAGGTCTCCAACAAAGCCCTCCCAGCCCCCATCGAGAAAACCATCTCCAA
AGCCAAAGGGCAGCCCCGAGAACCAGGTGTACACCCTGCCCCCATCCCGGGAAGAGATGACCAAGAACCAGGTCAGCC
TGACCTGCCTGGTCAAAGGCTTCTATCCCAGCGACATCGCCGTGGAGTGGGAGAGCAATGGGCAGCCGGAGAACAACTAC
AAGACCACGCCTCCCGTGCTGGACTCCGACGGCTCCTTCTTCCTCTACAGCAAGCTCACCGTGACAAGAGCAGGTGGCA
GCAGGGGAACGTCTTCTCATGCTCCGTGATGCATGAGGCTCTGCACAACCACTACACGCAGAAGAGCCTCTCCCTGTCTC
CGGGTAAA
><end h Fc {underline=1-3, dir=f, 5tag=}>
TGAGTGCGACGGCCCTAGA
><Sal {underline=1-6, dir=f, 5tag=}>
GTCGACCTGCAGAAGCT
><Xba>
TCTAGAGTCGACCTGCAGAAGCT Figure 59
SEQ ID: 20

><Cla (underline=1-6, dir=f, 5tag=)>ATCGATTAAACCACC
><Met (trans=1-s, dir=f, res=1)>
ATGGGGATCTTACTGGGCCTGCTACTCCTGGGGCACTTAGGGCACTAACAGTGGACACTTATGGCCGTCCCATCCTGAAGTGCCAGA
GAGTGTAACAGGACCTTGGAAAGGGGATGTGAATCTTCCCTGCACCTATGACCCCCTGCAAGGCTACACCCAAGTCTTGG
TGAAGTGGCTGGTACAACGTGGCTCAGACCCTGTCACCATCTTTCTACGTGACTCTTCTGGAGACCATATCCAGCAGGCA
AGTACCAGGGCCGCCTGCATGTGAGCCACAAGGTTCCAGGAGATGTATCCCTCCAATTGAGCACCCTGGAGATGGATGA
CCGGAGCCACTACACGTGTGAAGTCACCTGCAGACTCCTGATGCAACCAAGTCGTGAGAGATAAGATTACTGAGCTCC
GTGTCCAGAAACTCTCTGTCTCCAAGCCTCGGGGTTCTCCTCCATCAGTGACAACTGGACGCGGTTATGGCTTCACGGTGCCCAGGAATGAGG
ATTAGCCTTCAATGCCAGGCTCGGGGTTTCTCCCCATCAGTTATATTGGTATAAGCAACAGACTAATAACCAGGAACC
CATCAAAGTAGCAACCCTAAGTACCTTACTCTTCAAGCCTGCGGTGATAGCCGACTCAGGCTCCTATTTCTGCACTGCCA
AGGGCCAGTTGGCTCTGAGCAGCAGCACAGCGACATTGTGAAGTTTGTGGTCAAAGACTCCTCAAAGCTACTCAAGACCAAG
ACTGAGGCACCTACAACCATGACAACATACCCCTTGAAAGCAACATCTACAGTGAAGCAGTCCTGGACT
><Mutagenic Primer (underline=1-52, dir=f, 5tag=)>
GGACCACTGACATG
><begin hIgG1 - linker region (DKTHT)>
GATAAAACTCACACATGCCCACCGTGCCCAGCACCTGAACTCCTGGGGGACCGTCAGTCTTCCTCTTCCCCCCAAAACC
CAAGGACACCCTCATGATCTCCCGGACCCCTGAGGTCACATGCGTGGTGGTGGACGTGAGCCACGAAGACCCTGAGGTCA
AGTTCAACTGGTACGTGGACGGCGTGGAGGTGC
><Fc 3-1 (underline=1-29, dir=b, 5tag=)>
ATAATGCCAAGACAAAGCCGCGGGAGGAGCAGTACAACAGCACGTACCGTGTGGTCAGCGTCCTCACCGTCCTGCACCAG
GACTGGCTGAATGGCAAGGAGTACAAGTGCAAGGTCTCCAACAAAGCCCTCCCAGCCCCCATCGAGAAAACCATCTCCAA
AGCCAAAGGGCAGCCCCGAGAACCACAGGTGTACACCCTGCCCCCATCCCGGGAAGAGATGACCAAGAACCAGGTCAGCC
TGACCTGCCTGGTCAAAGGCTTCTATCCCAGCGACATCGCCGTGGAGTGGGAGAGCAATGGGCAGCCGGAGAACAACTAC
AAGACCACGCCTCCCGTGCTGGACTCCGACGGCTCCTTCTTCCTCTACAGCAAGCTCACCGTGGACAAGAGCAGGTGGCA
GCAGGGGAACGTCTTCTCATGCTCCGTGATGCATGAGGCTCTGCACAACCACTACACGCAGAAGAGCCTCTCCCTGTCTC
CGGGTAAA
><end h Fc (underline=1-3, dir=f, 5tag=)>
TGAGTGCGACGGCCCTAGA
><Sal (underline=1-6, dir=f, 5tag=)>
GTCGACCTGCAGAAGCT
><Xba>
TCTAGAGTCGACCTGCAGAAGCT Figure 60
SEQ ID: 21

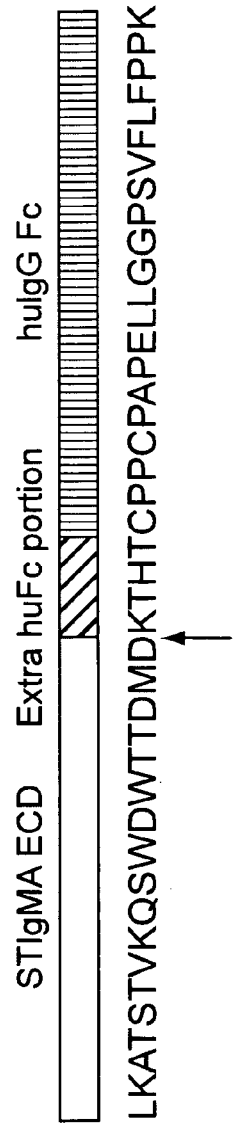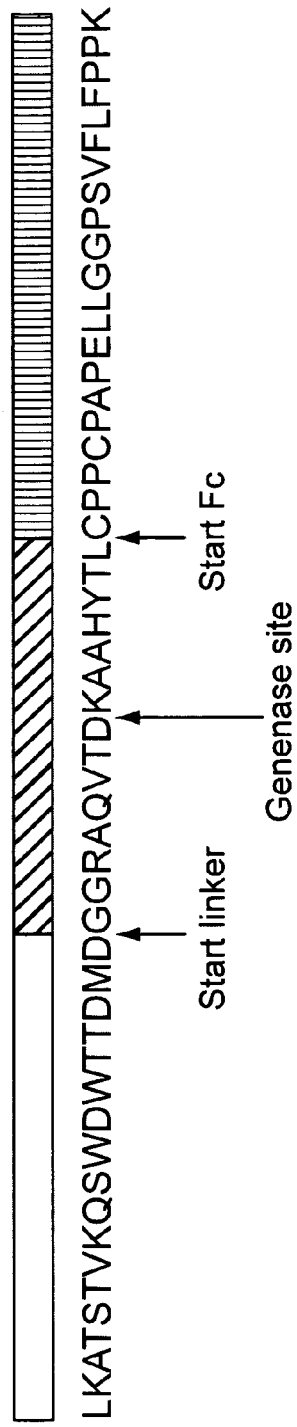
Figure 61

><Cla {underline=1-6, dir=f, 5tag=}>ATCGATTAAACCACC
><Met {trans=1-s, dir=f, res=1}>
ATGGGGATCTTACTGGGCCTGCTACTCCTGGGGCACCTAACAGTGGACACTTATGGCCGTCCCATC
CTGGAAGTGCCAGA
GAGTGTAACAGGACCTTGGAAAGGGGATGTGAATCTTCCCTGCACCTATGACCCCCTGCAAGGCTA
CACCCAAGTCTTGG
TGAAGTGGCTGGTACAACGTGGCTCAGACCCTGTCACCATCTTTCTACGTGACTCTTCTGGAGACCA
TATCCAGCAGGCA
AAGTACCAGGGCCGCCTGCATGTGAGCCACAAGGTTCCAGGAGATGTATCCCTCCAATTGAGCACC
CTGGAGATGGATGA
CCGGAGCCACTACACGTGTGAAGTCACCTGGCAGACTCCTGATGGCAACCAAGTCGTGAGAGATAA
GATTACTGAGCTCC
GTGTCCAGAAACTCTCTGTCTCCAAGCCCACAGTGACAACTGGCAGCGGTTATGGCTTCACGGTGC
CCCAGGGAATGAGG
ATTAGCCTTCAATGCCAGGCTCGGGGTTCTCCTCCCATCAGTTATATTTGGTATAAGCAACAGACTAA
TAACCAGGAACC
CATCAAAGTAGCAACCCTAAGTACCTTACTCTTCAAGCCTGCGGTGATAGCCGACTCAGGCTCCTAT
TTCTGCACTGCCA
AGGGCCAGGTTGGCTCTGAGCAGCACAGCGACATTGTGAAGTTTGTGGTCAAAGACTCC
><begin hIgG1 - linker region (DKTHT)>
GATAAAACTCACACATGCCCACCGTGCCCAGCACCTGAACTCCTGGGGGGACCGTCAGTCTTCCTC
TTCCCCCCAAAACC
CAAGGACACCCTCATGATCTCCCGGACCCCTGAGGTCACATGCGTGGTGGTGGACGTGAGCCACG
AAGACCCTGAGGTCA
AGTTCAACTGGTACGTGGACGGCGTGGAGGTGC
><Fc 3-1 {underline=1-29, dir=b, 5tag=}>
ATAATGCCAAGACAAAGCCGCGGGAGGAGCAGTACAACAGCACGTACCGTGTGGTCAGCGTCCTCA
CCGTCCTGCACCAG
GACTGGCTGAATGGCAAGGAGTACAAGTGCAAGGTCTCCAACAAAGCCCTCCCAGCCCCCATCGAG
AAAACCATCTCCAA
AGCCAAAGGGCAGCCCCGAGAACCACAGGTGTACACCCTGCCCCCATCCCGGGAAGAGATGACCA
AGAACCAGGTCAGCC
TGACCTGCCTGGTCAAAGGCTTCTATCCCAGCGACATCGCCGTGGAGTGGGAGAGCAATGGGCAG
CCGGAGAACAACTAC
AAGACCACGCCTCCCGTGCTGGACTCCGACGGCTCCTTCTTCCTCTACAGCAAGCTCACCGTGGAC
AAGAGCAGGTGGCA
GCAGGGGAACGTCTTCTCATGCTCCGTGATGCATGAGGCTCTGCACAACCACTACACGCAGAAGAG
CCTCTCCCTGTCTC
CGGGTAAA
><end h Fc {underline=1-3, dir=f, 5tag=}>
TGAGTGCGACGGCCCTAGA
><Sal {underline=1-6, dir=f, 5tag=}>
GTCGACCTGCAGAAGCT
><Xba>
TCTAGAGTCGACCTGCAGAAGCT

Figure 67

><Cla {underline=1-6, dir=f, 5tag=}>ATCGATTAAACCACC
><Met {trans=1-s, dir=f, res=1}>
ATGGGGATCTTACTGGGCCTGCTACTCCTGGGGCACCTAACAGTGGACACTTATGGCCGTCCCATC
CTGGAAGTGCCAGA
GAGTGTAACAGGACCTTGGAAAGGGGATGTGAATCTTCCCTGCACCTATGACCCCCTGCAAGGCTA
CACCCAAGTCTTGG
TGAAGTGGCTGGTACAACGTGGCTCAGACCCTGTCACCATCTTTCTACGTGACTCTTCTGGAGACCA
TATCCAGCAGGCA
AAGTACCAGGGCCGCCTGCATGTGAGCCACAAGGTTCCAGGAGATGTATCCCTCCAATTGAGCACC
CTGGAGATGGATGA
CCGGAGCCACTACACGTGTGAAGTCACCTGGCAGACTCCTGATGGCAACCAAGTCGTGAGAGATAA
GATTACTGAGCTCC
GTGTCCAGAAACTCTCTGTCTCCAAGCCCACAGTGACAACTGGCAGCGGTTATGGCTTCACGGTGC
CCCAGGGAATGAGG
ATTAGCCTTCAATGCCAGGCTCGGGGTTCTCCTCCCATCAGTTATATTTGGTATAAGCAACAGACTAA
TAACCAGGAACC
CATCAAAGTAGCAACCCTAAGTACCTTACTCTTCAAGCCTGCGGTGATAGCCGACTCAGGCTCCTAT
TTCTGCACTGCCA
AGGGCCAGGTTGGCTCTGAGCAGCACAGCGACATTGTGAAGTTTGTGGTCAAAGACTCCTCAAAGC
TACTCAAGACCAAG
ACTGAGGCACCTACAACCATGACATACCCCTTGAAAGCAACATCTACAGTGAAGCAGTCCTGGGACT
><Mutagenic Primer {underline=1-52, dir=f, 5tag=}>
GGACCACTGACATG
><begin hIgG1 - linker region (DKTHT)>
GATAAAACTCACACATGCCCACCGTGCCCAGCACCTGAACTCCTGGGGGGACCGTCAGTCTTCCTC
TTCCCCCCAAAACC
CAAGGACACCCTCATGATCTCCCGGACCCCTGAGGTCACATGCGTGGTGGTGGACGTGAGCCACG
AAGACCCTGAGGTCA
AGTTCAACTGGTACGTGGACGGCGTGGAGGTGC
><Fc 3-1 {underline=1-29, dir=b, 5tag=}>
ATAATGCCAAGACAAAGCCGCGGGAGGAGCAGTACAACAGCACGTACCGTGTGGTCAGCGTCCTCA
CCGTCCTGCACCAG
GACTGGCTGAATGGCAAGGAGTACAAGTGCAAGGTCTCCAACAAAGCCCTCCCAGCCCCCATCGAG
AAAACCATCTCCAA
AGCCAAAGGGCAGCCCCGAGAACCACAGGTGTACACCCTGCCCCCATCCCGGGAAGAGATGACCA
AGAACCAGGTCAGCC
TGACCTGCCTGGTCAAAGGCTTCTATCCCAGCGACATCGCCGTGGAGTGGGAGAGCAATGGGCAG
CCGGAGAACAACTAC
AAGACCACGCCTCCCGTGCTGGACTCCGACGGCTCCTTCTTCCTCTACAGCAAGCTCACCGTGGAC
AAGAGCAGGTGGCA
GCAGGGGAACGTCTTCTCATGCTCCGTGATGCATGAGGCTCTGCACAACCACTACACGCAGAAGAG
CCTCTCCCTGTCTC
CGGGTAAA
><end h Fc {underline=1-3, dir=f, 5tag=}>
TGAGTGCGACGGCCCTAGA
><Sal {underline=1-6, dir=f, 5tag=}>
GTCGACCTGCAGAAGCT
><Xba>
TCTAGAGTCGACCTGCAGAAGCT

Figure 68

```
><Cla {underline=1-6, dir=f, 5tag=}>ATCGATTAAACCACC
><Met {trans=1-s, dir=f, res=1}>
ATGGGGATCTTACTGGGCCTGCTACTCCTGGGGCACCTAACAGTGGACACTTATGGCCGTCCCATC
CTGGAAGTGCCAGA
GAGTGTAACAGGACCTTGGAAAGGGGATGTGAATCTTCCCTGCACCTATGACCCCCTGCAAGGCTA
CACCCAAGTCTTGG
TGAAGTGGCTGGTACAACGTGGCTCAGACCCTGTCACCATCTTTCTACGTGACTCTTCTGGAGACCA
TATCCAGCAGGCA
AAGTACCAGGGCCGCCTGCATGTGAGCCACAAGGTTCCAGGAGATGTATCCCTCCAATTGAGCACC
CTGGAGATGGATGA
CCGGAGCCACTACACGTGTGAAGTCACCTGGCAGACTCCTGATGGCAACCAAGTCGTGAGAGATAA
GATTACTGAGCTCC
GTGTCCAGAAACACTCC
><begin hIgG1 - linker region (DKTHT) {underline=1-15, dir=f, 5tag=}>
GACAAAACTCACACATGCCCACCGTGCCCAGCACCTGAACTCCTGGGGGGACCGTCAGTCTTCCTC
TTCCCCCCAAAACC
CAAGGACACCCTCATGATCTCCCGGACCCCTGAGGTCACATGCGTGGTGGTGGACGTGAGCCACG
AAGACCCTGAGGTCA
AGTTCAACTGGTACGTGGACGGCGTGGAGGTGC
><Fc 3-1 {underline=1-29, dir=b, 5tag=}>
ATAATGCCAAGACAAAGCCGCGGGAGGAGCAGTACAACAGCACGTACCGTGTGGTCAGCGTCCTCA
CCGTCCTGCACCAG
GACTGGCTGAATGGCAAGGAGTACAAGTGCAAGGTCTCCAACAAAGCCCTCCCAGCCCCCATCGAG
AAAACCATCTCCAA
AGCCAAAGGGCAGCCCCGAGAACCACAGGTGTACACCCTGCCCCCATCCCGGGAAGAGATGACCA
AGAACCAGGTCAGCC
TGACCTGCCTGGTCAAAGGCTTCTATCCCAGCGACATCGCCGTGGAGTGGGAGAGCAATGGGCAG
CCGGAGAACAACTAC
AAGACCACGCCTCCCGTGCTGGACTCCGACGGCTCCTTCTTCCTCTACAGCAAGCTCACCGTGGAC
AAGAGCAGGTGGCA
GCAGGGGAACGTCTTCTCATGCTCCGTGATGCATGAGGCTCTGCACAACCACTACACGCAGAAGAG
CCTCTCCCTGTCTC
CGGGTAAA
><end h Fc {underline=1-3, dir=f, 5tag=}>
TGAGTGCGACGGCCCTAGA
><Sal {underline=1-6, dir=f, 5tag=}>
GTCGACCTGCAGAAGCT
><Xba>
TCTAGAGTCGACCTGCAGAAGCT
```

Figure 69

A
><cloning linker>
CCTCGGTTCT
><Cla {underline=1-6, dir=f, 5tag=}>
ATCGATGCTCTCAATAAACCACC
><MET>
><DNA185041_ClaI_F_5'tag:ttttttttatcgattaaaccacc {underline=1-24, dir=f, 5tag=}>
<Comment {trans=1-s, dir=f, res=1}>
ATGGGGATCTTACTGGGCCTGCTACTCCTGGGGCACCTAACAGTGGACACTTATGGCCGTCCCATC
CTGGAAGTGCCAGA
GAGTGTAACAGGACCTTGGAAAGGGGATGTGAATCTTCCCTGCACCTATGACCCCCTGCAAGGCTA
CACCCAAGTCTTGG
TGAAGTGGCTGGTACAACGTGGCTCAGACCCTGTCACCATCTTTCTACGTGACTCTTCTGGAGACCA
TATCCAGCAGGCA
AAGTACCAGGGCCGCCTGCATGTGAGCCACAAGGTTCCAGGAGATGTATCCCTCCAATTGAGCACC
CTGGAGATGGATGA
CCGGAGCCACTACACGTGTGAAGTCACCTGGCAGACTCCTGATGGCAACCAAGTCGTGAGAGATAA
GATTACTGAGCTCC
GTGTCCAGAAACACTCCTCAAAGCTACTCAAGACCAAGACTGAGGCACCTACAACCATGACATACCC
CTTGAAAGCAACA
TCTACAGTGAAGCAGTCCTGGGACTGGACCACTGACATG
><begin hIgG1 - linker region (DKTHT) {underline=1-15, dir=f, 5tag=}>
GACAAAACTCACACATGCCCACCGTGCCCAGCACCTGAACTCCTGGGGGGACCGTCAGTCTTCCTC
TTCCCCCCAAAACC
CAAGGACACCCTCATGATCTCCCGGACCCCTGAGGTCACATGCGTGGTGGTGGACGTGAGCCACG
AAGACCCTGAGGTCA
AGTTCAACTGGTACGTGGACGGCGTGGAGGTGC
><Fc 3-1 {underline=1-29, dir=b, 5tag=}>
ATAATGCCAAGACAAAGCCGCGGGAGGAGCAGTACAACAGCACGTACCGTGTGGTCAGCGTCCTCA
CCGTCCTGCACCAG
GACTGGCTGAATGGCAAGGAGTACAAGTGCAAGGTCTCCAACAAAGCCCTCCCAGCCCCCATCGAG
AAAACCATCTCCAA
AGCCAAAGGGCAGCCCCGAGAACCACAGGTGTACACCCTGCCCCCATCCCGGGAAGAGATGACCA
AGAACCAGGTCAGCC
TGACCTGCCTGGTCAAAGGCTTCTATCCCAGCGACATCGCCGTGGAGTGGGAGAGCAATGGGCAG
CCGGAGAACAACTAC
AAGACCACGCCTCCCGTGCTGGACTCCGACGGCTCCTTCTTCCTCTACAGCAAGCTCACCGTGGAC
AAGAGCAGGTGGCA
GCAGGGGAACGTCTTCTCATGCTCCGTGATGCATGAGGCTCTGCACAACCACTACACGCAGAAGAG
CCTCTCCCTGTCTC
CGGGTAAA
><end h Fc {underline=1-3, dir=f, 5tag=}>
TGAGTGCGACGGCCCTAGA
><Sal {underline=1-6, dir=f, 5tag=}>
GTCGACCTGCAGAAGCT
><Xba>
TCTAGAGTCGACCTGCAGAAGCT

Figure 70

TREATMENT OF COMPLEMENT-ASSOCIATED DISORDERS

CROSS-REFERENCE TO RELATED APPLICATIONS

This application is a continuation-in-part of U.S. application Ser. No. 11/159,919 filed on Jun. 22, 2005, which is a continuation-in-part of U.S. application Ser. No. 10/964,263, filed on Oct. 12, 2004 now U.S. Pat. No. 7,419,663, which is a continuation-in-part of Ser. No. 10/767,374 now U.S. Pat. No. 7,282,565 and Ser. No. 10/767,904 now U.S. Pat. No. 7,211,400, each filed on Jan. 29, 2004, which are divisional applications of U.S. application Ser. No. 09/953,499 filed on Sep. 14, 2001 now U.S. Pat. No. 6,838,554. This application is also a continuation-in-part of PCT application No. PCT/US03/31207 filed on Oct. 1, 2003, which is a continuation-in-part of U.S. application Ser. No. 10/633,008 filed on Jul. 31, 2003 now U.S. Pat. No. 7,192,589, which is a continuation-in-part of U.S. application Ser. No. 10/265,542 filed on Oct. 3, 2002 now abandonded, which is a continuation-in-part of U.S. application Ser. No. 09/953,499 filed on Sep. 14, 2001 now U.S. Pat. No. 6,838,554, which is a continuation of application Ser. No. 09/254,465 filed on Mar. 5, 1999, now U.S. Pat. No. 6,410,708, and where U.S. application Ser. No. 09/953,499 is also a continuation-in-part of U.S. application Ser. No. 09/380,138 filed Aug. 25, 1999 (now abandoned), which is a national stage application under 35 U.S.C. §371 of PCT application No. PCT/US99/05028 filed Mar. 8, 1999, which is a continuation-in-part of U.S. application Ser. No. 09/254,465 filed on Mar. 5, 1999, now U.S. Pat. No. 6,410, 708, which is a national stage application under 35 U.S.C. §371 of PCT/US98/24855 filed Nov. 20, 1998, which claims priority under 35 U.S.C §119 to provisional application Ser. No. 60/078,936 filed on Mar. 20, 1998, now abandoned. The entire disclosures of all prior applications references herein are hereby expressly incorporated by reference.

FIELD OF THE INVENTION

The present invention concerns a recently discovered macrophage specific receptor, CRIg (earlier referred to as STIgMA), and its use in the prevention and/or treatment of complement-associated disorders, including complement-associated eye conditions, such as age-related macular degeneration (AMD) and choroidal neovascularization (CNV).

BACKGROUND OF THE INVENTION

The complement system is a complex enzyme cascade made up of a series of serum glycoproteins, that normally exist in inactive, pro-enzyme form. Three main pathways, the classical and the alternative pathway, can activate complement, which merge at the level of C3, where two similar C3 convertases cleave C3 into C3a and C3b. An additional pathway, the mannose-binding lectin (MBL) pathway has also been described.

Classical pathway components are labeled with a C and a number (e.g. C1, C3). Because of the sequence in which they were identified, the first four components are numbered C1, C4, C2, and C3. Alternative pathway components are lettered (e.g. B, P, D). Cleavage fragments are designated with a small letter following the designation of the component (e.g. C3a and C3b are fragments of C3). Inactive C3b is designated iC3b. Polypeptide chains of complement proteins are designated with a Greek letter after the component (eg, C3α and C3β are the α- and β-chains of C3). Cell membrane receptors for C3 are abbreviated CR1, CR2, CR3, and CR4.

The classical pathway of the complement system is a major effector of the humoral branch of the human immune response. The trigger activating the classical and MBL pathways is either IgG or IgM antibody bound to antigens or lectin on the target cells. Binding of antibody to antigen exposes a site on the antibody which is a binding site for the first complement component, C1. C1 binds to the exposed regions of at least two antigen-bound antibodies, and as a result, its C1r and C1s subunits are activated. Activated C1s is responsible for the cleavage of the next two involved complement components, C4 and C2. C4 is cleaved into two fragments, of which the larger C4b molecule attaches to the target membrane nearby while the small C4a molecule leaves. An exposed site on deposited C4b is available to interact with the next complement component, C2. Just as in the previous step, activated C1s cleaves the C2 molecule into two pieces, of which the fragment C2a remains, while the smaller C2b fragment leaves. C4b2a, also known as the C3 convertase, remains bound to the membrane. This C3 convertase converts the next complement component, C3 into its active form.

Activation of the alternative complement pathway begins when C3b binds to the cell wall and other cell components of the pathogens and/or to IgG antibodies. Factor B then combines with cell-bound C3b and forms C3bB. C3bB is then split into Bb and Ba by factor B, to forming the alternative pathway C3 convertase, C3bBb. Properdin, a serum protein, then binds C3bBb and forms C3bBbP that functions as a C3 convertase, which enzymatically splits C3 molecules into C3a and C3b. At this point, the alternative complement pathway is activated. Some of C3b binds to C3bBb to form C3bBb3b, which is capable of splitting C5 molecules into C5a and C5b.

The alternative pathway is a self-amplifying pathway and is important in the clearance and recognition of bacteria and other pathogens in the absence of antibodies. The alternative pathway can also amplify complement activation after initial complement activation by either the lectin and/or classical pathway. The rate-limiting step of activation of the alternative pathway in humans is the enzymatic action of factor D on the cleavage of factor B to form the alternative pathway C3 convertase, C3bBb. (Stahl et al., *American Journal of Pathology* 162:449-455 (2003)). There is strong evidence for the role of complement activation and deposition in adjuvant-induced arthritis (AIA), and collagen-induced arthritis (CIA) and in a variety of other diseases and conditions.

Recently, defective alternative pathway control has been implicated in the development of kidney and eye diseases, including hemolytic uremic syndrome (HUS) and AMD (Zipfel et al., *Mol. Immunol.* 43:97-106 (2006), available online at www.sciencedirect.com). C3 has been found to be essential for the development of CNV in mice (Bora et al., *J. Immunol.* 174(1):491-7 (2005)).

The role of the complement system in inflammatory conditions and associated tissue damage, autoimmune diseases, and complement-associated diseases is also well known.

It has been suggested that the alternative pathway plays an important role in inflammation (Mollnes et al., *Trends in Immunology* 23:61-64 (2002)), local and remote tissue injury after ischemia and reperfusion (Stahl et al., supra); adult respiratory distress syndrome (ARDS, Schein et al., *Chest* 91:850-854 (1987)); complement activation during cardiopulmonary bypass surgery (Fung et al, *J Thorac Cardiovasc Surg* 122:113-122 (2001)); dermatomyositis (Kissel, J T et al, *NEJM* 314:329-334 (1986)); and pemphigus (Honguchi et al, *J Invest Dermatol* 92:588-592 (1989)). The alternative complement pathway has also been implicated in autoimmune diseases, such as, for example, lupus nephritis and resultant glomerulonephritis and vasculitis (see, e.g. Watanabe et al., *J. Immunol.* 164:786-794 (2000)); and rheumatoid arthritis, such as juvenile rheumatoid arthritis (Aggarwal et al., *Rheumatology* 29:189-192 (2000); and Neumann E. et al, *Arthritis Rheum.* 4:934-45 (2002)).

Local increase in complement deposition and activation correlate with disease severity (Atkinson, *J Clin Invest* 112: 1639-1641 (2003)). C5a receptor antagonists, such as peptides and small organic molecules, have been tested for the treatment of arthritis (Woodruf et al., *Arthritis & Rheumatism* 46(9):2476-2485 (2002)), and various other immunoinflammatory diseases (Short et al., *Br J Pharmacol* 126:551-554 (1999); Finch et al., *J Med Chem* 42:1965-1074 (1999)); and companies, such as Promics (Australia) have been conducting human clinical trials to test the efficacy of C5a antagonists in similar indications. C5a has also been implicated in dermatomyositis, and pemphigus. (Kissel, J T et al, *NEJM* 314: 329-334 (1986)). Anti-C5a monoclonal antibodies have been shown to reduce cardiopulmonary bypass and cardioplegia-induced coronary endothelial dysfunction (Tofukuji et al., *J. Thorac. Cardiovasc. Surg.* 116:1060-1069 (1998)), prevent collagen-induced arthritis and ameliorate established disease (Wang et al., *Proc. Natl. Acad. Sci. USA* 92(19):8955-8959 (1995)).

Opsonophagocytosis, the process of deposition of complement fragments on the surface of particles and the subsequent uptake by phagocytic cells, is crucial for the clearance of circulating particles including immune complexes, apoptotic cells or cell debris and pathogens (Gasque, P., *Mol Immunol.* 41:1089-1098 (2004)). Tissue resident macrophages are known to play an important role in the complement mediated clearance of particles from the circulation. Kupffer cells, constituting over 90% of the tissue resident macrophages, are continuously exposed to blood from the hepatic portal vein and are strategically positioned in liver sinusoids to efficiently clear opsonized viruses, tumor cells, bacteria, fungi, parasites and noxious substances from the gastrointestinal tract. This clearance process is for a large part dependent on the presence of complement C3 as an opsonin (Fujita et al., Immunol. Rev. 198:185-202 (2004)). Upon binding to bacterial surfaces via a thoester, C3 is cleaved and amplifies the alternative pathway of complement. This reaction leads to further deposition of C3 fragments that can serve as ligands for complement receptors on macrophages. The importance of this pathway is shown by the high susceptibility of humans lacking C3 to bacterial and viral infections (ref).

The complement receptors characterized so far, CR1, 3 and 4 internalize C3b and phagocytosis C3 opsonized particles only after PKC activation or Fc receptor stimulation (Carpentier et al., Cell Regul 2, 41-55 (1991); Sengelov, Crit.Rev.Immunol. 15: 107-131 (1995); Sengelov et al., J. Immunol. 153:804-810 (1994). Moreover, CR1 is not expressed on the surface of murine Kupffer cells (Fang et al., J. Immunol. 160:5273-5279 (1998) Complement receptors that aid KCs in the constitutive clearance of circulating particles have not been described so far.

An anti-C3b(i) antibody has been reported to enhance complement activation, C3b(i) deposition, and killing of CD20$^+$ cells by rituximab (Kennedy et al., *Blood* 101(3): 1071-1079 (2003)).

In view of the known involvement of the complement cascade in a variety of diseases, there is a need for identification and development of new pharmaceuticals for the prevention and/or treatment of complement-associated diseases.

SUMMARY OF THE INVENTION

The present invention is based on the identification of a novel member of the complement receptor family and the first immunoglobulin (Ig) superfamily member that interacts with the complement system.

In one aspect, the invention concerns a method for the prevention or treatment of a complement-associated eye condition, comprising administering to the subject in need a prophylactically or therapeutically effective amount of a complement inhibitor, such as an inhibitor of the alternative complement pathway, e.g. a CRIg polypeptide or an agonist thereof.

The complement-associated eye condition may, for example, be age-related macular degeneration (AMD), choroidal neovascularization (CNV), uveitis, diabetic and other ischemia-related retinopathy, endophthalmitis, diabetic macula edema, pathological myopia, von Hippel-Lindau disease, istoplasmosis of the eye, Central Retinal Vein Occlusion (CRVO), corneal neovascularization, and retinal neovascularization. Preferably, the complement associated eye condition is AMD or CNV, including all stages of these conditions.

In another aspect, the invention concerns a method for the prevention of the development or progression of AMD, comprising administering to a subject at risk of developing or diagnosed with AMD in at least one eye, an effective amount of a complement inhibitor, such as an inhibitor of the alternative complement pathway, e.g. a CRIg polypeptide or an agonist thereof.

In yet another aspect, the invention concerns a method for the treatment of dry AMD, comprising administering to a subject in need a therapeutically effective amount of a complement inhibitor, such as an inhibitor of the alternative pathway, e.g. a CRIg polypeptide or an agonist thereof.

In all embodiments, the CRIg polypeptide may, for example, be selected from CRIg polypeptides of SEQ ID NOS: 2, 4, 6, and 8, and the extracellular domains (ECDs) of such polypeptides. The CRIg polypeptide, including the full-length polypeptides and their ECDs, can be fused to an immunoglobulin sequence, such as an immunoglobulin heavy chain constant region sequences, e.g. Fc region, and the resultant immunoadhesins can be used, as a CRIg agonist, in the preventative and treatment methods of the present invention. The immunoglobulin preferably is an IgG, such as IgG-1 or IgG-2, or IgG-3, or IgG-4, more preferably, IgG-1 or IgG-3. The IgG1 heavy chain constant region sequence may comprise at least the hinge, CH1, CH2 and CH3 region, or the hinge, CH2 and CH3 region, for example.

In a further aspect, the invention concerns a method for the prevention or treatment of a complement-associated diseases or condition, comprising treating a subject in need with a prophylactically or therapeutically effective amount of a complement inhibitor, such as an inhibitor of the alternative pathway, e.g. a CRIg polypeptide or an agonist thereof.

In another aspect, the invention concerns a method for inhibition of the production of C3b complement fragment in a mammal comprising administering to said mammal an effective amount of a complement inhibitor, such as an inhibitor of the alternative pathway, e.g. a CRIg polypeptide or an agonist thereof.

In yet another aspect, the invention concerns method for selective inhibition of the alternative complement pathway in a mammal, comprising administering to said mammal an effective amount of a CRIg polypeptide or an agonist thereof.

In all aspects, the CRIg polypeptide may, for example, be selected from the group consisting of CRIg polypeptides of SEQ ID NO: 2, 4, 6, 8, and the extracellular regions of such polypeptides. The agonist preferably is a CRIg-Ig fusion protein (immunoadhesin) as hereinabove described. The immunoglobulin sequence may, for example, be an immunoglobulin constant region sequence, such as a constant region sequence of an immunoglobulin heavy chain. In another embodiment, the immunoglobulin heavy chain constant region sequence is fused to an extracellular region of a CRIg polypeptide of SEQ ID NO: 2, 4, 6, or 8. In a further embodiment, the immunoglobulin heavy chain constant region sequence is that of an IgG, such as an IgG-1 or IgG-3, where the IgG-1 heavy chain constant region sequence may, for example, comprise at least a hinge, CH2 and CH3 region, or the hinge CH1, CH2 and CH3 regions.

The complement-associated disease may, for example, be an inflammatory disease or an autoimmune disease.

In one specific embodiment, the complement-associated disease is selected from the group consisting of rheumatoid arthritis (RA), adult respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, age-related macular degeneration, uveitis, diabetic retinopathy, allo-transplantation, hyperacute rejection, hemodialysis, chronic occlusive pulmonary distress syndrome (COPD), asthma, Alzheimer's disease, atherosclerosis, hereditary angioedema, paroxysmal nocturnal hemoglobinurea and aspiration pneumonia.

In another specific embodiment, the complement-associated disease is selected from the group consisting of inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease.

In yet another specific embodiment, the complement-associated disease is rheumatoid arthritis (RA), psoriasis or asthma.

In all embodiments, the subject may be a mammal, such as a human patient.

In a further aspect, the invention concerns a method for the prevention or treatment of age-related macular degeneration (AMD) or choroidal neovascularization (CNV) in a subject, comprising administering to the subject an effective amount of a complement inhibitor, such as an inhibitor of the alternative pathway, e.g. a CRIg polypeptide or an agonist thereof.

BRIEF DESCRIPTION OF THE DRAWINGS

FIGS. 1A-1B show the nucleotide and amino acid sequences of a 321-amino acid human CRIg polypeptide (SEQ ID NOS: 1 and 2, respectively).

FIGS. 2A-2B show the nucleotide and amino acid sequences of the 399-amino acid full-length long form of native human CRIg (huCRIg or huCRIg-long; SEQ ID NOS: 3 and 4, respectively).

FIGS. 3A-3B show the nucleotide and amino acid sequences of the 305-amino acid short form of native human CRIg (huCRIg-short, SEQ ID NOS: 5 and 6, respectively).

FIGS. 4A-4C show the nucleotide and amino acid sequence of the 280-amino acid native murine CRIg (muCRIg, SEQ ID NOS: 7 and 8, respectively).

FIG. 5 shows the amino acid sequence of full-length huCRIg (SEQ ID NO: 4; DNA185041) and huCRIg-short (SEQ ID NO: 6; DNA183026) in alignment with muCRIg (SEQ ID NO: 8; DNA22049). The hydrophobic signal sequence, IgV, IgC and transmembrane regions are shown. muCRIg has a predicted single N-linked glycosylation site at position 170 (NGTG). The Ig domain boundaries, deduced from the exon-intron boundaries of the human CRIg gene, are indicated.

FIG. 14 shows immunohistochemical analysis of CRIg in liver Kupffer cells.

FIG. 15 shows immunohistochemical analysis of CRIg in brain microglial cells.

FIG. 16 shows immunohistochemical analysis of CRIg in placental Hofbauer cells.

FIG. 22. Subcellular localization of CRIg in monocyte-derived macrophages. Monocytes were cultured for 7 days in macrophage differentiation medium, fixed in acetone and stained with polyclonal anti-CRIg antibody 6F1 or CD63 and secondary goat-anti-rabbit FITC. Cells were studied in a confocal microscope. CRIg is found in the cytoplasm were it co-localizes with the lysosomal membrane protein CD63. CRIg was also expressed at the trailing and leading edges of macrophages in a pattern similar to that of F-actin. Scale bar=10 μm.

FIG. 30. Cells expressing human CRIg showed increased adherence to human endothelial cells. (A) CRIg was stably expressed in a human Jurkat T-cell line. (B) Cells were preloaded with the fluorescent dye BCECF (Molecular Probes, Oregon) and added to a 96 well plate coated with a monolayer of human umbilical vein endothelial cells (HUVEC) treated with or without 10 ng/ml TNFα After 3 washes, fluorescence was counted in a spectro-fluorometer which indicated the number of cells that remain adherent to the HUVEC cells. The graph was representative of 4 independent experiments.

FIG. 32 is the nucleotide sequence of DNA42257 (consensus sequence) (SEQ ID NO: 9).

FIG. 34 shows that muCRIg inhibits joint inflammation.

FIG. 36 shows that CRIg-Fc treatment does not alter the number nor the morphology of tissue resident macrophages.

FIG. 41 shows that muCRIg inhibits joint inflammation in antibody-induced arhritis.

FIG. 44 shows that binding of human CRIg-Fc to E-IgM is C3 dependent.

Figure 6:
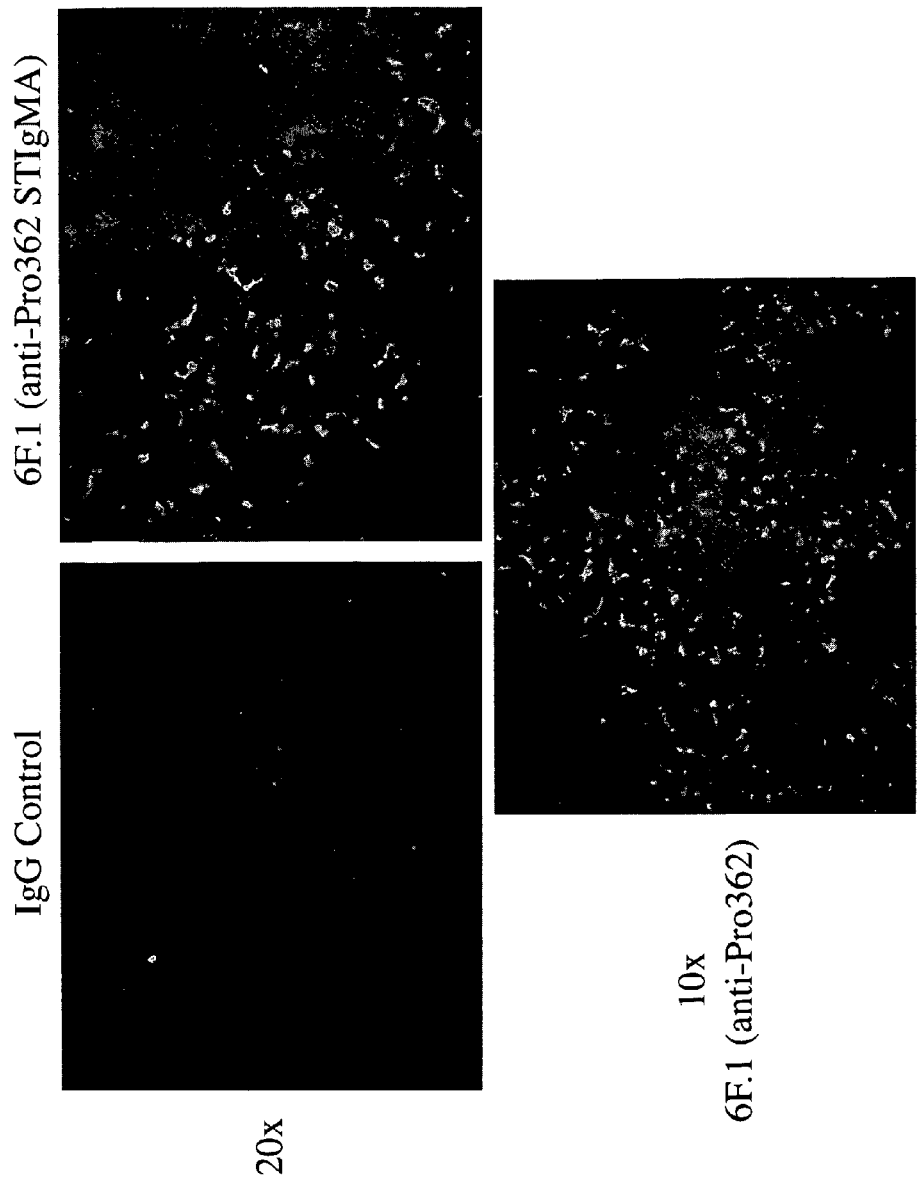
FIG. 6 shows in situ hybridization of CRIg in mouse liver frozen sections.

(A) CRIg is a single transmembrane immunoglobulin superfamily member consisting of one (human CRIg short (huCRIg(S)) and murine CRIg (muCRIg) or two (huCRIgL) immunoglobulin domains. The scale at the top of the left panel indicates size in amino acids. The panel on the right shows that hu and muCRIg are distantly related to junctional adhesion molecule-A (JAM-A) and A33 antigen. The scale on the top of the right panel indicates % amino acid similarity.

(B) CRIg is expressed in macrophages but not in monocytes human CD14+ monocytes and CD14+ monocytes cultured for 7 days in 10% autologous serum and 20% fetal bovine serum were analyzed for huCRIg staining by flow cytometry using anti-human CRIg MAb (3C9). Mouse CD11b+ and F4/80+ liver Kupffer cells were analyzed for muCRIg staining using an anti-muCRIg MAb (14G6).

(C) Western blot analysis of human and mouse macrophages. Lysates from human CD14+ monocytes cultured for the indicated periods of time or mouse peritoneal macrophages were boiled in reducing SDS buffer, loaded on a 4-10% Tris-glycine gel and incubated with a polyclonal anti-CRIg antibody (6F1, left panel) or an anti-muCRIg monoclonal antibody (14C6, right panel). Pre-immune IgG (left panel) and rat IgG2b (right panel) were used as isotype controls. Arrows in the left panel indicate the position of a 57 and 50 kDa band possibly representing huCRIg(L) and —(S).

(D) Co-localization of CRIg with CD68 on liver Kupffer cells. Immunostaining was performed on sections obtained from human and mouse liver using monoclonal anti-CRIg (3C9 human and 14G6 mouse), and monclonal anti-CD68 antibodies.

FIG. 51. Flow cytometry analysis of CRIg expression on peripheral blood leukocytes and analysis of binding of C3 fragments C3 opsonized particles to CRIg expressing CHO cells.

(A) Flow cytometry analysis of CRIg expression on human and mouse peripheral human and mouse lekocytes.

(B) Binding of soluble C3 fragments or complement opsonized pathogens to CHO cells expressing murine CRIg, but not to JAM-2 expressing CHO cells. Cells in suspension were incubated with A488-labeled complement opsonized particles under continuous rotation for 30 minutes at room temperature. Cells were washed three times and the binding of the particles was monitored by flow cytometric analyses. Results are representative of 3 independent experiments.

FIG. 52. Soluble and cell surface-expressed CRIg binds to C3 fragments in solution or deposited on the cell surface.

(A) CRIg(L)-transfected Jurkat cells (Jurkat-CRIg), but not empty vector-transfected Jurkat cells (Jurkat-control), form rosettes with C3 and IgM-opsonized sheep erythrocytes (E-IgM). Histogram (left panel) shows CRIg expression on Jurkat cells stably transfected with human CRIg(L). E-IgM opsonized with C3 deficient (C3−) or C3 sufficient (C3+) serum were mixed with CRIg or control vector transfected Jurkat for 1 hour. The experiment was representative of three independent experiments.

(B) CIg(L)-Fc binding to IgM-opsonized sheep red blood cells (E-IgM) is dependent on the presence of C3 in serum. E-IgM were opsonized with C3 depleted human serum to which increasing concentrations of purified human C3 were added. E-IgM were subsequently incubated with a huCRIg (L)-Fc fusion protein which was in turn detected with an anti-human Fc polyclonal antibody detected by flow cytometry. The experiment was representative of three independent experiments.

(C) ELISA showing binding of CRIg(L)- and CRIg(S)-Fc to C3b and iC3b. Increasing concentrations of huCRIg(L)- and huCRIg(S)-Fc fusion proteins were added to maxisorb plates coated with purified C3b and iC3b. Binding was detected using an HRPO-conjugated anti-huFc antibody. The results shown are representative of 4 independent experiments using different batches of fusion protein and purified complement components.

(D) Kinetic binding data showing soluble C3b dimers binding to huCRIg(L)-Fc. The affinity for C3b to the CRIg fusion proteins was determined using surface plasmon resonance. CRIg proteins were captured on a CM5 sensor chip via amine coupling of an antibody directed to the Fc fusion tag. Dimeric C3b was then injected for sufficient time to reach saturation. The Kd was calculated from a binding curve showing response at equilibrium plotted against the concentration. C3b dimers bound to huCRIg(S) with a calculated affinity of 44 nM and to huCRIg(L) with 131 nM affinity.

(E) CRIg expressed on the cell surface binds to A488-labeled C3b dimer (C3b)2) but not to native C3. Left panel shows expression levels of huCRIg(L) on transfected THP-1 cells by flow-cytometry analysis. (C3b)2 shows saturateable binding to CRIg-transfected THP-1 cells. (C3b)2 binding to THP-1 CRIg was competed off with (C3b)2, C3b and the extracellular domain of CRIg (CRIg-ECD), but not by C3. The results shown are representative of 3 independent experiments.

FIG. 53. Generation and characterization of CRIg ko mice (A) Generation of a targeting vector used for homologous recombination in ES cells.

(B) Southern blot confirmation of homologous recombination of the SRIg allele in heterozygous female offspring from chimeric mice bred to wt mice.

(C) Comparison of leukocyte numbers in the peripheral blood of wt and ko male and female mice.

(D) FACS analysis showing the absence of CR1, CR2 and CD11c expression in KCs.

(E) FACS analysis of C3-A488 and C3c-A488 binding to wt and ko KCs.

Figure 54A:
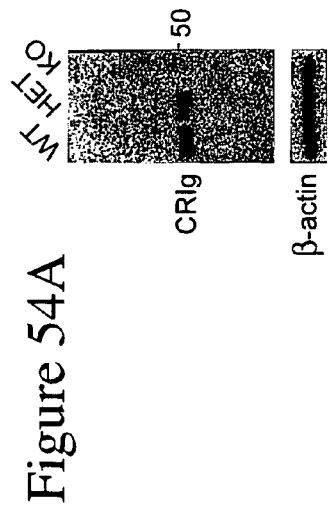

FIG. 54. Expression of CRIg on Kupffer cells is necessary for binding of C3b and iC3b (A) CRIg protein is absent on macrophages obtained from CRIg KO mice. Peritoneal macrophages obtained from CRIg wt, het or ko mice were incubated with an anti-muCRIg mAb (14G6; left panel). Kupffer cells (KCs) obtained from CRIg wt and ko mice were incubated with antibody 14G6 and analyzed by flow cytometry.

(B) Expression levels of CD11b and CD18, the alpha and beta chains of complement receptor 3 and Crry are similar on Kupffer cells obtained from CRIg we and CRIg ko mice. Kupffer cells isolated fro CRIg wt or ko mice were incubated with antibodies to CD11b, CD 18and Crry and analyzed by flow cytometry.

(C) Kupffer cells isolated from CRIg wt or ko mice were incubated with activated mouse serum (activated through incubations for 30 minutes at 37° C.), C3b, (C3b)2 and iC3b. Binding of the purified complement components to the cell surface was detected with a polyclonal antibody recognizing the various C3-deried fragments. Results shown are representative of 4 experiments.

(D) KCs isolated from CRIg ko mice show decreased resetting with IgM-coated sheep red blood cells (E-IgM) opsonized in C3 sufficient mouse serum. KCs isolated from livers of CRIg wt and ko mice were incubated with complement C3-opsonized E-IgM for 30 minutes in the presence of control IgG or anti-CR3 blocking antibody (M1/70). Cells were fixed and the number of KCs that formed rosettes with E-IgM were counted and expressed as a percentage of the total number of KCs. *=p<0.05. Results shown are representative of 2 independent experiments.

FIG. 55. CRIg on Kupffer cells recycles (A) Kupffer cells (KCs) from C3 wt (panels 1, 3, 4 and 6) or C3 ko mice (panels 2, 5) were incubated with A488-labeled anti-CRIg antibody (14G6) and (C3b)2 for one hour at 4° C. (panel 1-3) or for 10 minutes at 37° C. (panel 4-6). Cells were subsequently transferred to 4° C. and incubated with anti-A488 antibody (red histogram) or without antibody (black histogram) to distinguish cytoplasmic from cell surface expressed anti-CRIg or C3b.

(B) Internalization and co-localization of CRIg and C3b in CRIg wt, but not CRIg ko, KCs. KCs isolated from the livers of CRIg wt and ko mice were cultured in chamber slides for 2 days and incubated with A455-conjugated anti-CRIg antibodies and A488-conjugated C3b for 30 minutes at 37° C., mounted and photographed.

(C) CRIg, but not Lamp 1, antibodies recycle to the cell surface. Kupffer cells were loaded with A488-conjugated anti-muCRIg or anti-muLamp1 antibodies for 10 minutes at 37° C., washed and subsequently incubated for indicated time periods at 37° C. in the presence of anti-A488 quenching antibody. Results shown are representative of 3 independent experiments.

Figure 56A:
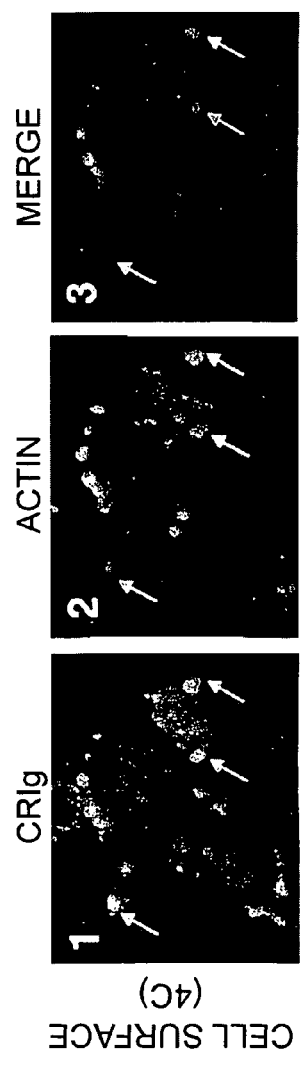
Figure 56B:
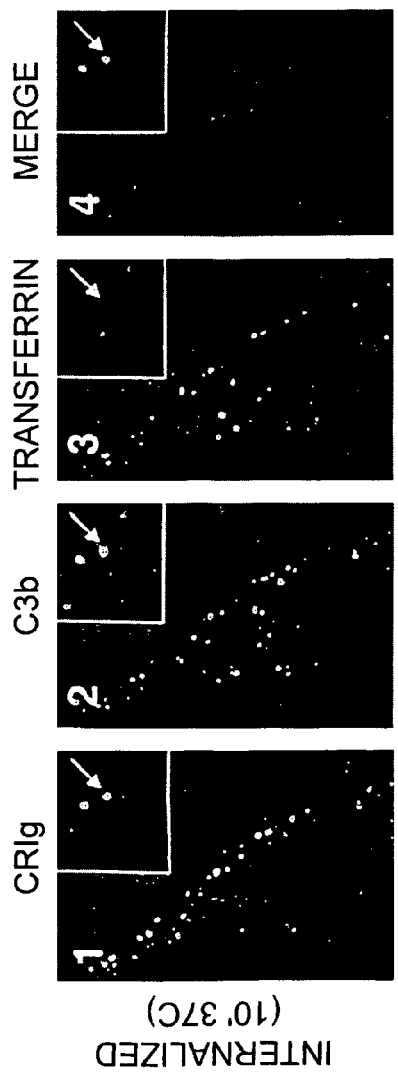

FIG. 56. CRIg is expressed on recycling endosomes that are recruited to sites of particle ingestion.

(A) Cell surface-expressed CRIg is localized to F-actin-positive membrane ruffles. Monocyte-derived macrophages cultures for 7 days were incubated at 4° C. with A488-conjugated anti-CRIg A488 mAb 3C9 (A1 and green channel in A3) and Alexa 546-phalloidin (A2 and red channel in A3). Arrowheads indicate membrane ruffles where both CRIg and actin staining are more intense than over the rest of the cell surface (yellow in the merged images in A3). Scale bar is 20 μm.

(B) CRIg and C3b co-localize with transferrin in recycling endosomes. Macrophages were incubated for 1 hour on ice with CRIg-A488 (B1, green channel in B4) or C30A488 (B2, red channel in B4) then chased for 10 minutes at 37° C. in the presence of A647-transferrin (B3, blue channel in B4). Scale bar=20 μm.

(C) CRIg is recruited to the phagocytic cup and the phagosome membrane. Macrophages were incubated with IgM-coated erythrocytes opsonized with C3 sufficient serum for 10 minutes (C1-4) or 2 hours (C5-8) at 37° C. in the presence of A647-labeled transferrin (C2, 6 and blue channel C4, 8). Cells were subsequently fixed, permeabilized and stained with anti-CRIg polyclonal antibodies (C1, 2 and green channel in C4, 5) and A555-conjugated antibody to LAMP-1 (C3, 7 and red channel in C4, 8).

FIG. 57. Trafficking of CRIg in human monocyte-derived macrophages (A) FACS plot showing saturatable binding of C3b-A488 to CRIg on day 7 MDMs.

(B) MDMs were pulsed for 10 minutes at 37° C. with anti-CRIg antibody and C3b-A488 n the presence of a 10 fold molar excess of huCRIg(L)-ECD. Binding and uptake of anti-CRIg antibody was specific for CRIg since it could be abolished by co-incubation of the antibody with a 10-fold molar excess of CRIg-ECD (panel 1) while leaving the uptake of transferrin intact (panel 2).

(C) MDMs 20h at 37° C. in the presence of lysosomal protease inhibitors, then the cells were washed, fixed with 1% PFA and the uptaken antibody detected with Cy3-labeled anti-ouse IgG (C panel 1, and red channel in panel 3). The cells were co-stained in 10 μg/ml rabbit anti-CRIg 6F1 followed by FITC-anti rabbit to detect the total CRIg distribution (C panel 2 and green channel in C panel 3). The uptaken antibody almost completely overlapped with the endogenous CRIg signal (yellow in the merged image in C panel 3), indicating that the antibody uptake does no influence CRIg trafficking. Scale bar is 20 μm and 5 μm in the 4× magnified inset of the boxed regions shown in the lower right of each channel. C panel 4 Human macrophages were incubated in C3-depleted serum for 13 h, then fixed and labeled with rabbit anti-CRIg F1 and FITC anti-rabbit. The CRIg distribution was essentially identical to that in C3 sufficient serum, both overlapping almost entirely with the recycling endosomal marker transferrin (data not shown). Scale bar is 20 μm.

(D) MDMs were incubated with 1 μg'ml anti-CRIg-A488 (panel 1) transferrin-A647 (panel 2) for 10 minutes at 37° C., fixe in 4% PFA, permeabilized with saponin buffer and incubated with mouse-anti-human Lamp-1-A555 (panel 3). Arrows indicate co-localization of CRIg and transferring in the recycling compartment.

(E) MDMs were incubated with 1 μg/ml anti-CRIg-A488 (panel 1, green channel in panel 4), transferrin-A647 (panel 2, blue channel in panel 4) for 30 minutes at 37° C., washed and incubate PKH-stained, compartment C3-opsonized sheep red blood cells (SRBCs, panel 3, red channel in panel 4) at a 1:10 macrophages: SRBC ratio.

FIG. 58. Mice lacking CRIg are susceptivle to *Listeria Monocytogenes* (LM) infection.

(A) Survival curves of female CRIg wt and CRIg ko mice infected with the indicated doses of LM following injection into the lateral tail vein, n=5-7 per group. Sttistical analysis (Wilcoxon): wt vs ko p<0.005 for 2×10e4 colony forming units (CFUs), p<0.0001 for 5×10e4 and 2×10e5 CFUs.\

(B) Analysis of bacterial counts in heart, liver, blood, and spleen 10 min following LM infection (2×10e7 CFUs, n=5 per groups). Statistical analysis (paired t-test): **p<0.01, *p<0.05.

(C) Increased concentrations of cytokines and chemokines in the serum of CRIg ko mice one day following LM infections. Statistical analysis (unpaired t-test): ***p<0.001.

(D) Reduced uptake of LM-A488 in KCs in CRIg ko mice. Mice were infected with 2×10e7 LM-A488. One hour later, livers were perfused, incubated with antibodies to F4/80 and analyzed by flow cytometry. F4/80 positive KCs were subsequently sorted by FACS and collected on poly-1-lysine coated slides for observation by fluorescent microscopy. The number of internalized LM-A488 was counted in a confocal microscope and the phagocytic index calculated. Results are representative of at least two experiments.

(E) CRIg mice have a reduced clearance of LM from the circulation. CRIg and C3 double or single ko mice were injected i.v. with 2×10e7 CFUs LM. CFUs in blood were counted 10 minutes post infection. In the presence of C3, CRIg ko mice had a significantly reduced clearance of LM from the circulation (p<0.001). In the absence of C3, there was no significant difference in clearance of LM in CRIg wt or ko mice.

FIG. 59 shows the nucleotide sequence of a human CRIg (short)-IgG fusion. (SEQ ID NO: 20).

FIG. 60 shows the nucleotide sequence of a human CRIg (long)-IgG fusion (SEQ ID NO: 21).

FIG. 61 illustrates the CRIg (STIgMA)-Fc junction in two different constructs, both of which are inserted into a pRK5 vector at a ClaI-XbaI site.

Figure 62:
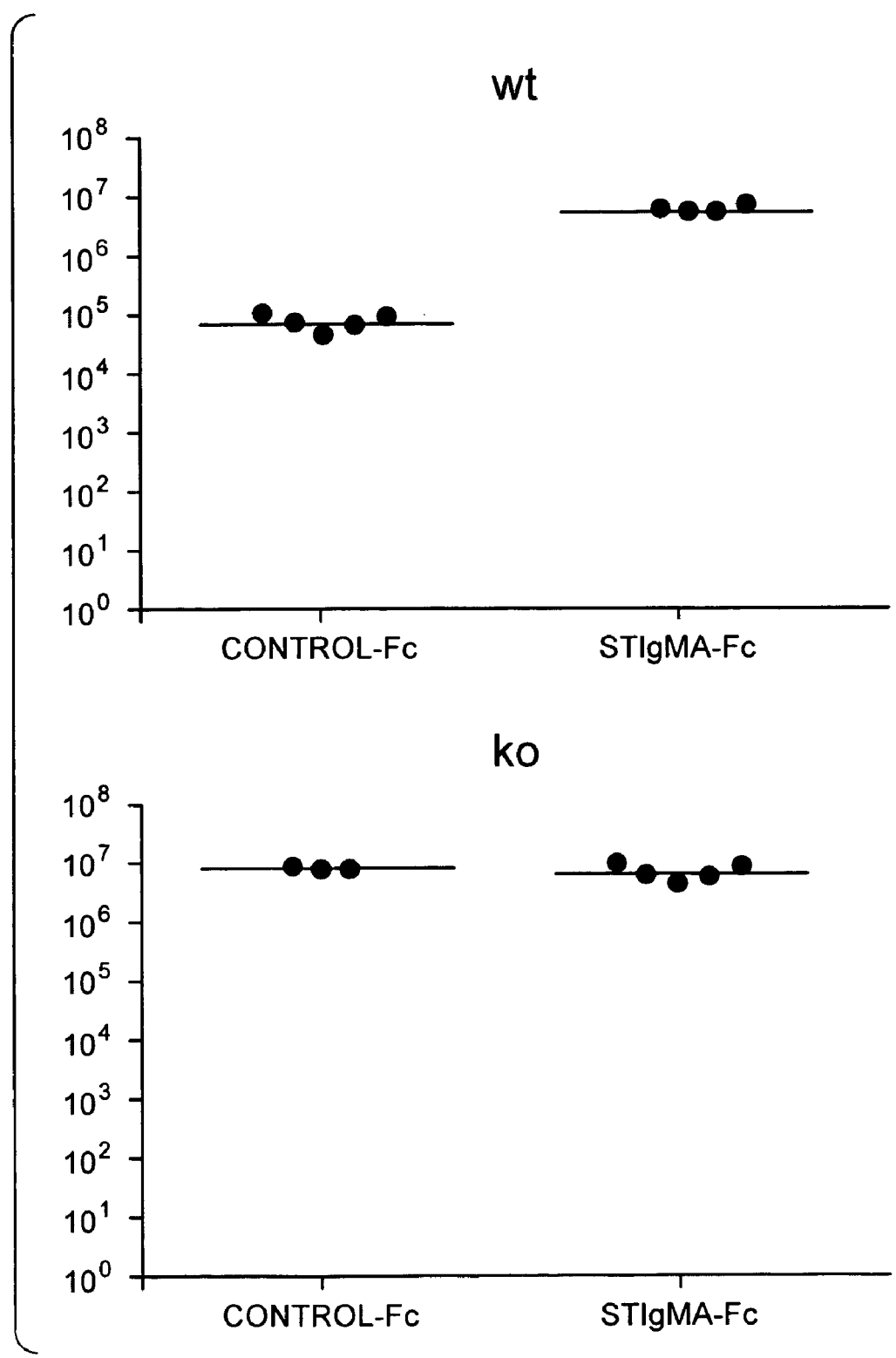

FIG. 62 shows that muCRIg-Fc fusion protein (but not control Fc fusion protein) inhibits clearance of LM from the circulation in wt but not CRIg ko cells. CRIg wt and ko mice were treated with 2 injections of 12 mg/kg muCRIg-Fc or control-Fc fusion proteins 24 hrs and 16 hrs prior to injection i.v. with $2 \times 10^7$ CFUs LM. CFUs in blood were counted 10 minutes post infection. CRIg wt mice treated with muCRIg-Fc had a significantly reduced clearance of LM from the circulation as compared to control-Fc treated wt mice (p<0.001, nonpaired Student's t-test). In CRIg ko mice, treatment with muCRIg-Fc had no effect on LM clearance.

Figure 63A:
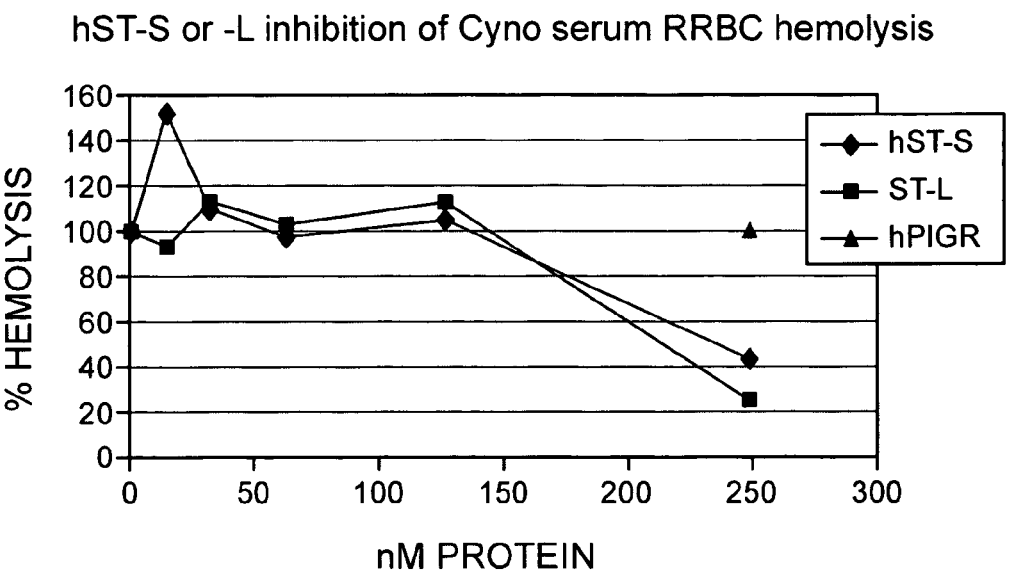
Figure 63B:
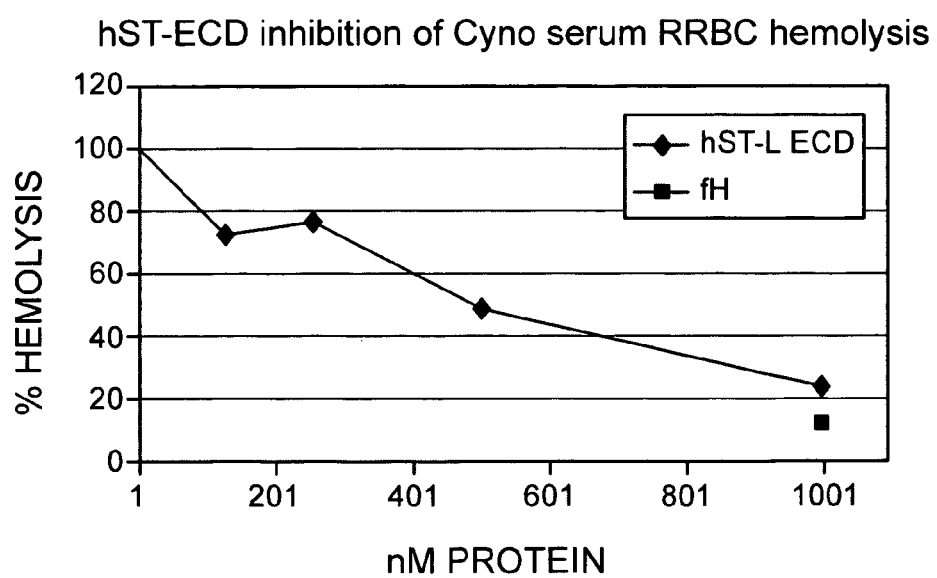

FIG. 63. Inhibition of complement-mediated immune hemolysis with huCRIg molecules A. Inhibition of Cyno serum RRBC hemolysis using hCRIg-short and -long fusion proteins. B. Inhibition of cyno serum RRBC hemolysis using hCRIg-long ECD.

Figure 64:
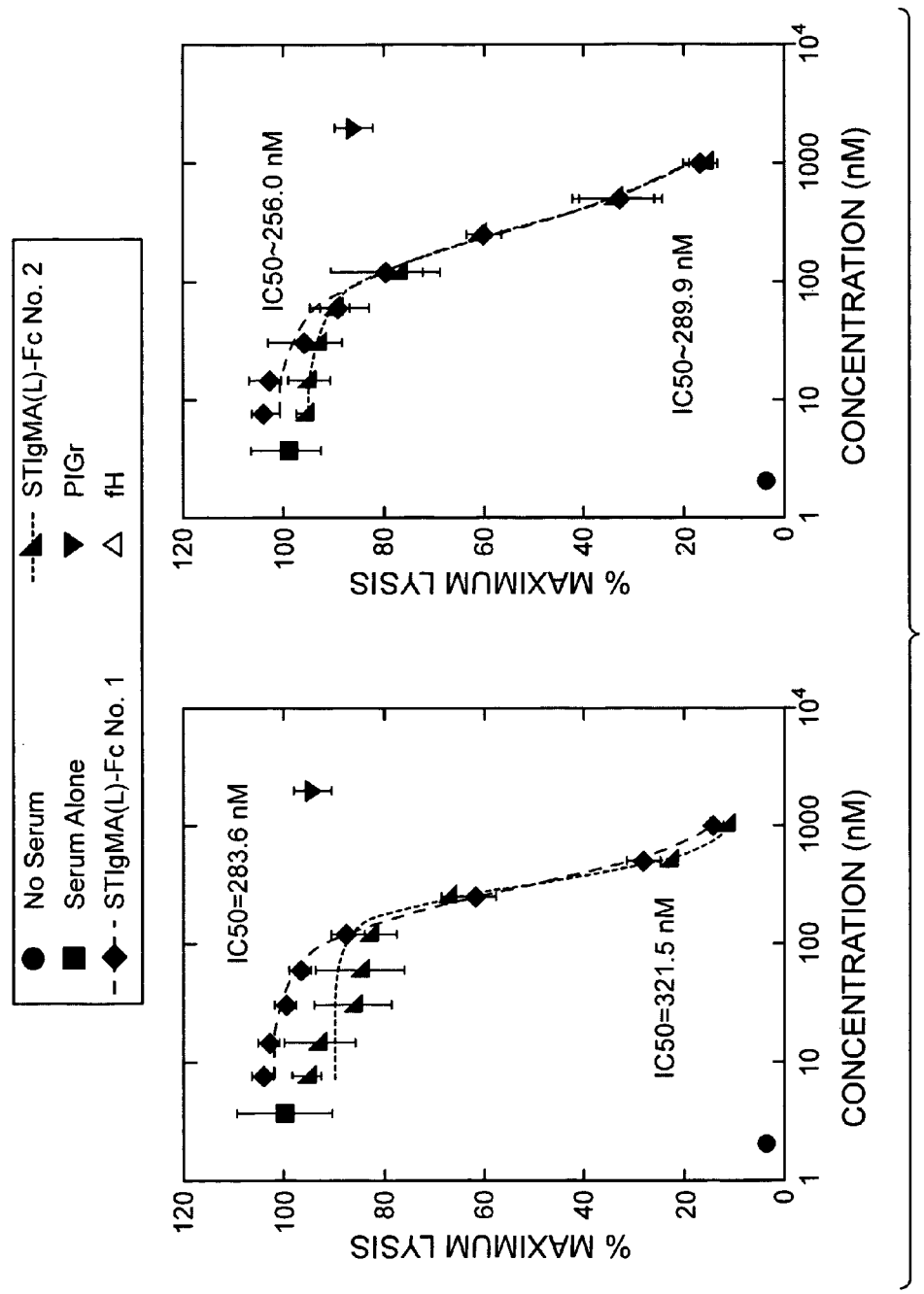

FIG. 64. Inhibition of human serum hemolysis with hCRIg-long in two different experiments.

Figure 65:
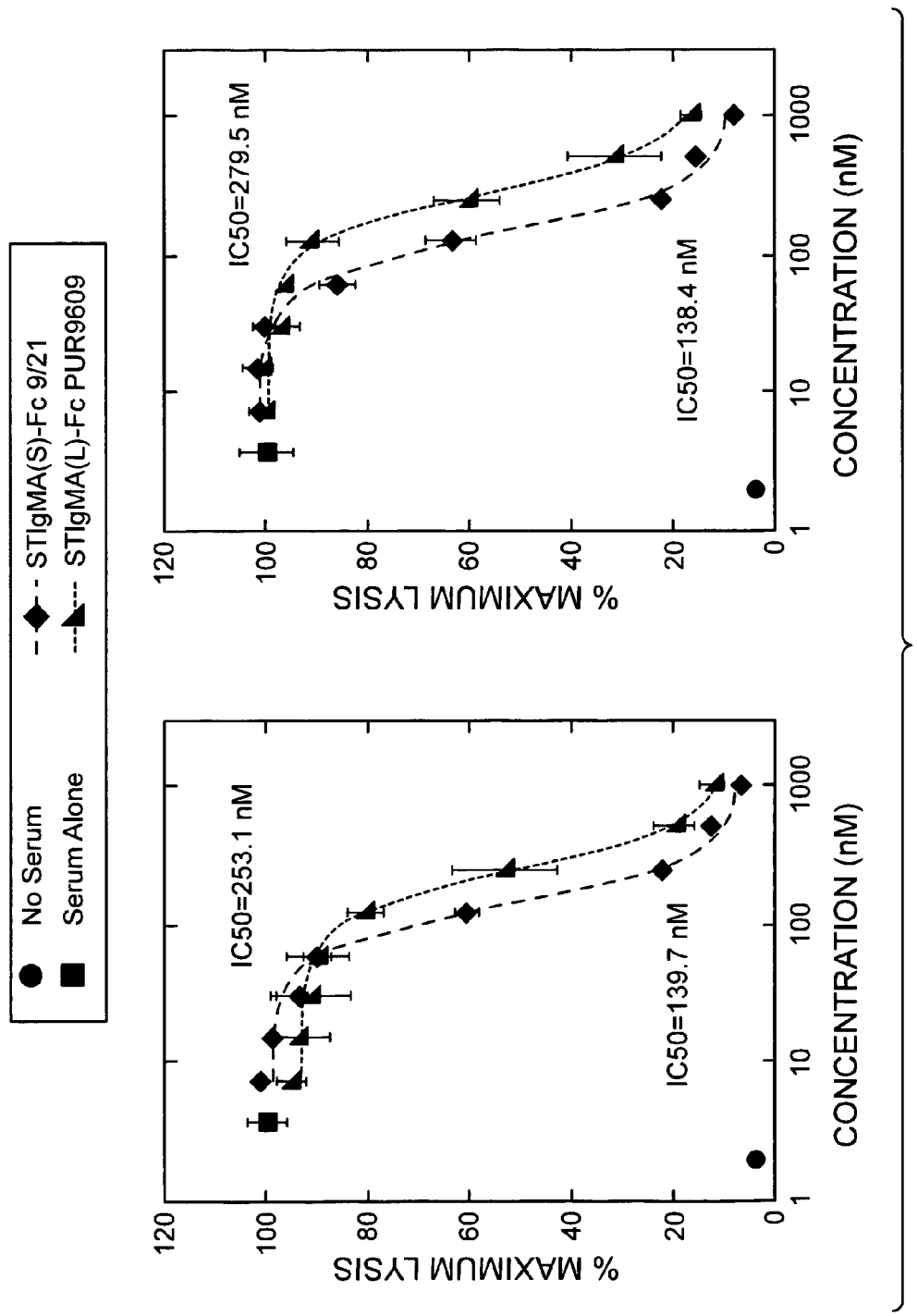

FIG. 65. Inhibition of human serum hemolysis with hCRIg-short-Fc and CRIg-long-Fc fusion proteins.

Figure 66:
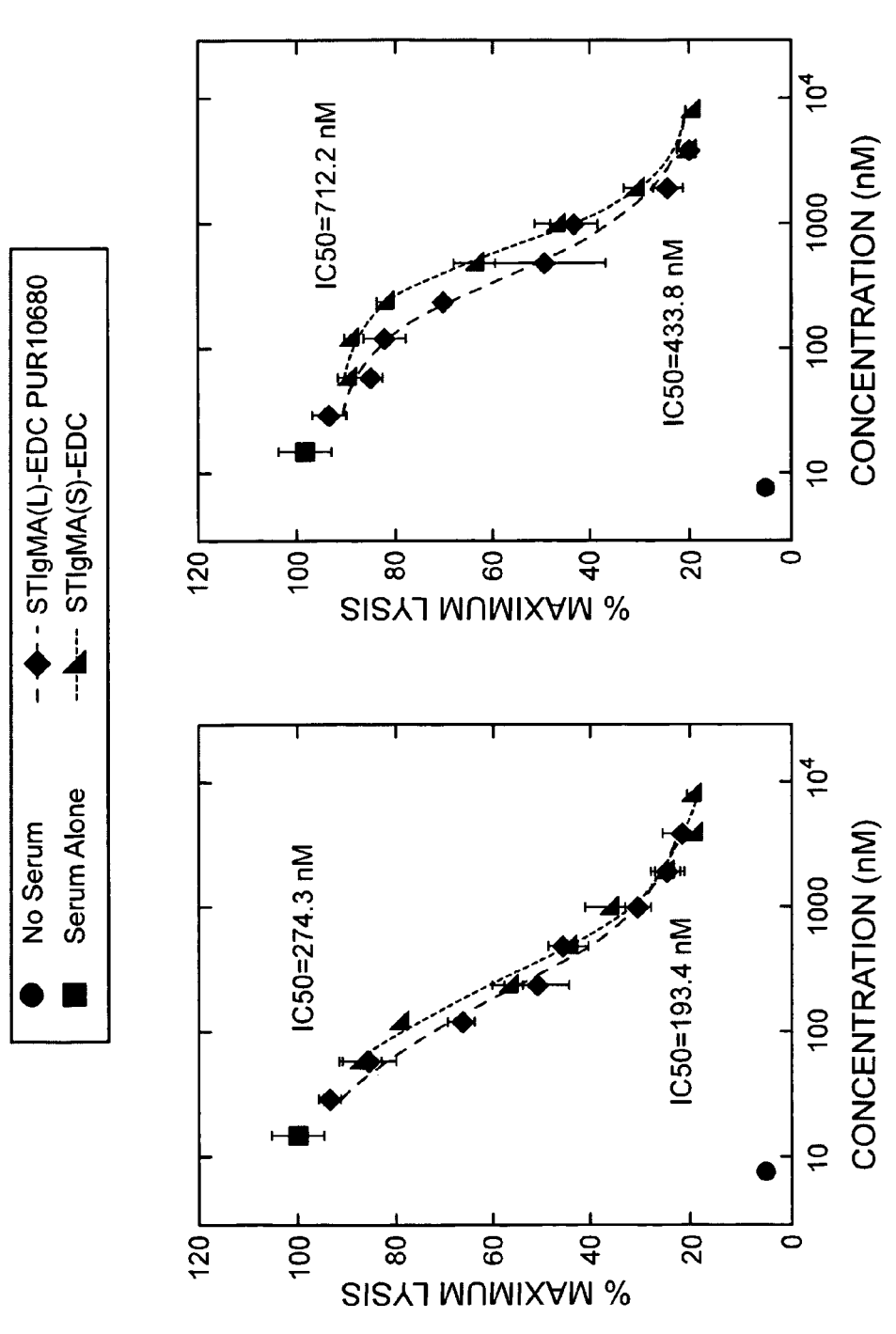

FIG. 66. Inhibition of human serum hemolysis with hCRIg-long-ECD and hCRIg-short-ECD, respectively.

FIG. 67 shows the nucleic acid sequence encoding huCRIg-long-Fc ("stalkless" construct) (SEQ ID NO: 25).

FIG. 68 shows the nucleic acid sequence encoding huCRIg-long-Fc having a "stalk" inserted between the transmembrane domain of CRIg and the Fc portion (SEQ ID NO: 26).

FIG. 69 shows the nucleic acid sequence encoding huCRIg-short-Fc ("stalkless" construct) (SEQ ID NO: 27).

FIG. 70 shows the nucleic acid sequence encoding huCRIg-short-Fc having a "stalk" inserted between the transmembrane domain of CRIg and the Fc portion (SEQ ID NO: 28).

Figure 71A:
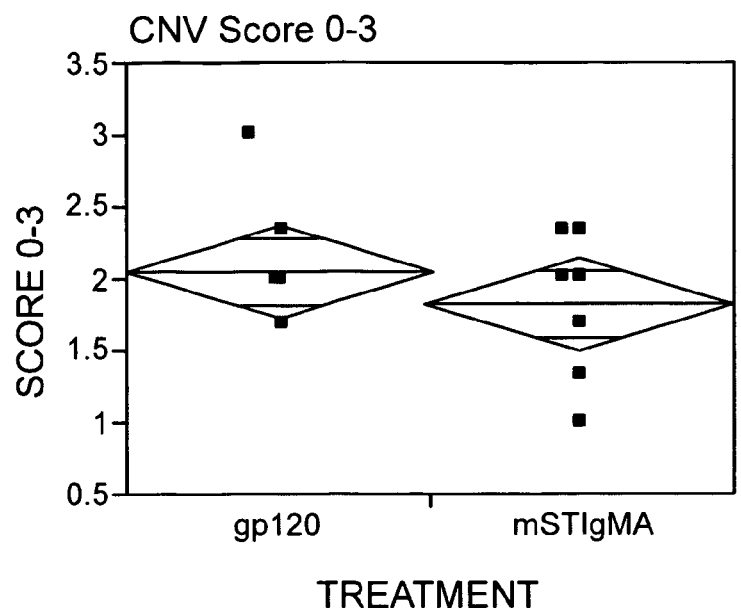
Figure 71B:
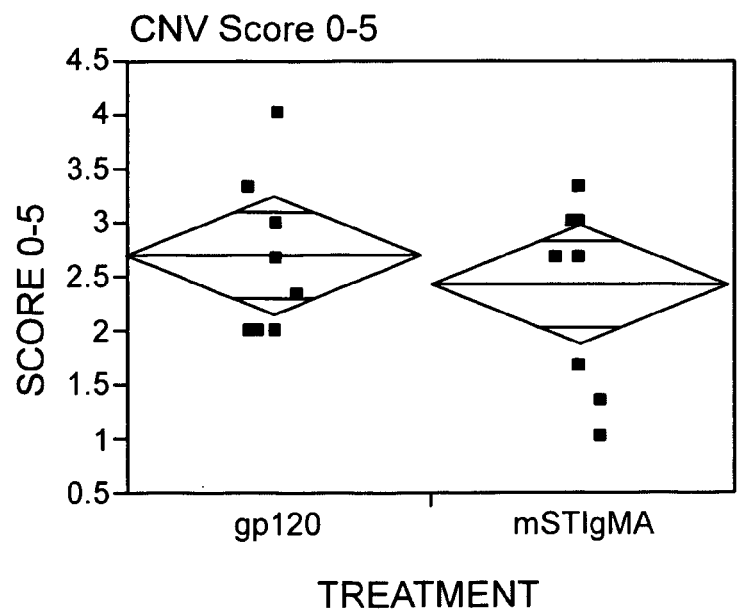

FIGS. 71A and B show the results of mouse CNV studies described in Example 23.

DETAILED DESCRIPTION OF THE PREFERRED EMBODIMENT

I. DEFINITIONS

The terms "PRO362," "JAM4," "STIgMA," and "CRIg" are used interchangeably, and refer to native sequence and variant CRIg polypeptides.

Figure 5:
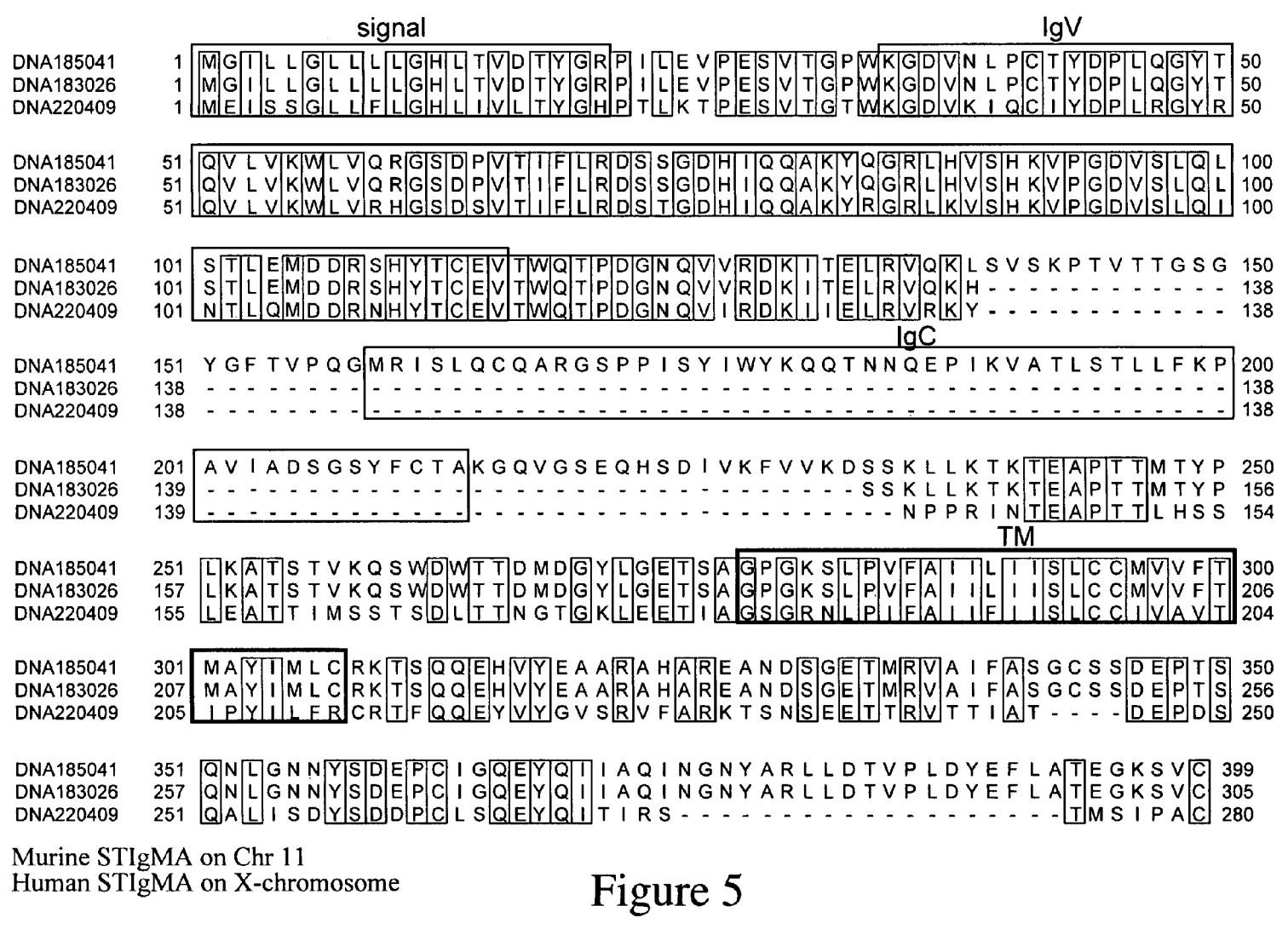

A "native sequence" CRIg, is a polypeptide having the same amino acid sequence as a CRIg polypeptide derived from nature, regardless of its mode of preparation. Thus, native sequence CRIg can be isolated from nature or can be produced by recombinant and/or synthetic means. The term "native sequence CRIg", specifically encompasses naturally-occurring truncated or secreted forms of CRIg (e.g., an extracellular domain sequence), naturally-occurring variant forms (e.g., alternatively spliced forms) and naturally-occurring allelic variants of CRIg. Native sequence CRIg polypeptides specifically include the 321 amino acids long human CRIg polypeptide of SEQ ID NO: 2 (shown in FIG. 1), with or without the N-terminal signal sequence, with or without the initiating methionine at position 1, and with or without any or all of the transmembrane domain at about amino acid positions 277 to 307 of SEQ ID NO: 2. Native sequence CRIg polypeptides further include the full-length 399 amino acids long human CRIg polypeptide of SEQ ID NO: 4 (huCRIg, or huCRIg-long, shown in FIGS. 2 and 5), with or without an N-terminal signal sequence, with or without the initiating methionine at position 1, and with or without any or all of the transmembrane domain at about amino acid positions 277 to 307 of SEQ ID NO: 4. In a still further embodiment, the native sequence CRIg polypeptide is the 305-amino acid, short form of human CRIg (huCRIg-short, SEQ ID NO: 6, shown in FIG. 3), with or without an N-terminal signal sequence, with or without the initiating methionine at position 1, and with or without any or all of the transmembrane domain at about positions 183 to 213 of SEQ ID NO: 6. In a different embodiment, the native sequence CRIg polypeptide is a 280 amino acids long, full-length murine CRIg polypeptide of SEQ ID NO: 8 (muCRIg, shown in FIGS. 4 and 5), with or without an N-terminal signal sequence, with or without the initiating methionine at position 1, and with or without any or all of the transmembrane domain at about amino acid positions 181 to 211 of SEQ ID NO: 8. CRIg polypeptides of other non-human animals, including higher primates and mammals, are specifically included within this definition.

"CRIg variant" means an active CRIg polypeptide as defined below having at least about 80% amino acid sequence identity to a native sequence CRIg polypeptide, including, without limitation, the C-terminally truncated 321-amino acid huCRIg (SEQ ID NO: 2), the fill-length huCRIg (SEQ ID NO: 4), huCRIg-short (SEQ ID NO: 6), and muCRIg (SEQ ID NO: 8), each with or without the N-terminal initiating methionine, with or without the N-terminal signal sequence, with or without all or part of the transmembrane domain and with or without the intracellular domain. In a particular embodiment, the CRIg variant has at least about 80% amino acid sequence homology with the mature, full-length polypeptide from within the sequence of the sequence of SEQ ID NO: 2. In another embodiment, the CRIg variant has at least about 80% amino acid sequence homology with the mature, fill-length polypeptide from within the sequence of SEQ ID NO: 4. In yet another embodiment, the CRIg variant has at least about 80% amino acid sequence homology with the mature, fill-length polypeptide from within the sequence of SEQ ID NO: 6. In a still further embodiment, the CRIg variant has at least about 80% amino acid sequence homology with the mature, full-length polypeptide from within the sequence of SEQ ID NO: 8. Such CRIg polypeptide variants include, for instance, CRIg polypeptides wherein one or more amino acid residues are inserted, substituted and/or deleted, at the N— or C-terminus of the sequence of SEQ ID NO: 2, 4, 6, or 8. Other variants have one or more amino acids inserted, substituted and/or deleted within the transmembrane regions of the indicated polypeptide sequences.

Ordinarily, a CRIg variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature amino acid sequence from within SEQ ID NO: 2, 4, 6, or 8. Preferably, the highest degree of sequence identity occurs within the extracellular domains (ECDs) (amino acids 1 or about 21 to X of SEQ ID NO: 2 or 4, where X is any amino acid residue from position 271 to 281; or amino acids 1 or about 21 to X of SEQ ID NO: 6, where X is any amino acid residue from position 178 to 186, or amino acids 1 or about 21 to X of SEQ ID NO: 8, where X is any amino acid residue from position 176 to 184).

The CRIg (PRO362) "extracellular domain" or "ECD" refers to a form of the CRIg polypeptide, which is essentially free of the transmembrane and cytoplasmic domains of the respective full length molecules. Ordinarily, the CRIg ECD will have less than 1% of such transmembrane and/or cytoplasmic domains and preferably, will have less than 0.5% of such domains. As discussed above, optionally, CRIg ECD will comprise amino acid residues 1 or about 21 to X of SEQ ID NO: 2, 4, 6, or 8, where X is any amino acid from about 271 to 281 in SEQ ID NO: 2 or 4, any amino acid from about 178 to 186 in SEQ ID NO: 6, and any amino acid from about 176 to 184 in SEQ ID NO: 8.

"Percent (%) amino acid sequence identity" with respect to the CRIg (PRO362) sequences identified herein is defined as the percentage of amino acid residues in a candidate sequence that are identical with the amino acid residues in the CRIg sequence, respectively, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) nucleic acid sequence identity" with respect to the CRIg (PRO362)-encoding sequences identified herein (e.g., DNA45416) is defined as the percentage of nucleotides in a candidate sequence that are identical with the nucleotides in the CRIg-encoding sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity wit a portion of a longer sequence, the overall sequence identity will be less than 100%.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an encoded polypeptide where, for example, the nucleic acid molecule is in a chromosomal location different from that of natural cells.

An "isolated" CRIg polypeptide-encoding nucleic acid molecule is a nucleic acid molecule that is identified and separated from at least one contaminant nucleic acid molecule with which it is ordinarily associated in the natural source of the CRIg-encoding nucleic acid. An isolated CRIg polypeptide-encoding nucleic acid molecule is other than in the form or setting in which it is found in nature. Isolated CRIg polypeptide-encoding nucleic acid molecules therefore are distinguished from the encoding nucleic acid molecule(s) as they exists in natural cells. However, an isolated CRIg-encoding nucleic acid molecule includes CRIg-encoding nucleic acid molecules contained in cells that ordinarily express CRIg where, for example, the nucleic acid molecule is in a chromosomal location different from that of natural cells.

The term "complement-associated disease" is used herein in the broadest sense and includes all diseases and pathological conditions the pathogenesis of which involves abnormalities of the activation of the complement system, such as, for example, complement deficiencies. The term specifically include diseases and pathological conditions that benefit from the inhibition of C3 convertase. The term additionally includes diseases and pathological conditions that benefit from inhibition, including selective inhibition, of the alternative complement pathway. Complement-associated diseases include, without limitation, inflammatory diseases and autoimmune diseases, such as, for example, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

The term "complement-associated eye condition" is used herein in the broadest sense and includes all eye conditions and diseases the pathology of which involves complement, including the classical and the alternative pathways, and in particular the alternative pathway of complement. Specifically included within this group are all eye conditions and diseases the associated with the alternative pathway, the occurrence, development, or progression of which can be controlled by the inhibition of the alternative pathway. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The term "inflammatory disease" and "inflammatory disorder" are used interchangeably and mean a disease or disorder in which a component of the immune system of a mammal causes, mediates or otherwise contributes to an inflammatory response contributing to morbidity in the mammal. Also included are diseases in which reduction of the inflammatory response has an ameliorative effect on progression of the disease. Included within this term are immune-mediated inflammatory diseases, including autoimmune diseases.

The term "T-cell mediated" disease means a disease in which T cells directly or indirectly mediate or otherwise contribute to morbidity in a mammal. The T cell mediated disease may be associated with cell mediated effects, lymphokine mediated effects, etc. and even effects associated with B cells if the B cells are stimulated, for example, by the lymphokines secreted by T cells.

Examples of immune-related and inflammatory diseases, some of which are T cell mediated, include, without limitation, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection, graft-versus host disease, Alzheimer's disease, and atherosclerosis.

"Tumor", as used herein, refers to all neoplastic cell growth and proliferation whether malignant or benign, and all pre-cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc. In treatment of complement-associated disease, treatment might, for example, prevent or slow down the progression of a disease. Thus, treatment of a complement-associated eye condition specifically includes the prevention, inhibition, or slowing down of the development of the condition, or of the progression from one stage of the condition to another, more advanced stage, or into a more severe, related condition.

The "pathology" of a disease, such as a complement-associated disease, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, drusen formation, loss of vision, etc.

The term "mammal" as used herein refers to any animal classified as a mammal, including, without limitation, humans, non-human primates, domestic and farm animals, and zoo, sports or pet animals such horses, pigs, cattle, dogs, cats and ferrets, etc. In a preferred embodiment of the invention, the mammal is a human, or a non-human primate, most preferably human.

Administration "in combination with" one or more further therapeutic agents includes simultaneous (concurrent) and consecutive administration in any order.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor, prolactin, placental lactogen, tumor necrosis factor-$\alpha$ and -$\beta$, mullerian-inhibiting substance, mouse gonadotropin-associated peptide, inhibin, activin, vascular endothelial growth factor, integrin, thrombopoietin (TPO), nerve growth factors such as NGF-β platelet-growth factor, transforming growth factors (TGFs) such as TGF-α and TGF.-β, insulin-like growth factor-I and -II, erythropoietin (EPO), osteoinductive factors, interferons such as interferon-α, -β, and -γ; colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1a, IL-2, IL-3, IL-4, IL-5, IL-6, IL-7, IL-8, IL-9, IL-11, IL-12, a tumor necrosis factor such as TNF-α or TNF-β, and other polypeptide factors including LIF and kit ligand (KL). As used herein, the term cytokine includes proteins from natural sources or from recombinant cell culture and biologically active equivalents of the native sequence cytokines.

"Therapeutically effective amount" is the amount of active CRIg, CRIg agonists and antagonists which is required to achieve a measurable improvement in the state, e.g. pathology, of the target disease or condition, such as, for example, a complement-associated (eye) disease or condition, or cancer.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42C; or (3) employ 50% formamide, 5×SSC (0.75 M NaCl, 0.075 M sodium citrate), 50 mM sodium mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of variants of the CRIg polypeptides of the invention refers to form(s) of such polypeptides which retain the biological and/or immunological activities of a native or naturally-occurring polypeptide of the invention. A preferred biological activity is the ability to bind C3b, and/or to affect complement or complement activation, in particular to inhibit the alternative complement pathway and/or C3 convertase. Inhibition of C3 convertase can, for example, be measured by measuring the inhibition of C3 turnover in normal serum during collagen- or antibody-induced arthritis, or inhibition of C3 deposition is arthritic joints.

"Biological activity" in the context of an antibody, polypeptide or another molecule that mimic CRIg biological activity, and can be identified by the screening assays disclosed herein (e.g. an organic or inorganic small molecule, peptide, etc.) refers, in part, to the ability of such molecules to bind C3b and/or to affect complement or complement activation, in particular, to inhibit the alternative complement pathway and/or C3 convertase.

The term CRIg "agonist" is used in the broadest sense, and includes any molecule that mimics a qualitative biological activity (as hereinabove defined) of a native sequence CRIg polypeptide. This CRIg agonists specifically include CRIg-Ig, e.g. CRIg-Fc fusion polypeptides (immunoadhesins), but also small molecules mimicking at least one CRIg biological activity. Preferably, the biological activity is the blocking of a complement pathway, especially of the alternative pathway of complement.

The term "antagonist" is used in the broadest sense, and includes any molecule that partially or fully blocks, inhibits, or neutralizes a qualitative biological activity of a native polypeptide, such as a native sequence CRIg polypeptide.

Suitable agonist or antagonist molecules specifically include agonist or antagonist antibodies or antibody fragments, fragments, fusions or amino acid sequence variants of native polypeptides of the invention, peptides, small molecules, including small organic molecules, etc.

A "small molecule" is defined herein to have a molecular weight below about 600, preferably below about 1000 daltons.

The term "antibody" is used in the broadest sense and specifically covers, without limitation, single anti-CRIg monoclonal antibodies (including agonist, antagonist, and neutralizing antibodies) and anti-CRIg antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *NIH Publ. No.* 91-3242, Vol. I, pages 647-669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 [1995]); single chain antibody molecules; and multispecific antibodies formed from antibody fragments. In particular, examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS (USA)* 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH—CH1-VH—CH1) which, together with complementary light chain polypeptides, form a pair of antigen binding regions (Zapata et al. *Protein Eng.* 8(10):1057 1062 (1995); and U.S. Pat. No. 5,641,870).

Papain digestion of antibodies produces two identical antigen-binding fragments, called "Fab" fragments, each with a single antigen-binding site, and a residual "Fc" fragment. The designation "Fc" reflects the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$—$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called γ, μ, δ, α, and ε, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 [1991] and Marks et al., J. Mol. Biol., 222: 581-597 (1991), for example. See also U.S. Pat. Nos. 5,750,373, 5,571,698, 5,403,484 and 5,223,409 which describe the preparation of antibodies using phagemid and phage vectors.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which several or all residues from a complementarity-determining region (CDR) of the recipient are replaced by residues from a CDR of a non-human species (donor antibody) such as mouse, rat or rabbit having the desired specificity, affinity, and capacity. In some instances, certain Fv framework region (FR) residues of the human immunoglobulin can also be replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 [1988]; and Presta, Curr. Op. Struct. Biol, 2: 593-596 (1992). The humanized antibody includes a "primatized" antibody where the antigen-binding region of the antibody is derived from an antibody produced by immunizing macaque monkeys with the antigen of interest. Antibodies containing residues from Old World monkeys are also possible within the invention. See, for example, U.S. Pat. Nos. 5,658,570; 5,693, 780; 5,681,722; 5,750,105; and 5,756,096.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

The "CH2 domain" of a human IgG Fc region (also referred to as "Cg2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol.22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "flexible linker" herein refers to a peptide comprising two or more amino acid residues joined by peptide bond(s), and provides more rotational freedom for two polypeptides (such as two Fd regions) linked thereby. Such rotational freedom allows two or more antigen binding sites joined by the flexible linker to each access target antigen(s) more efficiently. Examples of suitable flexible linker peptide sequences include gly-ser, gly-ser-gly-ser, ala-ser, and gly-gly-gly-ser.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

An "isolated" polypeptide, such as an antibody, is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide, including antibodies, will be purified (1) to greater than 95% by weight of the antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or other polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to a compound, e.g. antibody or polypeptide, so as to generate a "labeled" compound. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, ANGPTL3, ANGPTL4, etc. It would also include factors that accelerate wound healing, such as growth hormone, insulin-like growth factor-I (IGF-I), VIGF, epidermal growth factor (EGF), CTGF and members of its family, and TGF-α and TGF-β. See, e.g., Klagsbrun and D'Amore, *Annu. Rev. Physiol.*, 53:217-39 (1991); Streit and Detmar, *Oncogene*, 22:3172-3179 (2003); Ferrara & Alitalo, *Nature Medicine* 5(12):1359-1364 (1999); Tonini et al., *Oncogene*, 22:6549-6556 (2003) (e.g., Table 1 listing angiogenic factors); and, Sato *Int. J. Clin. Oncol.*, 8:200-206 (2003).

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668). Anti-angiogensis agents also include native angiogenesis inhibitors, e.g., angiostatin, endostatin, etc. See, e.g., Klagsbrun and D'Amore, *Annu. Rev. Physiol.*, 53:217-39 (1991); Streit and Detmar, *Oncogene*, 22:3172-3179 (2003).

The term "effective amount" refers to an amount of a drug effective to treat (including prevention) a disease or disorder in a mammal. Thus, in the case of age-related macular degeneration (AMD) or choroidal neovascularization (CNV), the effective amount of the drug can reduce or prevent vision loss. For AMD therapy, efficacy in vivo can, for example, be measured by one or more of the following: assessing the mean change in the best corrected visual acuity (BCVA) from baseline to a desired time, assessing the proportion of subjects who lose fewer than 15 letters in visual acuity at a desired time compared with baseline, assessing the proportion of subjects who gain greater than or equal to 15 letters in visual acuity at a desired time compared with baseline, assessing the proportion of subjects with a visual-acuity Snellen equivalent of 20/2000 or worse at desired time, assessing the NEI Visual Functioning Questionnaire, assessing the size of CNV and amount of leakage of CNV at a desired time, as assessed by fluorescein angiography, etc. If the indication is the prevention of the progression of dry to wet AMD, or from AMD to CMV, the effective amount of the drug can inhibit, slow down, or partially or fully block such progression. In this case, determination of the effective amount involves grading the disease, monitoring the time course of disease progression, and adjusting the dosage as necessary in order to achieve the desired result.

II. DETAILED DESCRIPTION

The present invention concerns the use of a novel macrophage-associated receptor with homology to the A33 antigen and JAM1, which was cloned from a fetal lung library and identified as a single transmembrane Ig superfamily member macrophage associated (STigMA) or Complement Receptor of the Immunoglobulin family (CRIg) polypeptide. Native human CRIg is expressed as two spliced variants, one containing an N-terminal IgV like domain and a C-terminal IgC2 like domain and a spliced form lacking the C-terminal domain (SEQ ID NOs: 4 and 6, respectively). Both receptors have a single transmembrane domain and a cytoplasmic domain, containing tyrosine residues which are constitutively phosphorylated in macrophages in vitro. A mouse homologue was found with 67% sequence homology to human CRIg (SEQ ID NO: 8). The full-length human CRIg polypeptide also has a shorter version, with an N-terminal segment missing (SEQ ID NO: 2).

As shown in the Examples below, CRIg binds complement C3b and inhibits C3 convertase. CRIg is selectively expressed on tissue resident macrophages, and its expression is upregulated by dexamethasone and IL-10, and down-regulated by LPS and IFN-γ, and inhibits collagen- and antibody-induced arthritis independent of B or T cell responses.

In addition it has been found that CRIg is highly expressed on Kupffer cells, binds to the C3b and iC3b opnonins and is requiresd for the rapid clearance of pathogens in the circulation. Structurally, CRIg differs from the known complement receptors in that it lacks combined C3b- and C4b-binding short consensus repeat sequences in CR1 and CR2, as well as the integring-line domains present in C3 and CR4. Wherease complement receptors CR1-4 are expressed on a wide variety of cell types, CRIg expression is confined to tissue resident macrophages including liver Kupffer cells.

Depletion studies have established a role for Kupffer cells in the rapid C3-dependent clearance of Listeria early during an infection (Kaufmann, *Annu Rev. Immunol.* 11:129-163 (1993); Gregory et al., *J. Immunol.* 168:308-315 (2002)) but the receptors involved in this process have do far not been identified. The studies presented in the Examples below demonstrate that macrophage-expressed CRIg binds C3b and iC3b deposited on the surface of pathogen. Due to this dual binding activity to C3b and iC3b, CRIg is required for efficient clearance of *Listeria Monocytogenes* (LM) opsonized with both C3 degradation components.

The importance of CRIg in the rapid hepatic clearance of C3 opsonized particles is further supported by the failure of CRIg knock out (ko) mice to efficiently clear C3-opsonized LM from the circulation, leading to elevted loads of pathogens in various organs and increased mortality. In the absence of C3, CRIg ko wild-type (wt) mice cleared Listeria equally well, indicating dependence of CRIg function on the presence of C3.

The role of complement receptors CR1-4 in clearance of LM by liver Kupffer cells has not been well established. CR1 and CR2 are absent on tissue resident macrophages and are predominantly expressed on follicular dendritic cells and B-cells whee they serve as role in regulating T- and B-cell responses (Krych-Goldber and Atkinson, *Immunol. Rev.* 180: 112-122 (2001); Molina et al., *J. Exp. Med.* 175:121-129 (1992)), and Examples). CR3 is expressed at low levels on KCs, but ko mice lacking the CD18 common beta chain of both CR3 and CR4 resulting in non-functional receptors showed reduced, rather than enhanced, susceptibility fo infection (Wu et al., *Infect. Immun.* 71:5986-5993 (2003)). Thus CRIg represents a major component of the reticulo-endothelial phagocytic system in rapid clearance of C3-opsonized particles.

In addition to its expression on liver Kupffer cells, CRIg is present on subpopulations of macrophages in various tissues including peritoneum, heart, lung, adrenal gland and intestine. These macrophages are known to serve a central role ion phagocytosis of dead cells and cell debris (Almeida et al., *Ann. N. Y Acad Sci.* 1019:135-140 (2004); Castellucci and Zaccheo, *Prog. Clin. Biol. Res.* 296:443-451 (1989); Taylor et al., *Annu. Rev. Immunol.* 23:901-944 (2005)). CRIg expression on these resident macrophages may mediate complement-dependent opsonophagocytosis of various particles. This is supported by the finding that CRIg ko mice exhibit decreased LM in their heart and liver tissues despite increased circulatory LM load. Hence, CRIg represents a novel receptor expressed in tissue macrophages and served as a kep portal for rapid clearance of complement opsonized pathogens.

The results presented in the Examples below further demonstrate that CRIg is expressed on an intracellular pool of recycling vesicles, thereby insuring a continuous supply of CRIg on the cell surface for binding to C3 opsonized particles. In addition, CRIg-expressing endosomes are rapidly recruited to sites of particle contact where they may aid in delivering membrane to the forming phagosome. The importance of CRIg in phagocytosis of C3-opsonized particles is shown by the inability of KCs lacking CRIg to bind C3b and iC3b resulting in reduced phagocytosis of C3 opsonized *Listeria Monocytogenes* (see Examples).

The subcellular localization and intracellular trafficking of CRIg differ from the known complement C3 receptors. Whereas CRIg is localized on constitutively recycling endosomes, CR1, CR3, and CR4 are located on secretory vesicles that fuse with the plasma membrane upon cytokine stimulation of the cells (Sengelov et al., *J. Immunol.* 153:804-810 (1994); and Sengelov et al., *Crit. Rev. Immunol.* 15:107-131 (1995)) and internalize ligand through a macropinocytotic process only after cross-linking of the receptor (Carpentier et al., *Cell Regul.* 2:41-55 (1991); Brown et al., *Curr. Opin. Immunol.* 3:76=82 (1991)). As a consequence, CRIg expression on the surface of cells is down/regulated following stimulation of the cells, whereas CR1 and CR3 cell surface expression increases following stimulation. This increase serves as an important step in binding and phagocytosis, and like CRIg, CR3 concentrates in the phagocytic cup and the phagosome surrounding C3 opsonized particles (Aderem and Underhill, *Annu. Rev. Immunol.* 17:593-623 (1999)). The constitutive recycling and endocytosis of ligand by CRIg in resting macrophages first with a role in binding of complement-opsonized particles during the initial phase of a bacterial infection prior to an inflammatory response (e.g. the recruitment of activated phagocytes), as well as during removal of particles from the circulation under non-inflammatory conditions.

Complement plays a crucial role in the body's defense, and, together with other components of the immune system, protect the individual from pathogens invading the body. However, if not properly activated or controlled, complement can also cause injury to host tissues. Inappropriate activation of complement is involved in the pathogenesis of a variety of diseases, referred to as complement associated diseases or disorders, such as immune complex and autoimmune diseases, and various inflammatory conditions, including complement-mediated inflammatory tissue damage. The pathology of complement-associated diseases varies, and might involve complement activation for a long or short period of time, activation of the whole cascade, only one of the cascades (e.g. classical or alternative pathway), only some components of the cascade, etc. In some diseases complement biological activities of complement fragments result in tissue injury and disease. Accordingly, inhibitors of complement have high therapeutic potential. Selective inhibitors of the alternative pathway would be particularly useful, because clearance of pathogens and other organisms from the blood through the classical pathway will remain intact.

C3b is known to covalently opsonize surfaces of microorganisms invading the body, and act as a ligand for complement receptors present on phagocytic cells, which ultimately leads to phagocytosis of the pathogens. In many pathological situations, such as those listed above, complement will be activated on cell surfaces, including the vascular wall, cartilage in the joints, glomeruli in the liver or cells which lack intrinsic complement inhibitors. Complement activation leads to inflammation caused by the chemoattractant properties of the anaphylatoxins C3a and C5a and can cause damage to self-cells by generating a membrane attack complex. Without being bound by any particular theory, by binding C3b, CRIg is believed to inhibit C3 convertase, thereby preventing or reducing complement-mediated diseases, examples of which have been listed hereinabove.

COMPOUNDS OF THE INVENTION

1. Native Sequence and Variant CRIg Polypeptides

The preparation of native CRIg molecules, along with their nucleic acid and polypeptide sequences, have been discussed above. Example 1 shows the cloning of full-length huCRIg of SEQ ID NO: 4. CRIg polypeptides can be produced by culturing cells transformed or transfected with a vector containing CRIg nucleic acid. It is, of course, contemplated that alternative methods, which are well known in the art, may be employed to prepare CRIg. For instance, the CRIg sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of CRIg may be chemically synthesized separately and combined using chemical or enzymatic methods to produce the full-length CRIg.

CRIg variants can be prepared by introducing appropriate nucleotide changes into the DNA encoding a native sequence CRIg polypeptide, or by synthesis of the desired CRIg polypeptide. Those skilled in the art will appreciate that amino acid changes may alter post-translational processes of CRIg, such as changing the number or position of glycosylation sites or altering the membrane anchoring characteristics.

Variations in the native sequence CRIg polypeptides described herein can be made, for example, using any of the techniques and guidelines for conservative and non-conservative mutations set forth, for instance, in U.S. Pat. No. 5,364,934. Variations may be a substitution, deletion or insertion of one or more codons encoding a native sequence or variant CRIg that results in a change in its amino acid sequence as compared with a corresponding native sequence or variant CRIg. Optionally the variation is by substitution of at least one amino acid with any other amino acid in one or more of the domains of a native sequence CRIg polypeptide. Guidance in determining which amino acid residue may be inserted, substituted or deleted without adversely affecting the desired activity may be found by comparing the sequence of the CRIg with that of homologous known protein molecules and minimizing the number of amino acid sequence changes made in regions of high homology.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res*, 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the CRIg variant DNA.

Scanning amino acid analysis can also be employed to identify one or more amino acids that may be varied along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.,* 150:1 (1976)]. If alanine substitution does not yield adequate amounts of variant, an isoteric amino acid can be used.

It has been found that removal or inactivation of all or part of the transmembrane region and/or cytoplasmic region does not compromise CRIg biological activity. Therefore, transmembrane region and/or cytoplasmic region deleted/inactivated CRIg variants are specifically within the scope herein. Similarly, the IgC2 region can be removed without compromising biological activity, as demonstrated by the existence of a biologically active native short form of huCRIg and a murine homologue.

Covalent modifications of native sequence and variant CRIg polypeptides are included within the scope of this invention. One type of covalent modification includes reacting targeted amino acid residues of CRIg with an organic derivatizing agent that is capable of reacting with selected side chains or the N— or C-terminal residues of the CRIg polypeptide. Derivatization with bifunctional agents is useful, for instance, for crosslinking CRIg to a water-insoluble support matrix or surface, for example, for use in the method for purifying anti-CRIg antibodies. Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of the CRIg polypeptides included within the scope of this invention comprises altering the native glycosylation pattern of the polypeptides. "Altering the native glycosylation pattern" is intended for purposes herein to mean deleting one or more carbohydrate moieties found in native sequence CRIg, and/or adding one or more glycosylation sites that are not present in the native sequence CRIg, and/or alteration of the ratio and/or composition of the sugar residues attached to the glycosylation site(s). A predicted native glycosylation site on murine CRIg is found at position 170 in the sequence NGTG.

Glycosylation of polypeptides is typically either N-linked or O-linked. N-linked glycosylation refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Native sequence CRIg has insignificant N-glycosylation. Addition of glycosylation sites to the CRIg polypeptide may be accomplished by altering the amino acid sequence. The alteration may be made, for example, by the addition of, or substitution by, one or more serine or threonine residues to the native sequence CRIg (for O-linked glycosylation sites), or the addition of a recognition sequence for N-linked glycosylation. The CRIg amino acid sequence may optionally be altered through changes at the DNA level, particularly by mutating the DNA encoding the CRIg polypeptide at preselected bases such that codons are generated that will translate into the desired amino acids.

Another means of increasing the number of carbohydrate moieties on the CRIg polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the a CRIg polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of CRIg comprises linking the CRIg polypeptide to one of a variety of nonproteinaceous polymers, e.g., polyethylene glycol, polypropylene glycol, or polyoxyalkylenes, for example in the manner set forth in U.S. Pat. Nos. 4,640,835; 4,496,689; 4,301,144; 4,670,417; 4,791,192 or 4,179,337.

The native sequence and variant CRIg of the present invention may also be modified in a way to form a chimeric molecule comprising CRIg, including fragments of CRIg, fused to another, heterologous polypeptide or amino acid sequence. In one embodiment, such a chimeric molecule comprises a fusion of CRIg with a tag polypeptide which provides an epitope to which an anti-tag antibody can selectively bind. The epitope tag is generally placed at the amino- or carboxyl-terminus of the CRIg polypeptide. The presence of such epitope-tagged forms of the CRIg polypeptide can be detected using an antibody against the tag polypeptide. Also, provision of the epitope tag enables the CRIg polypeptide to be readily purified by affinity purification using an anti-tag antibody or another type of affinity matrix that binds to the epitope tag. Various tag polypeptides and their respective antibodies are well known in the art. Examples include polyhistidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an □-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In another embodiment, the chimeric molecule may comprise a fusion of the CRIg polypeptide or a fragment thereof with an immunoglobulin or a particular region of an immunoglobulin. For a bivalent form of the chimeric molecule, such a fusion can be to the Fc region of an IgG molecule. These fusion polypeptides are antibody-like molecules which combine the binding specificity of a heterologous protein (an "adhesin") with the effector functions of immunoglobulin constant domains, and are often referred to as immunoadhesins. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

Chimeras constructed from a receptor sequence linked to an appropriate immunoglobulin constant domain sequence (immunoadhesins) are known in the art. Immunoadhesins reported in the literature include fusions of the T cell receptor (Gascoigne et al., Proc. Natl. Acad. Sci. USA, 84: 2936-2940 (1987)); CD4 (Capon et al., Nature 337: 525-531 (1989); Traunecker et al., Nature, 339: 68-70 (1989); Zettmeissl et al., DNA Cell Biol. USA, 9: 347-353 (1990); Byrn et al., Nature, 344: 667-670 (1990)); L-selectin (homing receptor) ((Watson et al., J. Cell. Biol., 110:2221-2229(1990); Watson et al., Nature, 349: 164-167 (1991)); CD44 (Aruffo et al., Cell, 61: 1303-1313 (1990)); CD28 and B7 (Linsley et al., J. Exp. Med., 173: 721-730 (1991)); CTLA-4 (Lisley et al., J. Exp. Med. 174: 561-569 (1991)); CD22 (Stamenkovic et al., Cell, 66:1133-11144 (1991)); TNF receptor (Ashkenazi et al., Proc. Natl. Acad. Sci. USA, 88: 10535-10539(1991); Lesslauer et al., Eur. J. Immunol., 27:2883-2886(1991); Peppel et al., J. Exp. Med., 174:1483-1489(1991)); NP receptors (Bennett et al., J. Biol. Chem. 266:23060-23067(1991)); and IgE receptor alpha. (Ridgway et al., J. Cell. Biol., 115:abstr. 1448 (1991)).

The simplest and most straightforward immunoadhesin design combines the binding region(s) of the "adhesin" protein with the hinge and Fc regions of an immunoglobulin heavy chain. Ordinarily, when preparing the CRIg-immunoglobulin chimeras of the present invention, nucleic acid encoding the a CRIg polypeptide, or the extracellular domain of a CRIg polypeptide, will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the CRIg-immunoglobulin chimeras.

In some embodiments, the CRIg-immunoglobulin chimeras are assembled as monomers, or hetero- or homo-multimer, and particularly as dimers or tetramers, essentially as illustrated in WO 91/08298.

In a preferred embodiment, the the sequence of a native-sequence human CRIg polypeptide, such as, for example, huCRIg(long) (SEQ ID NO: 4) or hyCRIg(short) (SEQ ID NO: 6), or a CRIg extracellular domain sequence (including the ECD of huCRIg(long) and huCRIg(short)) is fused to the N-terminus of the C-terminal portion of an antibody (in particular the Fc domain), containing the effector functions of an immunoglobulin, e.g. immunoglobulin $G_1$ (IgG 1). It is possible to fuse the entire heavy chain constant region to the CRIg or CRIg extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the CRIg amino acid sequence is fused to the hinge region and CH2 and CH3, or to the CH1, hinge, CH2 and CH3 domains of an IgG1, gG2, or IgG3 heavy chain. The precise site at which the fusion is made is not critical, and the optimal site can be determined by routine experimentation. Specific CRIg-Ig immunoadhesin structures are illustrated in FIGS. 59-61.

In some embodiments, the CRIg-immunoglobulin chimeras are assembled as multimer, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Alternatively, the CRIg or CRIg extracellular domain sequence can be inserted between immunoglobulin heavy chain and light chain sequences such that an immunoglobulin comprising a chimeric heavy chain is obtained. In this embodiment, the CRIg sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., Mol. Immunol., 28:1027-1037 (1991).

Although the presence of an immunoglobulin light chain is not required in the immunoadhesins of the present invention, an immunoglobulin light chain might be present either covalently associated to a CRIg-immunoglobulin heavy chain fusion polypeptide, or directly fused to the CRIg extracellular domain. In the former case, DNA encoding an immunoglobulin light chain is typically coexpressed with the DNA encoding the CRIg-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989.

The nucleotide sequences encoding certain CRIg-Ig fusion proteins of the invention are shown in FIGS. 59, 60, and 67-70. As shown in FIGS. 67-70, for example, the fusion proteins may contain a linker between the CRIg and immunoglobulin sequences, such as, for example, a short peptide sequence, e.g. DKTHT. In addition, in some contructs, the sequence between the CRIg transmembrane (TM) region and the immunoglobulin (Fc) region (referred to herein as the "stalk" sequence) can be deleted. The amino acid position where the linker starts in the various CRIg constructs shown in FIGS. 67-70 is as follows: huCRIg-long-Fc+stalk: position 267; huCRIg-long-Fc–stalk: position 233; huCRIg-short-Fc+stalk: position 173; huCRIg-short-Fc–stalk: position 140.

2. Preparation of Native Sequence and Variant CRIg Polypeptides

DNA encoding native sequence CRIg polypeptides may be obtained from a cDNA library prepared from tissue believed to possess the CRIg mRNA and to express it at a detectable level. Accordingly, human CRIg DNA can be conveniently obtained from a cDNA library prepared from human tissue, such as described in Example 1. The CRIg-encoding gene may also be obtained from a genomic library or by oligonucleotide synthesis.

Libraries can be screened with probes (such as antibodies to CRIg or oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding CRIg is to use PCR methodology [Sambrook et al., supra; Dieffenbach et al., *PCR Primer: A Laboratory Manual* (Cold Spring Harbor Laboratory Press, 1995).

Example 1 describes techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

Host cells are transfected or transformed with expression or cloning vectors described herein for CRIg production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Sambrook et al., supra.

Methods of transfection are known to the ordinarily skilled artisan, for example, CaPO4 and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transformations have been described in U.S. Pat. No. 4,399,216. Transformations into yeast are typically carried out according to the method of Van Solingen et al., *J. Bact,* 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for CRIg-encoding vectors. *Saccharomyces cerevisiae* is a commonly used lower eukaryotic host microorganism.

Suitable host cells for the expression of glycosylated CRIg are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 cells transformed by SV40 (COS-7, ATCC CRL 1651); human embryonic kidney cells (293 or 293 cells subcloned for growth in suspension culture, Graham et al., *J. Gen Virol.,* 36:59 (1977)); Chinese hamster ovary cells/-

DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art.

The nucleic acid (e.g., cDNA or genomic DNA) encoding CRIg may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The CRIg polypeptides may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the CRIg DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* "—factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the CRIg nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39(1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the CRIg nucleic acid sequence to direct mRNA synthesis. Promoters recognized by a variety of potential host cells are well known. Promoters suitable for use with prokaryotic hosts include the □-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding CRIg.

Examples of suitable promoting sequences for use with yeast hosts include the promoters for 3-phosphoglycerate kinase [Hitzeman et al., *J. Biol. Chem*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

CRIg transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the CRIg polypeptides by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the CRIg coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding CRIg.

Still other methods, vectors, and host cells suitable for adaptation to the synthesis of CRIg in recombinant vertebrate cell culture are described in Gething et al., *Nature,* 293:620-625 (1981); Mantei et al., *Nature,* 281:4046 (1979); EP 117,060; and EP 117,058.

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence CRIg polypeptide or against a synthetic peptide based on the DNA sequences provided herein or against exogenous sequence fused to CRIg DNA and encoding a specific antibody epitope.

Forms of CRIg may be recovered from culture medium or from host cell lysates. If membrane-bound, it can be released from the membrane using a suitable detergent solution (e.g. Triton-X 100) or by enzymatic cleavage. Cells employed in expression of CRIg can be disrupted by various physical or chemical means, such as freeze-thaw cycling, sonication, mechanical disruption, or cell lysing agents.

It may be desired to purify CRIg from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the CRIg polypeptide. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular CRIg produced.

3. Agonists of CRIg Polypeptides

Agonists of the CRIg polypeptides will mimic a qualitative biological activity of a native sequence CRIg polypeptide. Preferably, the biological activity is the ability to bind C3b, and/or to affect complement or complement activation, in particular to inhibit the alternative complement pathway and/or C3 convertase. Agonists include, for example, the immunoadhesins, peptide mimetics, and non-peptide small organic molecules mimicking a qualitative biological activity of a native CRIg.

CRIg-Ig immunoadhesins have been discussed above.

Another group of CRIg agonists are peptide mimetics of native sequence CRIg polypeptides. Peptide mimetics include, for example, peptides containing non-naturally occurring amino acids provided the compound retains CRIg biological activity as described herein. Similarly, peptide mimetics and analogs may include non-amino acid chemical structures that mimic the structure of important structural elements of the CRIg polypeptides of the present invention and retain CRIg biological activity. The term "peptide" is used herein to refer to constrained (that is, having some element of structure as, for example, the presence of amino acids which initiate a .beta. turn or .beta. pleated sheet, or for example, cyclized by the presence of disulfide bonded Cys residues) or unconstrained (e.g., linear) amino acid sequences of less than about 50 amino acid residues, and preferably less than about 40 amino acids residues, including multimers, such as dimers thereof or there between. Of the peptides of less than about 40 amino acid residues, preferred are the peptides of between about 10 and about 30 amino acid residues and especially the peptides of about 20 amino acid residues. However, upon reading the instant disclosure, the skilled artisan will recognize that it is not the length of a particular peptide but its ability to bind C3b and inhibit C3 convertase, in particular C3 convertase of the alternative complement pathway, that distinguishes the peptide.

Peptides can be conveniently prepared using solid phase peptide synthesis (Merrifield, J. Am. Chem. Soc. 85:2149 (1964); Houghten, Proc. Natl. Acad. Sci. USA 82:5132 (1985)). Solid phase synthesis begins at the carboxyl terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g., a polyamide or polystyrene resin), as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the .alpha.-amino group of the blocked amino acids in peptide synthesis. If a base-labile alpha.-protecting group is used, then it is desirable to use an acid-labile link between the peptide and the solid support. For example, an acid-labile ether resin is effective for base-labile Fmoc-amino acid peptide synthesis, as described on page 16 of Stewart and Young, supra. Alternatively, a peptide anchor link and .alpha.-protecting group that are differentially labile to acidolysis can be used. For example, an aminomethyl resin such as the phenylacetamidomethyl (Pam) resin works well in conjunction with Boc-amino acid peptide synthesis, as described on pages 11-12 of Stewart and Young, supra.

After the initial amino acid is coupled to an inert solid support, the .alpha.-amino protecting group of the initial amino acid is removed with, for example, trifluoroacetic acid (TFA) in methylene chloride and neutralizing in, for example, triethylamine (TEA). Following deprotection of the initial amino acid's .alpha.-amino group, the next .alpha.-amino and sidechain protected amino acid in the synthesis is added. The remaining .alpha.-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino]phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the .alpha.-amino group on an amino acid or peptide fragment while the C-terminal carboxyl group of the amino acid or peptide fragment reacts with the free N-terminal amino group of the growing solid phase polypeptide chain, followed by the selective removal of the .alpha.-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

α- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO$_2$)], p-methoxybenzyloxycarbonyl [Z(OMe))], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxyl functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem Calif. (Torrence, Calif.) or Peninsula Labs (Belmont, Calif.).

Stewart and Young, supra, provides detailed information regarding procedures for preparing peptides. Protection of α-amino groups is described on pages 14-18, and side chain blockage is described on pages 18-28. A table of protecting groups for amine, hydroxyl and sulfhydryl functions is provided on pages 149-151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

4. Antagonists of CRIg Polypeptides

Antagonists of native sequence CRIg polypeptides find utility in the treatment of condition benefiting from excessive complement activation, including the treatment of tumors.

A preferred group of antagonists includes antibodies specifically binding a native CRIg. Exemplary antibodies include polyclonal, monoclonal, humanized, bispecific and heteroconjugate antibodies.

Methods of preparing polyclonal antibodies are known to skilled artisan. Polyclonal antibodies can be raised in a mammal, for example, by one or more injections of an immunizing agent, and, if desired, an adjuvant. Typically, the immunizing agent and/or adjuvant will be injected in the mammal by multiple subcutaneous or intraperitoneal injections. The immunizing agent may include the CRIg polypeptide of the invention or a fragment or fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Antibodies which recognize and bind to the polypeptides of the invention or which act as antagonists thereto may, alternatively be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the CRIg polypeptide of the invention, an antigenic fragment or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide of the invention or having similar activity as the polypeptide of the invention. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies are preferably monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et a, *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immunol*, 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature*_Biotechnology 14, 845-51 (1996); Neuberger, *Nature Biotechnology* 14, 826 (1996); Lonberg and Huszar, *Intern. Rev. Immunol.* 13 65-93 (1995).

Bispecific antibodies are monoclonal, preferably human or humanized, antibodies that have binding specificities for at least two different antigens. In the present case, one of the binding specificities may be for the polypeptide of the invention, the other one is for any other antigen, and preferably for a cell-surface protein or receptor or receptor subunit.

Methods for making bispecific antibodies are known in the art. Traditionally, the recombinant production of bispecific antibodies is based on the coexpression of two immunoglobulin heavy-chain/light-chain pairs, where the two heavy chains have different specificities (Milstein and Cuello, *Nature*, 305:537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are cotransfected into a suitable host organism. For further details of generating bispecific antibodies see, for example, Suresh et al., *Methods in Enzymology*, 121:210 (1986).

Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It may be desirable to modify the antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B., *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design,* 3:219-230 (1989).

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}$Bi, $^{131}$i, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tissue pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

5. Target Diseases 5.1 Complement-Associated Diseases and Conditions

The CRIg polypeptides of the present invention and their agonists, especially CRIg-Ig immunoadhesins, find utility in the prevention and/or treatment of complement-associated diseases and pathological conditions. Such diseases and conditions include, without limitation, inflammatory and autoimmune diseases.

Specific examples of complement-associated diseases include, without limitation, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

5.2 Complement-Associated Eye Conditions

The CRIg polypeptides and their agonists, especially CRIg-Ig immunoadhesins, are particularly useful for the prevention and treatment of complement-associated eye conditions (all eye conditions and diseases the pathology of which involves complement, including the classical and the alternative pathways, and in particular the alternative pathway of complement), such as, for example, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

AMD is age-related degeneration of the macula, which is the leading cause of irreversible visual dysfunction in individuals over the age of 60. Two types of AMD exist, non-exudative (dry) and exudative (wet) AMD. The dry, or non-exudative, form involves atrophic and hypertrophic changes in the retinal pigment epithelium (RPE) underlying the central retina (macula) as well as deposits (drusen) on the RPE. Patients with nonexudative AMD can progress to the wet, or exudative, form of AMD, in which abnormal blood vessels called choroidal neovascular membranes (CNVMs) develop under the retina, leak fluid and blood, and ultimately cause a blinding disciform scar in and under the retina. Nonexudative AMD, which is usually a precursor of exudative AMD, is more common. The presentation of nonexudative AMD varies; hard drusen, soft drusen, RPE geographic atrophy, and pigment clumping can be present. Complement components are deposited on the RPE early in AMD and are major constituents of drusen.

The present invention specifically concerns the treatment of high risk AMD, including category 3 and category 4 AMD. Category 3 AMD is characterized by the absence of advanced AMD in both eyes, at least one eye having a visual acuity of 20/32 or better with at least one large druse (e.g. 125 μm), extensive (as measured by drusen area) intermediate drusen, or geographic atrophy (GA) that does not involve the center of the macula, or any combination of these. Category 3 AMD (which is still considered "dry" AMD) has a high risk of cinversion to choroidal neovascularization (CNV).

Category 4 high risk AMD (classified as "wet AMD) is characterized by a visual acuity of 20/32 or better and no advanced AMD (GA involving the center of the macula or features of choroidal neovascularization) in index eye. The fellow eye is characterized by advanced AMD, or visual acuity less than 20/32 attributable to AMD maculopathy. Typically, high risk AMD, if untreated, rapidly progresses into choroidal neovascularization (CNV), at a rate about 10-30-times higher than the rate of progression for category 1 or 2 (not high risk) AMD.

CRIg and its agonists, such as CRIg-Ig immunoadhesins, find particular utility in the prevention of the progression of AMD (in particular, category 3 or category 4 AMD) into CNV, and/or the prevention of the development/progression of AMD or CNV in the non- or less effected fellow eye. In this context, the term "prevention" is used in the broadest sense to include, complete or partial blocking and slowing down of the progression of the disease as well as the delay of the onset of the more serious form of the disease. Patients who are at high risk of developing or progressing into high risk (category 4) AMD or CMV especially benefit from this aspect of the invention.

It is known that complement factor H (CFH) polymorphism is associated with the risk of an individual to develop AMD and/or CNV. Muations in CFH can activate complement, which in turn may lead to AMD/CNV. It has been recently reported that complement factor H (CFH) polymorphism accounts for 50% of the attributable risk of AMD (Klein et al., *Science* 308:385-9 (2005)). A common halpotype in CFH (HF1/CFH) has been found to predispose individuals to age-related macular degeneration (Hageman et al., *Proc. Natl. Acad. Sci. USA*, 102(2):7227-7232 (2005)). AMD has been segregated as an autosomal-dominant trait, with the disease locus mapping to chromosome 1q25-q31 between markers D1S466 and D1S413, with a maximum lod score of about 3.20 (Klein et al., *Arch Opthalmol.* 116(8): 1082-9 (1998); Majewski et al., *Am. J. Hum. Genet.* 73(3):540-50 (2003); Seddon et al., *Am. J. Hum. Genet.* 73(4):780-90 (2003); Weeks et al., *Am. J. Ophthalmol.* 132(5):682-92 (2001); Iyengar et al., *Am. J. Hum. Genet.* 74(1):20-39 (2004)); chromosome 2q3/2q32 between markers D12S1391 and D2S1384, with a maximum lode score of 2.32/2.03 (Seddon et al., supra); 3p13, between markers D12S1300 and D12S1763, with a maximum lode score of 2.19 (Majewski et al., supra; Schick et al., *Am. J Hum. Genet.* 72(6):1412-24 (2003)); 6q14 between markers D6S1056 and DS249 with a maximum lode score of 3.59/3.17 (Kniazeva et al., *Am. J. Ophthlmol.* 130(2):197-202 (2000)); 9q33, at marker D9S934, with a maximum lode score of 2.06 (Mejwski et al., supra); 10q26 at th marker D10S1230, with a maximum lode score of 3.06 (Majewski et al., supra; Iyengar et al., supra; Kenealy et al., *Mol. Vis.* 10:57-61 (2004); 17q25 at marker D17S928, maximum lode score of 3.16 (Weeks et al., supra); and 22q12 at marker D22S1045, maximum lode score of 2.0 (Seddon et al., supra). Accordingly, genetic screening is an important part of identifying patients who are particularly good candidates for preventative treatment, including prevention of the progression of the disease into a more severe form, such as from AMD to CNV.

In addition, in view of strong evidence for a link of complement activation and age-related macular degeneration (AMD), the present invention provides a new method for the prevention and treatment of CNV and AMD by complement inhibition, in particular, by inhibiting the alternative pathway. Inhibitors of the alternative pathway, other than CRIg, include fusion proteins (e.g. immunoadhesins), agonist anti-CRIg antibodies and peptide and non-peptide small molecules.

5.3 Inflammatory Conditions and Autoimmune Diseases

A more extensive list of inflammatory conditions as examples of complement-associated diseases includes, for example, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid is infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stages have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+T lymphocytes are the predominant cell type at lesions. The mechanism of oligodendrocyte cell death and subsequent demyelination is not known but is likely T lymphocyte driven.

Inflammatory and Fibrotic Lung Disease, including eosinophilic pneumonia, idiopathic pulmonary fibrosis and hypersensitivity pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils. Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

6. Treatment Methods

For the prevention, treatment or reduction in the severity of complement-associated (immune related) disease, the appropriate dosage of a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments. Preferably, it is desirable to determine the dose-response curve and the pharmaceutical composition of the invention first in vitro, and then in useful animal models prior to testing in humans.

For example, depending on the type and severity of the disease, about 1 µg/kg to 15 mg/kg (e.g. 0.1-20 mg/kg) of polypeptide is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The compounds of the invention for prevention or treatment of an ocular disease or condition are typically administered by ocular, intraocular, and/or intravitreal injection. Other methods administration by also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred. In the case of CRIg, all forms, including the ECD of huCRIg short and long forms, their Ig (Fc) fusions, the full-length huCRIg long and short forms, and their Ig (Fc) fusions are all suitable for intraocular (including intravitreal) delivery.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ET-DRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performiing eye exam, measuring intraocular pressure, assessing visual acuity, measuring slitlamp pressure, assessing intraocular inflammation, etc.

CRIg antagonists, such as antibodies to CRIg, can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al, (1996) *Proc. Natl. Acad. Sci. USA,* 93:7149. It has been shown that costimulation of T cells induces tumor regression and an antitumor response both in vitro and in vivo. Melero, I. et al, *Nature Medicine* (1997) 3:682; Kwon, E. D. et al, *Proc. Natl. Acad. Sci. USA* (1997) 94:8099; Lynch, D. H. et al, *Nature Medicine* (1997) 3:625; Finn, O. J. and Lotze, M. T., *J. Immuno.* (1998) 21:114. The CRIg antagonists of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the CRIg antagonists of the invention allows reduced amounts of the growth regulating, cytotoxic, or chemotherapeutic agents thereby potentially lowering the toxicity to the patient.

Although some macrophages are involved in tumor eradication, many solid tumors are known to contain macrophages that support tumor growth (Bingle et al., *J. Pathol* 196:254-265 (2002); Mantovani et al., *Trends Immunol* 23:549-555 (2002)). These macrophages may contain CRIg on their surface Antibodies that block the capacity of CRIg to inhibit complement activation could be used to activate complement on tumor cells and help irradicate the tumor through complement-mediated lysis. This approach would be particularly useful in tumors that contain CRIg positive macrophages.

In the treatment methods of the present invention, the compositions herein can be combined with one more further treatment modalities for the prevention or treatment of the target disease or condition. Thus, for example, if the target is prevention or treatment of complement-associated eye conditions, the administration of CRIg (including all forms and their EC regions and/or Ig fusions) can be combined with or supplement the administration of the anti-VEGF-A antibody ranibizumab (Lucenitis™, Genentech, Inc.), which is in clinical development for the treatment of AMD. In a recently concluded Phase III clinical trial, in addition to meeting the study's primary efficacy endpoint of maintaining vision in patients with wet AMD, 25 percent (59/238) of patients treated with 0.3 mg of Lucentis and 34 percent (81/240) treated with 0.5 mg of Lucentis™ improved vision by a gain of 15 letters or more compared to approximately 5 percent (11/238) of patients in the control group as measured by the Early Treatment of Diabetic Retinopathy (ETDRS) eye chart. Nearly 40 percent (188/478) of Lucentis™-treated patients achieved a visual acuity score of 20/40 or better at 12 months compared to 11 percent (26/238) in the control group. At 12 months, patients treated with Lucentis™ gained an average of seven letters in visual acuity compared to study entry, while those in the control group lost an average of 10.5 letters.

If the target is the treatment of a complement-associated inflammatory or autoimmune disease, the administration of CRIg (including all forms) can be combined with other therapies for such indications. Thus, for example, if the target is rheumatoid arthritis (RA), other arthritis medications, such as salicialates (e.g. aspirin), traditional non-steroid anti-inflammatory molecules (NSAIDs), such as, e.g. Asaid, Arthrotec, Cataflam, Naproxen, etc., COX-2 inhibitors, e.g. Celebrex, Vioxx. In this context, "combination" means concurrent or consecutive administration in any order, and in any dose form, in the same or different routes of delivery.

7. Screening Assays and Animal Models

CRIg and CRIg agonists, including Ig fusions of CRIg and CRIg ECD, can be evaluated in a variety of cell-based assays and animal models of complement-associated diseases or disorders.

Thus, for example, efficacy in the prevention and/or treatment of arthritis can be evaluated in a collagen-induced arthritis model (Terato et al. *Brit. J. Rheum.* 35:828-838 (1966)), as shown in Example 7 below. Potential arthritis prophylactics/therapeutics can also be screened in a model of antibody-mediated arthritis induced by the intravenous injection of a cocktail of four monoclonal antibodies, as described by Terato et al., *J. Immunol.* 148:2103-8 (1992); Terato et al., *Autoimmunity* 22:137-47 (1995), and in Example 8 below. Candidates for the prevention and/or treatment of arthritis can also be studied in transgenic animal models, such as, for example, TNF-α transgenic mice (Taconic). These animals express human tumor necrosis factor (TNF-α), a cytokine which has been implicated in the pathogenesis of human rheumatoid arthritis. The expression of TNF-α in these mice results in severe chronic arthritis of the forepaws and hind paws, and provides a simple mouse model of inflammatory arthritis.

In recent years, animal models of psoriasis have also been developed. Thus, Asebia (ab), flaky skin (fsn), and chronic proliferative dermatitis (cpd) are spontaneous mouse mutations with psoriasis-like skin alterations. Transgenic mice with cutaneous overexpression of cytokines, such as interferon-γ, interleukin-1α, keratinocyte growth factor, transforming growth factor-α, interferon-6, vascular endothelial growth factor, or bone morphogenic protein-6, can also be used to study in vivo psoriasis and to identify therapeutics for the treatment of psoriasis. Psoriasis-like lesions were also described in $B_2$-integrin hypomorphic mice backcrossed to the PL/J strain and in $β_1$-integrin transgenic mice, scid/scid mice reconstituted with CD4$^+$/CD45RB$^{hi}$T lymphocytes as well as in HLA-B27/h$β_2$m transgenic rats. Xenotransplantation models using human skin grafted on to immunodeficient mice are also known. Thus, the compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path.* (1995) 146:580. For further details see, e.g. Schon, M. P., *J Invest Dermatology* 112:405-410 (1999).

Recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with CRIg or a candidate agonist to determine the extent of effects on complement and complement activation, including the classical and alternative pathways, or T cell proliferation. In these experiments, blocking antibodies which bind to the polypeptide of the invention, are administered to the animal and the biological effect of interest is monitored.

Alternatively, "knock out" animals can be constructed which have a defective or altered gene encoding CRIg, as a result of homologous recombination between the endogenous gene encoding the CRIg polypeptide and altered genomic DNA encoding the same polypeptide introduced into an embryonic cell of the animal. For example, cDNA encoding CRIg can be used to clone genomic DNA encoding CRIg in accordance with established techniques. A portion of the genomic DNA encoding CRIg can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the CRIg polypeptide.

Thus, the biological activity of CRIg or its potential agonists can be further studied in murine CRIg knock-out mice, as described in Example 7 below.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test CRIg and CRIg agonists for activity and effectiveness in the treatment of asthma are described by Wolyniec, W. W. et al, *Am. J. Respir. Cell Mol. Biol.* (1998) 18:777 and the references cited therein.

Contact hypersensitivity is a simple in vivo assay of cell mediated immune function. In this procedure, epidermal cells are exposed to exogenous haptens which give rise to a delayed type hypersensitivity reaction which is measured and quantitated. Contact sensitivity involves an initial sensitizing phase followed by an elicitation phase. The elicitation phase occurs when the epidermal cells encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19(1):37-44 (1998).

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, supra, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, supra, unit 4.4. Other transplant rejection models which can be used to test CRIg and CRIg agonists are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. CRIg and its agonists and antagonists can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

An animal model of age-related macular degeneration (AMD) consists of mice with a null mutation in Ccl-2 or Ccr-2 gnes. These mice develop cardinal features of AMD, including accumulation of lipofuscin in and drusen beneath the retinal pigmented epithelium (RPE), photoreceptor atrophy and choroidal neovascularization (CNV). These features develop beyond 6 months of age. CRIg and CRIg agonists can be tested for the formation of drusen, photoreceptor atrophy and choroidal neovascularization.

CNV can be tested in various models of laser-induced choroidal neovascularization. Thus, for example CNV can be induced in rats and cynomolgus monkeys by intense laser photocoagulation, which results in choroidal neovascularization. Progess and treatment of this condition can be evaluated, e.g. by fluorescein angiography, histopathologic and immunohistochemical evaluation, and by pharmacokinetics, hemolytic, antibody screening and complement activation assays of serum collected from the animals before and after treatmen, in different time intervals. Efficacy of preventative administration can be monitored by similar methods, including monitoring of vascular leakage by fluorescein angiography, inhibition of complement deposition at the site of laser burn, ocular exam, ocuar photography, harvest of vitreous and retinal tissue, and the like. Further details are provided in the examples below.

Models of myocardial ischemia-reperfusion can be performed in mice or rats. Animals are tracheostomized and ventilated with a small animal ventilator. Polyethylene catheters are placed in the internal carotid artery and the external jugular vein for measurement of mean arterial blood pressure. Myocardial ischemia reperfusion is initiated by ligating the left anterior descending artery (LAD) with a 6-O suture. Ischemia is produced by tightening the reversible ligature around the LAD to completely occlude the vessel. The ligature is removed after 30 min and the heart perfused for 4 hours. CRIg and CRIg agonists can be tested for their efficacy by measuring heart infarct size, heart creatine kinase activity, myeloperoxidase activity and immunohistochemistry using anti C3 antibodies A model of diabetic retinopathy involves treatment of mice or rats with streptozotocin. CRIg and CRIg agonists can be tested on their effect on venule dilatation, intraretinal microvascular abnormalities, and neovascularization of the retina and vitreous cavity.

A model for membranoproliferative glomerulonephritis can be established as follows: Female mice are immunized i.p. with 0.5 mg control rabbit IgG in CFA (day −7). Seven days later (day 0), 1 mg of the rabbit anti-mouse glomerular basement membrane (GBM) antibody is injected i.v. via the tail vein. Elevation of anti-rabbit IgG antibody in the serum is measured by ELISA. 24-h urine samples are collected from the mice in metabolic cages, and mouse renal function is assessed by the measurement of urinary protein in addition to blood urea nitrogen.

7. Pharmaceutical Compositions

The active molecules of the invention, including polypeptides and their agonists, as well as other molecules identified by the screening assays disclosed above, can be administered for the treatment of inflammatory diseases, in the form of pharmaceutical compositions.

Therapeutic formulations of the active molecule, preferably a CRIg polypeptide or CRIg agonist of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Compounds identified by the screening assays of the present invention can be formulated in an analogous manner, using standard techniques well known in the art.

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and □ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37C, resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

For intraocular administration, typically injection formulations are used, usually given about six weeks apart. The eye is numbed before each injection.

However, it is also possible to use implants with sustained released formulations of CRIg or an agonist, such as a CRIg-Ig or CRIg ECD-Ig fusion, for intravitreal release.

The following examples are offered for illustrative purposes only, and are not intended to limit the scope of the present invention in any way.

All patent and literature references cited in the present specification are hereby expressly incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1

Isolation of cDNA Clones Encoding Human CRIg (PRO362)

The extracellular domain (ECD) sequences (including the secretion signal, if any) of about 950 known secreted proteins from the Swiss-Prot public protein database were used to search expressed sequences tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST-2 (e.g., Altshul et al., *Methods in Enzymology* 266: 460-480 (1996)) as a comparison of the ECD protein sequences to a 6 frame translation of the EST sequence. Those comparisons resulting in a BLAST score 70 (or in some cases 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated DNA42257 (SEQ ID NO: 9) (see FIG. 32).

Based on the DNA42257 (SEQ ID NO: 9) consensus sequence shown in FIG. 32, oligonucleotides were synthesized: 1) to identify by PCR a cDNA library that contained the sequence of interest, and 2) for use as probes to isolate a clone of the full-length coding sequence for CRIg. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers (forward and reverse) were synthesized:

```
forward PCR primer 1 (42257.f1)
5'-TATCCCTCCAATTGAGCACCCTGG-3'    (SEQ ID NO: 10)

forward PCR primer 2 (42257.f2)
5'-GTCGGAAGACATCCCAACAAG-3'       (SEQ ID NO: 11)

reverse PCR primer 1 (42257.r1)
5'-CTTCACAATGTCGCTGTGCTGCTC-3'    (SEQ ID NO: 12)

reverse PCR primer 2 (42257.r2)
5'-AGCCAAATCCAGCAGCTGGCTTAC-3'    (SEQ ID NO: 13)
```

Additionally, a synthetic oligonucleotide hybridization probe was constructed from the consensus DNA42257 sequence which had the following nucleotide sequence: Hybridization probe (42257.p1)

```
Hybridization probe (42257.p1)
5'-TGGATGACCGGAGCCACTACACGTGTGAA   (SEQ ID NO: 14)

GTCACCTGGCAGACTCCTGAT-3'.
```

In order to screen several libraries for a source of a full-length clone, DNA from the libraries was screened by PCR amplification with the PCR primer pairs identified above. A positive library was then used to isolate clones encoding the CRIg gene using the probe oligonucleotide and one of the PCR primers.

RNA for construction of the cDNA libraries was isolated from human fetal brain tissue (LIB153). The cDNA libraries used to isolate the cDNA clones were constructed by standard methods using commercially available reagents such as those from Invitrogen, San Diego, Calif. The cDNA was primed with oligo dT containing a NotI site linked with blunt to SalI hemikinased adaptors, cleaved with NotI, sized appropriately be gel electrophoresis, and cloned in a defined orientation into a suitable cloning vector (such as pRKB or pRKD; pRK5B is a precursor of pRK5D that does not contain the SfiI site; see Holmes et al., *Science* 253: 1278-1280 (1991)) in the unique XhoI and NotI sites.

DNA sequencing of the clones isolated as described gave the DNA sequence for an isolated CRIg polypeptide (herein designated as UNQ317 (DNA45416-1251) (SEQ ID NO: 1).

The entire nucleotide sequence of UNQ317 (DNA45416-1251) is shown in FIG. 1 (SEQ ID NO: 1). Clone UNQ367 (DNA45416-1251) (SEQ ID NO: 1) contains a single open reading frame with an apparent translational initiation site at nucleotide positions 1082-1084 (FIG. 1, SEQ ID NO: 1). The predicted polypeptide precursor is 321 amino acids long (FIG. 1, SEQ ID NO: 2). The CRIg protein shown in FIG. 1 has an estimated molecular weight of about 35,544 daltons and a pI of about 8.51. Analysis of the 321-amino acid CRIg polypeptide as shown in FIG. 1 (SEQ ID NO: 2) evidences the presence of a glycosaminoglycan attachment site at about amino acid 149 to about amino acid 152 and a transmembrane domain from about amino acid 276 to about amino acid 306. Clone UNQ317 (DNA45416-1251) has been deposited with ATCC deposit No.: 209620.

Similar to JAM family members, CRIg (PRO362), more recently referred to as CRIg, is a type 1 transmembrane molecule and a member of the immunoglobulin superfamily. The extracellular domain of the long form of human CRIg (hu-CRIg(L)) encodes both V and a C2 type terminal Ig domains (Smith and Xue, *J. Mol. Biol.* 274:530-545 (1997)), while the short form (huCRIg(S)) encodes only a single V-type Ig, resembling murine CRIg (muCRIg) (FIG. 42A). The C terminal cytoplasmic domain of human and murine CRIg contain consensus AP-2 internalization motifs (YARL and DSQALI, respectively Bonafacino & Traub Ann Rev Biochem 72 p 395 (2003)). HuCRIgs and muCRIg share 67% overall sequence homology with 83% homology residing in the IgV domain. Among the JAM family members, huCRIg is most closely related to JAM-A. Sequence similarity is confined to a conserved stretch of residues forming the Ig domain fold (FIG. 42A). Both human and murine CRIg are located on chromosome X position Xq12 and have a syntenic position on the chromosome flanked by hephaestin and moesin.

Example 2

Protein Production and Purification

The extracellular domains of hu and muCRIg were cloned into a modified pRK5 expression vector encoding the human or murine IgG1 Fc region downstream of the CRIg sequence. The Fc portion of mouse IgG1 contains a double mutation (D265A, N297A) preventing Fc receptor binding (Gong et al, *J. Immunol.* 174:817-826 (2005)) was used to control for Fc receptor regulation. Human IREM-1 and mouse CLM-1 Fc fusion protein or a murine anti-gp120 IgG antibody were used as controls. LFH tagged CRIg was made by fusing the ECD of CRIg to a yeast leucine zipper, a Flag and an C-terminal (6) histidine. Proteins were overexpressed in CHO cells by transient transfections. Cells were grown in fully automated bioreactors using F-12/Dulbecco's modified Eagle's medium-based media supplemented with Ultra-Low IgG serum (Invitrogen) and Primatone HS (Sigma). The culture was maintained for 7-12 days until harvest. Fc fusion proteins were purified by protein A affinity chromatography and subsequent Sephacryl S-300 gel filtration. LFH fuson protein was purified over a nickle column. Human CRIg-ECD protein was affinity-purified over a Millipore Glyceryl-CPG (173700404) column to which monoclonal antibody 3C9 was absorbed. Protein was eluted at pH 3.0. hu and muCRIg-HIS were generated by cloning the CRIg ECD into a baculovirus expression vector containing C-terminal (6) histidines. Plasmid DNA was transfected into Sf9 cells, the supernatant was used to infect H5 cells and proteins were purified over a nickel column. The identities of all purified proteins were verified by N-terminal sequence analysis and the lipopolysaccharide concentration was <5 Eu/mg for all human or murine CRIg preparations.

Example 3

Preparation of Antibodies

Polyclonal antibodies were generated by immunizing New Zealand rabbits with 200 μg huCRIg(L)-His in complete Freuds adjuvant followed by a boost 6 weeks following first immunization. Monoclonal antibodies to muCRIg and huCRIg were generated by immuniziling Wistar rats and Balb/c mice with 50 μg of his-tagged CRIg fusion protein via footpad injection. Clones were selected based on reactivity with human and murine CRIg-ECD by ELISA, FACS, Western blotting and immunohistochemistry. Unless otherwise indicated, the antibodies obtained were used in subsequent tests.

Example 4

Inflammatory Cell infiltrates into Guinea Pig Skin

The following example shows that huCRIg (PRO362) is proinflammatory in that it stimulates inflammatory cell infiltrates (i.e., neutrophilic, eosinophilic, monocytic or lymphocytic) into guinea pig skin. The assay described herein monitors the capacity of this protein to induce an inflammatory cell infiltrate into the skin of a guinea pig. Compounds which stimulate inflammatory infiltration are useful therapeutically where enhancement of an inflammatory response is beneficial. Compounds which inhibit proliferation of lymphocytes are useful therapeutically where suppression of an inflammatory response is beneficial. A therapeutic agent may take the form, for example, of murine-human chimeric, humanized or human antibodies against CRIg, small molecules, peptides, etc. that mimic CRIg biological activity, CRIg-Ig fusion proteins, CRIg extracellular region, and the like.

Hairless guinea pigs (Charles River Labs) weighing 350 grams or more were anesthetized with ketamine (75-80 mg/kg body weight) and xylazine (5 mg/kg body weight) intramuscularly. The protein samples of huCRig and control proteins were injected intradermally into the backs of each animal at a volume of 100 μl per injection site. There were approximately 16-24 injection sites per animal. One mL of Evans blue dye (1% in physiological buffered saline) was injected intracardially. The animals were euthanized after 6 hours and each skin injection site was biopsied and fixed in formalin. The skins were prepared for histopathological evaluation. Each site was evaluated for inflammatory cell infiltration into the skin. Sites with visible inflammatory cells were scored as positive. Samples inducing an inflammatory cell infiltrate were scored as proinflammatory substances. CRIg tested positive in this assay, which indicates antiinflammatory activity.

Example 5

CRIg (PRO362) mRNA and Polypeptide Expression

A. In Situ Hybridization and Immunohistochemistry

Expression of CRIg mRNA was evaluated by in situ hybridization, immunohistochemistry and RT-PCR in various types of tissues.

For in situ hybridization, tissues were fixed (4% formalin), paraffin-embedded, sectioned (3-5 μm thick), deparaffinized, deproteinated (20 μg/ml) with proteinase K (15 minutes at 37° C.), and processed for in situ hybridization. Probes to the polypeptides of the invention were produced by PCR. Primers included T7 or T3 RNA polymerase initiation sites to allow for in vitro transcription of sense or antisense probes from the amplified products. $^{33}$P-UTP labeled sense and antisense probes were hybridized overnight (55° C.), washed (0.1×SSC for 2 hours at 55° C.), dipped in NBT2 nuclear track emulsion (Eastman Kodak, Rochester, N.Y.), exposed 4-6 weeks at 4° C.), and developed and counterstained with hematoxylin and eosin. Representative paired bright and darkfield images are typically shown.

Immunohistochemical staining was performed on 5 mm thick frozen sections using a DAKO Autostainer. Endogenous peroxidase activity was blocked with Kirkegaard and Perry Blocking Solution (1:10, 4 minutes at 20° C.). 10% NGS in TBS/0.05% Tween-20 (DAKO) was used for dilution and blocking. MAb 4F722.2 anti-CRIg (anti-PRO362) or mouse IgG was used at 0.13 mg/ml. Biotinylated goat anti-mouse IgG (Vector Labs, Burlingame, Calif.) was used at 1:200 and detected with Vector Labs Standard ABC Elite Kit (Vector Labs, Burlingame, Calif.). Slides were developed using Pierce metal-enhanced diaminobenzidine (Pierce Chemicals, Rockford, Ill.). Dual immunohistochemistry for CRIg (PRO362) and CD68 expression was performed on frozen sections to demonstrate localization of CRIg expression to macrophages. mAb 4F7.22.2 anti-CRIg and anti-CD68 mAb KP-1 from (DAKO) were utilized and detected by phycoerythrin and FITC markers, respectively.

Expression was examined in a wide variety of tissues and cell types from humans and other mammals.

a. Normal Tissue

Normal human adult tissues that were examined included tonsil, lymph node, spleen, kidney, urinary bladder, lung, heart, aorta, coronary artery, liver, gall bladder, prostate, stomach, small intestine, colon, pancreas, thyroid gland, skin, adrenal gland, placenta, uterus, ovary, testis, retina, and brain (cerebellum, brainstem, cerebral cortex). Normal human fetal tissues including E12-E16 week-old brain, spleen, bowel and thyroid were also tested. In addition, expression was investigated in murine liver.

b. Inflamed Tissue

Inflamed tissues examined by in situ hybridization included tissues with chronic inflammatory disease such as lungs with chronic asthma, chronic bronchopneumonia, chronic bronchitis/chronic obstructive pulmonary disease, kidneys with chronic lymphocytic interstitial nephritis, and livers with chronic inflammation and cirrhosis due to chronic hepatitis C infection, autoimmune hepatitis or alcoholic cirrhosis.

c. Primary Neoplasms

Primary human neoplasms that were examined by in situ hybridization for PRO362 expression included breast carcinoma, pulmonary squamous cell carcinoma, pulmonary adenocarcinoma, prostatic adenocarcinoma, and colonic adenocarcinoma.

2. Results

Figure 7:
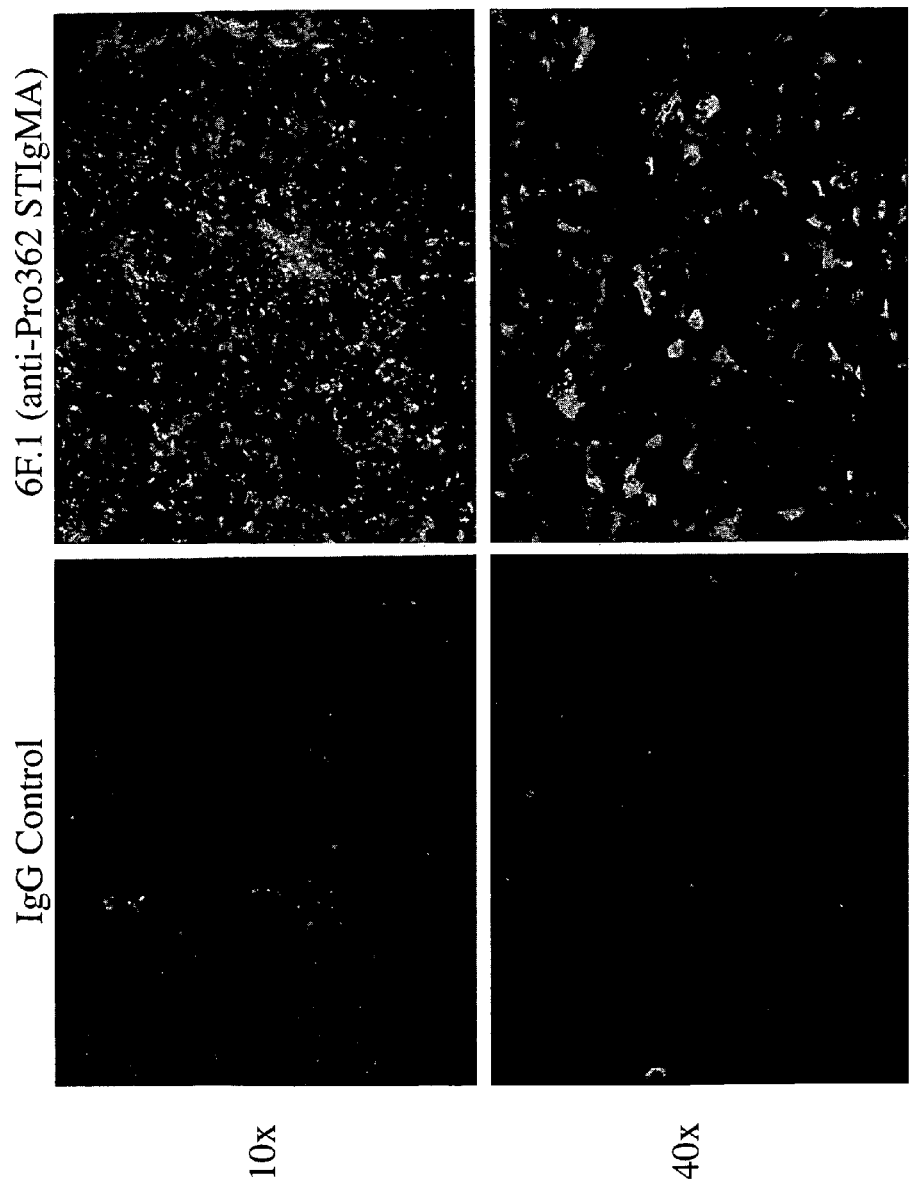
FIG. 7 shows in situ hybridization of CRIg in human liver frozen sections.
Figure 8:
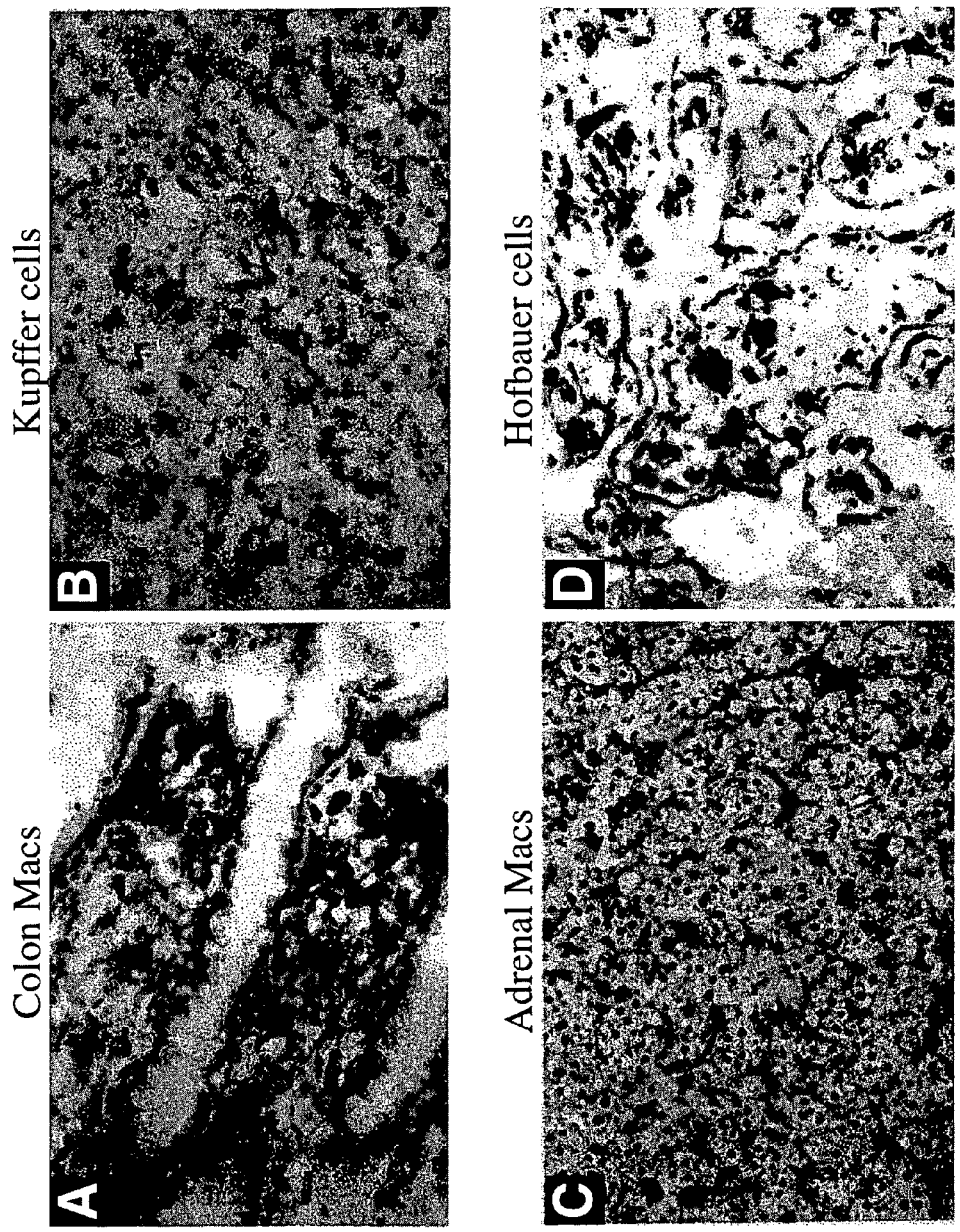
FIG. 8 shows in situ hybridization of CRIg in activated colon and adrenal macrophages, Kupffer cells, and placental Hofbauer cells.
Figure 9:
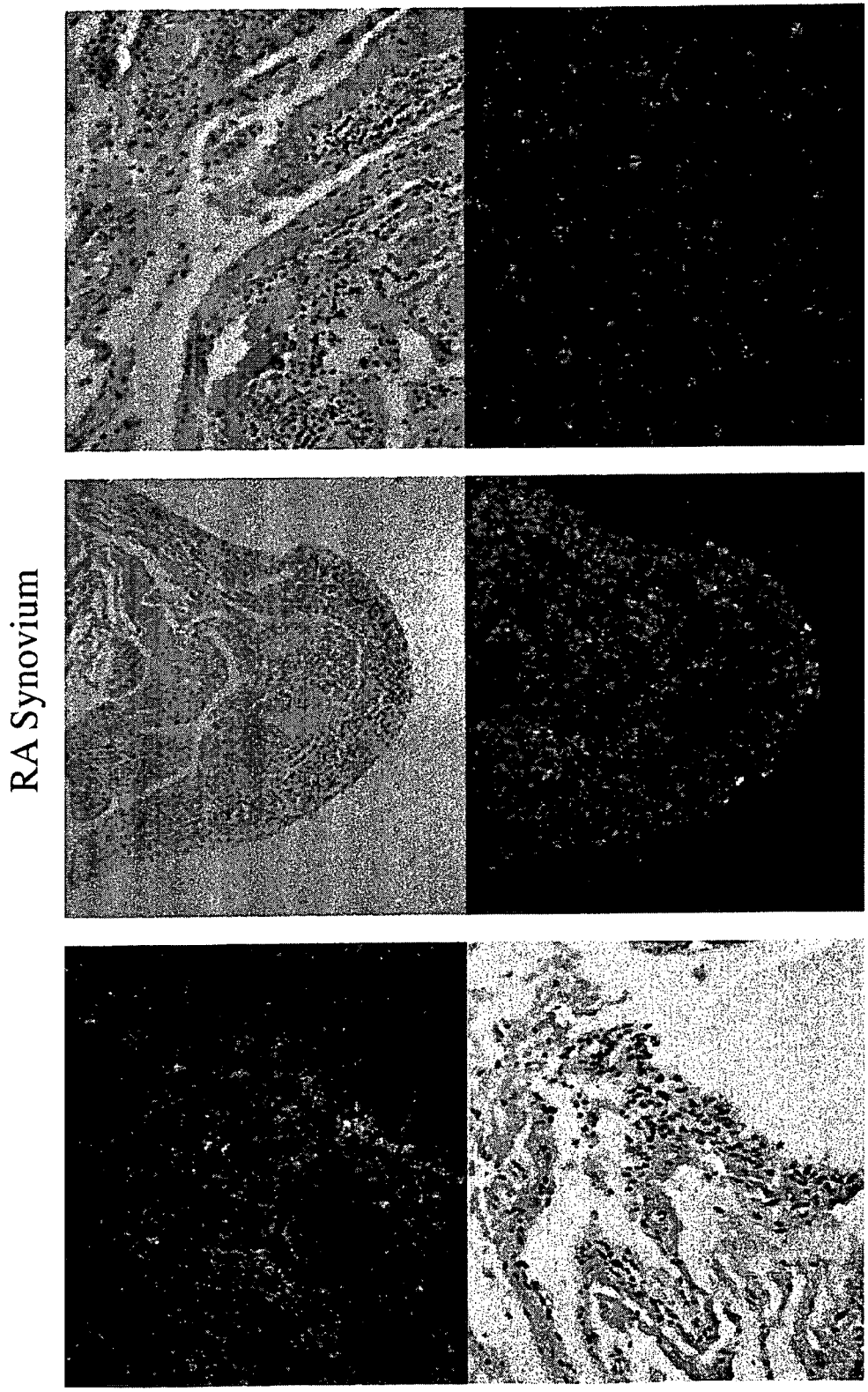
FIG. 9 shows in situ hybridization of CRIg mRNA in RA synovial cells.
Figure 10:
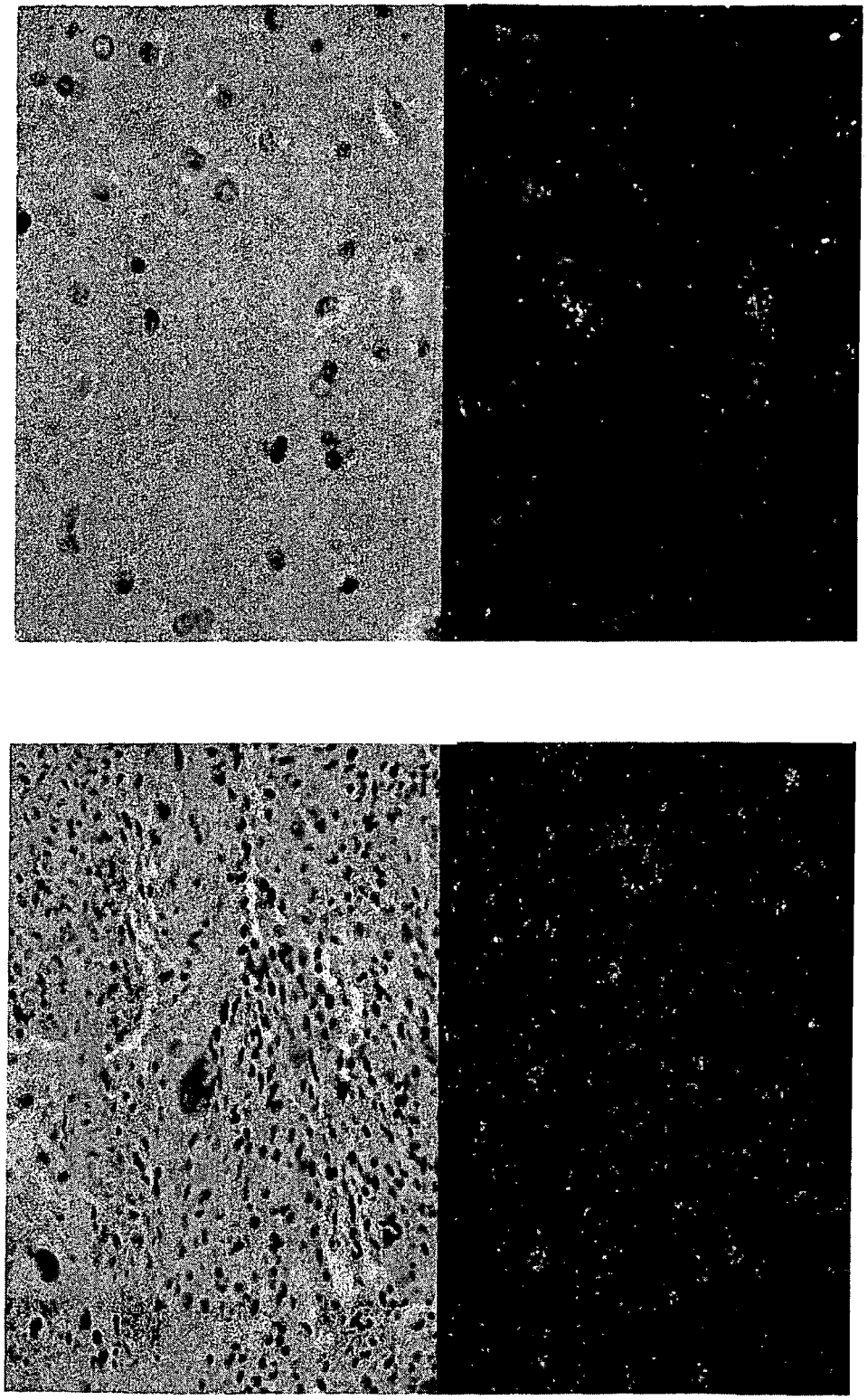
FIG. 10 shows in situ hybridization of CRIg mRNA in brain microglia cells.
Figure 11:
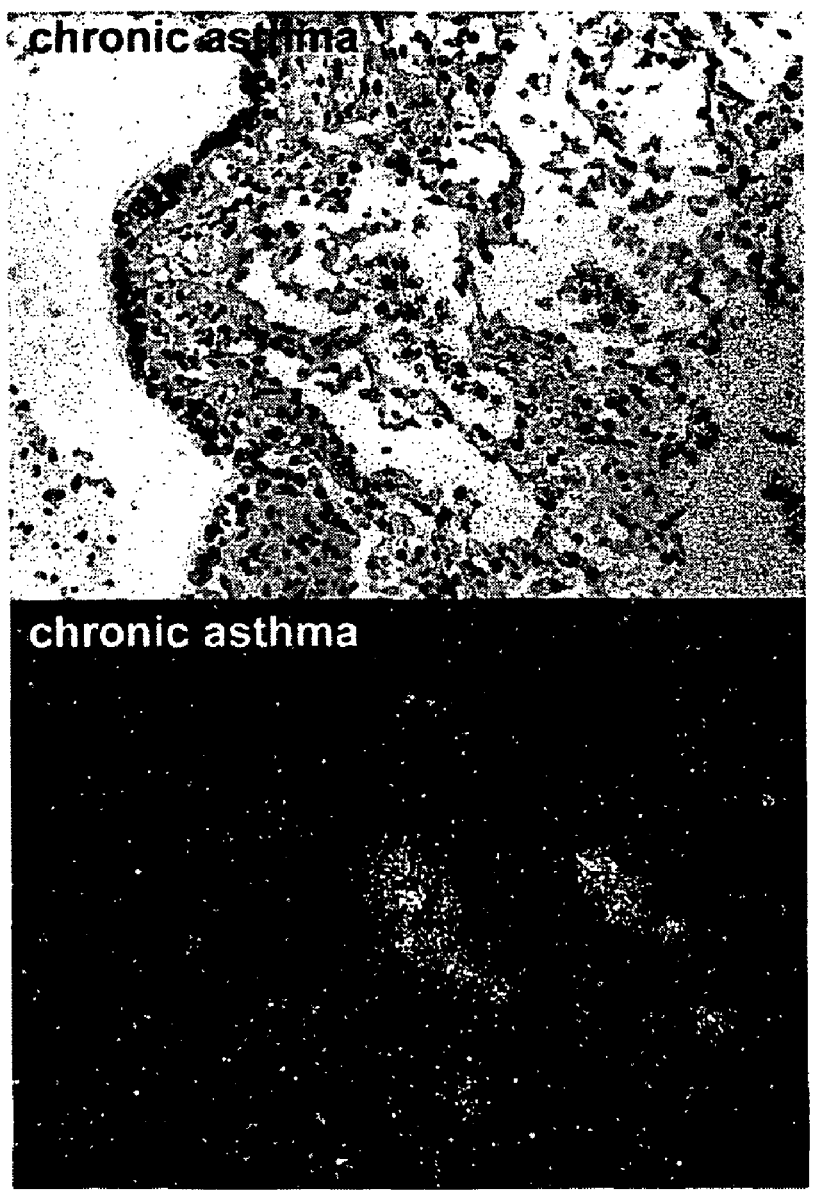
FIG. 11 shows in situ hybridization of CRIg mRNA in cells from human asthmatic tissue.
Figure 12:
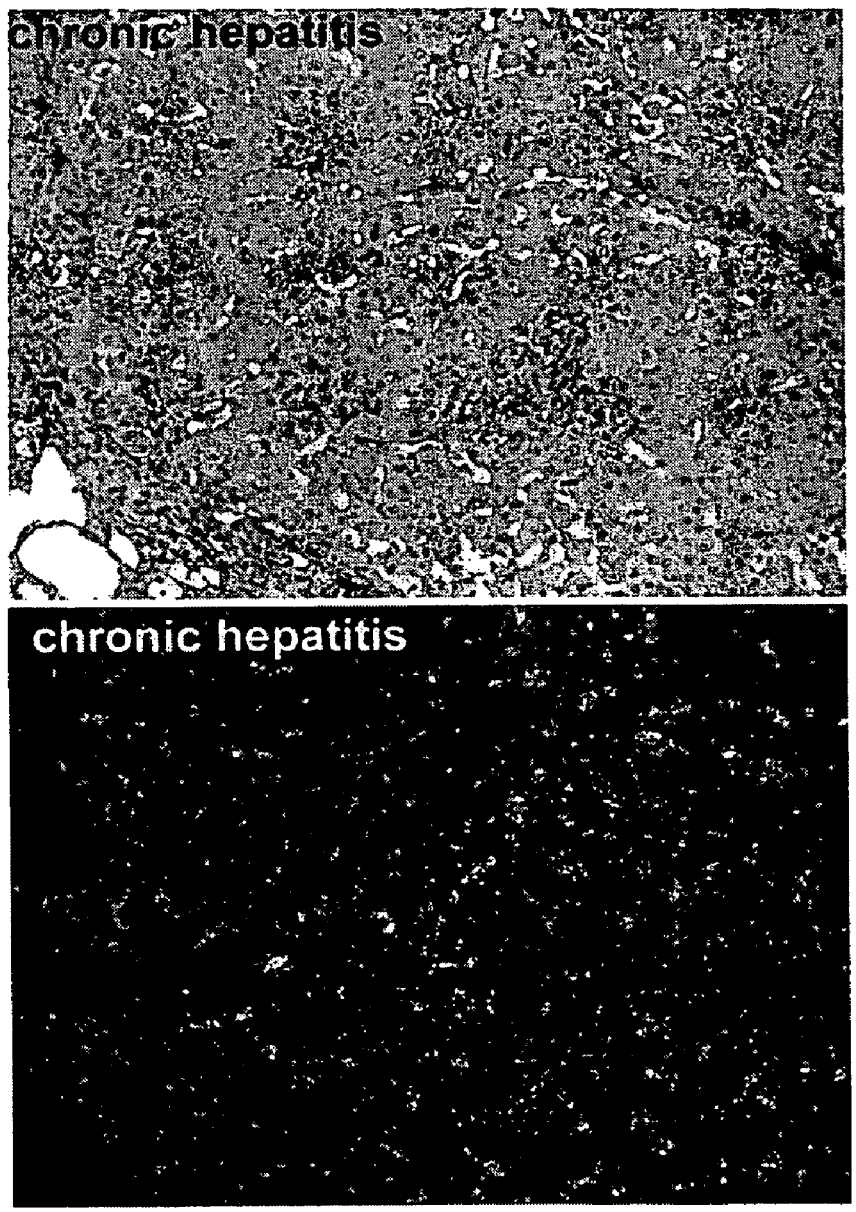
FIG. 12 shows in situ hybridization of CRIg mRNA in cells from human chronic hepatitis tissue.

CRIg (PRO362) was found to be expressed in mouse liver frozen sections (FIG. 6), human live frozen sections (FIG. 7) and a number of tissue macrophage-like cells, including colon macrophages (FIG. 8A), Kupffer cells (FIG. 8B), adrenal macrophages (FIG. 8C), Hofbauer cells (FIG. 8D), synovial cells (FIG. 9), alveolar macrophages, resident macrophages in the intestinal lamina propria and interstitial macrophages in many tissues. CRIg was also significantly expressed in brain microglia (FIG. 10). The expression of CRIg was significantly increased in these tissues when activated by the presence of neoplasia or inflammatory disease, including rheumatoid arthritis (FIG. 9), inflammatory bowel disease, chronic hepatitis (FIG. 12), pneumonia, chronic asthma (FIG. 11), glioma, and bronchitis.

To further examine expression of CRIg, immunohistochemical staining was performed on various tissue types. Dual immunohistochemical staining for CRIg and CD68 was performed on tissue macrophages, including adrenal gland macrophages, liver Kupffer cells, brain microglial cells, and placental Hofbauer cells was performed to determine whether CRIg and CD68 are expressed in the same tissues.

Figure 13:
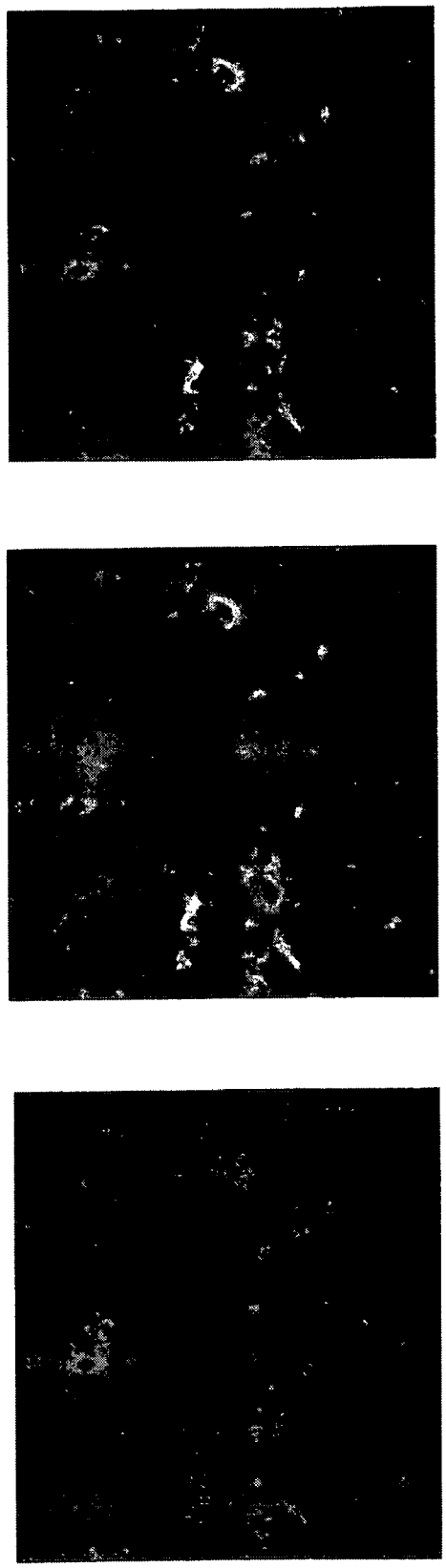
FIG. 13 shows immunohistochemical analysis of CRIg in adrenal gland macrophages.

CRIg was found to be coexpressed with CD68 on adrenal gland macrophages (FIG. 13), liver Kupffer cells (FIG. 14), brain microglial cells (FIG. 15), and placental Hofbauer cells (FIG. 16).

Example 6

Involvement of CRIg (PRO362) in Chronic Inflammation

The novel macrophage associated receptor with homology to A33 antigen and JAM1 was cloned as described in Example 1 and below, and was identified as a single transmembrane Ig superfamily member macrophage associated polypeptide (CRIg or PRO362).

CRIg is expressed as two spliced variants. One variant is a 399-amino acid polypeptide containing an N-terminal IgV like domain and a C-terminal IgC2 like domain, referred to as huCRIg or huCRig-long (SEQ ID NO: 4). The spliced form, which is 355 amino acids long, lacking the C-terminal domain, is referred to as huCRIg-short (SEQ ID NO: 6). Both receptors have a single transmembrane domain and a cytoplasmic domain containing tyrosine residues which are constitutively phosphorylated in macrophages in vitro.

The present study demonstrates that CRIg is selectively expressed on a subset of tissue resident macrophages, and is associated with chronic inflammation.

Materials and Methods

Cells

Blood was obtained from healthy adult volunteers after informed consent by venous puncture and separated using Ficoll-Paque PLUS (Amersham Pharmacia Biotech) per manufacturers instruction. PBMCs were obtained from the interface, washed in cold PBS, lysed with 0.2% NaCl for 30 s and neutralized with 1.6% NaCl. Cells were counted and kept on ice until use. To isolate peripheral blood subsets, untouched MACS kits (Miltenyi Biotech, Auburn, Calif.) were used following the manufacturer's instructions. Differentiation to a macrophage phenotype was induced by culturing $CD14^+$ monocytes for up to 2 weeks in HG-DMEM medium containing 10% (v/v) autologous human serum, 20% fetal bovine serum and 10 mM 1-glutamine, penicillin and streptomycin. Medium was replaced at day 5. For flow cytometric analysis, cells were dissociated from the culture dish using ice-cold cell dissociation solution (Sigma). Lysates for Western blot analysis were prepared by adding 0.5 ml lysis buffer directly to the wells. Lysates were mixed with sample buffer containing SDS and beta-mercaptoethanol, run on a Tris-Glycine gel and transferred to a nitrocellulose membrane. Cell viability was assessed by trypan blue exclusion.

Flow Cytometry

Cells for use in flow cytometric analysis were blocked for 30 min at 4 C with PBS containing 2% fetal bovine serum and 5 μg/ml human IgG (Calbiochem, San Diego, Calif.). Next, cells were incubated with 3C9, an anti-CRIg (anti-PRO362) monoclonal antibody. After washing in PBS, cells were stained with phycoerythrin (PE)-conjugated antibodies to CD11b, CD14, CD163, CD15, CD68 were obtained from Pharmingen.

Cell-cell Adhesion Studies

A pRK expression vector containing full length CRIg was stably expressed in a human Jurkat T-cell line using neomycin selection and autoclone sorting as described elsewhere. Cells were preloaded with the fluorescent dye BCECF (Molecular Probes, Oregon) and added to a 96 well Maxisorb plate (CORNING™) coated with a monolayer of human umbilical vein endothelial cells (HUVEC) treated with or without 10 ng/ml TNFalpha. Cells were gently washed by loading the wells with incubation buffer (HBSS contained 10 mM CaCl, 10 mM magnesium and 1.5 mM NaCl) followed by inverting the plate on a piece of blotting paper. After 3 washes, fluorescence was counted in a fluorospectrometer. The fluorescent readout is representative of the number of cells that remain adherent to the HUVEC cells.

Northern Blot Analysis

Multiple tissue Northern blots (CLONTECH) were probed with a $^{32}P$ labeled probe of random-primed full-length CRIg cDNA using Ambion kit according to manufacturers recommendations. Blots were exposed to a phosphorimaging screen for 4 hours at 22° C. Blots were stripped and re-probed with a commercially available probe to human or mouse β-actin (Clontech) to assess the loading and quantity of RNA in each lane, and analyzed with a Storm® phosphorImager (Molecular Dynamics, Sunnyvale, Calif.).

Real Time RtPCR Analysis

For quantitative PCR analysis (TAQMAN™), total mRNA from human tissues or primary cells (100 ng) was recommended (PerkinElmer Life Sciences) with primers based on the coding sequence of CRIg.

Fc- and His-fusion Protein Production

Human CRIg was cloned into the baculovirus expression vector pHIF (Pharmingen). The HIS-tagged CRIg fusion protein consisted of the extracellular domain of CRIg fused to 8 histidines. His-tagged fusion protein was purified from the supernatant of baculovirus-infected insect cells grown in suspension using nickel affinity resin.

Monoclonal and Polyclonal Antibody Production

For the present experiments, BALBc females were immunized and boosted with 10 μg CRIg-His8 via footpad injections, as previously described Ghilardi et al, *J. Biol. Chem.* 277: 16831-16836 (2002). Single clones were screened against CRIg-His by ELISA. Selected clones selected clones were tested against JAM family members and human IgG Fc. Clones were titrated out to single cell densities and rescreened. Clone 3C9 (IgG1) was found to be selectively reactive to CRIg. Clones were used for ascites generation and purified over protein G (Amersham Pharmacia Biotech); protein concentration was determined using the Pierce BCA reagent (Pierce, Rockford, Ill.).

Polyclonal antibodies were generated by injecting 150 μg CRIg-His in New Zealand Rabbits. Serum titers were determined by ELISA. Serum was collected at the peak of circulating IgG levels and purified over a protein A column.

In Situ Hybridization

PCR primers (upper 5'-TCTCTGTCTCCAAGCCCA-CAG (SEQ ID NO: 18), and lower, 5'-CTTTGAG-GAGTCTTTGACC (SEQ ID NO: 19) were designed to amplify a 700 bp fragment of huJAM4. Primers included T7 or T3 RNA polymerase initiation sites to allow for in vitro transcription of sense or antisense probes, respectively, from the amplified products. Normal human tissues included tonsil, lymph node, spleen, kidney, lung and heart. Tissues with chronic inflammatory disease included lung with chronic asthma, chronic bronchitis, livers with chronic inflammation and cirrhosis due to chronic hepatitis C infection. Tissues were fixed in 4% formalin, paraffin embedded, sectioned (3-5 μm thick) deparaffinized, deproteinated with 20 μg/ml proteinase K (15 min at 37° C.) and processed for in situ hybridization as described elsewhere.

Immunohistochemistry

Human liver was obtained from Ardais Corporation, Lexington, Mass. Immunohistochemical staining was performed on 5-6-μm thick frozen liver sections using a DAKO autostainer. Endogenous peroxidase activity was blocked with Kirkegaard and Perry blocking solution (1:10, 4 min 20° C.). Normal goat serum (NGS) at 10% in TBS/0.05% Tween-20 was used for dilution and blocking. Mab 3C9 was used at 1 ug/ml. Slides were developed using metal-enhanced diaminobenzidine (Pierce Chemicals). For immunofluoresence staining of sections, sections were blocked with PBS/10% NGS and incubated with mAb 3C9 for 1 hr at 20° C. A rabbit-anti mouse FITC-labeled secondary antibody conjugated to FITS was used as detections agent. For double staining procedure, sections were subsequently stained with a PE-conjugated monoclonal antibody to human CD68.

Results

As described in Example 1, huCRIg was cloned from a human fetal cDNA library using degenerate primers recognizing conserved Ig domains of human JAM1. Sequencing of several clones revealed an open reading frame of 321 amino acids (FIG. 1, SEQ ID NO: 2). Blast searches confirmed similarity to Z39Ig, a type 1 transmembrane protein (Langnaese et al., *Biochim Biophys Acta* 1492:522-525 (2000)). It was later found that this 321-amino acid protein missed some C-terminal amino acid residues. The full-length huSIgMA protein has been determined to have 399 amino acid residues, as shown in FIG. 2 (SEQ ID NO: 4). The extracellular region of CRIg consisted of 2 Ig-like domains, comprising an N-terminal V-set domain and a C-terminal C2-set domain. Using 3' and 5' primers, a splice variant of CRIg, CRIg-short (305 amino acids, FIG. 3, SEQ ID NO: 6), which lacks the membrane proximal IgC domain, was cloned.

Cloning of Murine CRIg and Sequence Comparison with Human CRIg

The murine expressed sequence tags (EST) database was searched using the full open reading frame of huCRIg and the tblastn algorithm. DNA sequencing of 3 clones gave rise to identical complete open reading frames of 280 amino acids. Primers to the 3 prime regions were used to clone a full length transcript from a mouse spleen library. The murine clone resembled the spliced form of huCRIg in that, it lacked the C-terminal Ig-like domain. The extracellular IgV-domain was well conserved between the human and murine receptor with 93% identity. The murine cytoplasmic domain was poorly conserved being 20 amino acids shorter than its human counterpart and was 40% identical. The nucleic acid encoding murine CRIg (muCRIg) and the deduced amino acid sequence are shown in FIG. 4 and as SEQ ID NOS: 7 and 8, respectively.

Figure 17:
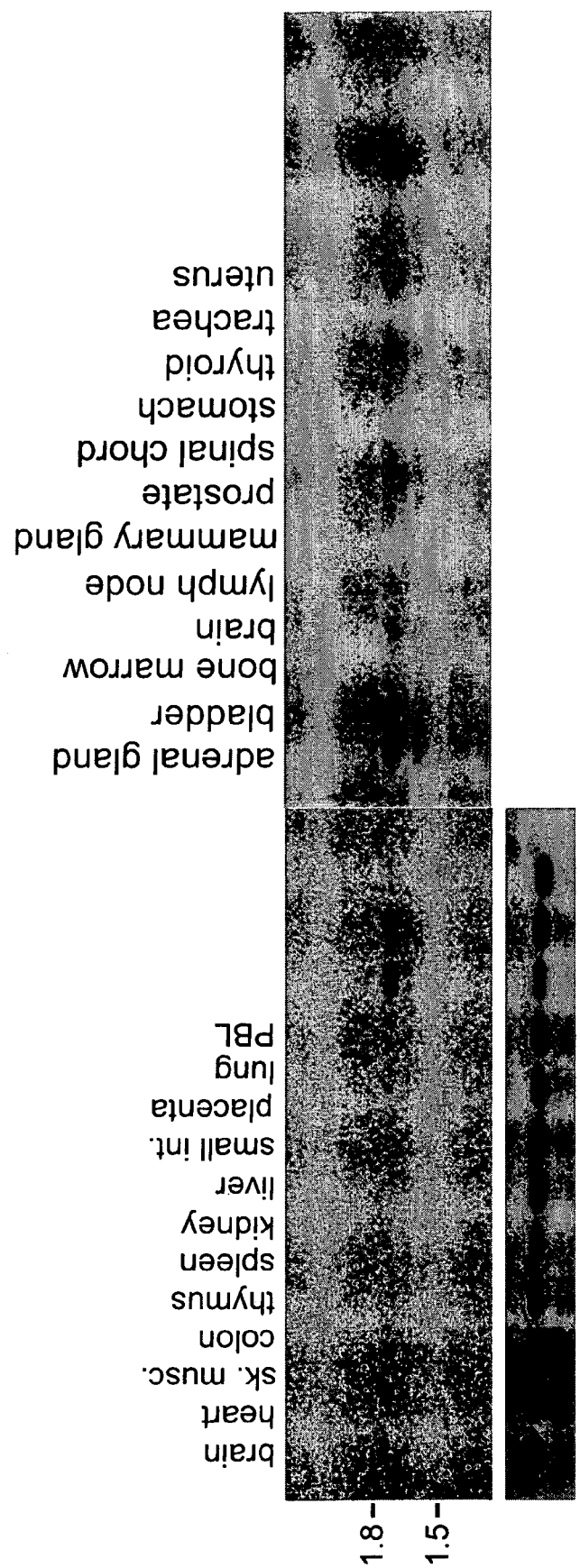
FIG. 17. Northern blot analysis showing expression of huCRIg in a variety of tissues. Two transcripts of 1.5 and 1.8 kb were present in the human tissues expressing CRIg.

CRIg is Expressed on a Subset of Resident Macrophages in Diverse Tissues and its Expression is Increased in Inflammation Northern blot analysis of huCRIg showed two transcripts of 1.5 and 1.8 kb (FIG. 17), with highest expression in the adrenal gland, lung, heart and placenta, and lower expression in other organs, such as, spinal chord, thyroid gland, mammary gland, and lymph node. In all tissues, the 1.8 kb transcript was the most abundantly expressed transcript and presumably, encodes the long form of CRIg. A single transcript of about 1.4 kb was detected in mouse liver and heart.

TAQMAN™ Real-time PCR Analysis

Figure 18:
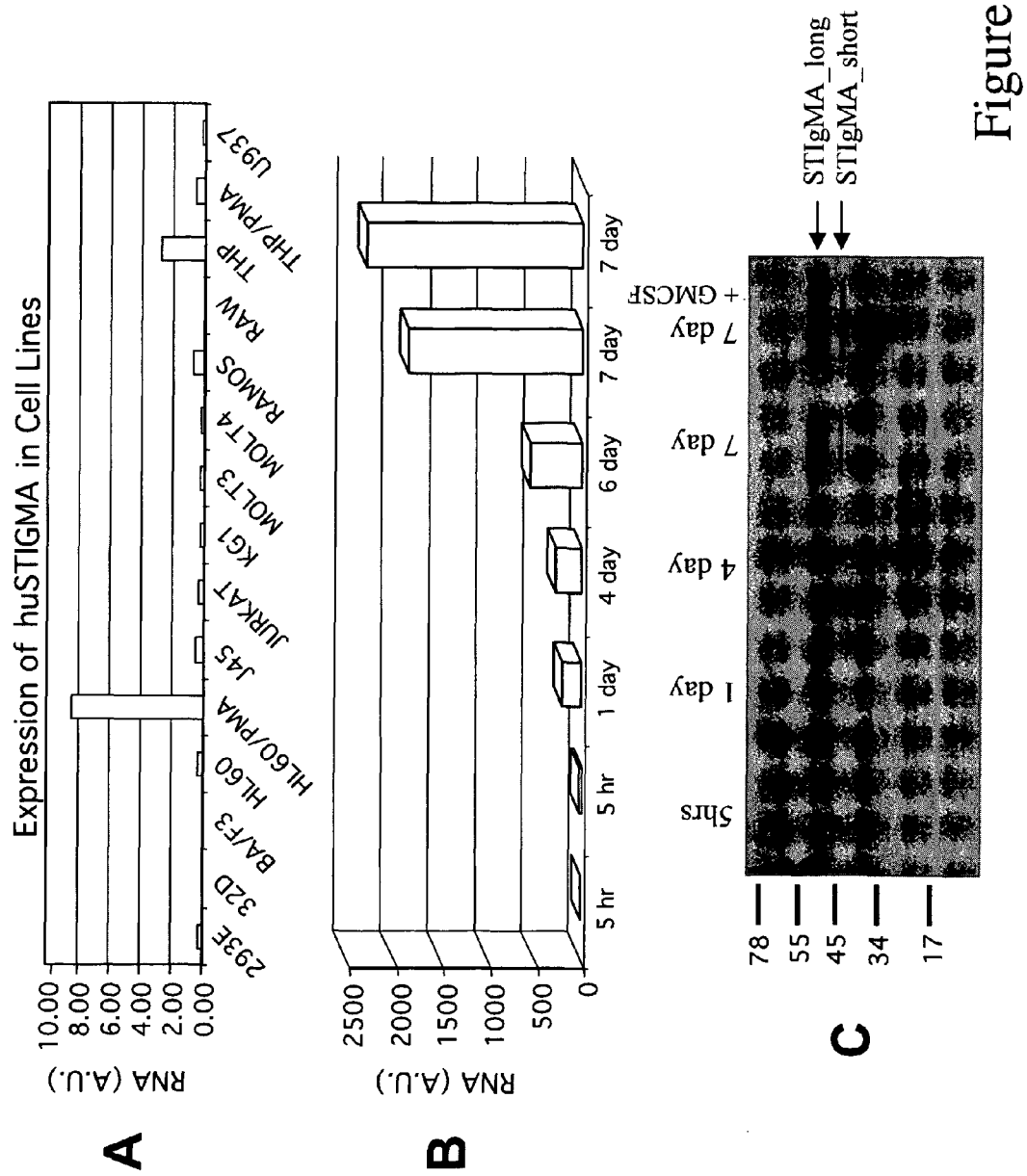
FIG. 18. (A) TAQMAN™ PCR analysis showing increased expression of huCRIg in myelomonocytic cell lines HL60 and THP-1 and in differentiated macrophages. Low levels of expression were found in Jurkat T cells, MOLT3, MOLT4 and RAMOS B-cell lines. (B) Increased expression of huCRIg mRNA during in vitro monocyte differentiation. Monocytes isolated from human peripheral blood were differentiated by adhering to plastic over 7 day period. Total RNA was extracted at different time points during differentiation. (C) Increased expression of huCRIg protein during monocyte to macrophage differentiation. Monocytes were treated as indicated in (B), whole cell lysates were run on a gel and transferred to nitrocellulose membrane that was incubated with a polyclonal antibody (4F7) to huCRIg. The polyclonal antibody recognized a 48 and 38 kDa band possibly representing the long and the short form of huCRIg.

To identify specific cell lines expressing CRIg, real-time quantitative PCR and primers/probes specific for the N-terminal Ig domain were used. Low but detectable mRNA expression was found in the myeloid cell line HL-60 treated with PMA and the monocytic cell line THP-1. Expression was absent in B- and T-cell lines (FIG. 18A).

CRIg Expression on Differentiated Monocytes.

In order to establish details of when CRIg was expressed in differentiating monocytes/macrophages, we determined CRIg mRNA levels in non-adherent monocytes and in adherent monocytes, induced to differentiate in the presence of human autologous serum. CRIg mRNA levels gradually increased over time and reached maximum levels at 7 days following plating (FIG. 18B). At this differentiation stage, mRNA levels were 100 fold higher as compared to those in undifferentiated monocytes.

Western blotting of monocyte/macrophage lysates showed an increase in CRIg protein expression (FIG. 18C) in parallel with the increase in CRIg mRNA expression, indicating that CRIg was expressed when monocytes differentiated to form macrophages. A band of 48 kDa and a band of 40 kDa appeared on the blot, presumably representing the long and the short forms of human CRIg.

Molecular Characterization of CRIg

Figure 19:
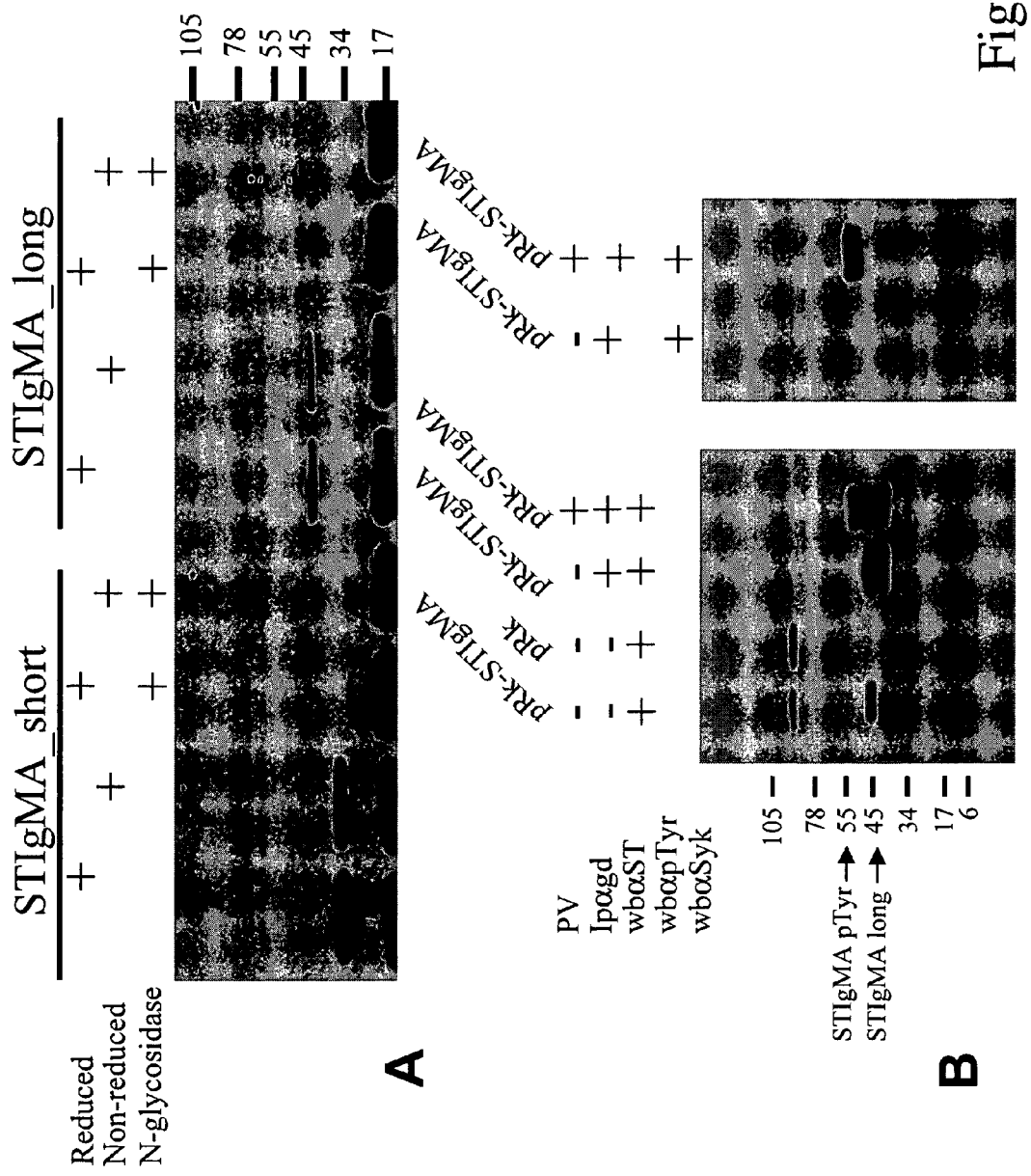
FIG. 19. Molecular characterization of huCRIg protein in cell lines. (A) huCRIg-gd was transiently expressed in 293E cells, immunoprecipitated with anti-gd and blots incubated with anti-gd or a polyclonal antibody to the extracellular domain of CRIg. (B) huCRIg expressed in 293 cells is a monomeric N-glycosylated protein. CRIg is tyrosine phosphorylated upon treatment of HEK293 cells with sodium pervanadate but does not recruit Syk kinase. Phosphorylated CRIg migrated at a slightly higher molecular mass compared to non-phosphorylated CRIg.

CRIg migrated similarly under reduced and non-reduced conditions indicating that it was expressed as a monomer (FIG. 19A). Only slight changes in migration patterns were observed when CRIg was deglycosylated using PNGase F, indicating insignificant N-glycosylation. CRIg was phosphorylated when CRIg overexpressing cells were treated with pervanadate (FIG. 19B). Phosphorylated CRIg migrated as a slightly higher Mw protein (55 kDa). In human HEK 293 cells, tyrosine-phosphorylated CRIg cytoplasmic domain does not recruit Syk kinase (results not shown).

Figure 20:
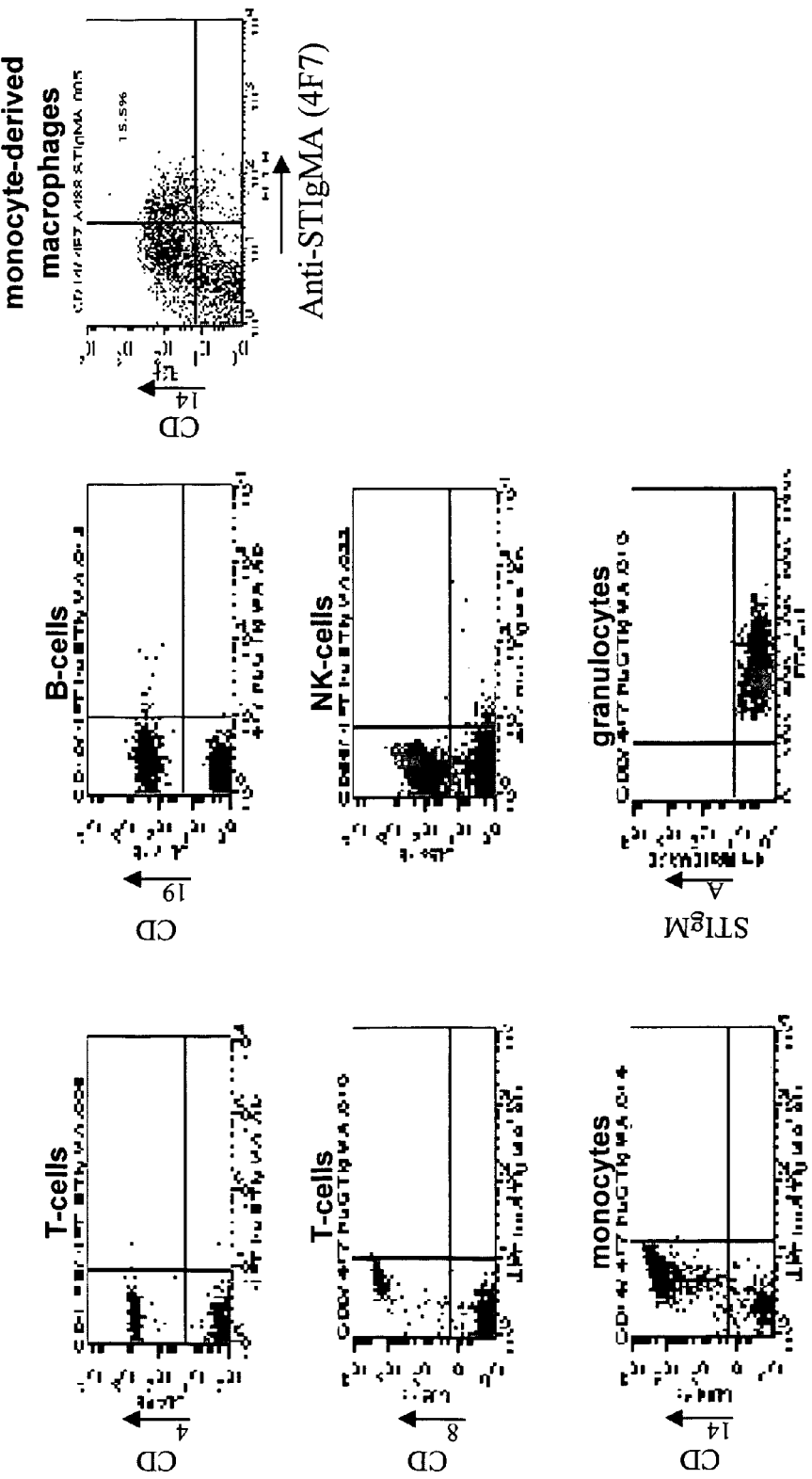
FIG. 20. Selective expression of huCRIg on human monocyte-derived macrophages. Peripheral blood mononuclear cells were stained with antibodies specific for B, T, NK cells, monocytes and with a ALEXA™ A488 conjugated monoclonal antibody (3C9) to CRIg. Expression was absent in all peripheral blood leukocytes as well as in monocyte derived dendritic cells, but was expressed in in vitro differentiated macrophages.

Flow Cytometry Analysis of CRIg Expression on Peripheral Blood Mononuclear Cells In order to determine the expression pattern of CRIg in circulating leukocytes, flow cytometric analysis was performed on lymphocytes isolated from blood from a healthy donor using monoclonal anti-human CRIg antibody 3C9. Antibodies were made by immunizing Balb/C mice with octa-His-tagged human CRIg extracellular domain. The antibody is a non-blocking antibody that can be used to detect native protein in acetone-fixed frozen sections directly conjugated with ALEXA™ A488. Counterstaining was performed with PE conjugate antibodies to several immune-cell surface antigens. CRIg was absent on the surface of all leukocytes, including B-T-NK cells, monocytes and granulocytes (FIG. 20). CRIg was however expressed on monocytes cultured for 7 days in macrophage differentiation medium.

Regulation of CRIg Expression in Monocytes

Figure 21A:
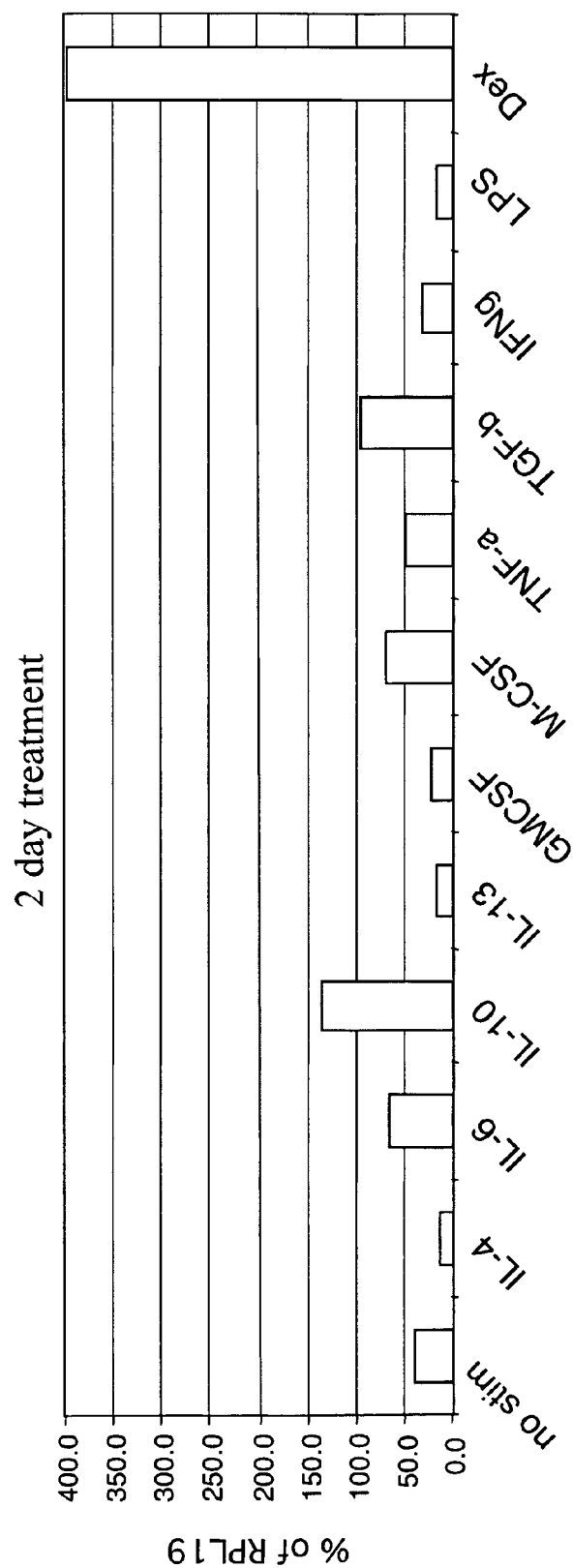
FIG. 21. CRIg mRNA and protein expression was increased by IL-10 and dexamethasone. (A) Real-time PCR shows increased expression of CRIg mRNA following treatment with IL-10, TGFβ and was highly induced by dexamethasone but was down-regulated by treatment with LPS, IFNγ, and TNFα (B) Ficoll-separated peripheral blood mononuclear cells were treated with various cytokines and dexamethasone for 5 days and double-stained with anti-CD14 and anti-CRIg. Flow analysis showed a dramatic increase in CRIg expression on the surface of monocytes treated with dexamethasone and after treatment with IL-10 and LPS.
Figure 21B:
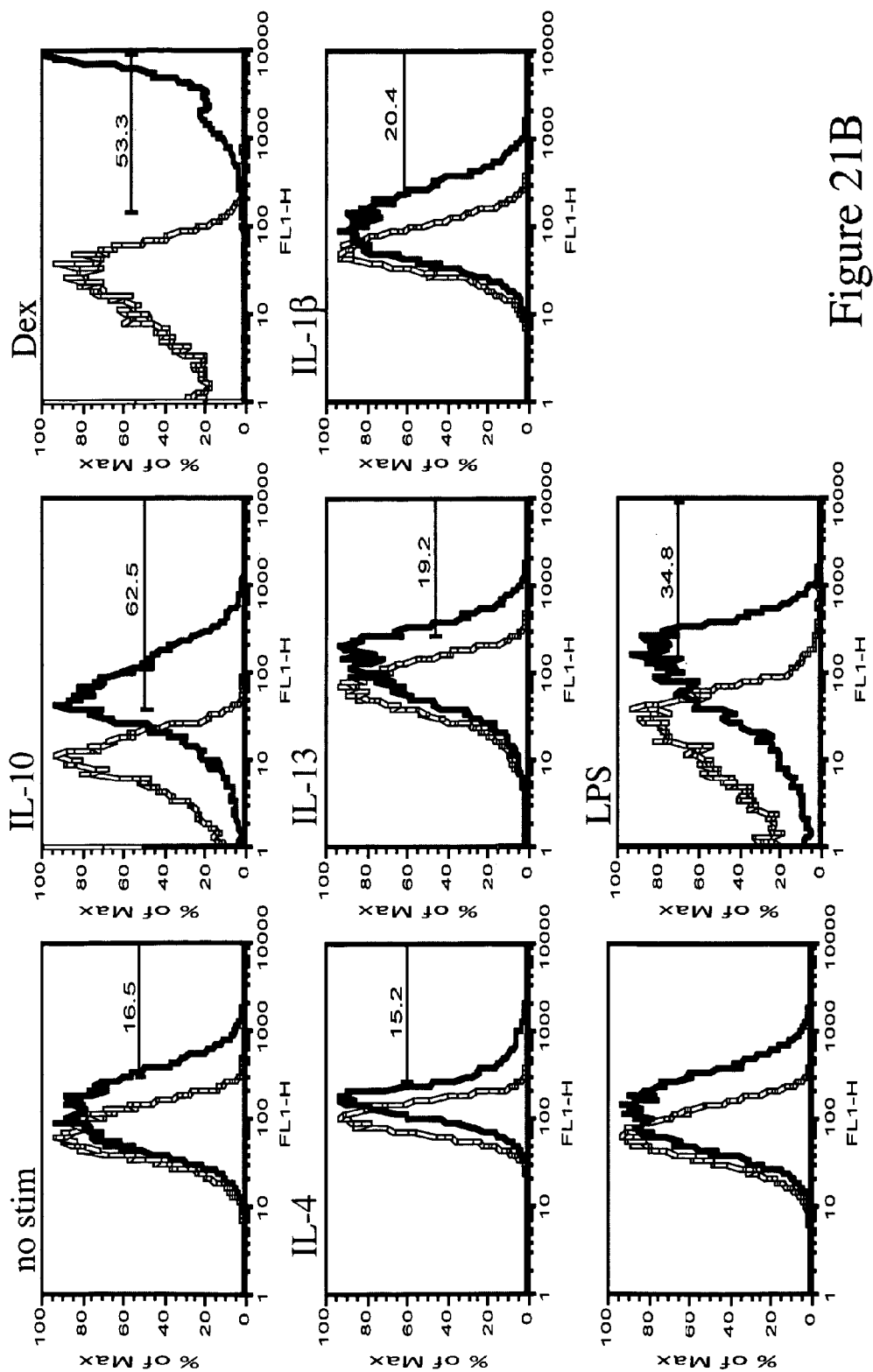

In order to study the regulation of expression of CRIg, 7 day macrophages were cultured in the presence of various pro-and anti-inflammatory cytokines and CRIg expression levels were determined by real-time PCR or flow analysis. Expression of CRIg mRNA was increased after treatment of macrophages for 2 days with IL-10 and TGF-β and down regulated by IL-4, IL13 and LPS (FIG. 21A). Treatment with dexamethasone increased expression to 5 fold compared to control non-treated macrophages. In order to determine the regulation of cell-surface expressed CRIg, flow cytometry was performed on peripheral blood monocytes treated with various cytokines and dexamethasone for 5 days. CRIg was detected using monoclonal antibody clone 3C9 conjugated to ALEXA™ A488. Cells were co-stained with anti CD-14 antibodies. Increased surface expression of CRIg was found following treatment of monocytes with IL-10 and LPS for 5 days (FIG. 21B). A dramatic increase in surface CRIg expression was found after treatment with dexamethasone.

Subcellular Distribution of CRIg

In order to study the subcellular distribution of CRIg, monocyte-derived macrophages (MDMs) were kept in culture for 15 days after which they were fixed and stained with a monoclonal antibody (clone 3C9) or polyclonal rabbit antibody 4F7 followed by FITC conjugated secondary antibody and a PE-labeled anti CD63 antibody. Confocal microscopy showed high expression of CRIg in the perinuclear cytoplasm, overlapping with the expression of the lysosomal membrane protein CD63 (FIG. 22). CRIg was also expressed in the leading and trailing edges of the macrophages where its staining pattern did not overlap with that of CD63.

Expression of CRIg in Normal and Disease Tissues

Figure 23:
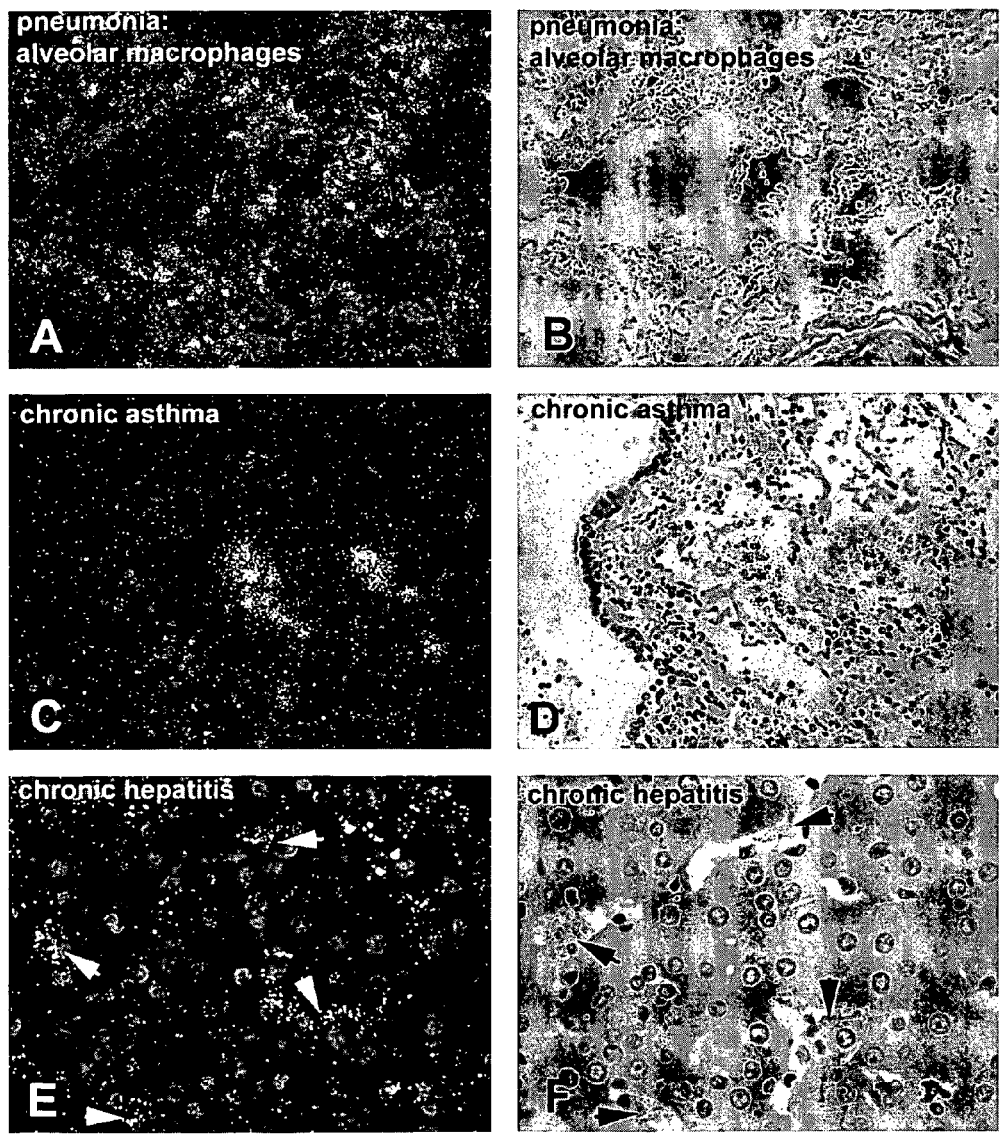
FIG. 23. Localization of CRIg mRNA in chronic inflammatory diseases. In situ hybridization showed the presence of CRIg mRNA in alveolar macrophages obtained from tissue of a patient with pneumonia (A, B) or a patient with chronic asthma (C, D). CRIg mRNA was also expressed in liver Kupffer cells in tissue obtained from a liver biopsy of a patient with chronic hepatitis (E, F).

CRIg expression in tissue resident macrophages and changes in its expression in tissues with chronic inflammatory diseases was studied. Using in situ hybridization, CRIg mRNA expression was determined on panels of paraformaldehyde-fixed human tissues. High expression levels were found in alveolar macrophages obtained from a lung autopsy of a patient with pneumonia or chronic asthma (FIG. 23, A, B, C, and D). High mRNA expression was found in Kupffer cells in the liver of a patient with chronic hepatitis (FIG. 23, E and F).

Figure 24:
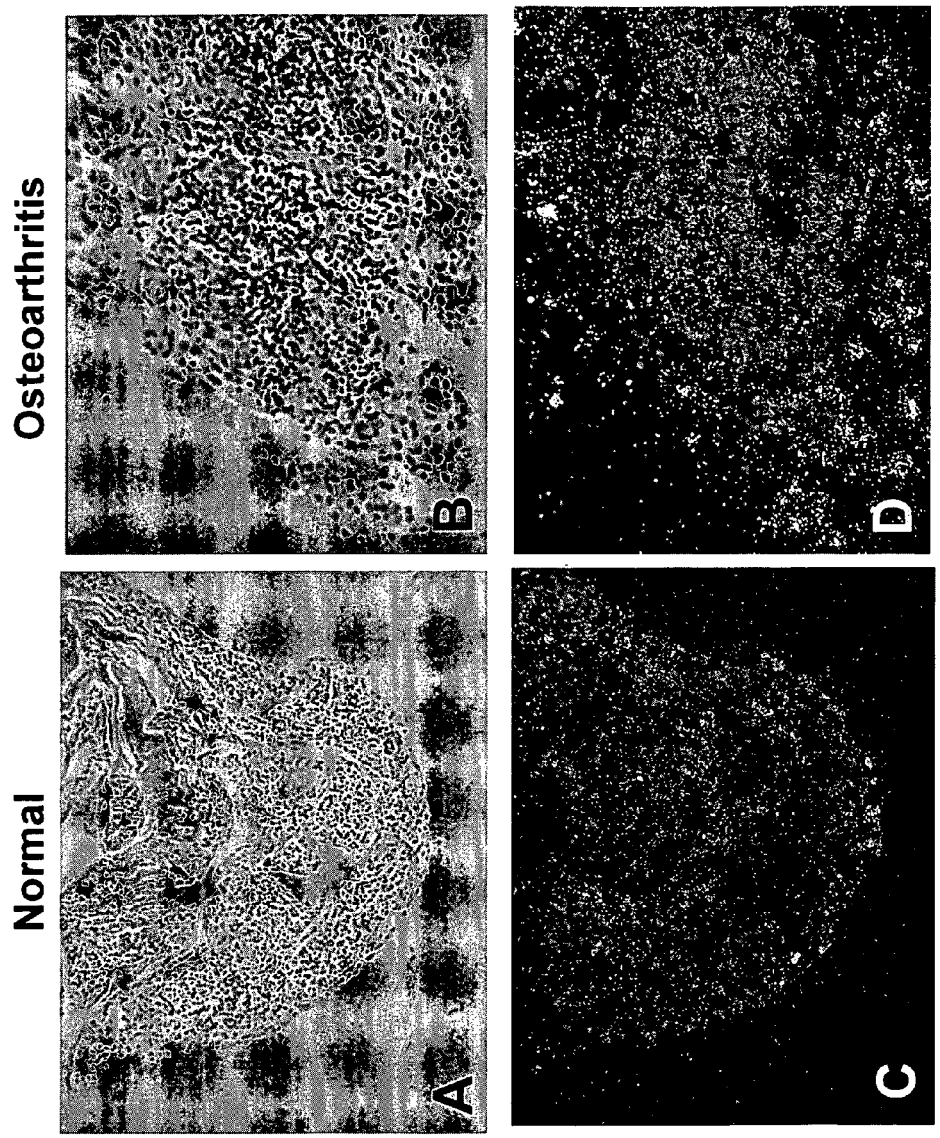
FIG. 24. CRIg mRNA expression was increased in inflamed synovium. CRIg mRNA was low or absent in synovial membranes of a joint obtained from a knee replacement of a patient with no joint inflammation (A, C) but was highly expressed in cells, potentially synoviocytes or synovial macrophages, in the pannus of a patient with osteoarthritis (B, D).
Figure 25:
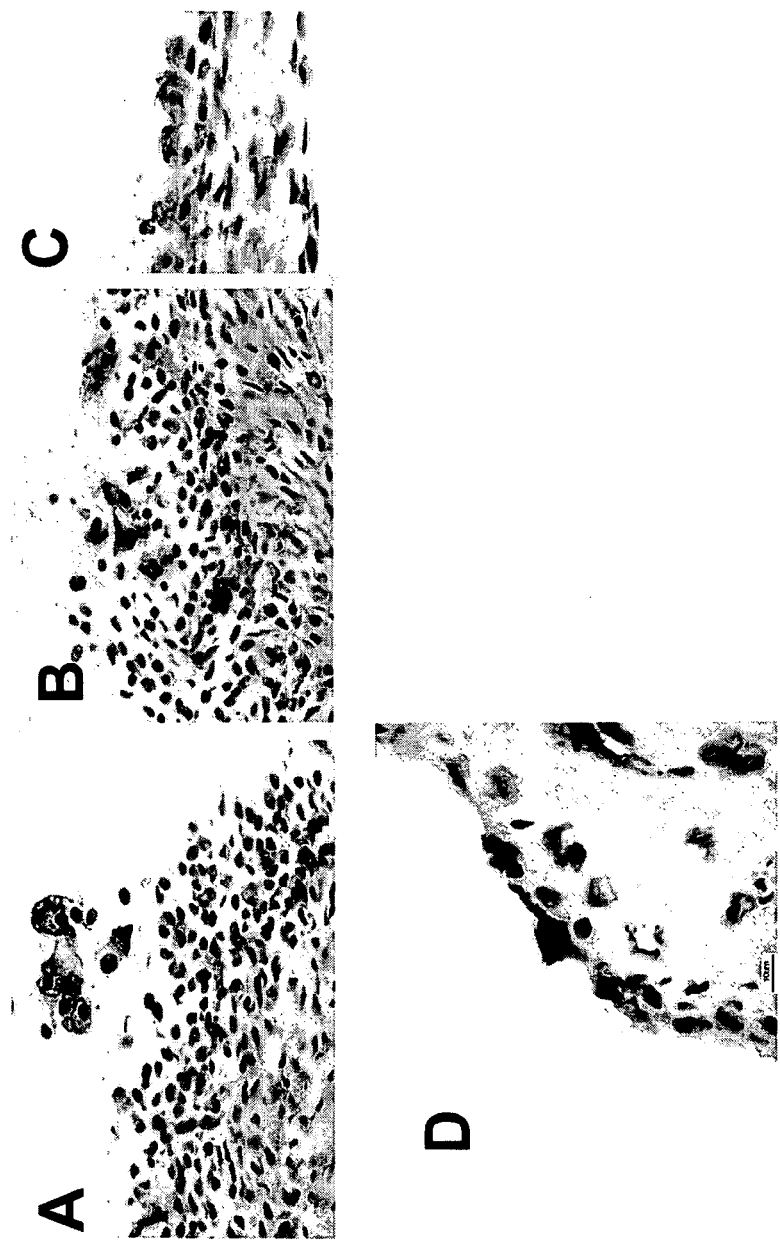
FIG. 25. Detection of CRIg protein with polyclonal antibody 6F1 in cells lining the synovium of a patient with degenerative joint disease (A, B, C). No immunohistochemical detection of CRIg was found in a control synovium (D).

In a previous study (Walker, Biochimica et, *Biophysica Acta* 1574:387-390(2002)), and in electronic screening of libraries, high expression of CRIg mRNA was found in the synovium of patients with rheumatoid arthritis. Therefore, the expression pattern of CRIg in synovium obtained from patients with rheumatoid arthritis, osteoarthritis and degenerative bone disease was studied. High expression of CRIg mRNA was found in synovial cells obtained from a patient with osteoarthritis (FIG. 24, B). Synovial cells in the superficial layers had the highest expression of CRIg (FIG. 24, D). In addition, polyclonal antibody 6F1 was used to study CRIg expression in frozen sections of human synovium obtained from a patient with rheumatoid arthritis. CRIg was expressed in a subset of synovial cells (20-40%) and in tissue macrophages in the synovium (FIG. 25, A, B, C. These cells were, most likely, type A macrophage-like synovial cells. Staining was absent in control synovium (FIG. 25, D).

Figure 26:
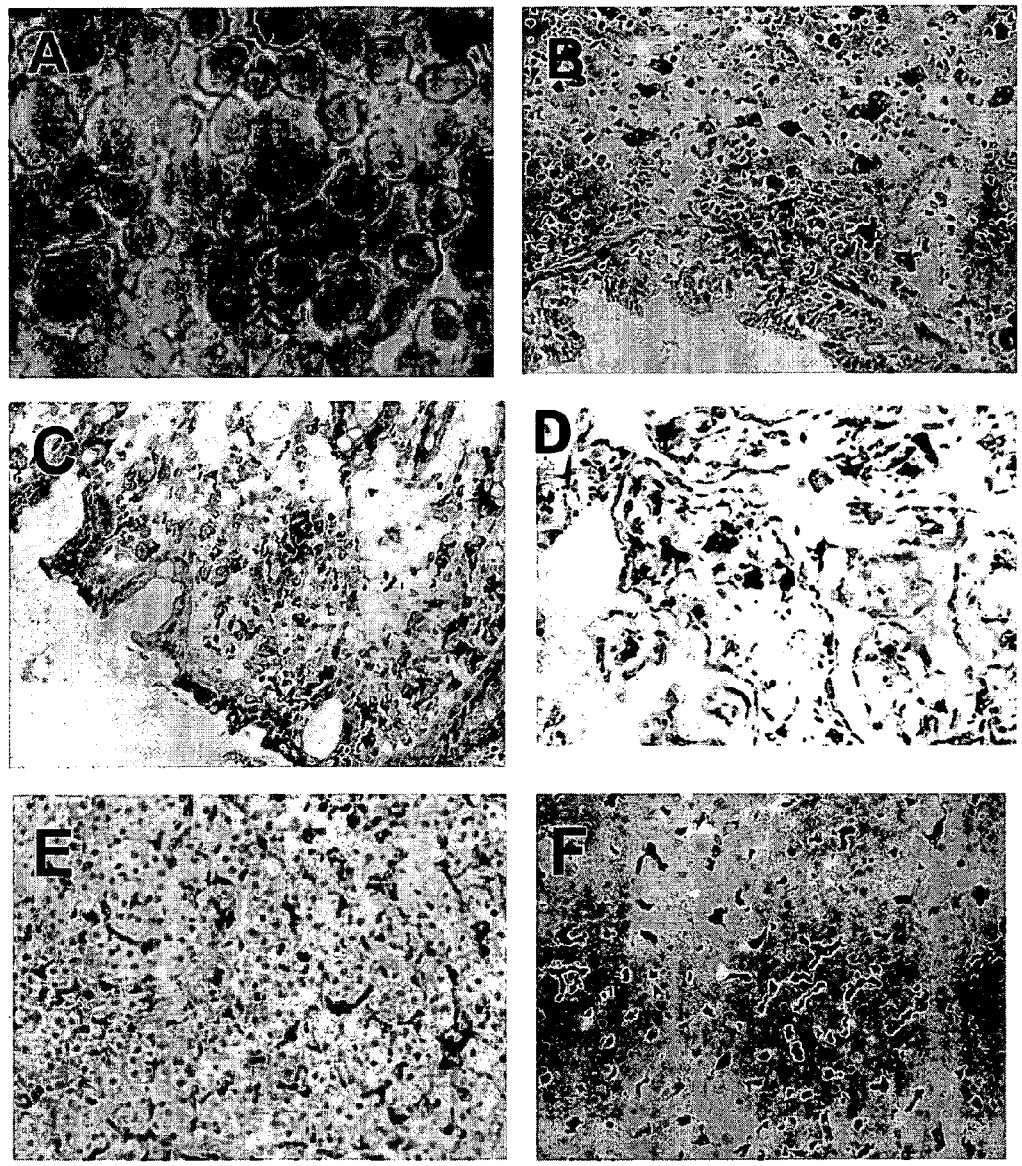
FIG. 26. CRIg protein was expressed in a subtype of tissue resident macrophages and its expression was increased in chronic inflammatory diseases. (A) CRIg was expressed on the membrane of CHO cells stably expressing CRIg. High expression of CRIg protein was found in alveolar macrophages (B) in tissues obtained from a patient with chronic asthma. (C) Expression of CRIg in histiocytes of the human small intestine. The section was obtained from surgically removed tissue and could have contained a neoplasm. (D) Expression of CRIg protein in Hofbauer cells in human preterm placenta. High expression of CRIg protein in macrophages was present in the adrenal gland (E) and in Kupffer cells of human liver (F). Staining was performed on 5 μm thick acetone-fixed sections using DAB as the chromogen. Images were photographed at a 20× and 40× magnification.

Expression of CRIg protein was found on macrophages in a number of different tissues. Frozen sections prepared from CHO cells stably expressing CRIg show membrane localization of CRIg (FIG. 26A). CRIg protein was found in alveolar macrophages (FIG. 26, B), histiocytes in the lamina propria of the small intestine (FIG. 26, C), Hofbauer cells in the placenta (FIG. 26, D), macrophages in the adrenal gland (FIG. 26, E) and Kupffer cells in the liver (FIG. 26, F).

Figure 27:
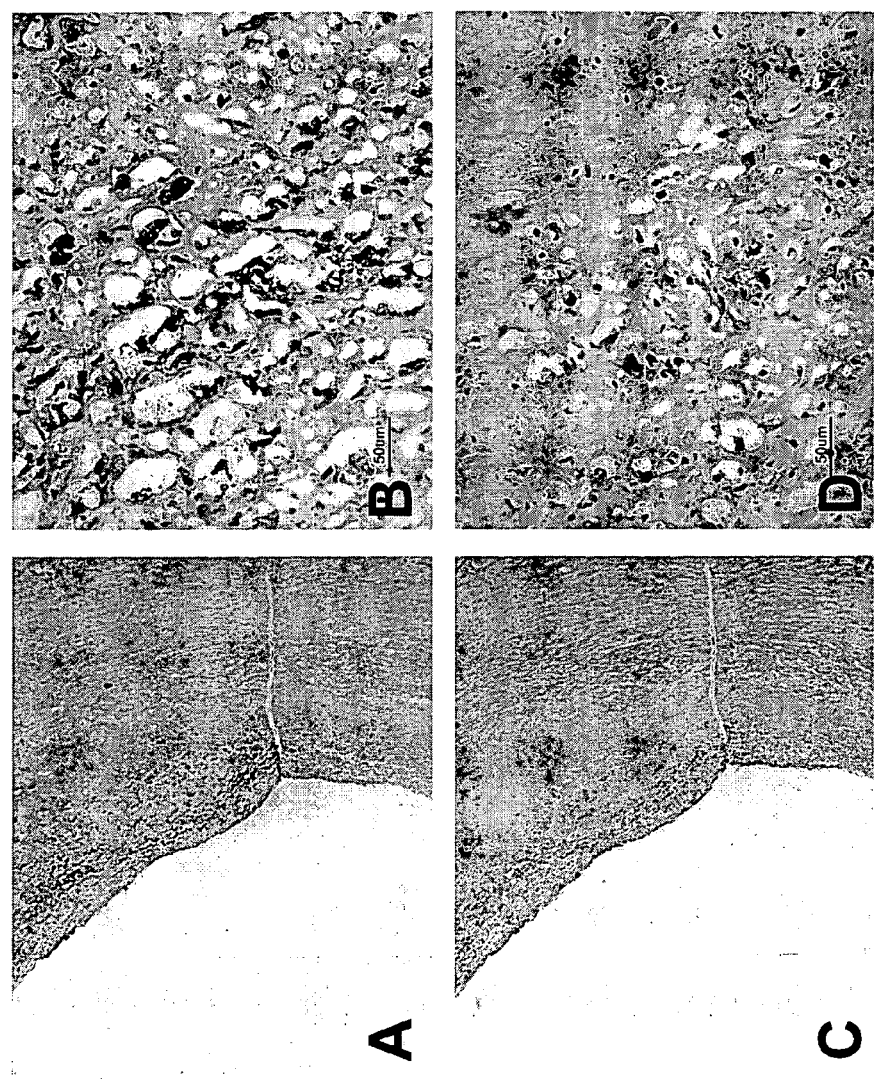
FIG. 27. Immunohistochemical staining of CD68 and CRIg on a vascular plaque obtained from a patient with atherosclerosis. Consecutive sections were fixed and stained with a monoclonal antibody to human CD68 (A, B) and a polyclonal antibody 6F 1 raised against human CRIg (C, D). CRIg appeared in a population of macrophages and phoam cells present in the atherosclerotic plaque, and overlapped with CD68 positive macrophages, as judged from staining on consecutive sections. Magnification: 10× (A, C) and 20× (B, D).

Atherosclerotic plaques contained a high number of macrophages or macrophage-foam cells that adhered tightly to the luminal wall of the aorta. Considering a role for CRIg in macrophage-endothelium adhesion, the expression of CRIg in atherosclerotic plaques was studied. Alternate sections of plaques were stained with anti-CD63 (FIG. 27, A and B) or anti-CRIg (FIG. 27, C and D). Overlapping staining patterns of anti-CD63 and CRIg was found on foam cells aligning the vessel wall indicating a role for CRIg in atherosclerosis.

Figure 28:
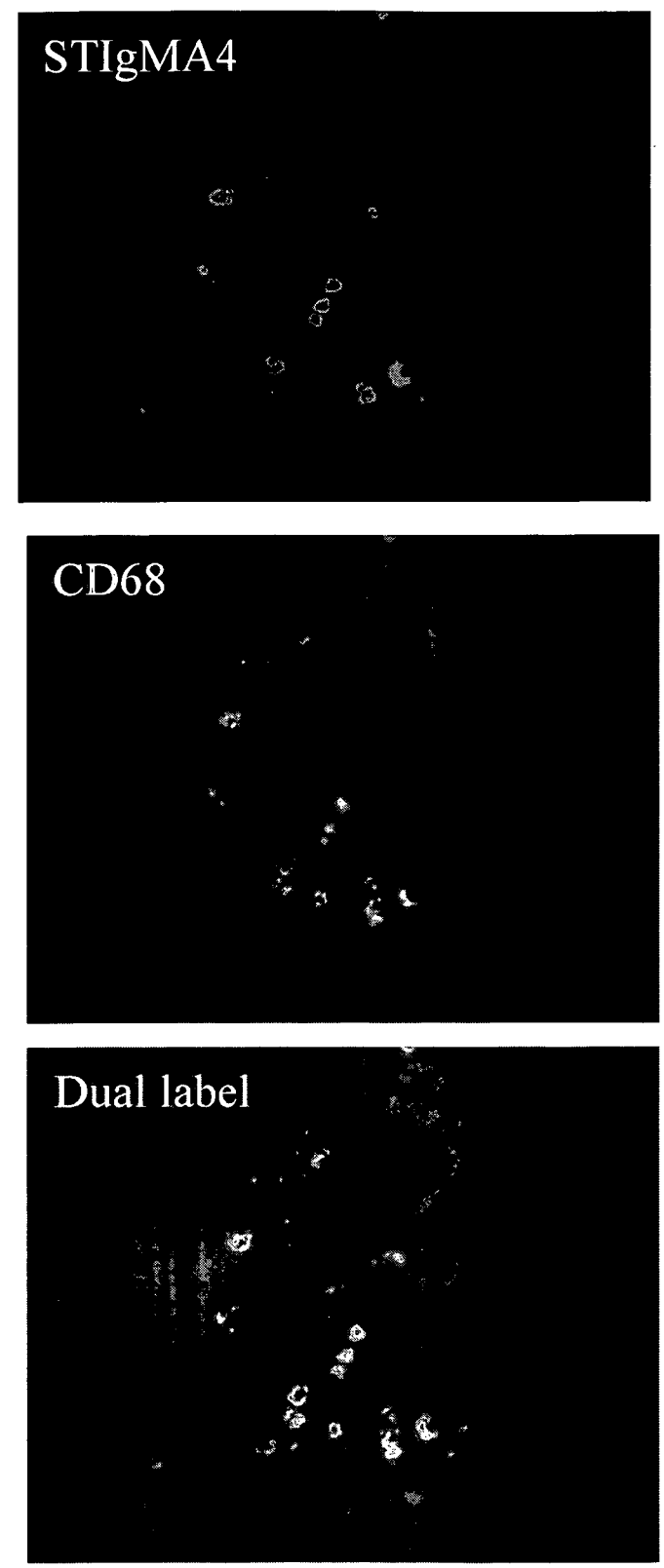
FIG. 28. Co-staining of CRIg and CD68 on heart interstitial macrophages. 5 μm sections were obtained from a human heart (autopsy) and stained with a monoclonal antibody to CRIg (3C9) and a secondary anti-mouse FITC-labeled antibody. CD68 was detected by staining with a PE-labeled monoclonal antibody to CD68. Magnification: 20×.

In order to determine whether CRIg was selectively expressed on macrophages, double staining immunofluorescence was performed on heart interstitial macrophages (FIG. 28). As shown in the overlay (FIG. 28, third panel) most of the interstitial macrophages positive for CRIg were also positive for CD68. Not all CD68 positive macrophages were positive for CRIg, indicating that the latter was specific for a subtype of tissue resident macrophages.

Figure 29:
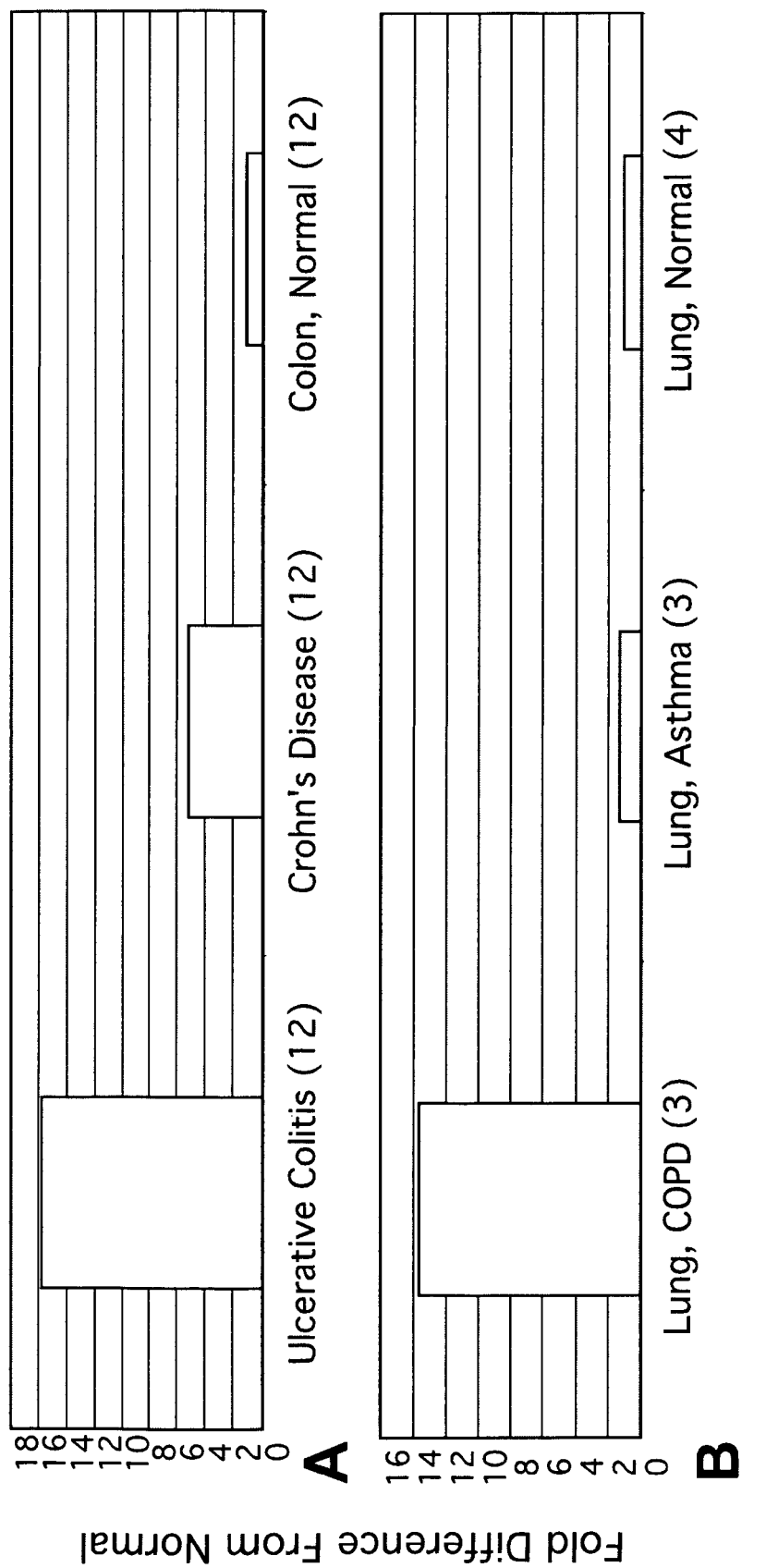
FIG. 29. CRIg mRNA levels are significantly elevated in colon tissue obtained from patients with ulcerative colitis, Crohn's disease, chronic occlusive pulmonary disease (COPD) and asthma. Real-time PCR was performed on total RNA extracted from the various tissues. mRNA for CRIg was significantly increased in tissues obtained from patients with ulcerative colitis, Crohn's disease and COPD. Statistical analysis was performed using the Mann-Whitney U-test.

In order to quantitatively determine mRNA expression levels in inflammatory bowel disease (IBD) syndrome, mRNA was extracted from colon tissue obtained from patients with ulcerative colitis, Crohn's disease or from patients with no manifestation of IBD. Real time PCR was performed using primers specific for CRIg, to measure relative expression levels. Expression levels were 16 fold higher in a patient with ulcerative colitis and, 5 fold higher in a patient with Crohn's disease, as compared to control tissue (FIG. 29, A). Similarly, relative RNA equivalents were determined in lung tissue and was found to be highest in tissue from a patient with chronic occlusive pulmonary disease (COPD: 14 fold over normal) and was not significantly different from normal in a patient with asthma (FIG. 29, B).

Molecules of the Ig superfamily are well known to mediate cell surface recognition and cell-cell adhesion. Since CRIg expression was high in interstitial macrophages aligning blood vessels, CRIg involvement in macrophage-endothelial cell adhesion was studied. A Jurkat cell line, stably transfected with full length CRIg-long (FIG. 30A) was loaded with the fluorescent dye BCECF and added to the wells of a 96 well maxisorb plate on which a monolayer of HUVEC cells had been cultured. Adhesion was measured by the amount of fluorescence retained after 3 gentle washes. Jurkat cells expressing CRIg were more adherent to both, control and TNFα stimulated endothelium, as compared to Jurkat cells stably transfected with a control plasmid (FIG. 30B).

Discussion

This study, for the first time, described the tissue distribution, regulation of expression and molecular characterization of a novel Ig superfamily member CRIg/Z39Ig and confirmed its selective expression in tissue resident macrophages.

CRIg expression was found on resident macrophages which had a fully differentiated phenotype. Its expression was increased in tissues with chronic inflammation like, rheumatoid arthritis and inflammatory bowel disease. The increase of CRIg expression in these diseases, which was often characterized as Th2 type diseases, may be in line with the regulation of its expression by Th2 cytokines in vitro. Whether this increased expression is due to an increased presence of CRIg positive macrophages or an increased expression on the inflammatory macrophages has yet to be determined.

CRIg may mediate one of the effector functions of human macrophages, which include bacterial recognition, phagocytosis, antigen presentation and cytokine release. These results indicated a role for CRIg in adhesion, and possibly motility, of macrophages to the endothelial cell wall of vessels.

CRIg expression was increased in non-microbial inflammatory diseases like ulcerative colitis and chronic occlusive pulmonary disease (COPD) but was downregulated in isolated macrophages upon treatment with LPS or other bacterial cell wall components like lipoteichoic acid and bacterial lipoprotein. Long term treatment, over 2 days, with LPS caused an increase in the expression of CRIg. This could be due to an autocrine effect of IL-10 secreted by LPS-stimulated macrophages. A striking up-regulation of CRIg, both at the mRNA and protein levels, was observed upon treatment of monocytes or macrophages with dexamethasone. Few monocyte/macrophage surface receptors have been found to increase in expression upon dexamethasone treatment. One example is CD163, but its induction by dexamethasone is far less dramatic. The up-regulation of CRIg by anti-inflammatory cytokines IL10 and TGFβ was of considerable interest and indicates that CRIg may mediate the anti-inflammatory role of glucocorticosteroids.

As described here, CRIg was expressed on a subset of CD68 positive macrophages which may represent activated macrophages. Using blocking and activating antibodies to CRIg and CRIg-Fc fusion protein, its role in macrophage effector function, adhesion and migration and its role in chronic inflammatory diseases has been investigated, and is described in Example 7.

Only few cell surface markers were specifically expressed on differentiated macrophages, such as CD68 and CD163. Although CD68 was apparently expressed on all human macrophage populations, the antigen could also be detected on other myeloid cells and also on certain non-myeloid cells. Therefore, CRIg represents the first cell surface antigen selectively expressed on a subset of interstitial mature macrophages.

Example 7

CRIg Fusion Proteins in Collagen-Induced Arthritis (CIA) in DBA-1J Mice

This experiment aimed to compare CRIg fusion proteins to control murine IgG1 in the development of disease and progression of CIA (collagen-induced arthritis, an experimental animal model system of rheumatoid arthritis).

As discussed in Example 4, CRIg is highly and specifically expressed on a subset of macrophages and is elevated in tissues with chronic inflammation. Murine CRIg is highly expressed in macrophages and synoviocytes in inflamed joints of mice with collagen-induced arthritis. In vitro studies have shown that CRIg is involved in adhesion of macrophages to endothelium. CRIg-Fc fusion protein influences the course of an autoimmune disease, in this case collagen-induced arthritis in mice, either by influencing the properties of tissue macrophages or by influencing immune response of other cells (e.g. T cells, B cell, epithelial cells, endothelial cells). This may result in alleviation of inflammation, swelling and long term bone erosion in joints.

A muCRIg-Fc fusion protein was generated by fusing the hinge, CH2 and CH3 domains of murine IgG1 to the extra cellular domain (aa 1-200) of murine CRIg. A fusion containing a double mutation preventing Fc receptor binding was used to control for Fc receptor regulation. The nucleotide sequence of the muCRIg-Fc fusion protein is shown as SEQ ID NO: 17. (The coding sequences of similar huCRIg-Ig and huCRIg-short-Ig are shown as SEQ ID NOS: 15 and 16, respectively.) Protein was produced in CHO cells by transient transfections of plasmid DNA. The fusion protein was purified by running the cell supernatant over a protein A column followed by ion-exchange chromatography to eliminate aggregates. Serum half life was estimated by injecting a single dose of 4 mg/kg CRIg-Fc in a C57B6 mouse followed by obtaining serum from the mice at specified time intervals. The serum levels of murine CRIg-Fc was determined by a sandwich ELISA using to anti CRIg mAbs recognizing different epiotpes on the extracellular domain of CRIg.

Animal Model Species: Mouse
Strain(s): DBA-1J
Supplier(s): JACKSON
Age Range: 7 to 8 week old The mouse was chosen as the species to study collagen-induced arthritis (CIA) because CIA is an inflammatory polyarthritis with clinical and pathological features similar to human rheumatoid arthritis (RA). This animal model has been used by many laboratories and the histopathology of CIA resembles those seen in RA with synovial proliferation that progresses to pannus formation, cartilage degeneration/destruction and marginal bone erosions with subsequent joint deformities. Also, mouse is phylogenetically the lowest mammal. In addition, there is no in vitro model available to mimic the complex, multifactorial pathogenesis of RA.

Experimental Design
Treatment groups:
1) mIgG1 isotype 6 mg/kg in 200 µl saline subcutaneous (SC) 3 times/wk for 7 weeks (n=8).
2) muCRIg 4 mg/kg in 100 µl saline SC 3 times/wk for 7 weeks (n=8).

Figure 31:
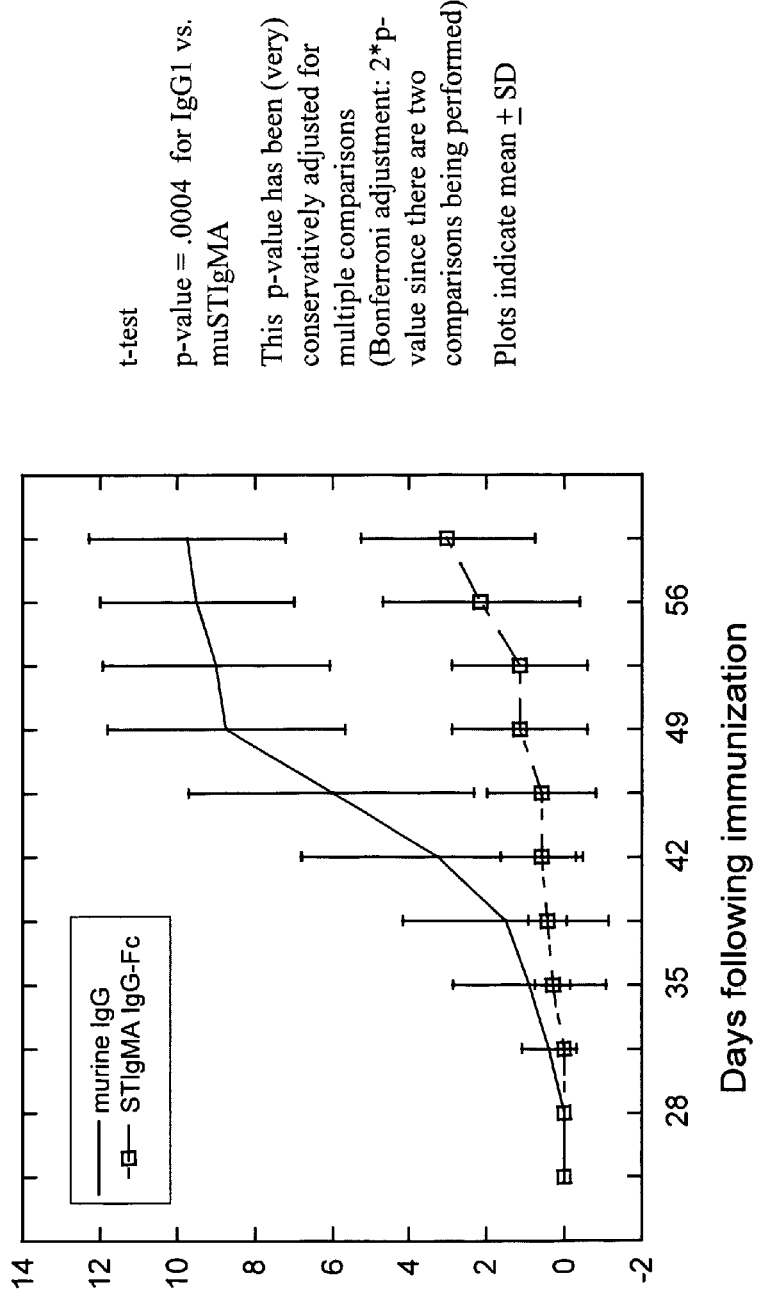
FIG. 31. Inhibition of progression of collagen-induced arthritis (CIA) mouse model by muCRIg IgG-Fc fusion protein. A group of (CIA) mice (n=7) was given 100 μg of muCRIg IgG-Fc fusion protein (squares), whereas a CIA mouse control group (n=8) received 100 μg of murine IgG1 (circles), 3 times per week for 6 weeks. Mice were examined daily for signs of inflammation and scored on a scale of 0-16 (details in Example 25) and the results were plotted graphically (mean±SD, Student's T test p-value=0.0004 for control IgG1 vs. test muCRIg protein).

Mice were immunized interdermally with bovine CII (100 ug, Sigma, St. Louis) emulsified in CFS (Difco). Mice were rechallenged with CII in IFA (Difco) 21 days later. Starting on day 24, one group of mice (n=7) was given 100 ug muCRIg (PRO362) Fc three times per week for 6 weeks, and the second group (n=8) received 100 ug of murine IgG1, as a control. Mice were examined daily for signs of joint inflammation and scored as follows: 0, normal; 1, erythema and mild swelling confined to the ankle joint; 2, erythema and mild swelling extending from the ankle to metatarsal and metacarpal joints;, 3 erythema and moderate swelling extending from the ankle to metatarsal or metacarpal joints. 4, erythema and severe swelling extending from the ankle to the digits. The maximum arthritic score per paw was 4, and the maximal score per mouse was 16 (FIG. 31).

All mice were immunized with 100 µg bovine collagen type II in 100 µl complete Freunds Adjuvant (CFA) on day 0. Collagen type II in CFA was injected intradermally at the base of the tail on the right side. On day 21, a 2nd immunization with 100 µg bovine collagen type II in 100 µl of incomplete Freunds adjuvant was given i.d. at the left side of the tail. Animals were checked daily (M-F) by the investigative staff. Nestlets were used as an enrichment device, and to provide extra padding for the animals. If necessary, moistened food was provided at the bottom of the cages. Debilitated animals were sacrificed after consultation with the veterinary staff. Terminal faxitron X-Rays and microCT were taken at the end of study and joint lesion/erosion was evaluated. In addition, animals were weighed before treatment and at termination.

On day 35 and at the termination of the study, mice in Groups 1 to 8 were bled for serum pK and to determine anti-collagen type II antibody titer (100 µl orbital bleed).

On day 70 all mice were terminally bled intracardially under 3% isoflurane for a terminal hemogram, for a differential leukocyte count and for serum pK (G3) evaluation.

The mice were euthanized at day 70, post induction of arthritis. All four limbs were collected for radiographs, 5CT and histopathology.

Results

Systemic injection of the CRIg fusion protein, muCRIg-Fc, into a collagen-induced arthritic mouse (animal model for rheumatoid arthritis) showed significant (see FIG. 31: p-value=0.0004) reduction in the progression of CIA in the test group of mice that received the CRIg fusion protein (squares) versus the control group of mice that received IgG1 (circles). Collagen-induced arthritis was induced by injection of bovine collagen type II emulsified in complete Freud's adjuvant. A booster immunization was given 21 days after the first immunization Animals were treated 3× per week with either murine CRIg-Fc fusion protein or with anti gp120 IgG1. Dosing was 4 mg/kg in 100 ul PBS subcutaneous. Treatment started on day 21 and continued until day 70. Mice were observed daily for swelling of the hind paw as a sign of arthritis. The severity of arthritis was graded on a 1-16 scale as follows: 0=No evidence of erythema and swelling, 1=Erythema and mild swelling confined to the mid-foot (tarsal) or ankle, 2=Erythema and mild swelling extending from the ankle to the mid-foot, 3=Erythema and moderate swelling extending from the ankle to the metatarsal joints, 4=Erythema and severe swelling encompass the ankle, foot and digits.

Repeat Experiment

The protocol described above was modified to repeat and confirm the results of the previous experiment in the collagen-induced arthritis (CIA) model. The modified protocol included investigation of the potential effect of radiation exposure as a result of in vivo microCT imagig on disease and development progression.

70 DBA-1J 7 to mice (7 to 8 weeks old, Jackson Laboratories) were divided into 5 treatment groups, two groups (G1 and G3) with 15 mice per group, two groups (G4 and G5) with 10 mice per group, and one group (G2) with 20 mice.

Treatment Groups:
G1: MuIgG1 isotype 4 mg/kg in 100 µl saline, s.c., 3-times per week for 7 weeks (n=15).
G2: MuCRIg-IgG1 4 mg/kg in 100 µl saline, s.c., 3-times per week for 7 weeks (n=20).
G3: MuTNFRII-IgG1 isotype 4 mg/kg in 100 µl saline, s.c., 3-times per week for 7 weeks (n=15).
G4: MuIgG1 isotype 4 mg/kg in 100 µl saline, s.c., 3-times per week for 7 weeks, anaesthesia with in vivo microCT (n=10).
G5: MuTNFRII-IgG1 1.0 mg/kg in 100 µl saline, s.c., 3-times per week for 7 weeks, anesthesia with in vivo microCT (n=10).

TNF is a cytokine secreted by mononuclear phagocytes, Ag-stimulated T cells, NK cells and mast cells. It is involved in normal inflammatory and immune responses. TNF-α plays an important role in the pathogenesis of rheumatoid arthritis (RA). Elevated levels of TNF were found in synovial fluid of RA patients. In this protocol, mTNFRII-Fc was used as a positive control, to block the interaction between TNF and its cell surface receptors.

All mice from G1 to G5 were immunized with 100 µg bovine collagen type II in 100 µl Complete Freund's Adjuvant (CFA) on day). The collagen type II in CFA was injected intradermally at the base of the tail on the right side. At day 21, a second immunization with 100 µg bovine collagen type II in 100 µl of incomplete Freund's Adjuvant was given intradermally at the left side of the tail.

Animals were checked daily. Mice in the G4-5 groups were anesthesized with isoflurane and in vivo microCt was performed weekly. Terminal faxitron X-Rays and microCT were taken at the end of study, ad joint lesion/erosion was evaluated.

On day 35 and at the termination of the study, mice in groups G1-5 were bled fro serum pK and anti-collagen type II antibody titer (100 µl orbital bleed). On day 70 all mice were terminally bled intracardiac under 3% isoflurane for terminal hemogram and differential leukocyte count and serum for pK (G3).

The mice were euthanized at day 70 pest induction of arthritis. All four limbs were collected for radiographs, microCT and histopathology.

Figure 33:
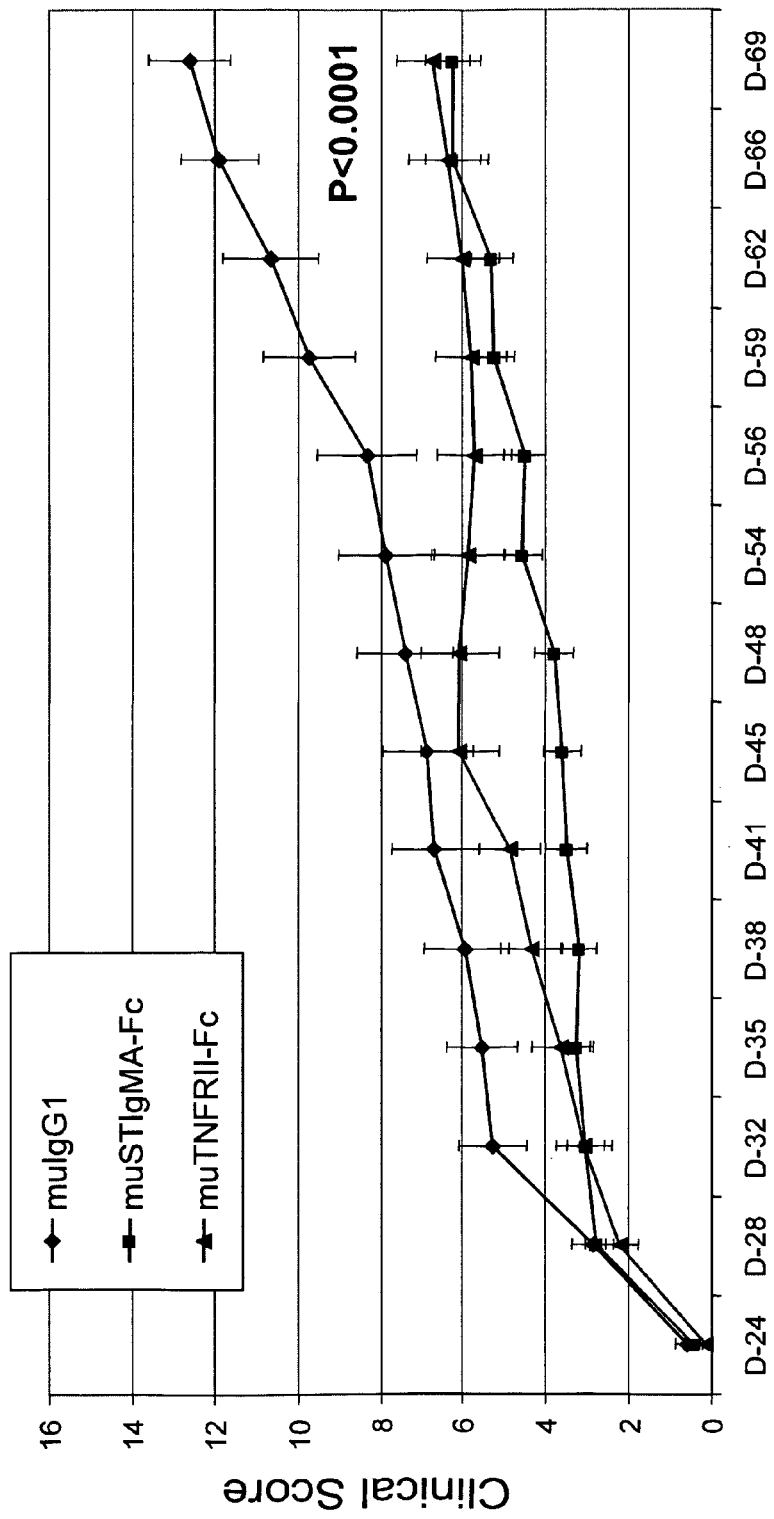
FIG. 33 shows reduction in joint swelling in CRIg-Fc treated mice.

FIG. 33 shows significant reduction in joint swelling in CRIg-Fc treated mice.

Immunohistochemistry performed on formalin-fixed, paraffin-embedded tissue (H&E staining), obtained from muCRIg-Fc treated animals at day 70, shows inhibition of joint inflammation as a result of treatment. FIG. 34 shows H&E stained sections of a meta-tarsal joint of a DBA1/J mouse 70 days after immunization with collagen type II. A. Massive inflammatory cell infiltrate is found in the areas surrounding tendon sheats and the area surrounding the joint cavity; B. Detail of A; C. Low degree of inflammatory infiltrate in the joint of a mouse treated with CRIg-Fc. Few inflammatory cells were found in the areas surrounding the tendon sheats and the joint cavity; D. Detail of B.

Figure 35:
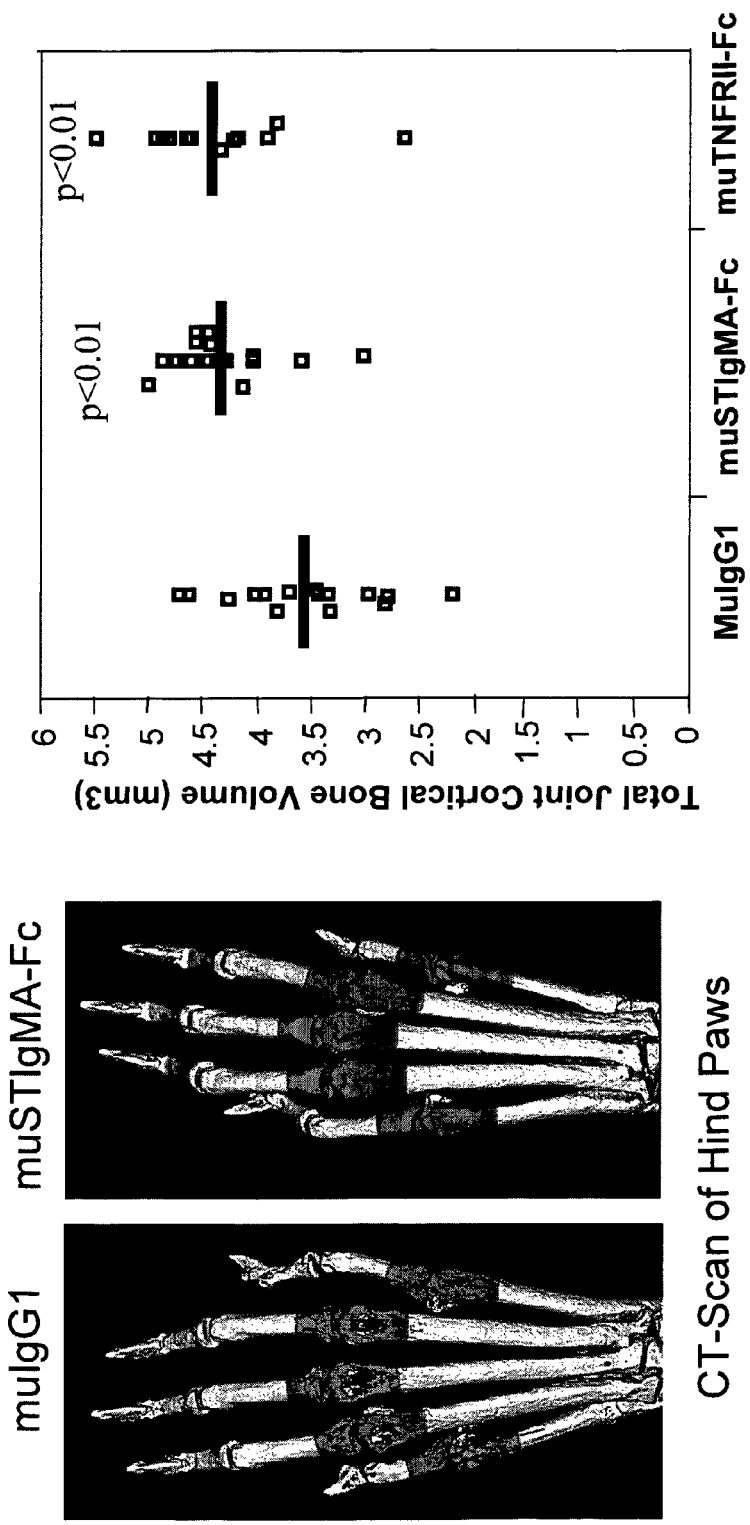
FIG. 35 shows preservation of cortical bone volume in joints of mice treated with muCRIg-Fc.

FIG. 35 shows that cortical bone volume was preserved in joints of mice treated with muCRIg-Fc. Mice in control IgG- and CRIg-Fc-treated groups were sacrificed 70 days after collagen injection, and joints were scanned by µCT. Bone erosion and loss of bone density in joints of mice representative of CRIg-Fc and control IgG groups are shown in the left figure as compared to muIgG1 treated animals. Preservation of cortical bone volume was significantly greater in muCRIg-Fc treated animals. The images are a three-dimensional surface rendering created from the µCT data using Analyze image analysis software.

Figure 37:
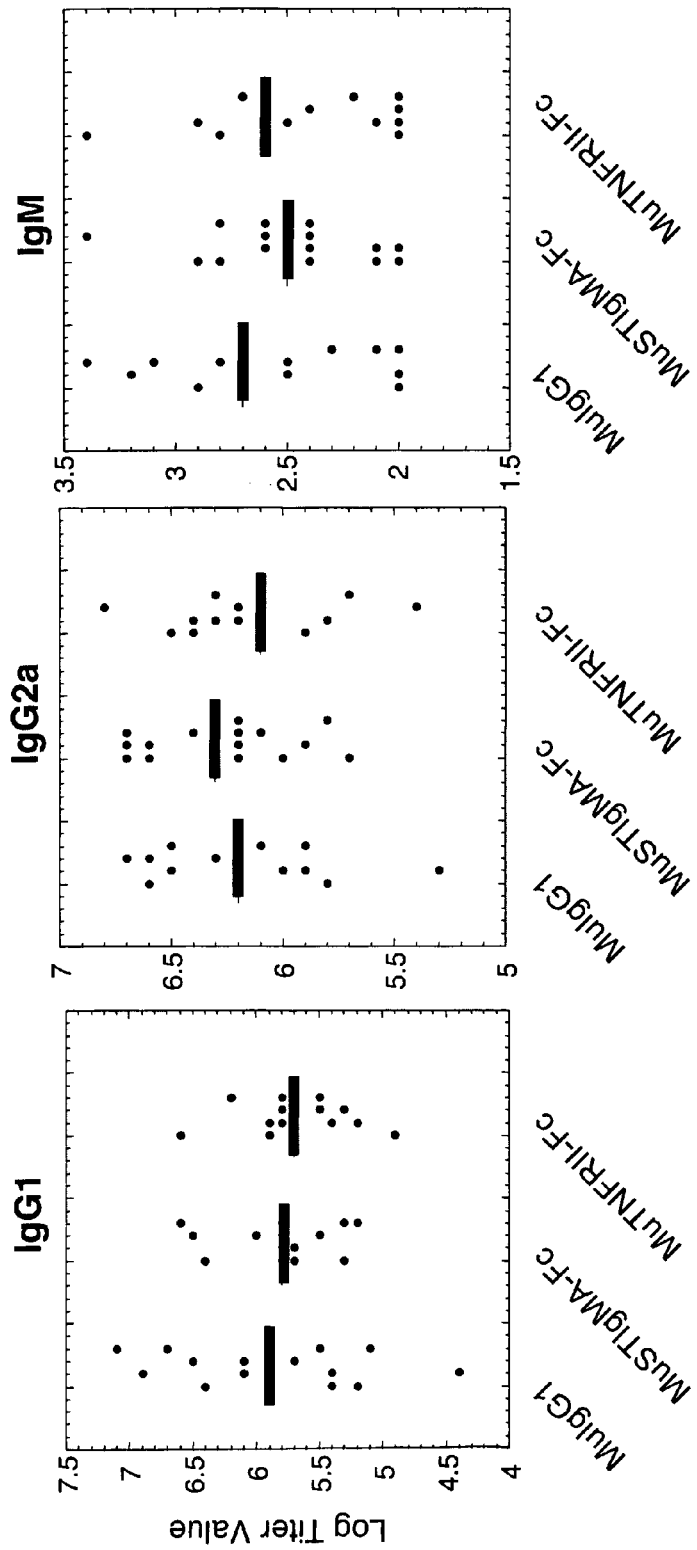
FIG. 37 shows that muCRIg treatment does not affect serum anti-collagen antibody titers.
Figure 38:
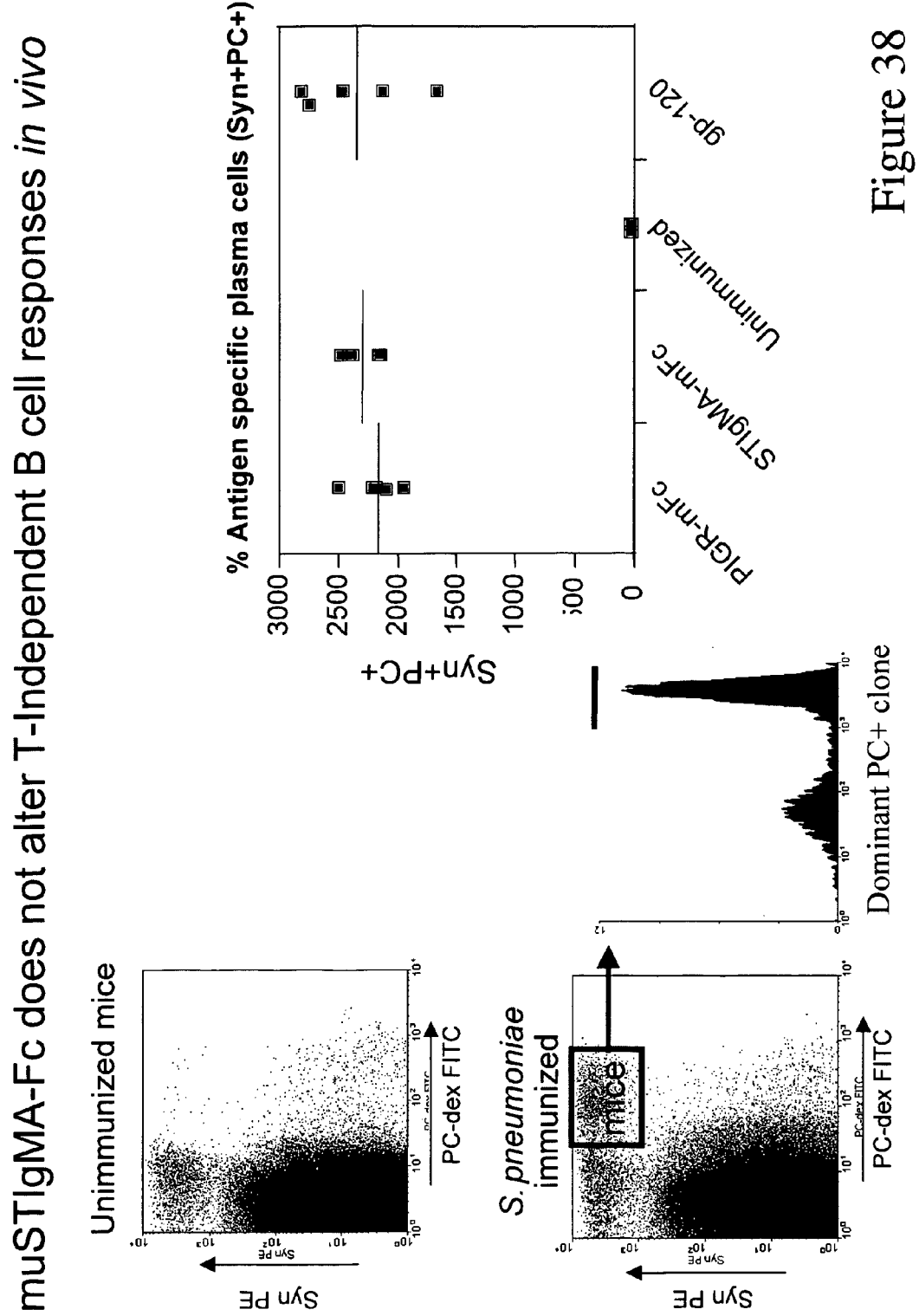
FIG. 38 shows that muCRIg does not alter T-independent B cell responses in vivo.

FIG. 36 shows that CRIg-Fc treatment does not alter the number nor the morphology of tissue resident macrophages. Livers and lungs from mice treated with either anti-gp 120 IgG1 (left figures) or CRIg-Fc (right figures) were dissected, fixed in formalin and embedded in paraffin wax. Seven micron sections were stained using an antibody to F4/80. Careful examination of the sections shows equal numbers of F4/80 positive macrophages in both treatment groups. In addition, there were no differences observed in the morphology of the macrophages FIG. 37 shows that muCRIg-Fc treatment does not affect serum anti-collagen antibody titers. Serum titers of anti collagen antibodies were determined 70 days following immunization. No differences were found in the serum titers of IgG1, IgG2a and IgM subclasses of antibodies in CRIg-Fc treated versus anti gp 120 treated animals. This means that CRIg-Fc does not affect antibody responses in mice immunized with collagen type II. FIG. 38 shows that muCRIg-Fc decreases the number of circulating inflammatory macrophages. Peripheral blood was obtained from CRIg-Fc and anti gp-120 treated animals 70 days after immunization and analysed by flow cytometry using markers for inflammatory and non-inflammatory monocytes. CRIg-Fc treated animals showed a significant increase in the number of inflammatory monocytes and a decrease in the number of non-inflammatory monocytes as compared to the anti gp 120 treated group.

In conclusion, the results of the experiments described in the present Example demonstrate that the muCRIg-Fc fusion protein inhibits collagen-induced arthritis. In particular, the results show that CRIg-Fc inhibits joint swelling, inhibits inflammation, preserves cortical joint bone volume, and decreases the number of circulating inflammatory macrophages.

Other experiments have shown that CRIg-Fc does not affect in vivo B- or T-cell responses.

Example 8

CRIg Fusion Proteins in Antibody-mediated CIA in Mice

Antibody-mediated arthritis differs from collagen-induced arthritis in that instead of injecting the antigen (bovine collagen type II), antibodies recognizing type II collagen are injected. In this way, adaptive B and T cell responses are circumvented to directly induce effector functions on macrophages and neutrophils through Fc receptor and complement-mediated activation.

Antibody-mediated CIA can be induced by i.v. injection of a combination of four different monoclonal antibodies generated by the Arthrogen-CIA® mouse B-hybridoma cell lines (Terato et al., J. Immunol. 148:2103-8 (1992)). Three of the monoclonal antibodies recognize autoantigenic epitopes clustered within an 84 amino acid residue fragment, LyC2 (the smallest arthritogenic fragment of type II collagen) of CB11 and the fourth monoclonal antibody reacts with LyC1. All four antibodies recognize the conserved epitopes shared by various species of type II collagen and cross-react with homologous and heterologous type II collagen (Terato et al., supra; Terato et al., Autoimmunity 22:137-47 (1995)). The Arthrogen-CIA® arthritis inducing monoclonal antibody cocktail is commercially available (Chemicon International, Inc., Temecula, Calif., catalog No. 90035).

Protocol

10 BALB-c mice(CR/Hollister) of 4-5 weeks, were divide into two groups, with 5 mice in each group.

Animals were treated daily with 100 μg muCRIg-Fc or 100 μg control-Fc (anti-gp120 IgG1), starting the day prior to the injection of the antibody cocktail (day −1), and continuing until day 14. At day 14. Animals were checked at least two-times per day, and written records of observations were kept. The extent of disease was scored by visual observation.

Visual scoring system:
0=No evidence of erythema and swelling
1=Erythema and mild swelling confined to the mid-foot
2=Erythema and mild swelling extending from the ankle to the mid-foot
3=Erythema and moderate swelling extending from the ankle to the metatarsal joints
4=Erythema and severe swelling encompass the ankle, foot and digits Nestlets were used as an enrichment device and to provide extra padding for the animals.

All animals were sacrificed on day 14, and joints were harvested for immunohistochemical staining or haematoxylin-eosin staining. Blood was sampled for hematological analysis.

Results

Figure 39:
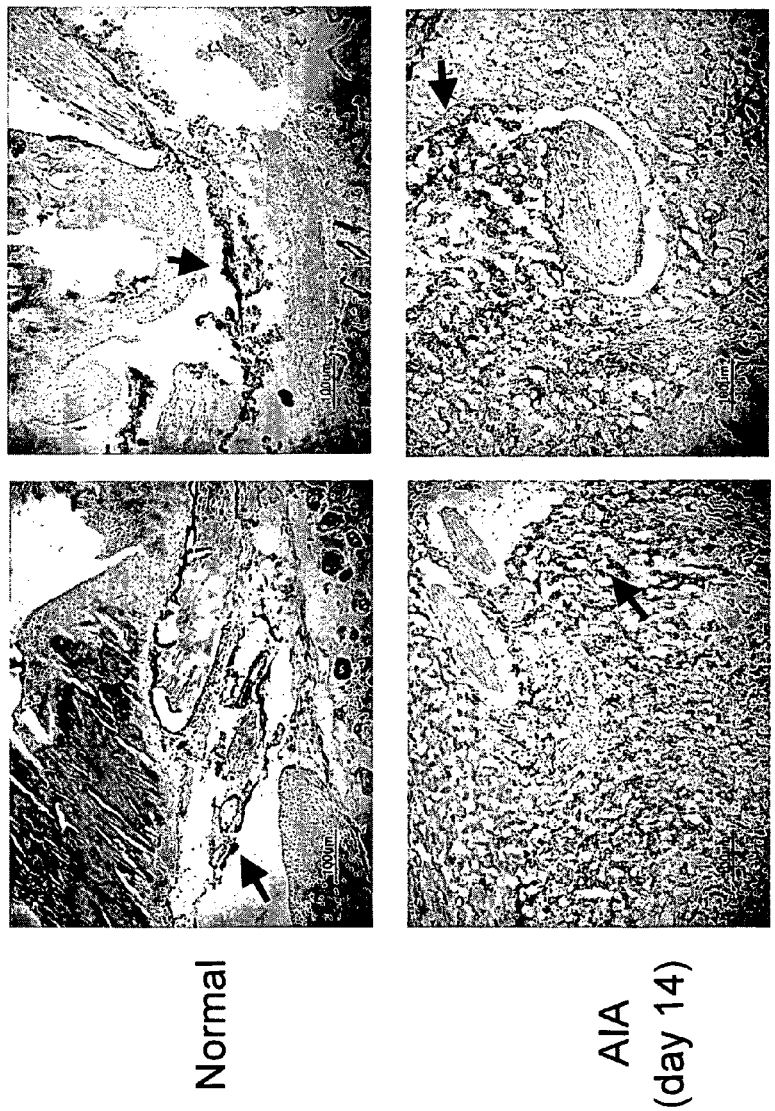
FIG. 39 shows macrophage infiltration in joints following antibody-induced arthritis (AIA), generated with F4/80 staining in undecalcified frozen joints.

FIG. 39 shows macrophage infiltration in joints following antibody-induced arthritis (AIA), generated with F4/80 staining in undecalcified frozen joints. Female Balb/C mice were injected with 2 mg of anti collagen antibodies (arthrogen) i.v. followed 3 days later by injection with 25 ug LPS i.p. 14 days following antibody injection, mice were euthanized and the paws were collected, and embedded in polyvinyl alcohol. 7 μm thick sections were cut from the frozen joints and stained with antibodies to murine CRIg and to F4/80, a macrophage specific marker.

Figure 40:
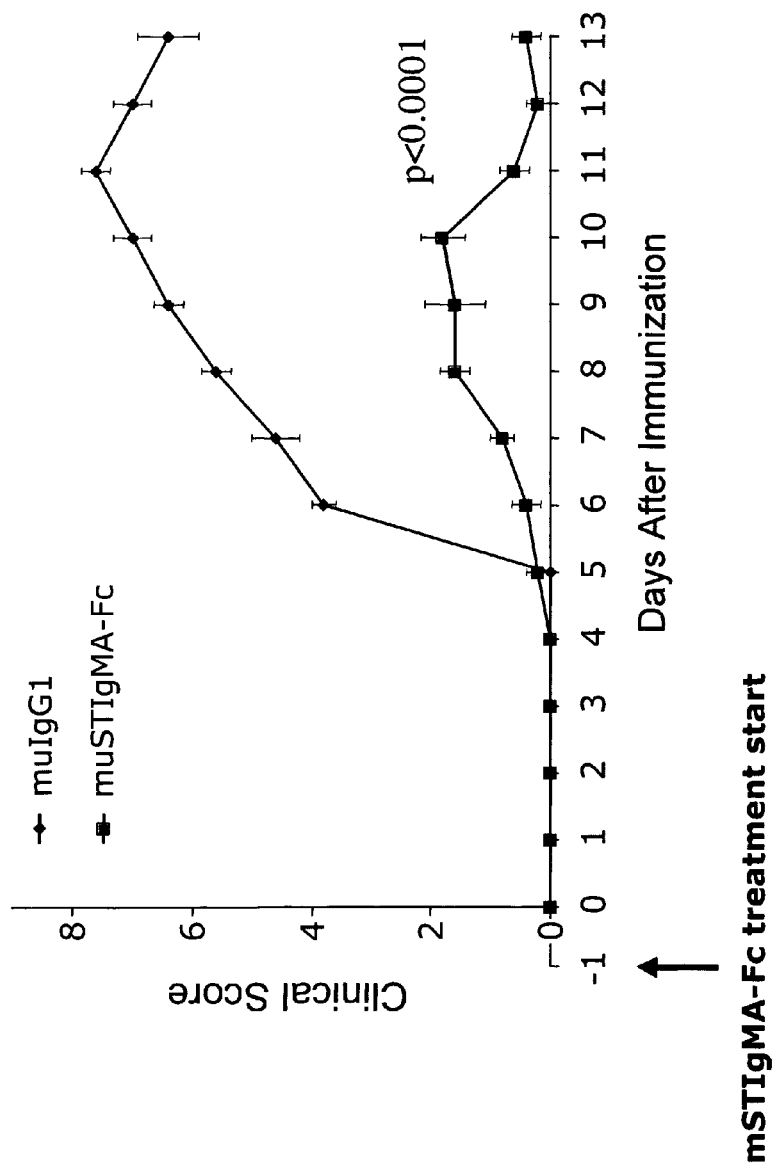
FIG. 40 shows that muCRIg-Fc prevents joint swelling following antibody-induced arthritis in balb/c mice.

FIG. 40 demonstrates that muCRIg prevents joint swelling following antibody-induced arthritis in Balb/c mice. Arthritis was induced by the method of Terato and colleagues (Terato et al., (1992), supra; Terato et al., (1995) supra) using a mixture of 4 monoclonal antibodies recognizing a conserved epitope on callegn type II (Chemicon). Female Balb/C mice, 6 weeks old, were injected i.v. with 2 mg anti CII antibody followed 3 days later with an i.p. injection of 25 μg LPS. Animals were treated daily either with murine CRIg-Fc fusion protein or with a control-Fc fusion protein. Dosing was 4 mg/kg in 100 μl PBS subcutaneous. Treatment started the day prior to anti collagen antibody injection and continued until them ice were euthanized at day 14. Mice were observed daily post LPS injection for swelling of the hind paw as a sign of arthritis. The severety of arthritis was graded on a 1-16 scale as follows: 0=No evidence of erythema and swelling, 1=Erythema and mild swelling confined to the mid-foot (tarsal) or ankle, 2=Erythema and mild swelling extending from the ankle to the mid-foot, 3=Erythema and moderate swelling extending from the ankle to the metatarsal joints, 4=Erythema and severe swelling encompass the ankle, foot and digits.

Therapeutic treatment was performed similar to prophylactic treatment apart from the treatment start which was at day 4 rather than day −1. muCRIg-Fc treatment reduced levels of inflammatory cytokines in paws of AIA mice. Measurement of cytokine, C3a and C5a concentration in arthritic hindpaw performed according to the method of Kagari et al, J. Immunol. 169:1459-66 (2002). In short, at the indicated time points following the induction of antibody-induced arthritis, paws were collected and frozen in liquid nitrogen. Subsequently, paws were pulverized on a liquid nitrogen-cooled metal plate and dispersed in ice-cold PBS containing 0.1% PMSF (Sigma). The samples were homogenized with a Vitatron (NL) homogenizer on ice, insoluble parts were removed by spinning at 14000 g for 10 min and collection of supernatant. Cytokines in the supernatant were measure using cytokine ELISA's from BD Pharmingen.

muCRIg-Fc treatment inhibits deposition of complement C3 but not of IgG2a on cartilage in AIA. Female Balb/C mice were injected with 2 mg of anti collagen antibodies (arthrogen) i.v. followed 3 days later by injection with 25 ug LPS i.p. 14 days following antibody injection, mice were euthanized and the paws were collected, embedded in polyvinyl alcohol and frozen in ispenthane cooled on dry iced. 7 um thick sections were cut from the frozen joints and stained with a FITC-coupled polyclonal antibody to murine C3 (Calbiochem) and a polyclonal A594-coupled antibody to murine IgG2a (Jackson Immunoresearch). Sections were photographed in a Leitz fluorescent microscope.

The results of immunohistochemistry performed with H&E staining are shown in FIG. 41. Control-treated mice (muIgG1) had moderate to severe arthritis (left panel), muCRIg-treated mice has minimal to no arthritis (right panel). The results show that muCRIg inhibits joint inflammation in antibody-induced arthritis.

In conclusion, animals treated with murine CRIg-Fc had significantly reduced clinical scores as compared to animals treated with anti-gp120 IgG1. CRIg demonstrated both prophylactic and therapeutic efficacy in this animal model. The decrease in severity of arthritis was also reflected by a decrease in inflammatory cells, especially neutrophils, in the joints. There was an increased number of neutrophils in the circulation possibly reflecting a decrease in neutrophil migration into the joint. muCRIg-Fc inhibited local IL-1β and IL-6 production in parallel with clinical manifestation of RA. muCRIg treatment did not affect immune complex deposition, but inhibited complement C3 deposition on cartilage. The effector function was found to be independent of Fc receptor binding. huCRIg-short-Fc has also demonstrated significant prophylactic activity.

Example 9

Murine CRIg-Fc Binds to C3-Opsonized Sheep Red Blood Cells (E-IgM)

SRBC (MP Biomedicals, ICN/Cappel) were coated with rat IgM (E-IgM) (Forssman Ag, Pharmingen). E-IgM were opsonized with normal mouse serum or serum from a C3 knockout mouse. Opsonized E-IgM were incubated with different concentrations of murine CRIg-Fc. Binding of the fusion protein to E-IgM was monitored by flow cytometry using a FITC-labeled antibody to the Fc portion of the fusion protein.

Figure 42:
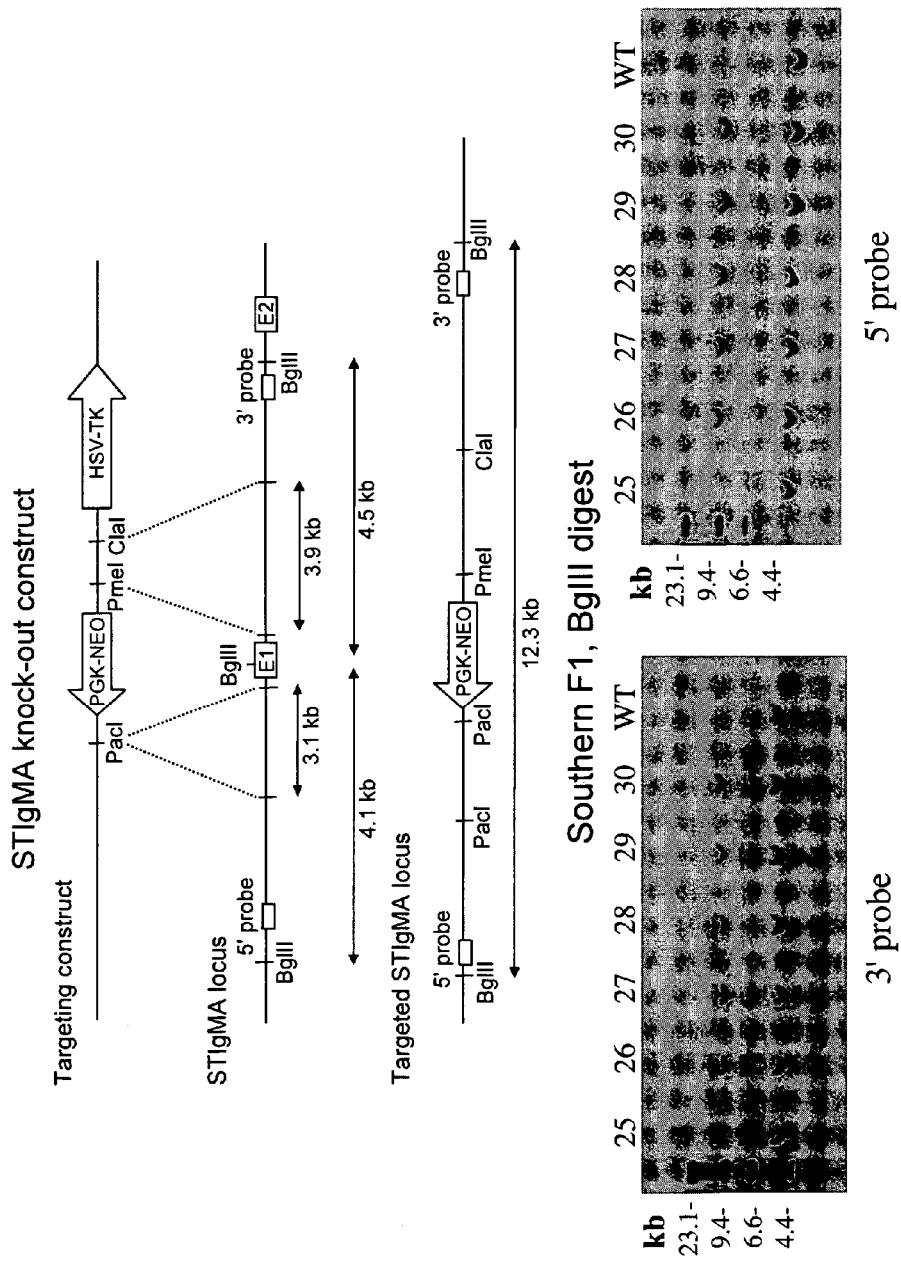
FIG. 42 shows generation of muCRIg knock-out mice.

As shown in FIG. 42, murine CRIg bound dose-dependently to E-IgM opsonized with normal mouse serum but not to E-IgM opsonized with C3 deficient serum, indicating selective binding of CRIg to murine C3 or a fragment of C3.

Example 10

Binding of Human CRIg-Fc to E-IgM is C3 Dependent

SRBC (MP Biomedicals, ICN/Cappel) were coated with rat IgM (E-IgM) (Forssman Ag, Pharmingen). E-IgM was opsonized with human serum deficient in C3 or C5. Opsonized E-IgM were incubated with different concentrations of human CRIg-Fc. Binding of the fusion protein to E-IgM was monitored by flow cytometry using a FITC-labeled antibody to the Fc portion of the fusion protein.

Figure 43:
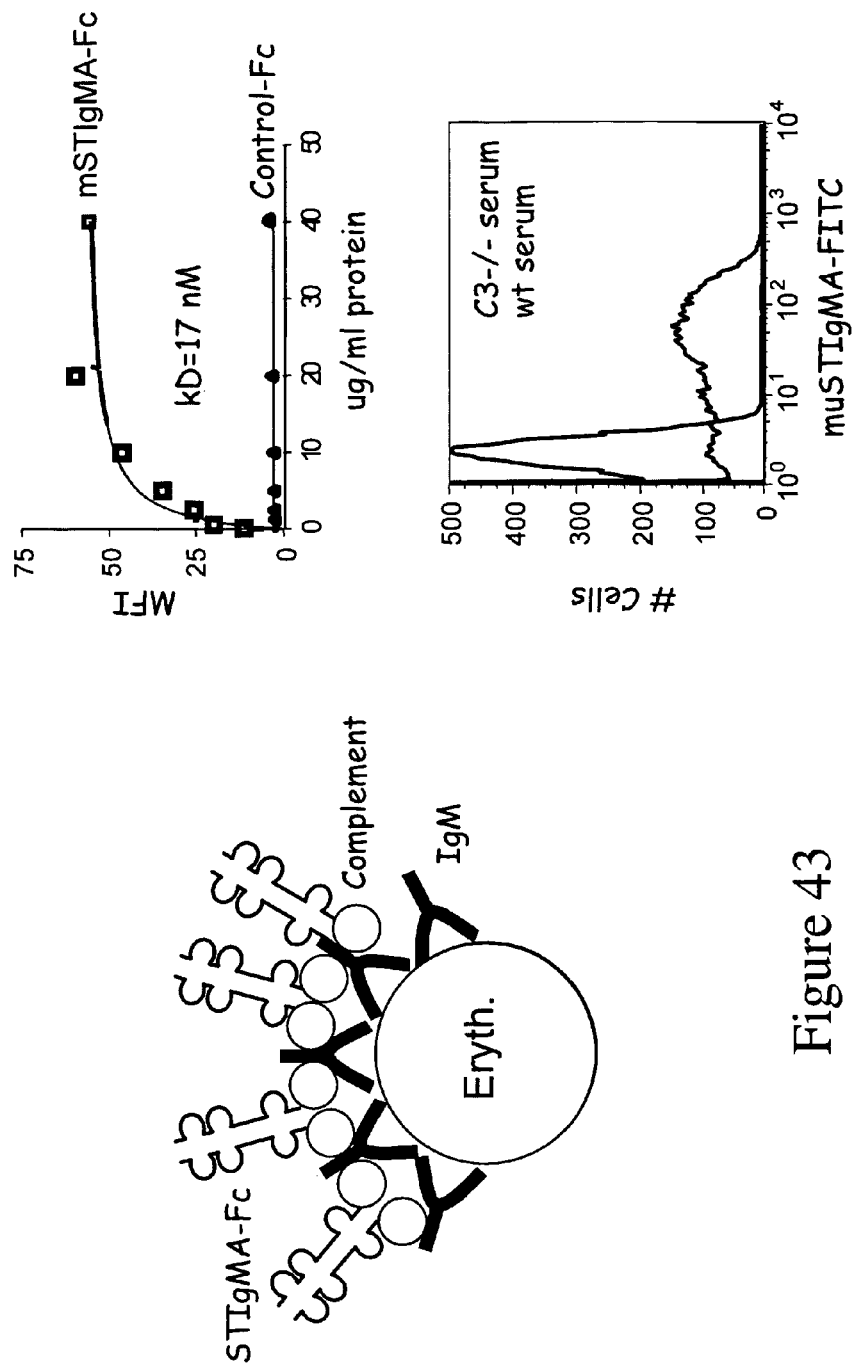
FIG. 43 shows that murine CRIg-Fc fusion protein binds to C3-opsonized sheep red blood cells (E-IgM).

As shown in FIG. 43, human CRIg bound dose-dependently to E-IgM opsonized with C5 deficient serum but not to E-IgM opsonized with C3 deficient serum, indicating selective binding of CRIg to human C3 or a fragment of C3. Similar results were obtained with human CRIg ECD.

Example 11

Binding of Serum-Opsonized Particles to CRIg-Expressing CHO Cells

50 µl fresh C57B6 female serum +20 ug/ml mCRIg-mFc (PUR5270-B) or mPIGR-mFc (4699) were mixed together. A488 particles, zymosan, *S. aureus* or *E. coli* from Molecular Probes were added for 60 min at 37° C. in PBS/0.2% gelatin/0.18% glucose/1 mM MgC12 (PBSgg++). Opsonized particles were washed 2× in PBS and added to CHO cells expressing murine CRIg (clone 5C10) or human JAM2 in the presence or absence of CRIg-Fc or control-Fc protein for 30 min at 37° C. Cells washed 2× inPBS and analysed for binding of particles to the cell surface in a FACS Caliber.

As shown in FIG. 44, particles opsonized with C3 sufficient serum bound to CRIg expressing CHO cells but not to JAM2 expressing CHO cells. Binding was abrogated in the presence of a CRIg-Fc fusion protein but not in the presence of a control-Fc fusion protein indicating that the binding site for CRIg to C3b resides in the extracellular domain.

Example 12

MuCRIg Fc Binds C3b

Real-time monitored surface plasmon resonance assays were performed using a Biacore®-2000 instrument, and the data were analyzed using the BiaEvaluation 3.0 software (Biacore AB, Uppsala, Sweden). Carboxylated dextran chips (sensor chip CM5, research grade from Biacore AB) were used in all the assays. Flow cells of the CM5 chips were used either for a standard amine coupling procedure or prepared for the direct enzymatic coupling of C3b by using a standard activation-deactivation procedure without adding any protein between the steps. The activation step was performed with fresh solution containing N-hydroxysuccinimide and N-ethyl-N'-(dimethylaminopropyl)-carbodiimide (Biacore AB, 7-15-min injection at a flow rate of 5 µl/min) and was followed by deactivation with ethanolamine-HCl (1.0 M at pH 8.5) (Biacore AB, 7-15-min injection). Hepes-buffered saline (Biagrade, Biacore AB) or VBS was used as the flow buffer throughout. After these initial steps VBS or VBS was used as the continuous flow buffer at 5 µl/min; only degassed buffers were used.

Amine Coupling of Proteins onto the Biacore® Chip—C3b, iC3b, C3c, and C3d were coupled onto the CM5 chip using the standard amine coupling procedure as recommended by the manufacturer. The proteins to be coupled were dialyzed against 10 mM acetate buffer (pH 5.0-5.7) to achieve a negative net charge for the amine coupling. Briefly, the chip surface was activated with N-ethyl-N'-(dimethylaminopropyl)-carbodiimide (7-15-min injection, 5 µl/min), and either purified C3b (50 µg/ml, 20 µl), C3c (70 µg/ml, 30 µl), or C3d (130 µg/ml, 20 µl) was injected to reach an appropriate level of coupling for the binding experiments, i.e. 1,000-5,000 resonance units (RU). Afterward, the flow cells were deactivated as described above. Before the experiments, the flow cells were washed thoroughly with VBS and 3 M NaCl in 10 mM acetate buffer, pH 4.6

Binding Assays Using Biacore®—We tested the binding of CRIg-Fc to amine-coupled C3b, C3c, and C3d. For Biacore® injections the reagents were dialyzed against VBS, diluted with VBS, and filtered (0.20 µm Minisart®, Sartorius Corp., Edgewood, N.Y.) or centrifuged (10 min at 14,000×g). The protein concentrations of the dialyzed reagents were measured using the BCA Protein Assay (Pierce). The fusion proteins were injected separately through a control flow cell (activated and deactivated flow cell without any coupled proteins, "blank channel") and through the flow cell with the coupled protein using a flow rate of 5 µl/min at 22° C. All the binding assays were performed at least in duplicate using independently prepared sensor chips.

Figure 45:
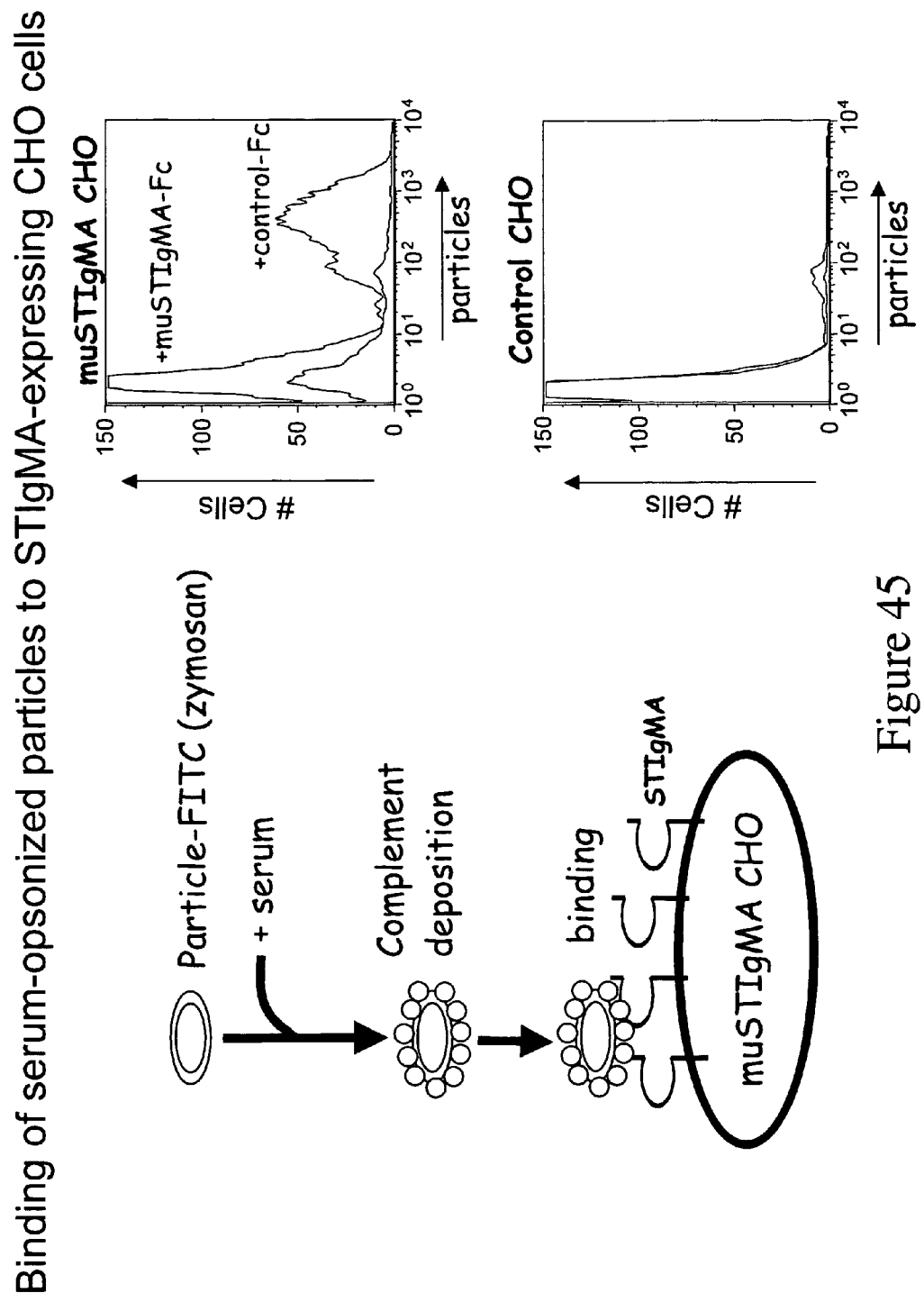
FIG. 45 shows the binding of serum-opsonized particles to CRIg-expressing CHO cells.

As shown in FIG. 45, murine CRIg-Fc shows specific binding of C3b to the sensor chip with a calculated Kd of 250 nM.

Example 13

Mouse and Human CRIg-Fc Bind Complement C3b

Maxisorb plates were coated o/n with 3 ug/ml C1, C3a,b,c,d, C4, C6 in PBS. Plates were blocked for 2 hrs in PBS+4% BSA and incubated with various concentrations of murine or human CRIg-Fc fusion protein for 1 hr at Rt in PBS+4% BSA+0.1% Tween. Plates were washed and incubated with a goat-anti mouse or goat-anti human Fc antibody conjugated to peroxidase. Following washes, the plates were incubated with TNB sustrate and OD read on a plate reader.

Figure 46:
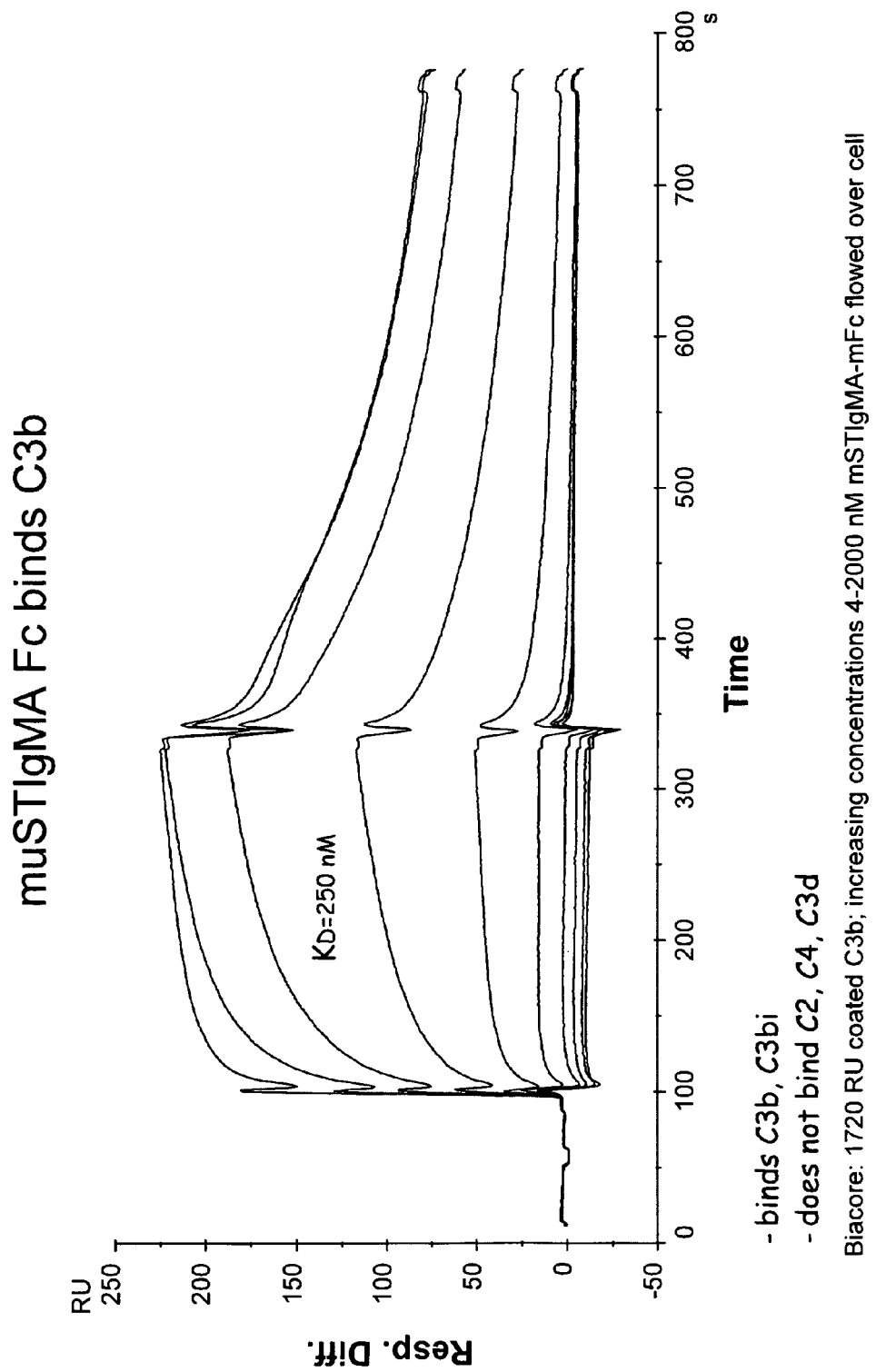
FIG. 46 shows that murine CRIg-Fc binds complement C3b and iC3b but does not bind C2, C4, and C3d.

Results shown in FIG. 46 represent a concentration dependent increase in murine and human CRIg binding to C3b, C3c and C3bi and absence of binding to C1, C2, C4, C3a, and C3d.

Example 14

Mouse and Human CRIg-Fc Inhibit C3 Deposition on Zymosan

Inhibition of the alternative pathway was studied using a method that utilizes flow cytometric analysis of C3 deposition on zymosan A particles (Sigma) (Quigg et al., *J. Immunol.* 160:4553-4560 (1998)). Briefly, 50 mg of zymosan particles in 10 ml of 0.15 M NaCl were first activated by boiling for 60 min, followed by washing twice in PBS. In each alternative pathway assay condition, $2 \times 10^7$ particles were added to reaction tubes containing a final concentration of 10 mM EGTA and 5 mM $MgCl_2$. Samples as described in the text were then added containing either 10 mM EDTA (negative control) or increasing amounts of murine CRIg-Fc. Ten microliters of BALB/c serum as a source of complement were added, and all samples were brought to 100 µl with PBS. Samples were incubated at 37° C. for 20 min, and the reaction was stopped by adding 10 mM EDTA. The particles were centrifuged, and supernatants were removed and frozen for later analysis. The particles were then washed twice with cold PBS, 1% BSA, and then incubated with FITC-conjugated goat anti-mouse C3 (Cappel, Durham, N.C.) for 1 h on ice. The samples were then washed twice in cold PBS, 1% BSA, resuspended in PBS, and then analyzed by flow cytometry using an EPICS cytometer (Coulter, Hialeah, Fla.). Percentage inhibition was calculated using the formula [1−[sample mean channel fluorescence−background (10 mM EDTA condition)/positive control mean channel fluorescence (no Crry-Ig)−background]]×100.

Supernatants from the reaction were also analyzed by Western blotting to determine the extent of C3 cleavage. In this analysis, 5 µl of the supernatant was mixed with an equal amount of SDS-PAGE loading buffer with 10% 2-ME. The samples were subjected to SDS-PAGE on a 7.5% acrylamide gel, transferred to Hybond enhanced chemoluminescence (ECL) paper (Amersham, Arlington Heights, Ill.) overnight in 0.19 M Tris, 0.025 M glycine, 20% methanol buffer. Following this, membranes were blocked in PBS,0.1% Tween with 10% milk for 1 h. Anti-C3 mAb RmC11H9 (Quigg et al., supra) that had been pretitered was then added to the blot in the same buffer with 1% BSA. Following washing, horseradish peroxidase-conjugated goat anti-rat IgG (Southern Biotechnology, Birmingham, Ala.) (preadsorbed against mouse IgG) was added for 1 h, and then the blot was washed and developed using the enhanced chemoluminescence (ECL) system (Amersham).

Figure 47:
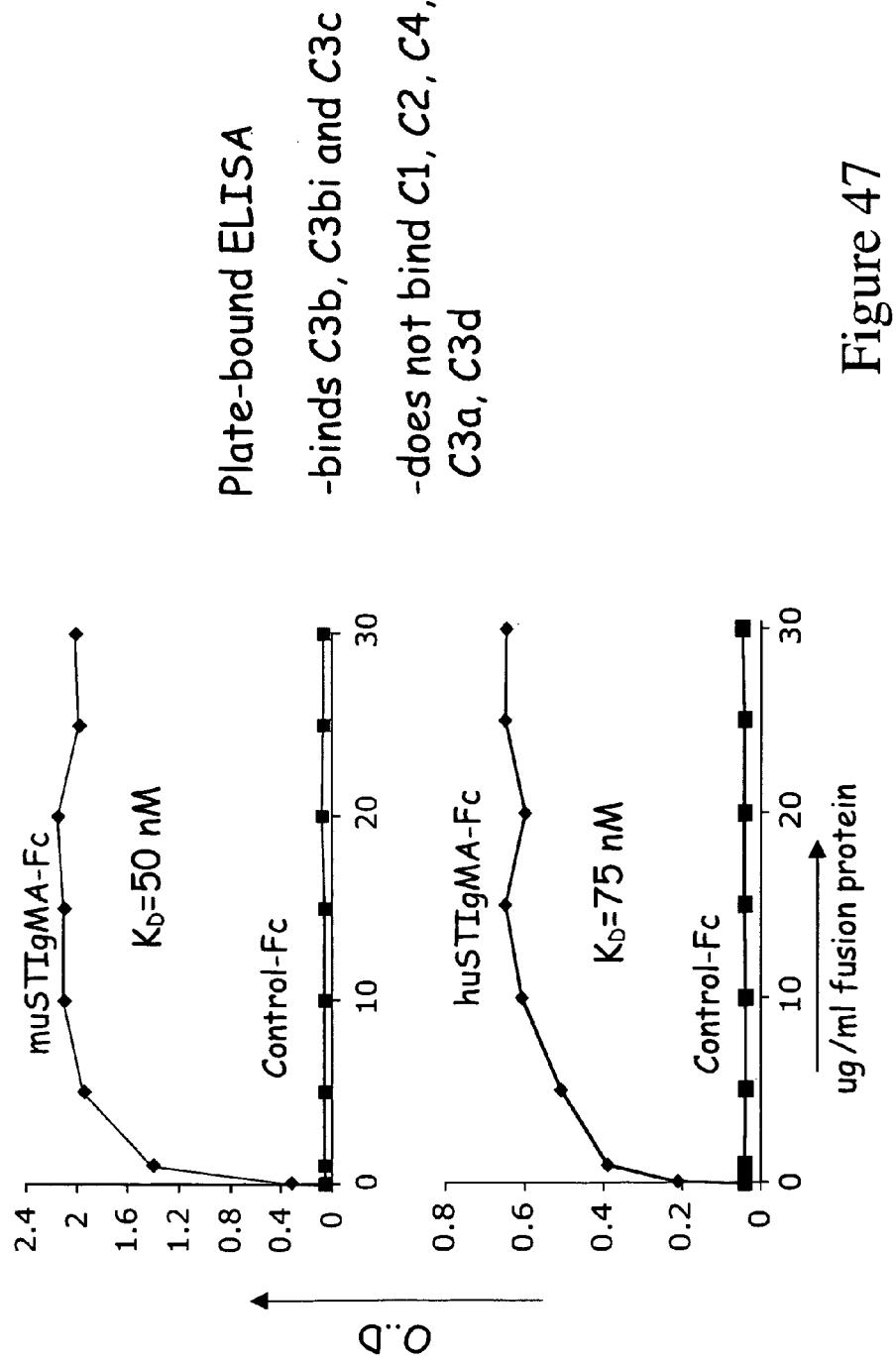
FIG. 47 shows that murine and human CRIg-Fc bind complement C3b, C3bi and C3c but do not bind C1, C2, C4, C3a, and C3d.

The inhibition of complement activation by CRIg-Fc on zymosan particles was analyzed following flow cytometry to detect surface-bound C3 (FIG. 47A), or when an aliquot of the zymosan reaction supernatant was analyzed by Western blotting and detection using anti-C3 mAb (FIG. 47B). Positions of the intact C3 and C3' chains in B are shown by arrows at right. The 10 mM EDTA lane represents the negative control, and increasing doses of CRIg-Fc are shown at the top in lanes 2 to 7.

Example 15

CRIg Inhibits Alternative Pathway Hemolysis of SRBC

For alternative pathway: Rabbit-red blood cells (RRBCs) were washed in veronal buffer (Bio Whittacker) containing 0.1% gelating and resuspend to 1×10e9 cells/ml in GVB. 10 µl of the cell suspension was added to 10 µl of C1q depleted serum containing the inhibitors. The mixture was incubated for 35 min at 37C in a warm room while shaking. 200 ul GVB containing 10 mM EDTA was added, cells were centrifuged at 2500 rpm for 5 min and 100 µl aliquots were read at 412 nm wavelength.

Figure 48A:
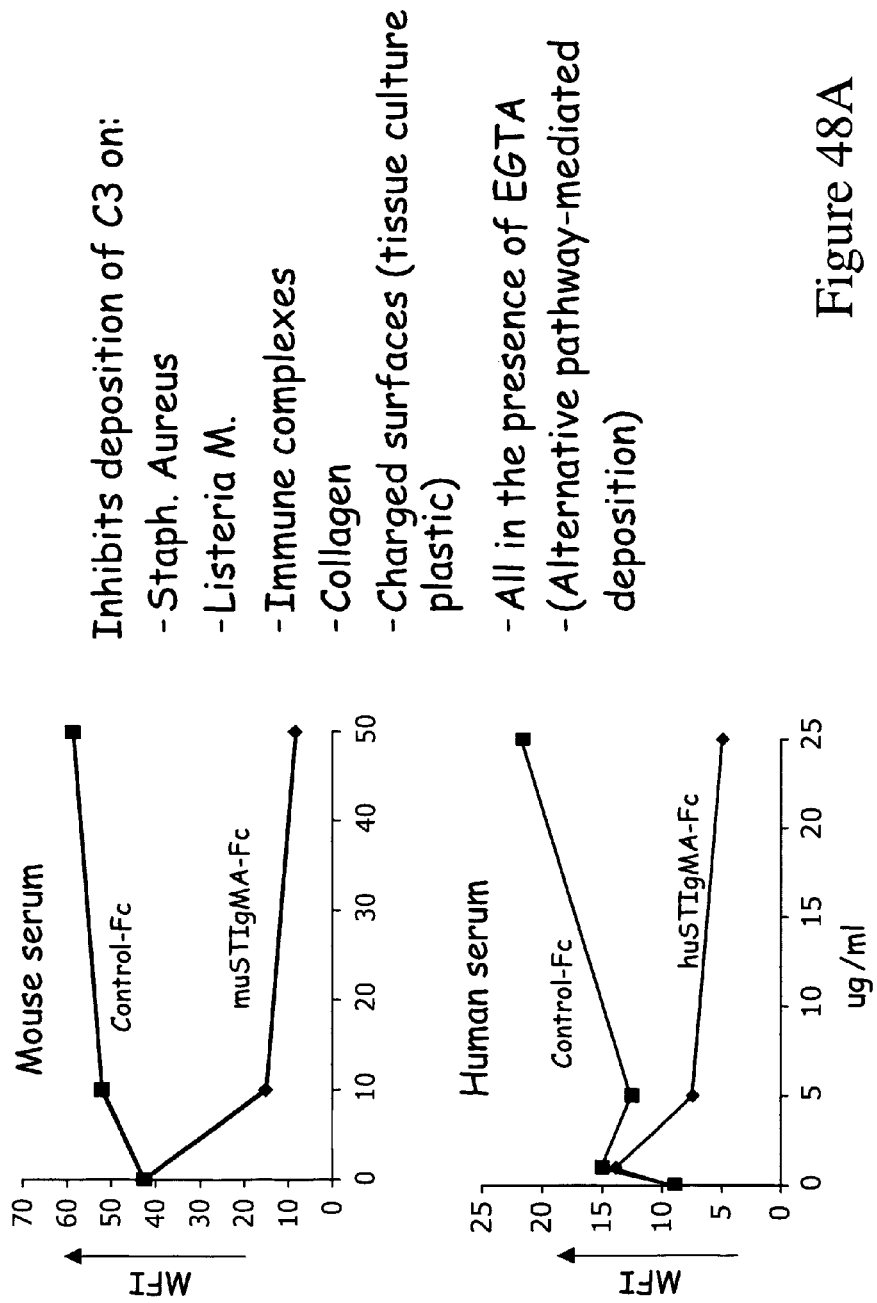
FIG. 48A shows that murine and human CRIg-Fc inhibit C3 deposition of zymosan.
Figure 48B:
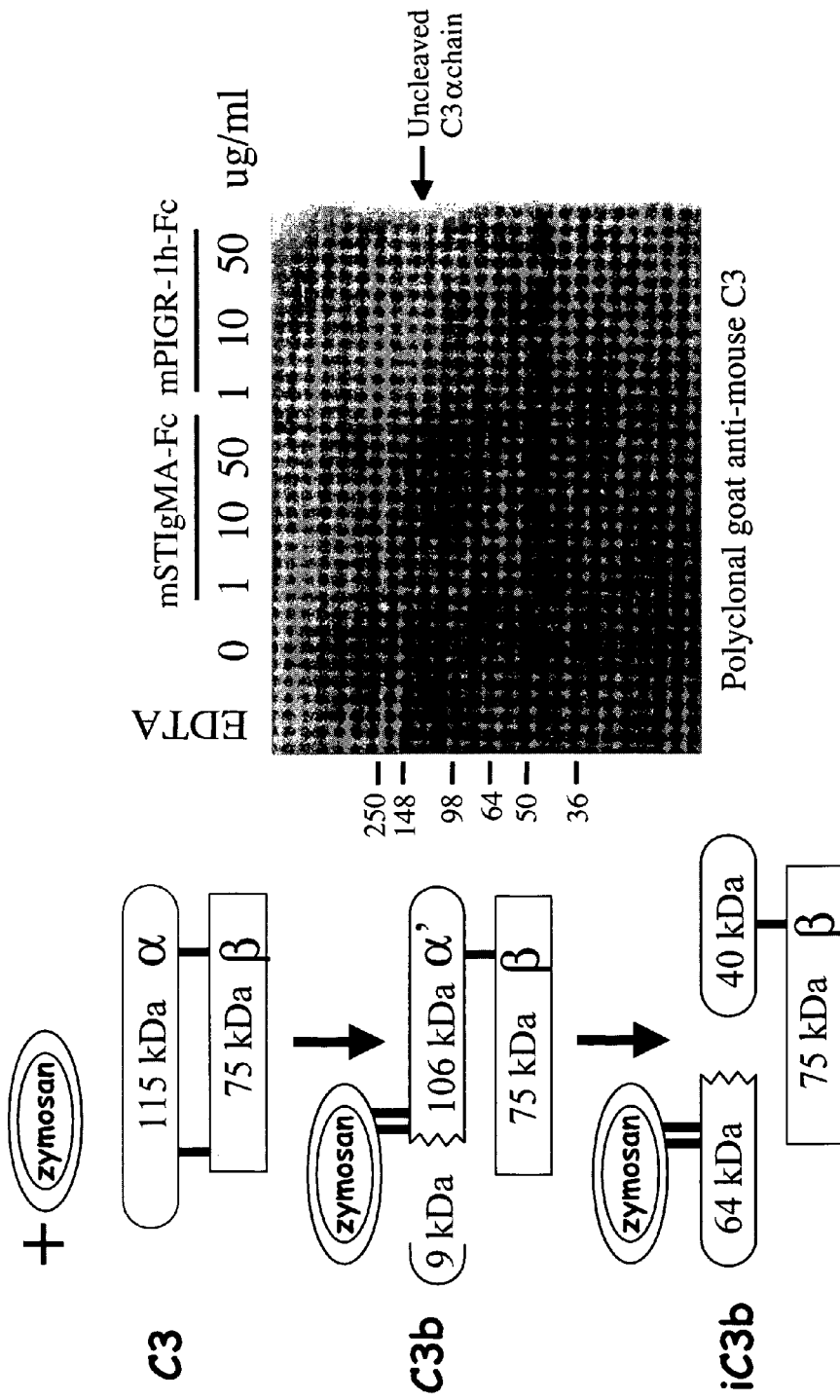
FIG. 48B shows that murine CRIg-Fc inhibits C3 activation is serum.

For classical pathway, sheep erythrocytes opsonized with IgM (E-IgM) were incubated in fB deficient serum. Methodology was similar to alternative pathway measurements The results set forth in FIG. 48 show that murine CRIg inhibits alternative pathway-induced hemolysis but does not affect classical pathway hemolysis. Similar results were obtained with human CRIg.

Example 16

CRIg Selectively Inhibits Alternative Pathway of Complement

Hemolytic Assays Using Whole Serum

Alternative pathway of complement was assessed with rabbit erythrocytes (Er) as described y Kostavasili et al. (J. Immunol. 158:1763-71 (1997)). Briefly, Er (Colorado Serum, Denver, Colo.) were washed 3× in GVB and resuspended to 1×109/ml. 10 µl Er were added to 10 µl GVB/EGTA (0.1 M EGTA/0.1 M MgCl2), inhibitors, 10 µl C1q depleted human serum and volume adjusted to 100 µl with GVB then incubated at 37° C. for 30 minutes. 250 µl GVB/10 mM EDTA was added to stop the reaction, and centrifuged for 5 min at 500×g. Hemolysis was determined by absorbance of 200 µg supernatant at 412 nm. The percentage of lysis was normalized by considering 100% lysis equal to the lysis occurring in the absence of the inhibitor.

To determine the effect of CRIg on the classical pathway of complement, a similar procedure was followed, except that Er were replaced with E-IgM and the assay was performed in fB deficient human serum in GVB++.

Measurement of C3 Convertase-mediated Cleavage of C3

The effect of CRIg on fluid phase C3 cleavage by C3 convertase (C3b.Bb) (from Kostavasili et al., supra) was examined by incubating 0.4 µM purified C3 with huCRIg-long, huCRIg-short, muCRIg or factor H in GVB (20 µl volume) at 37° C. for 15 minutes. Thereafter, 0.4 µM factor B and 0.04 µM factor D were added in the presence of 50 mM MgEGTA, in a total volume of 30 µl to activate the pathway. After 30 minutes at 37° C., the reaction mixtures were stopped with 30 µl Laemmli's sample buffer (BioRad) containing 2-ME, boiled for 3 minutes, and electrophoresed on an 8% SDS-PAGE gel (Invitrogen). Proteins were visualized by staining the gel with SimplyBlue stain (Invitrogen, Carlsbad, Calif.). The gel was scanned for densitometric analyis, and the percentage of C3 cleaved was calculated. Controls were incubated in GVBE (GVB with 10 mM EDTA) to inhibit cleavage.

The microtiter plate assay for the alternative pathway DAA was performed as described previously (Krych-Goldberg et al. J. Biol. Chem. 274:31160-8 (1999)). Microtiter plates were coated overnight with 5 µg/ml C3b (Advanced Research Technologies) in phosphate-buffered saline. Plates were blocked for 2 hours at 37° C. with phosphate-buffered saline containing 1% bovine serum albumin and 0.1% Tween 20 and incubated for 15 minutes at 37° C. with 10 ng of factor B, 1 ng of factor D, and 0.8 mM NiCl2 in 2.5 mM veronal buffer, pH 7.4, containing 71 mM NaCL and 0.05% Tween 20. Using the same buffer, sequential 1-hour incubations were performed with 0.01-1 µg of CRIg-Fc, 0.129 µg of goat anti-human factor B antibody, and 100 µg of a 1:15,000 dilution of anti-goal antibody conjugated to horseradish perozidase (Jackson Immunoresearch Laboratories, West Grove, Pa.). Color was developed with O-phenylenediamine. In this assay, DAF and factor H behave as expected, as mediators of decoy accelerating activity, and C3a release was deteted using the Amersham Pharmacia Biotech des-Arg RIA kit.

C5 Convertase Assay

C3b was deposited on zymosan by resuspending $1 \times 10^{10}$ zymosan particles in 0.2 ml of 10 mg/ml C3 and adding 5 µg of trypsin, followed y a 10-minute incubation at 22° C. The deposition of C3b by trypsin was repeated and the cells washed six times with 5 ml GVB. The zymosan particles were resuspended in 100 µl GVB and mixed with 50 µl GVB containing factors B (35 µg) and D (0.5 µg) and 50 µl of 10 mM NiCl2. After 5 minutes of incubation at 22° C., 5 µl of 0.2 M EDTA was added. The bound C3b was amplified by adding 50 µl C3 (500 µg) and incubating the cells for 30 minutes at 22° C. The zymosan particles bear C3b were washed and the amplification procedure was repeated until the desired numbers of C3b/zymosan were obtained.

Because formation of C5 convertase took less than one minute, enzyme was formed in the same reaction mixture in which the assays were performed. Enzyme velocities were determined under saturating concentrations of factors B and D, and C6, in 0.5 ml siliconized microfuge tubes as described previously. Assay mixtures contained varying concentrations of C5 (preincubated for 20 minutes at 37° C. to eliminate freeze/thaw-generated background C5b,6-like activity), factor B (1.2 µg, 516 nM0, factor D (0.1 µg, 167 nM), C6 (2.5 µg, 833 nM0, and 0.5 mM NiCl2. The reaction was started by the addition of ZymC3b, ESC3b, or ERC3b. Depending on the density of C3b per cell, the concentration of cells was adjusted so as to have 9-35 ng of bound C3b in a final volume of 25 µg GVB resulting in 2-8 nM enzyme concentration. After 15 minutes of incubation at 37° C., further cleavage of C5 was prevented by transferring the assay tubes to an ice bath and adding ice-cold GVBE. Appropriately diluted assay mixtures were immediately titrated for C5b,6 formation by hemolytic assays using EC. C5b,6 was quantitate using standard curves generated with purified C5b,6. Controls established that the cold temperature and the dilution were sufficient to reduce the cleavage of C5 during subsequent steps to undetectable levels. Lysis of rabbit erythrocytes (ER) or sheep erythrocytes (ES) was shown to contribute <2% to C5b,6 titers using lysis of EC as the endpoint.

C5b,6 was measured hemolytically using the sensitivity of EC to hemolytic lysis by human C5b-9, To an aliquot (25 μl) of the diluted sample from C5 convertase assays was added a mixture of 1.2×107 EC and 5 μl of pooled normal human serum (NHS) as a source of complement proteins C7-C9 in a final volume of 225 μl GVBE. The reaction mixtures were incubated for 10 minutes at 37° C. after which the unlysed cells were removed by centrifugation for I minute at 10,000× g. The amount of hemoglobin released was quantitated spectrophotometrically at 414 nm. One-hundred percent lysis was measured as EC lysed in 2% Nonidet P-40. Controls containing C5 and C6 but no C5 convertase, were subtracted as the background. Controls containing C5 convertase but no purified C5 or C6 demonstrated that no significant amount of C5b,6 was formed from NHS used as a source of C7-9 during the lysis of EC.

Results

The results are shown in FIGS. 49(A)-(E).

Figure 49:
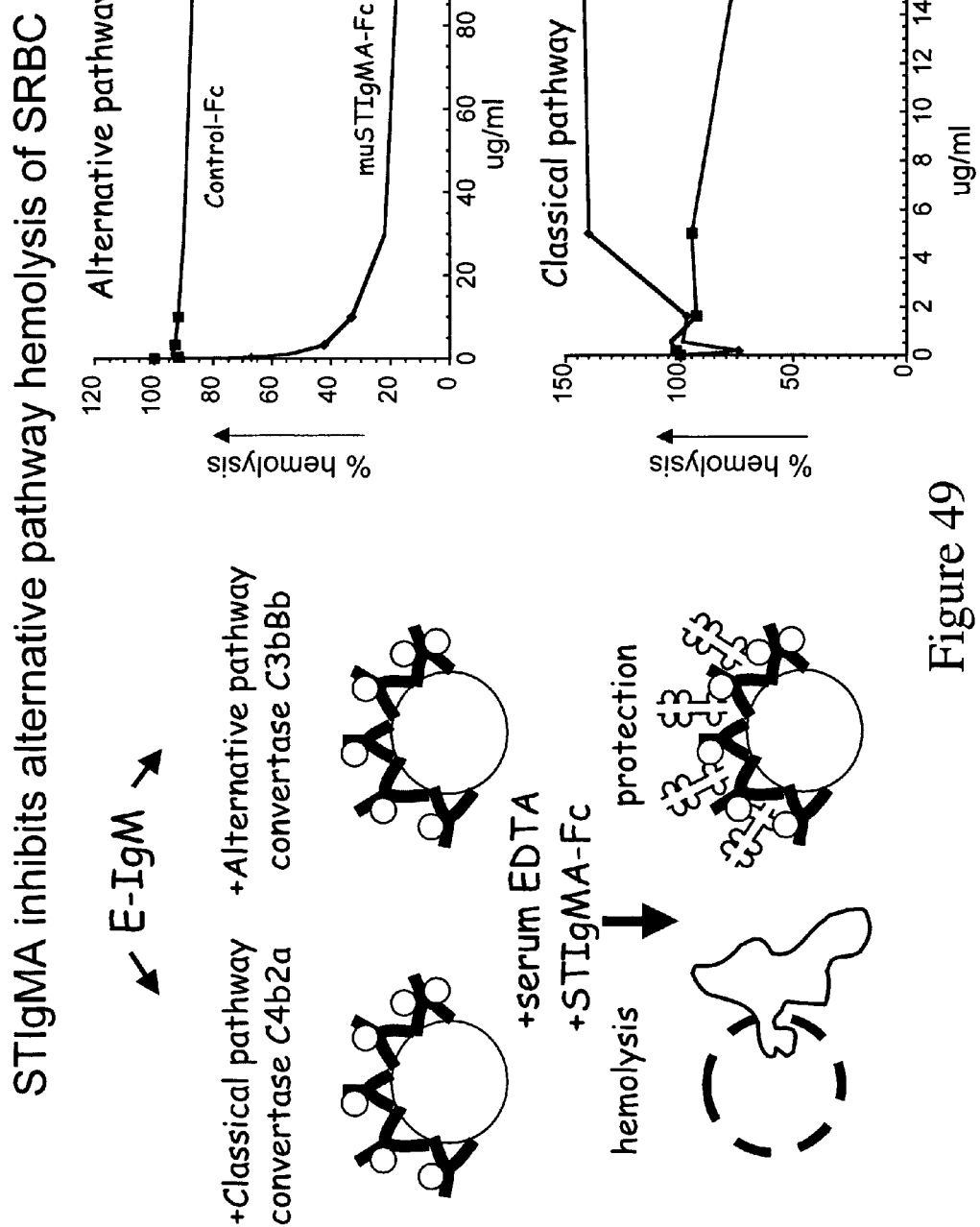
FIG. 49 shows that murine CRIg inhibits alternative pathway-induced hemolysis but does not affect classical pathway hemolysis.

FIG. 49(A) shows that CRIg inhibits hemolysis of rabbit erythrocytes in C1q deficient serum (alternative pathway) but not of IgM-opsonized sheep erythrocytes in fB deficient serum (classical pathway) indicating hat CRIg selectively inhibits the alternative pathway of complement.

As shown in FIG. 49(B), CRIg inhibits fluid phase C3 convertagse activity. The gel shows inhibition of the cleavage of the 115 kDa alpha chain of C3 with increasing concentration of human CRIg-ECD (10-100 nM).

FIGS. 49(C) and (D) show that CRIg does not function as a cofactor of factor I mediated cleavage of C3 nor as an accelerator of decay of the C3 convertase.

The data set forth in FIG. 49(E) show that CRIg inhibits alternative pathway C5 convertase formed on zymosan particles.

Example 17

CRIg is Expressed on a Subset of Tissue Macrophages

Figure 50A:
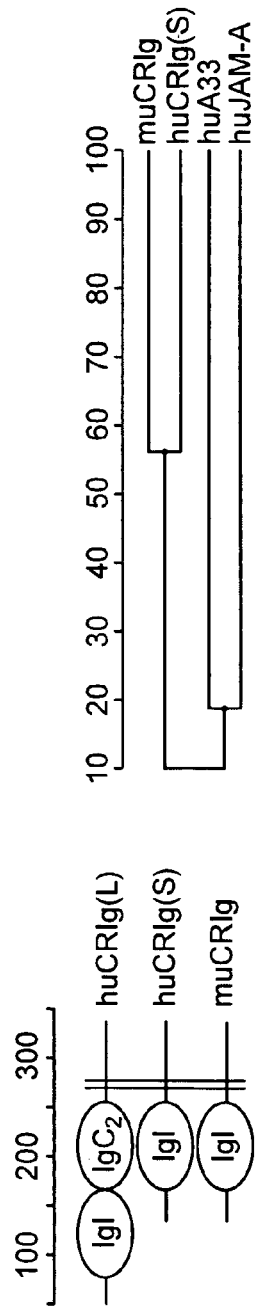
FIG. 50 CRIg is selectively expressed on a subpopulation of tissue resident macrophages.
Figure 50B:
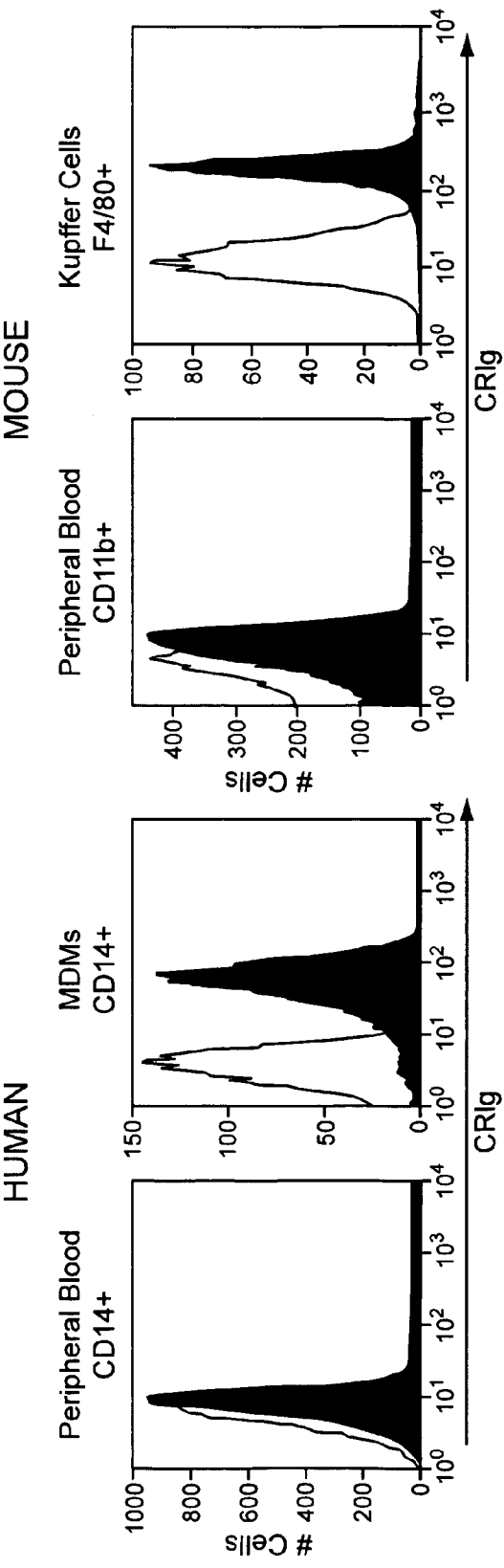
Figure 50C:
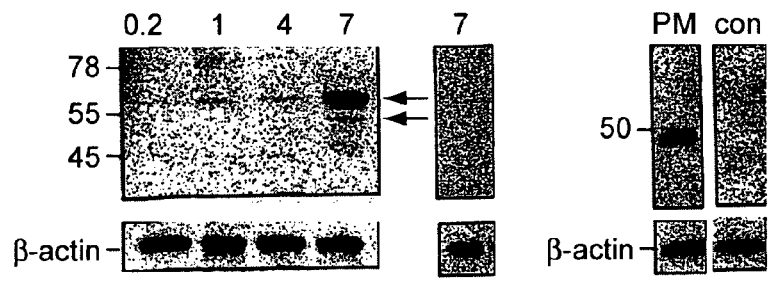
Figure 50D:
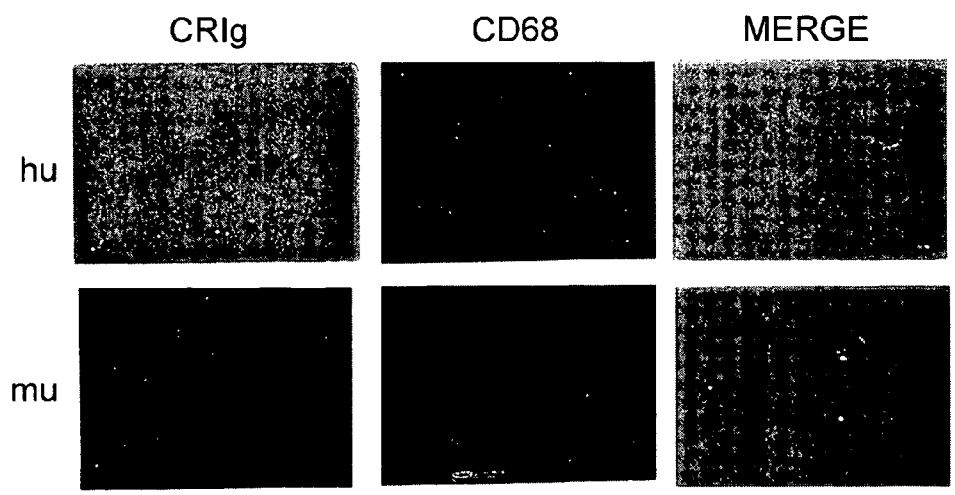
Figure 51A:
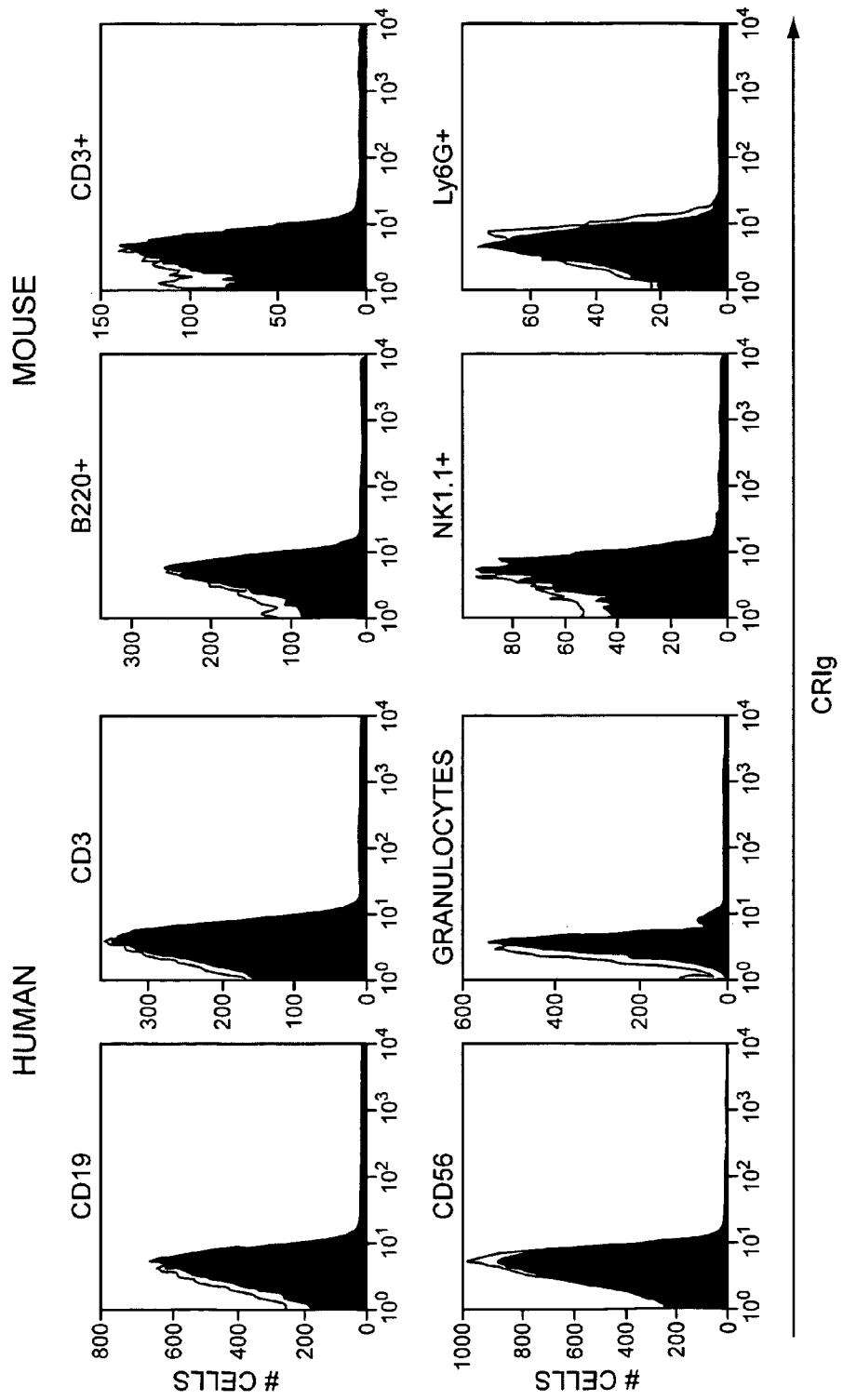

Monoclonal antibodies specific for human and mouse CRIg were generated and utilized to define the expression of CRIg, as described in Example 3. While CRIg was absent on peripheral blood C14+ monocytes, it was readily detected on monocyte-derived macrophages by flow cytometry (FIG. 50B). huCRIg was absent on peripheral blood $CD4^+$ and $CD8^+$ T cells, $CD19^+$ B-cells, $CD56^+$ NK cells, $CD15^+$ granulocytes (FIG. 51A). Similar to huCRIg, muCRIg was absent on peripheral blood and splenic leukocytes, including $CD11b^+$ myeloid cells, but detected on liver Kupffer cells (KCs, FIG. 50B). Expression of huCRIg(L) and (S) protein was confirmed at 55 and 48 K Mr proteins as monocytes differentiated into macrophages (FIG. 50C). Similarly mouse CRIg was detected as a 48 K Mr glycoprotein in peritoneal macrophages (PM). MuCRIg has a predicted N-linked glycosylation site and is glycosylated, accounting for a ~5 kDa mobility shift on a gel (results ot shown).

As CRIg mRNA was highly detected in the liver, CRIg expression in the liver was further analyzed by immunohisochemistry. CRIg was expressed in expressed on CD68+ KCs in human and mouse liver but was also detected on macrophages of the adrenal gland, placenta, synovium, intestine and peritoneum (data not shown). CRIg was absent from human splenic macrophages, Langerhan cells, microgial cells and bone-marrow derived macrophages, as well as a variety of human and mouse macrophage cell lines (THP-1, RAW275, PU1.1, J774; results not shown). Together, these results indicate that CRIg is highly expressed on a population of resident macrophages in diverse tissues.

Example 18

CRIg Binds C3b and iC3b

Materials and Methods

Complement Proteins

Human and mouse C3 was isolated according to the method of Hammer et al. (*J. Biol. Chem.* 256(8):3995-4006 (1981)) with an additional Protein A column to remove contaminating IgGs. To obtain hC3b, hC3 was incubated with CVF, hfB, ug, hfD in 10:10:1 molar ratio at 37° C. for one hour in the presence of 10 mM MgC12. The hC3b fragment was subsequently isolated by a strong anion exchanger monoQ 5/50 (Amersham Biosciences, Piscataway, N.J.) and Superdex S-200 10/300 GL gel filtration column (Amersham Biosciences, Piscataway, N.J.) for a purity of >95% by Coomassie Blue-stained gel. To generate C3b dimers, C3b prepared as above was reacted for 3 days at 4° C. in PBS pH 7.0 with bismaleiidohexane (Pierce) in methanol in a 2.2:1 molar ratio. Cross-linking was generated through the free sulfhdryl group by breaking the thioeser bond. With this procedure, the yield was over 50%. The dimers were purifiee by a Superdex S-200 10/300 GL gel filtration column (Amersham Biosciences, Piscataway, N.J.). The dimers were 95% pure based on a Coomassie Blue-stained gel. Hydrolyzed C3 was produced with an addition of 2M methylamine pH 7.0 to C3 in PBS with 10 mM EDTA for a final concentration of 50 mM in the reaction volumn. The reaction was run for 4 hours at 37° C., after which time it was purified over a Superdex S-200 10/300 GL gel filtration column (Amersham Biosciences, Piscataway, N.J.), iC3b and C3c (Advanced Research Technologies) were purified over an Superdex S-200 10/300 GL gel filtration column to separate monomers from dimers. C3d, Factors B, D, and P, complement components C1-9, antibody-sensitices sheep erythrocytes and cobra venom factor were obtained from Advanced Research Techologes (San Diego, Calif.).

Results

The expression of CRIg on a population of highly phagocytic cells, prompted us to explore whether CRIg is involved in binding of opsonized particles. Complement and Fc receptors have been demonstrated to mediate phagocytosis. (reviewed by Aderem and Underhill, Annu. Rev. Immunol. 17:593-623 (1999), Underhill and Ozinsky, Annu Rev. Immunol. 20:825-852 (2002)). In order to determine whether CRIg binds to complement C3, sheep erythrocytes coated with either rabbit IgG (E-IgG) or mouse IgM (E-IgM) were analyzed for their ability to rosette with a Jurkat T-cell line expressing CRIgL in the presence of C3 or C5-deficient human serum. CRIg(L) expressing but not control Jurkat cells, formed rosettes with E-IgM in the presence (C3+), but not absence (C3−), of C3 (FIG. 52A) CRIg did not appear to be involved in Fc-receptor mediated binding since Es opsonized with IgG did not rosette with Jurkat CRIg cells (results not shown).

Figures 52A, 52B:
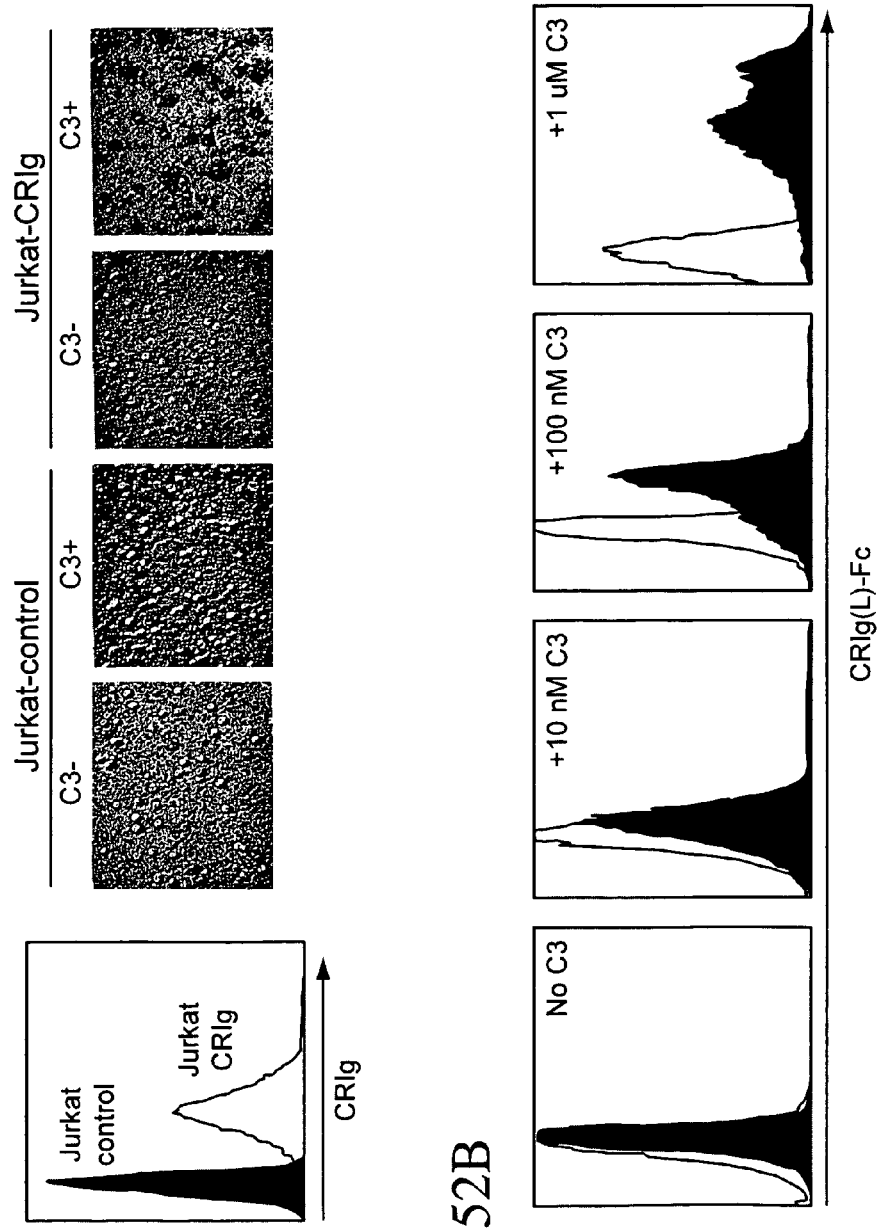
Figure 52C:
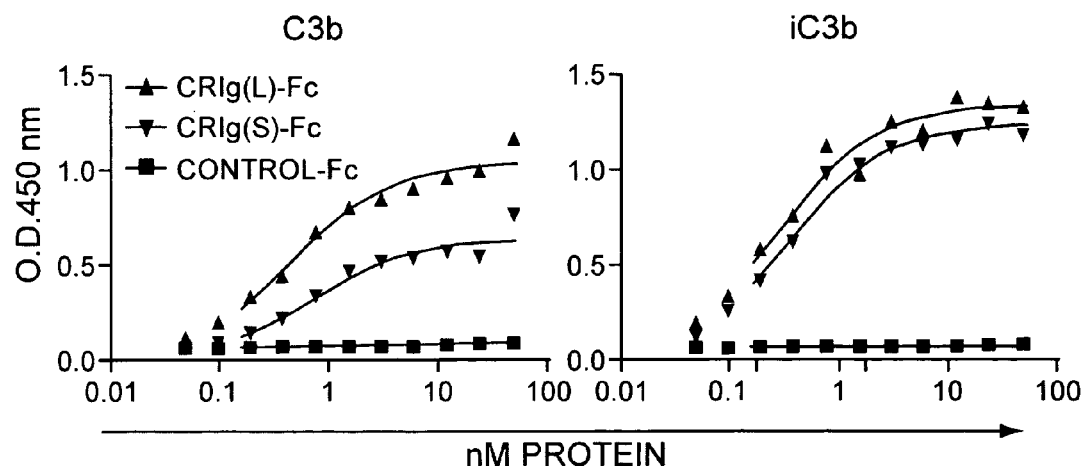

To test whether CRIg can directly bind to complement components on cell surfaces, a soluble form of human CRIg was generated in which the ECD of CRIg was fused to the Fc portion of human IgG1. The huCRIg-long-Fc, but not control-Fc, fusion protein bound to E-IgM opsonized in the presence, but not in the absence, of C3 (FIG. 52B). Binding was restored when C3 deficient serum was reconstituted with purified human C3. The V-type Ig domain was sufficient for binding since both huCRIg(S)-Fc and muCRIg-Fc were capable of binding to E-Igm (results not shown).

Figure 52D:
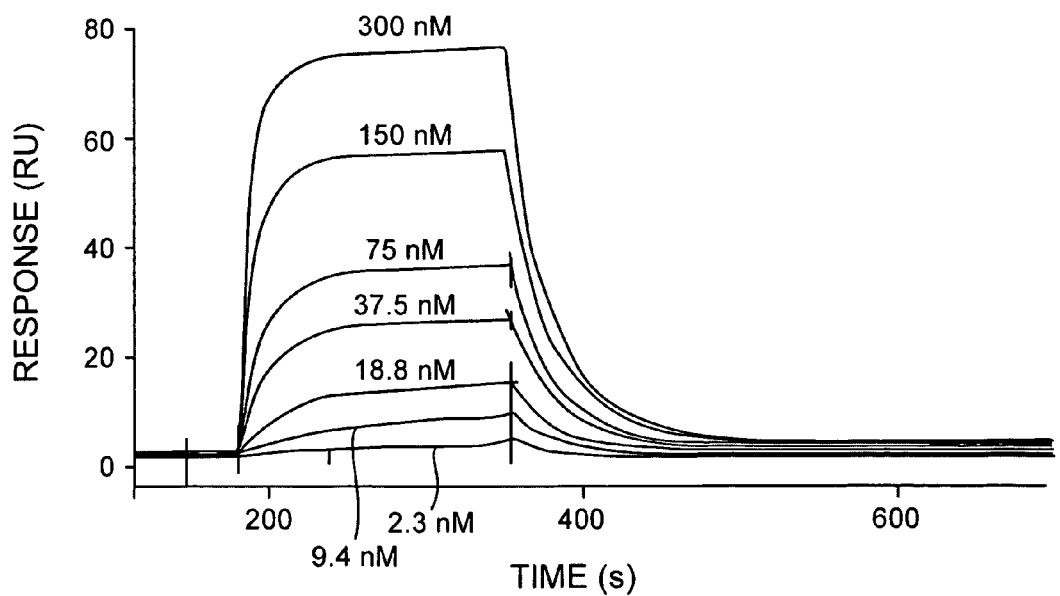

As a result of complement activation inducing a cascade of enzymatic reactions, C3 is cleaved into its muptiple breakdown products C3b, iC3b, C3c, C3dg and C3d, each of which could serve as a binding partner for CRIg. Using a plate bound ELISA, huCRIg(L) and huCRIg(S)-Fc, but not control Fc demonstrated satureable binding to C3b nd iC3b (FIG. 52C), but not to C3, C3a, C3c or C3d (results not shown). Similar binding was observed for huCRIgL-ECD, lacking the Fc portion, and muCRIg-Fc, and binding to iC3b was greater than to C3b (results not shown). Conversely, soluble C3b also bound to plate-coated huCRIg(L)-Fc and was competed for by huCRIg(L)-ECD (results not shown). Hence, CRIg can bind C3b and iC3b in solution or when C3b and iC3b are bound to a substrate. Since C3b is present as a multimeric form when deposited on cell surfaces, the binding of CRIg was further assessed to artificially assembled C3b dimers (C3b2). C3b2 bound to huCRIg(L) with a Kd of 131 nM (FIG. 52D) and to huCRIg(S) with a Kd of 44 nM, as measured by surface plasmon resonance (FIG. 52D).

Figure 51B:
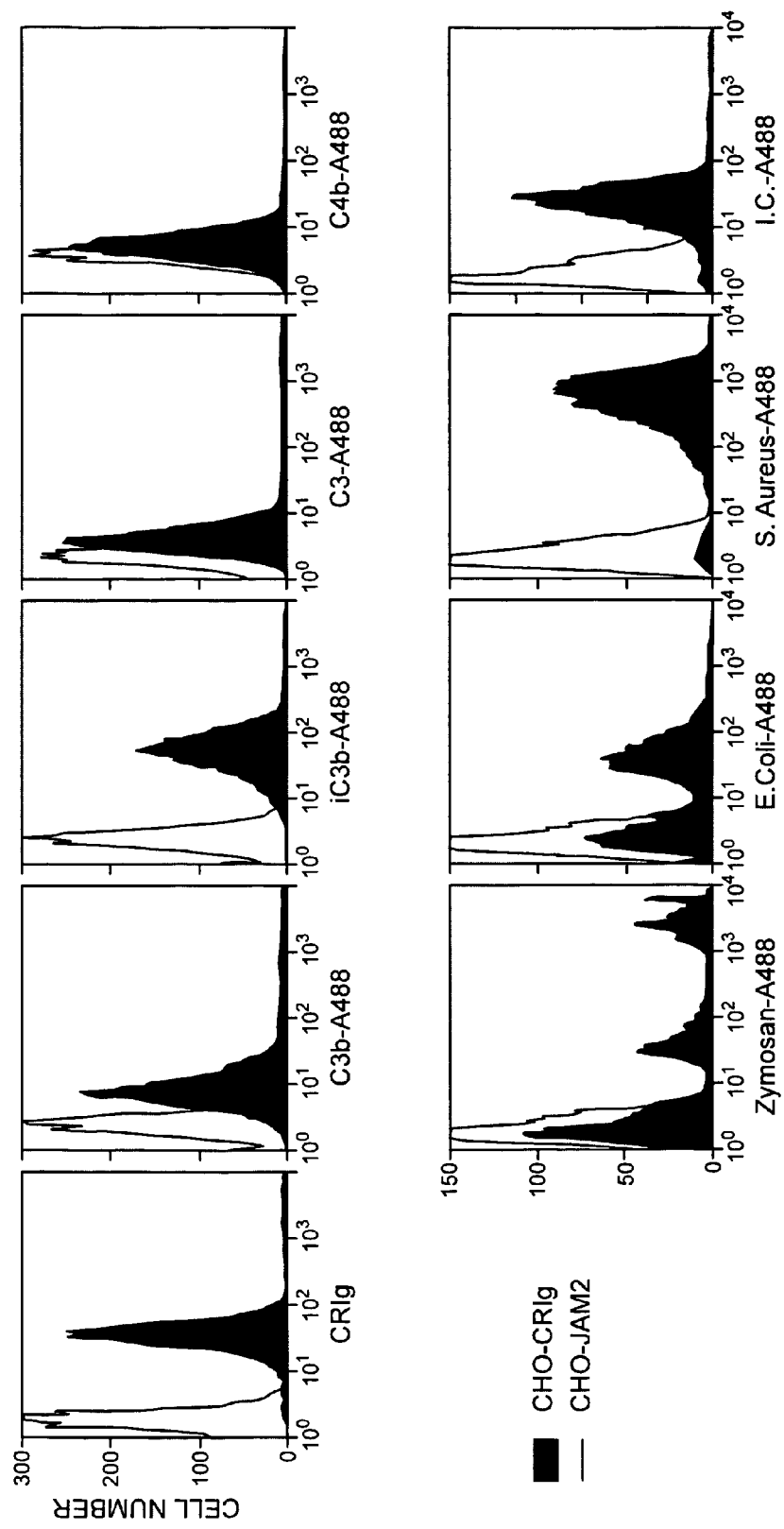
Figure 52E:
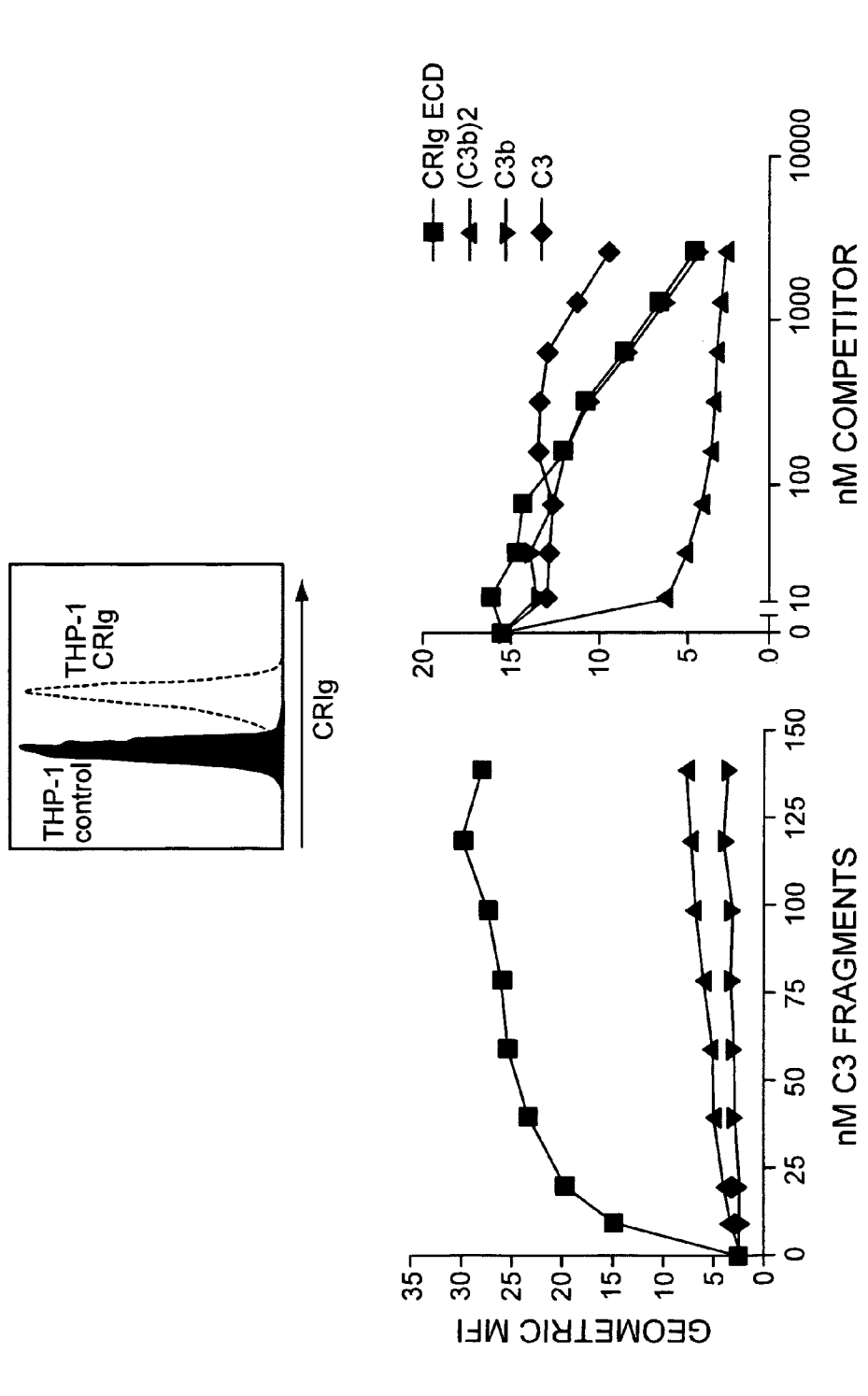

To complement these biochemical studies, we evaluated the binding specificity of cell surface CRIg for C3-derived products. A488-labeled dimeric form of C3b2 bound to the surface of CRIg+, but not CRIg–, THP-1 cells (FIG. 52E). Binding was specific since it was competed for by the addition of soluble unlabeled C3b2, C3b monomer, and huCRIg (L)-ECD but not by native C3. In addition to binding to soluble complement fragments, muCIg expressed on the surface of a CHO cell line also bound to various particles opsonized in C3 sufficient, but not in C3 deficient, serum (FIG. 51B). Together, these studies demonstrate that CRIg expressed on the cell surface as well as soluble CRIg (CRIg-FC) is a receptor for iC3b and C3b.

Example 19

CRIg Expression on Kupffer Cells in Necessary for Binding of Soluble or Particle-bound C3 Fragments
Materials and Methods
1. Generation of CRIg Knock Out (ko) Mice
All animals were held under Sterile Pathogen Free conditions and animal experiments were approved by the institutional animal care and use committee of Genentech. CRIg ko embryonic stem cells were generated by electroporation of a linearized targeting vector replacing exon I with a neomycin-resistance gene (FIG. 53A) into C2B6 embryonic stem (ES) cells. Clones resistant to neomycin were selected, and homologous recombination was confirmed by Southern blotting. Seven out of 100 clones screened were positive for homologous recombination Two targeted clones were injected into C57VL/6 blastocysts and transferred to pseudopregnant foster mothers, and the resultant male chimeric mice were bred to C57BL/6 females to obtain +/– mice. Germline transmission was verified for the 2ES cloned by Southern blot analysis or tail DNA from F1 offspring (FIG. 42B). Interbreeding of +/– mice was performed to generate –/– CRIg mice. The phenotypes of the two clones were identical. For routine genotyping by a PCR method, a common sense primer 5'-CCACTGGTCCCAGAGAAAGT-3' (SEQ ID NO: 22), and a wild-type specific (5'-CACTATTAGGTG-GCCCAGGA-3') (SEQ ID NO: 23) and knock out specific (5'-GGGAGGATTGGGAAGACAAT-3') (SEQ ID NO: 24) antisense primer were used, amplifying a 306 bp fragment for the wild-type allele and a 406 bp fragment for the mutant allele. The generation of C3 ko mice has been described previously (Naughton et al., Immunol. 156:3051-3056 (1996). To generate CRIg/C3 double knock out mice, C3 ko mice on a mixed s129/B6 background (F2) were crossed with CRIg ko mice. The F1 females heterozygous for both alleles were subsequently crossed with C3 heterozygous males, heterozygous for the CRIg allele. The offspring from this mating was used in the studies. C57B6 mice used for analysis of CRIg expression by flow cytometry were purchased from Jackson Laboratories (Bar Harbor).

Figure 53C:
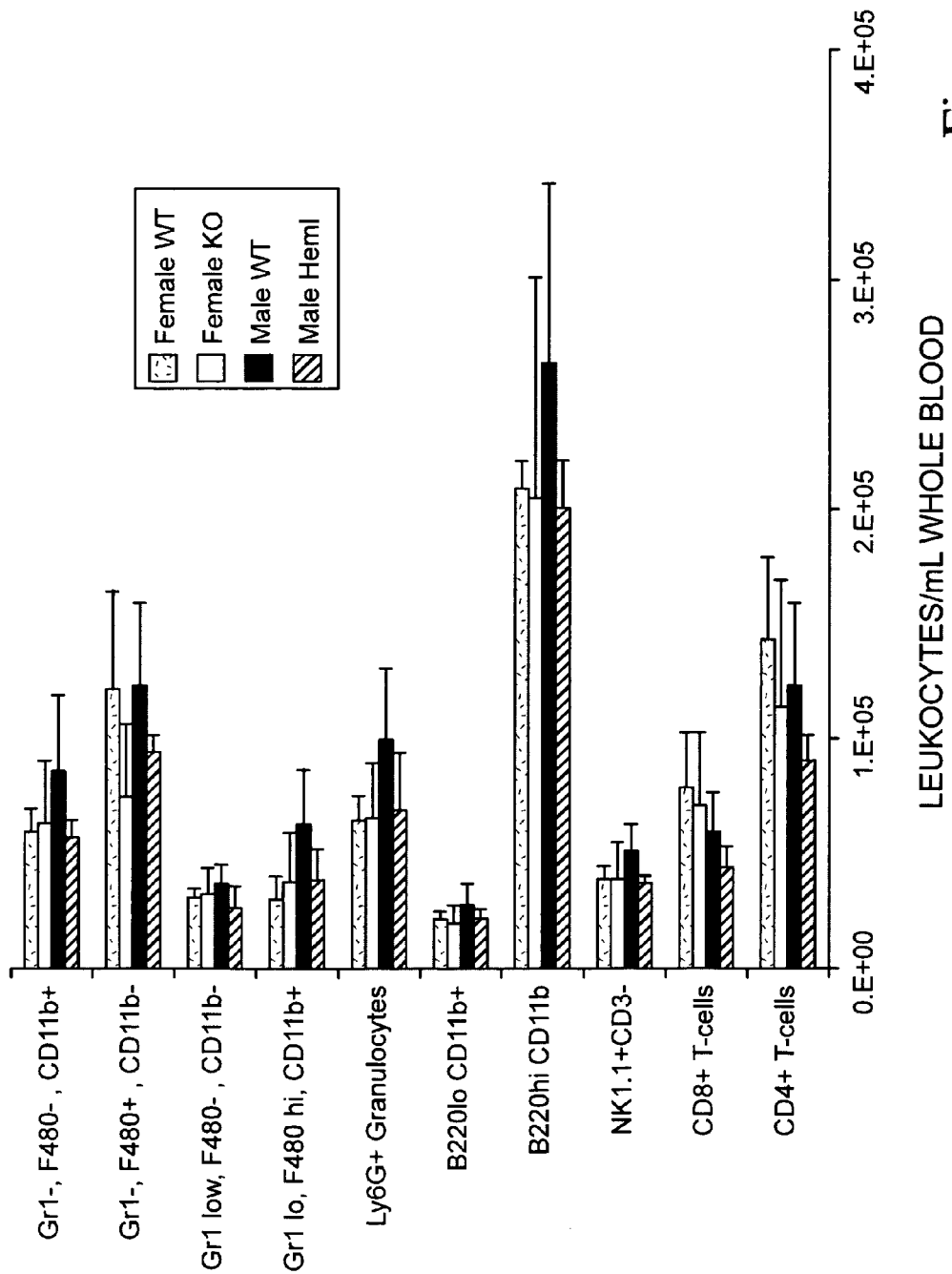
Figure 53D:
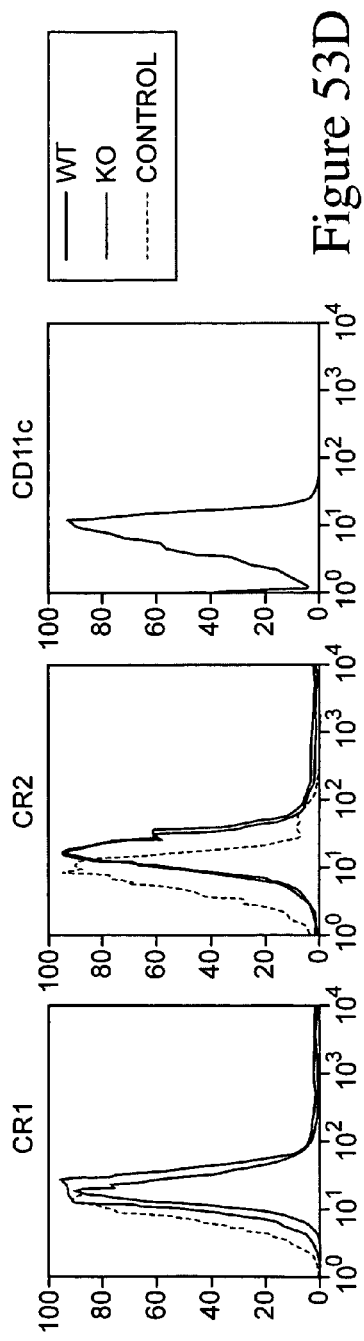
Figure 54B:
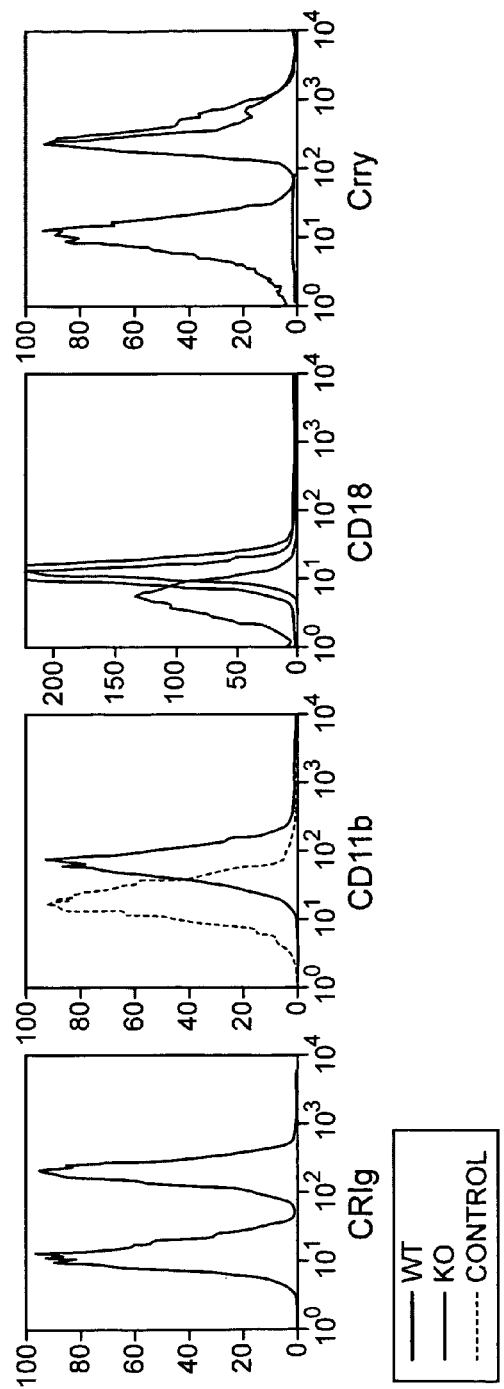
Figure 54C:
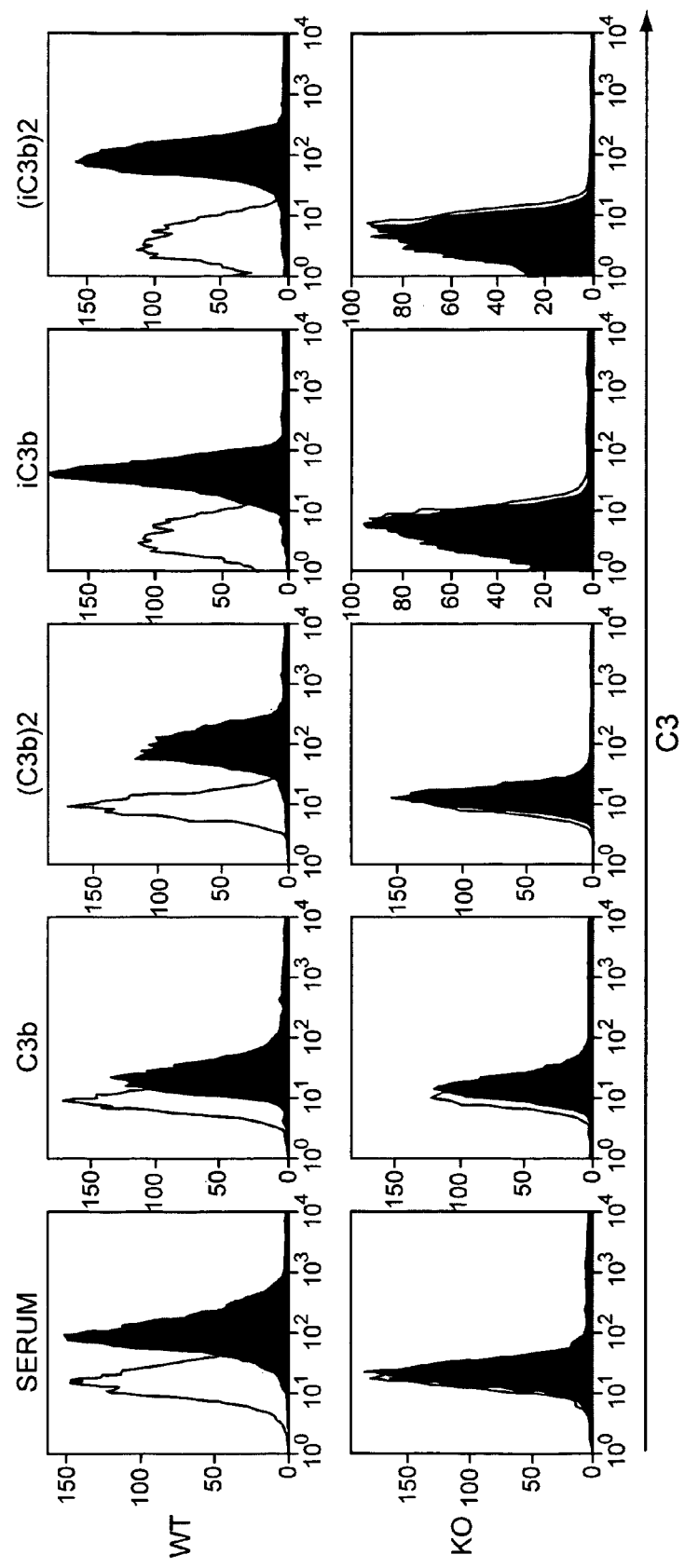

2. Western Blotting and Deglycosylation
Human and murins macrophages were lysed in PBS containing 1% SDS, 0.1% Triton X-100 and a protease inhibitor cocktil (Boehringer). Following cntrifugation at 10,000 g, the soluble fraction was run on a SDS gel and transferred to nitrocellulose membranes. CRIg protein was visualized using ani-CRIg antibodies and HRPO-conjugated secondary antibodied followed by chemiluminescence detection of bound antibody by ECL (Amersham). For determination of the glycosylation state of CRIg, CRIg-gD expressing cells were immunoprecipitated wi\th an anti-gD antibody, treated with PNGase, O-glycosydase and neuraminidse according to the manufacturer's instructions (Biolabs, NE), and subjected to Western blot analysis using bioinylated anti-gD antibodies.
Results
To study the biological function of CRIg, mice with a null mutation in the CRIg gene were generated by homologous recombination as described above and shown in FIG. 42A. Deletion was confirmed by Southern blotting (FIG. 53B), Western blotting of peritoneal exudates cell lysates (FIG. 54A) and flow cytometry (FIG. 54B). Mice were bodn at the expected Mendelian ratios and exhibited no gross phenotypic or histopathological abnormalities. Absolute numbers of immune cells in different lymphoid compartments were similar in blood, spleen and lymph nodes from wt and ko animals (FIG. 53C). In addition, no differences were observed in the number of F4/80+ KCs and hert macrophages when analyzed by flow cytometry and immunohistochemistry, respectively (results not shown). Expression levels of other compartment inding proteins, including the α and β chains of CR3 and complement-receptor related gene y (Crry) on KCs were not altered (FIG. 54C). Similarly, the low or undetectable expression CR1, CR2 or CD11c, the beta chain of CR4, were comparable between wt or ko KCs (FIG. 53D).

Figure 53E:
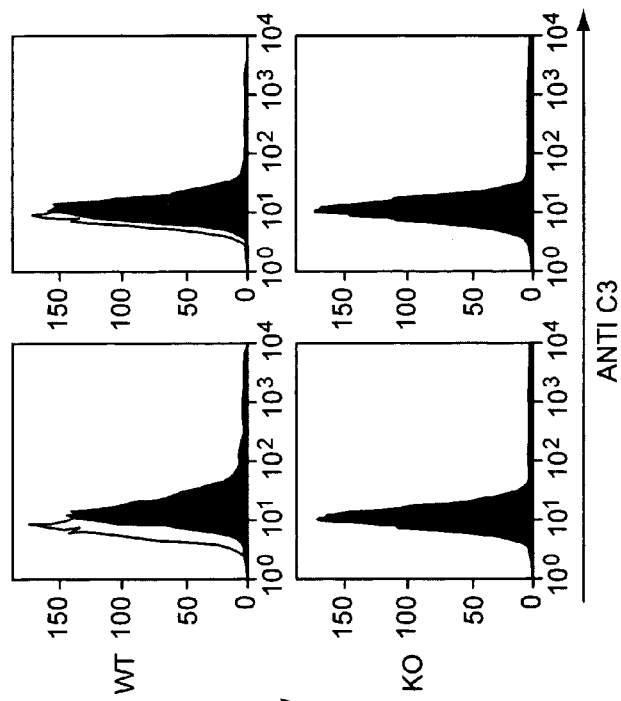

Next, the binding capacity of CRIg wt and CRIg ko KCs for C3 degradation products was tested. The C3 fragments (C3b, C3b2 and iC3b) were readily deposited on the surface of CRIg wt KCs (FIG. 54B). In contrast, no binding of C3b, C3b2, iC3b or iC3b2 were detected in CRIg ko KCs. Little or no binding of C3 and C3c to either wt or ko KCs was detected (FIG. 53E).

To extend the analysis from the binding of soluble C3 fragments to the binding of C3 fragments bound to cell surfaces, the role for CRIg on KCs to bind C3-opsonized IgM-coated erythrocytes was examined. CRIg ko KCs demonstrated an ~60% reduction in E-IgM rosetting when compared to CRIg wt KCs (FIG. 54D). CR3 had a minor contribution to the total binding activity as a further reduction (<20%) in rosette formation was observed with the addition of CR3 blocking antibody. Hence, CRIg expression is necessary for binding of C3 degradation products and C3-opsonized particles to Kupffer cells.

Example 20

CRIg Internalizes and is Expressed on Recycling Endosomes
As binding of C3 opsonized particles to its receptors may trigger their subsequent endocytosis (Fearon et al., *J. Exp.*

Figure 55A:
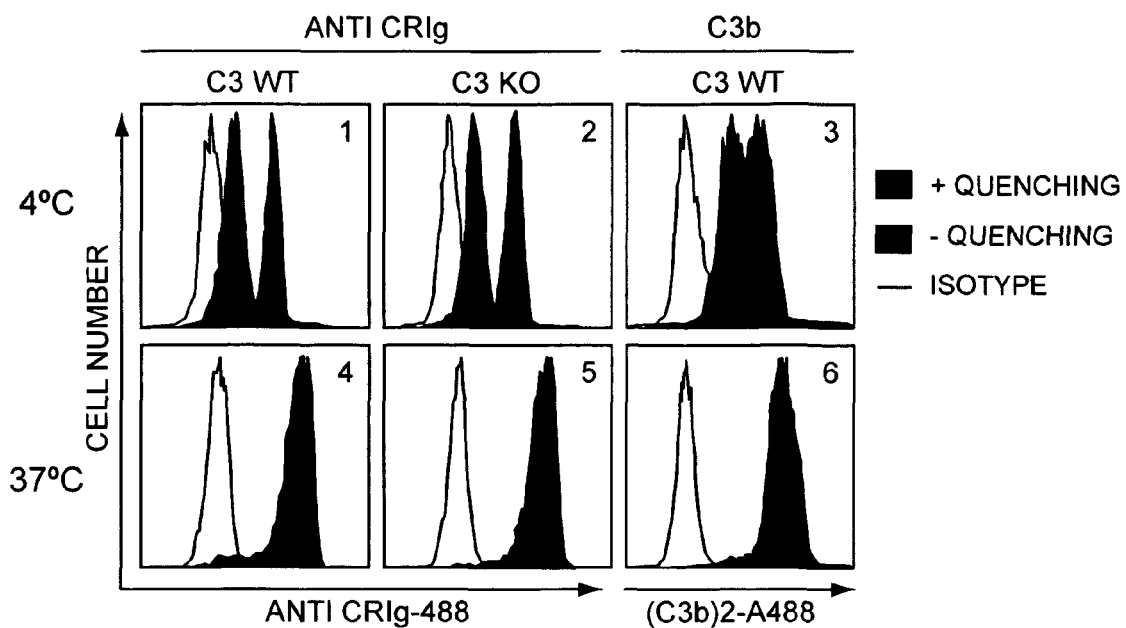
Figure 55B:
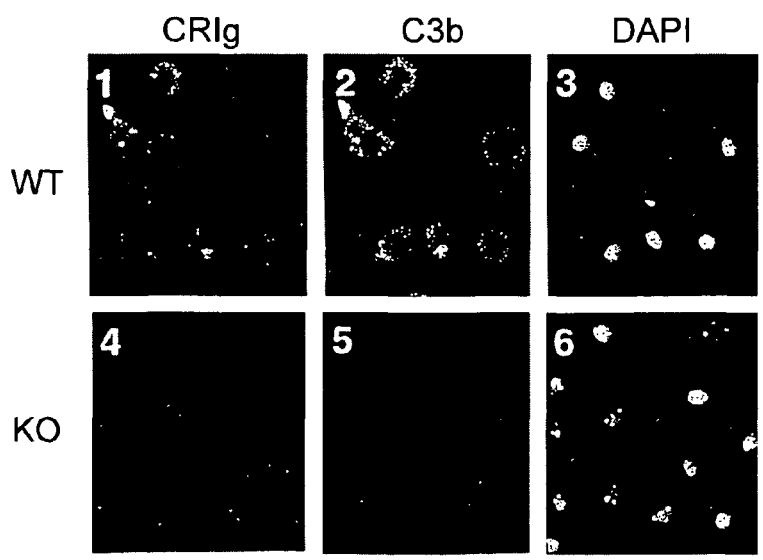
Figure 55C:
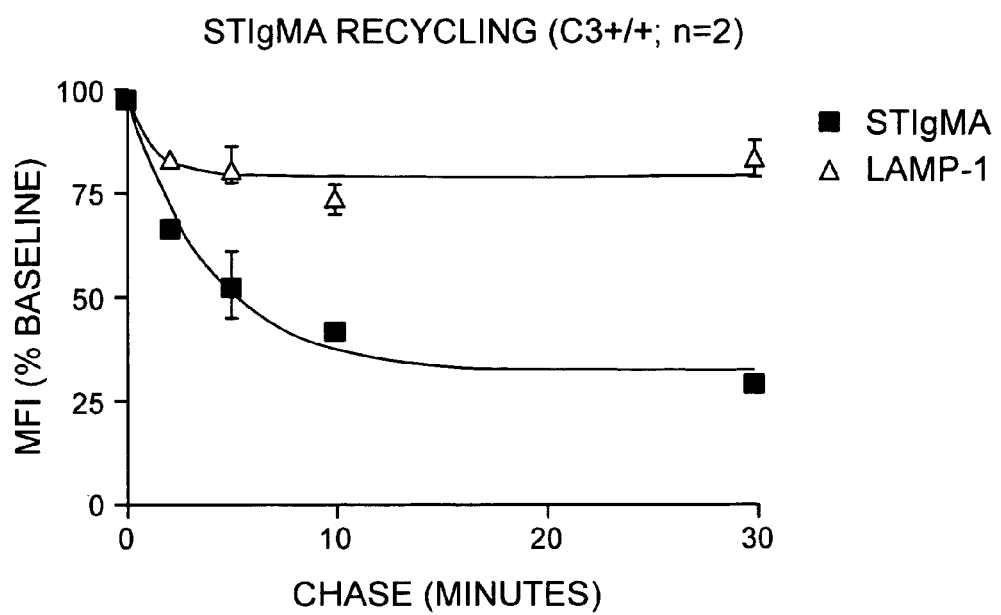

*Med.* 153:1615-1628 (1981); Sengelov, *Crit Rev. Immunol.* 15:107-131 (1995)), polyclonal antibodies that quench the Alexa488 fluorochrome (Austin et al., *Mol. Biol. Cell* 15:5268-5282 (2004)) were used to analyze whether CRIg and C3b internalize in KCs. A488-conjugated anti-CRIg mAbs were pre-incubated with KCs at 4° C. Addition of anti-A488 antibody at 4° C. suppressed fluorescence of surface-bound anti-CRIg antibodies as shown in FIG. 47A, panel 1. When A488-conjugated anti-CRIg mAbs were incubated with KCs at 37° C. for 30 minutes followed by incubation with anti-A488 antibodies, fluorescence was no suppressed (FIG. 55A, panel 4) indicating that the anti-CRIg antibodies internalized upon transfer of cells from 4° C. to 37° C. and therefore were not accessible to the quenching anti-A488 antibodies. A similar result was found for C3b (FIG. 55A, panels 3 and 6). Internalization of anti-CRIg antibodies was not dependent on the presence of C3 since uptake of the antibody occurred in KCs isolated from C3 ko mice (FIG. 55A, panels 2 and 5) and in the absence of serum (results not shown). Immunohistochemistry further confirmed the presence of anti-CRIg antibodies and C3b in the cytoplasm of KCs from CRIg wt, but not ko, mice (FIG. 55B). Over time, when KCs coated with A488-conjugated anti-CRIg antibodies were incubated in the presence of extracellular anti-A488 antibodies, a decrease in fluorescence over time was observed and suggests that anti-CRIg antibodies recycle back to the cell surface (FIG. 55C). The time course of recycling was again independent of C3 since the kinetics of quenching was similar in the presence and absence of C3 (results not shown). In contrast, antibodies to the lysosomal protein Lamp1 remained intracellular and did not diminish with time. These results indicate that CRIg functions as a receptor for C3b located on a pool of constitutively recycling membranes.

Figure 57A:
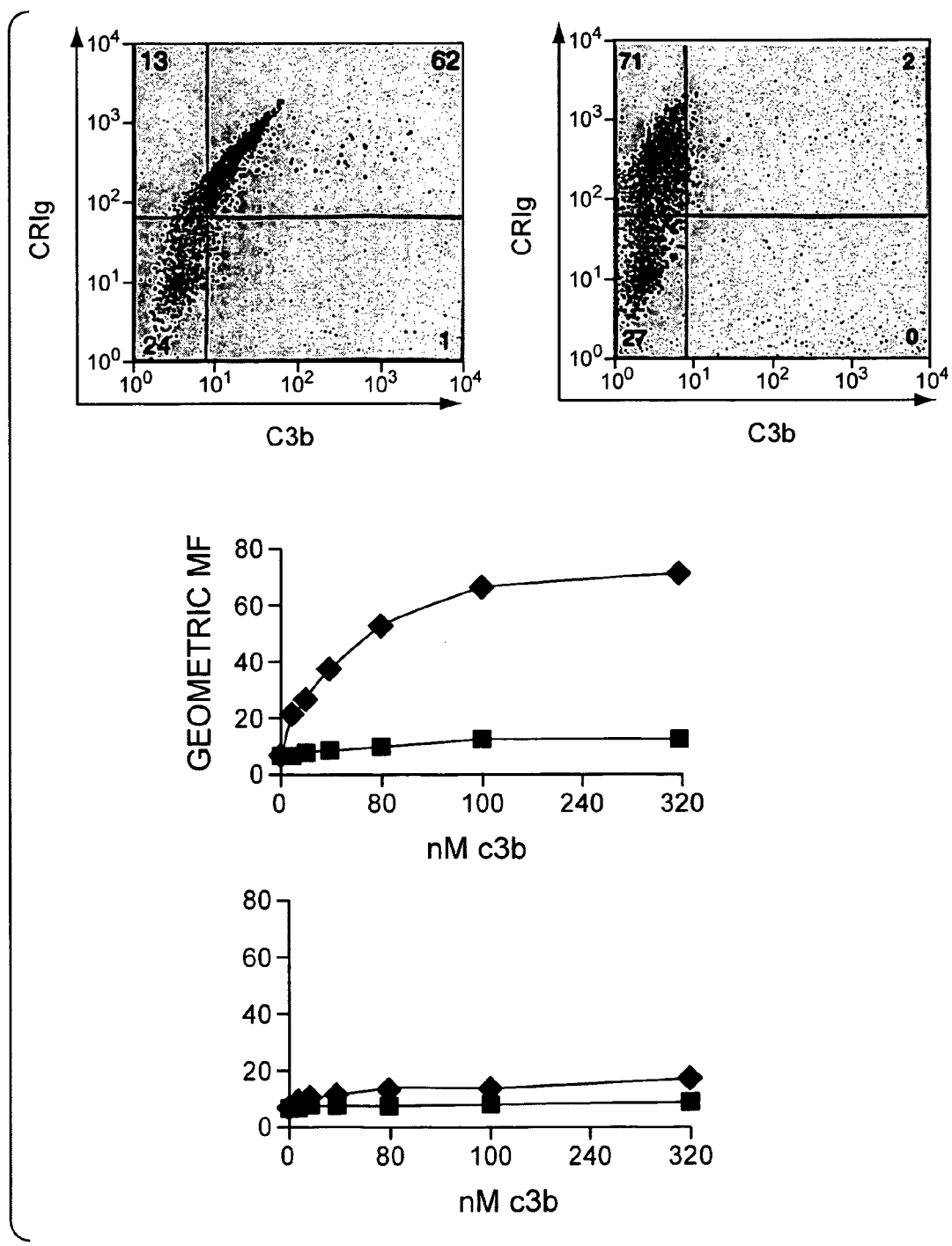
Figure 57B:
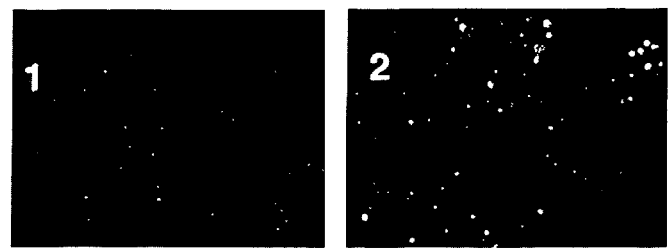
Figure 57C:
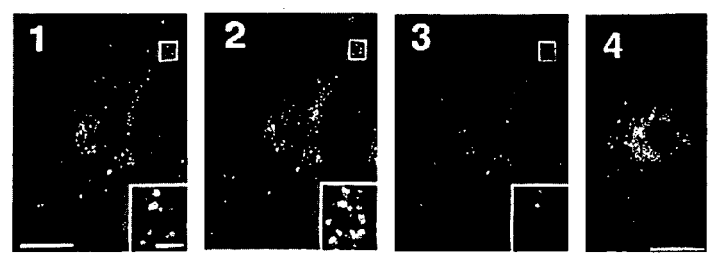
Figure 57D:
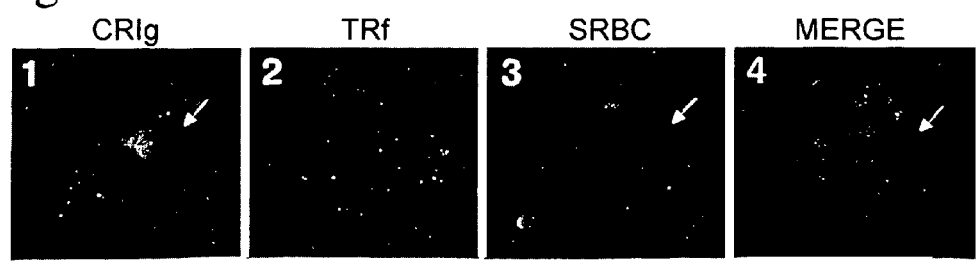
Figure 57E:
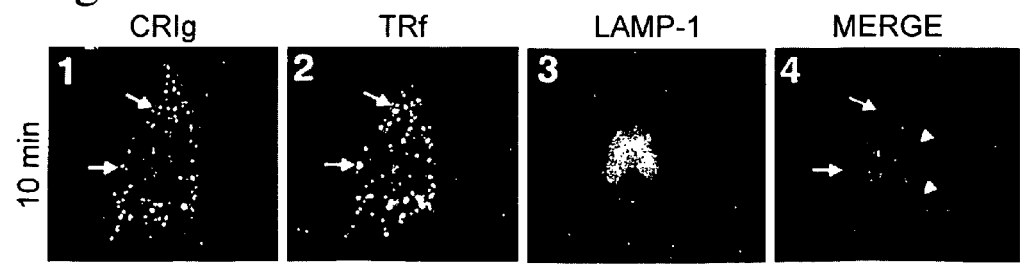

To further determine the subcellular compartments in which CRIg recycles, human monocyte-derived macrophages (MDMs) were visualized using deconvolution microscopy using transferring as a marker for recycling endosomes and Lamp1 as a marker for lysosomes. MDMs cultured for 7 days express CRIg on 60% of the cells that show saturatable binding of C3b (FIG. 55A) that can be competed off with the extracellular domain of huCRIg(L) (results not shown). Macrophages coated with anti-CRIg antibody at 4° C. demonstrate focal CRIg expression in F-actin rich filopodial extensions (arrowheads, FIG. 56A, panels 1-3). In addition, the CRIg antibody co-localized with C3b to the cell surface (results not shown). Transfer of cells from 4° C. to 37° C. followed by a 10 minute incubation at 37° C. (FIG. 56B) resulted in rapid intern CRIg antibody and C3b into a transferrin+ endosome compartment located in the periphery of the cell (FIG. 56B, panels 14, arrows) and bordering the Lamp1+ compartment (arrows FIG. 57D, panel 14). CRIg remained localized within the endosomal compartment and was not degraded in the lysosome with prolonged chase times up to 24 hours (results not shown). Incubation of macrophages with anti-CRIg antibodies did not influence CRIg distribution since internalized CRIg antibody completely overlapped with the total pool of CRIg detected post fixation with a polyclonal antibody (FIG. 57C, panels 1-3) and was independent of the presence of C3 in the medium (FIG. 57C, panel 4). Together, these results indicate that CRIg is present on recycling and early endosomes and that internalization of CRIg takes place in the absence of ligand or cross-linking antibody.

Figure 56C:
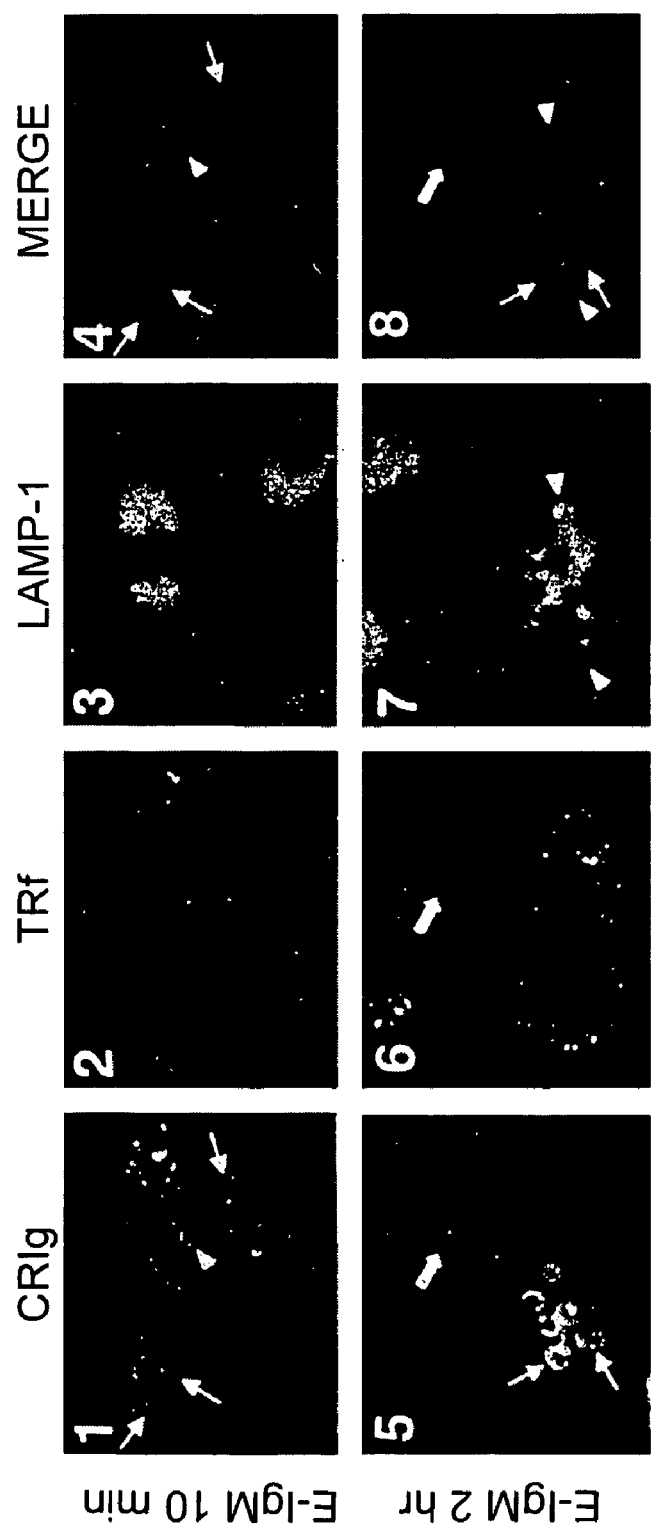

Since the majority of C3b and iC3b was deposited on particles exposed to seum (Brown, *Curr. Opin. Immunol.* 3:76-82 (1991)), next we explored the localization of CRIg positive endosomes in macrophages during phagocytosis of C3 opsonized particles. Upon encounter with iC3b-opsonized sheep red blood cells (E-IgM), CRIg rapidly (10 minutes) redistributed from transferrin positive vesicles to the forming phagosome visible as a ring around the engulfed erythrocytes (FIG. 56C, panels 1 and 4, arrows). After 2 hours following incubation of macrophages with C3 opsonized particles, phagosomes had matured as shown by their translocation into the lysosomal compartment (FIG. 56C, panels 5-8). CRIg was highly expressed on the phagosomal membranes surrounding the C3 opsonized particles (FIG. 56C, panels 5 and 8, arrows) and in most macrophages were no longer present within the transferrin+ endosomal compartment. While CRIg retained present on a subset of phagosomes in the lysosomal compartment, its expression did not overlap with that of LAMP-1 (FIG. 56C, panels 7 ad 8, arrowheads). The absence of CRIg in the LAMP-1+ membranes was unlikely the result of lysosomal degradation of CRIg since protease inhibitors were continuously present during incubation. In some of the macrophages that has ingested E-IgM but lck CRIg+ phagosomes, CRIg+ was co-localized with the transferrin+ compartment (thick arrow, FIG. 56C5, panels 5 and 8, thick arrows) suggesting CRIg+ returns to the recycling compartment following transfer of the E-IgM to the lysosomal compartment.

Taken together, these results indicate that CRIg is recruited from endosomes to sites of particle ingestion and participates in the initial stages of Phagosome formation, but excapes from the phagosome upon phagosome-lysome fusion to return to the endosome compartment.

Example 21

Mice Lacking CRIg are Susceptible to Infection with *Listeria Monoctogenes*

Materials and Methods

1. Microorganisms, Infection of Mice and Evaluation of Listerial Growth by Determination of CFU Counts Virulent *L. monocytogenes* (LM) (ATCC strain 43251), was used in all experiments. Bacterial virulence was maintained by serial passage in BALB/c mice. Fresh isolates were obtained from infected spleens, grown in brain heart infusion (liquid) or brain heart infusion plates (Difco Laboratories, Detroit, Mich.). Bacteria were washed repeatedly, resuspended in sterile phosphate-buffered saline (PBS), and then stored at −80° C. in small aliquots in PBS containing 40% glycerol. Mice were inoculated intraveneously in the tail vein with *L. monocytogenes* at various doses. For the observation of bacterial growth in the various organs, we injected intravenously $1 \times 10^4$ colony-forming units (CFUs) of Listeria, a dose not lethal to either CRIg ko or CRIg wt mice. The number of viable bacteria in the inoculum, homogenates of the liver and spleen, and infected cells was determined by plating 10-fold serial dilutions on brain-heart infusion agar (Difco Laboratories) plates. The numbers of CFUs were counted after incubation for 24 hours at 37° C.

2. Determination of Listeria-A488 Uptake in Kupffer Cells

Live L. Monocytogenes was labeled with A-488 labeling kit according to the manufacturers instructions (Molecular Probes, Oregon). The number of live Listeria after the labeling procedure was assessed by colony counts. CRIg wt or CRIg ko mice were injected intravenously with 10 million CFU LM. One hour later, livers were perfused and Kupffer cells were isolated according to the methods described above. Cells were stained with a PE-labelled antibody to F4/80, and positive cells were isolated using anti PE beads (Miletnyi) followed by sorting with a MoFlo flow cytometer (DakoCytomation, Ft. Collins, Colo.). F4/80 positive cells were collected on coverslips and the number of internalized labeled bacteria was estimated using confocal and light microscopy. Number of bacteria per cell was counted in 400 cells from 4 different fields per slide. Phagocytic index was calculated by multiplying average number of bacteria per cell with percentage of kupffer cells containing at least one bacteria. The results show average and standard deviations of phagocytic index obtained from four different animals.

Results

Figure 58A:
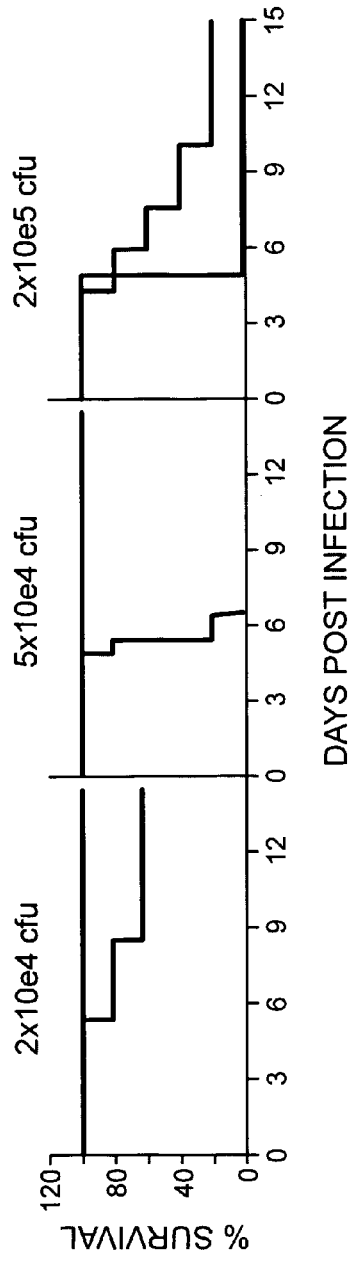

Based on the binding of CRIg to C3b/iC3b-opsonized particles, to explore a role for CRIg in phagocytosis of complement opsonized particles in vivo, CRIg wt and KO mice were infected with various doses of Listeria Monocytogenes (LM), a gram-positive facultative bacterium that, when exposed to serum, activates the alternative pathway of complement which predominantly depostis C3b and iC3b on the bacterial surface (Croize et al., Infec Immunol. 61:5134-5139 (1993)). CRIg KO mice were significantly more susceptible to LM infection as shown by an increased lethality (FIG. 58A). Conversely, pretreatment with CRIg-Ig fusion protein increased susceptibility of CRIg wt, but not CRIg ko mice (FIG. 62).

Figure 58C:
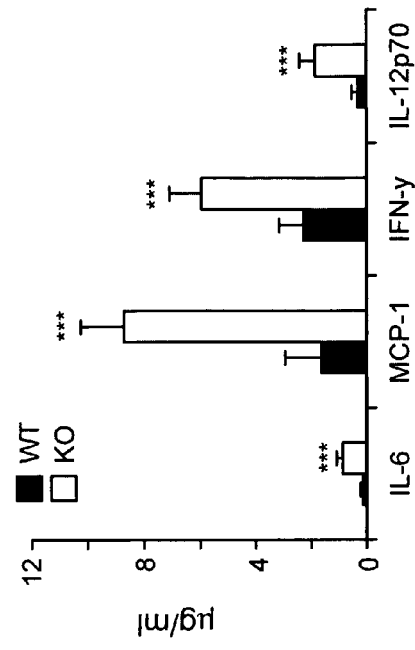
Figure 58B:
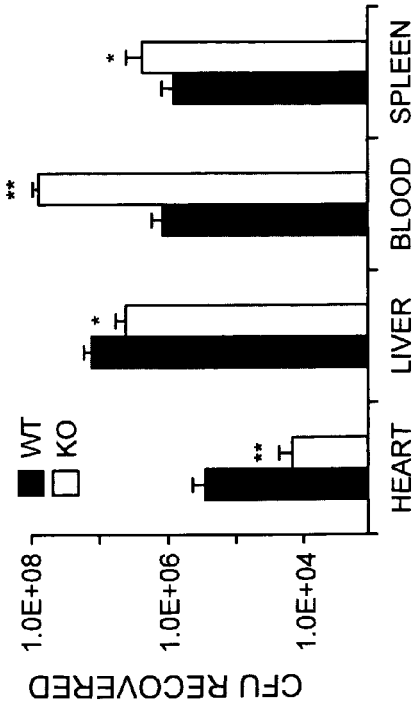
Figure 58D:
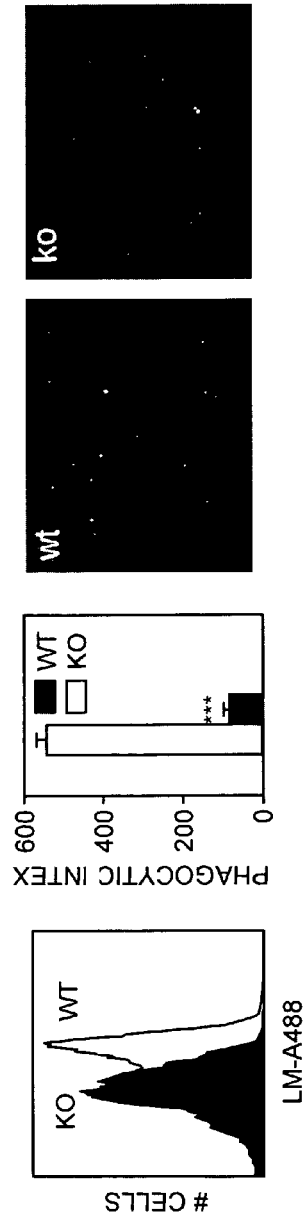
Figure 58E:
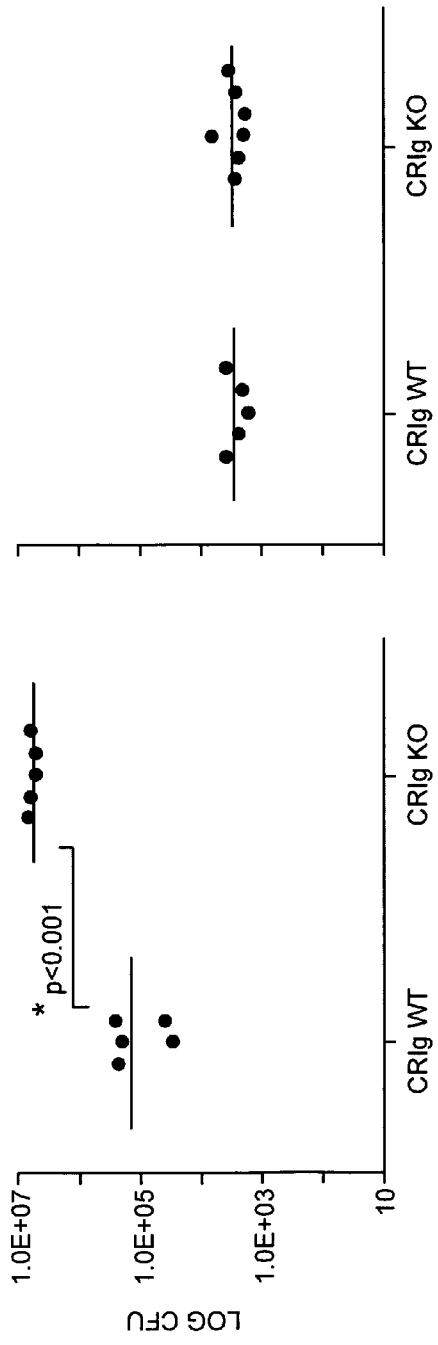

4881 In line with a role of CRIg in binding and phagocytosis of complement C3 opsonized particles, CRIg ko mice had a reduced clearance of LM from the blood that resulted in an increased LM burden in the spleen and lung (FIG. 58B). There was also a decreased LM burden in the liver and heart of infected mice which likely reflects the presence of CRIg expressing macrophages in these tissues (FIG. 58B). Inflammation responses were elevated in CRIg ko mice reflected by increased serum levels of IFN-γ, TNF-α and IL-6 (FIG. 58C). Consistent with the requirement of CRIg in the clearance of C3-opsonized particles, CRIg ko KCs demonstrated significantly reduced binding and phagocytosis of LM as compared to CRIg wt KCs (FIG. 58D). Finally, the increased Listeria load detected in the blood of CRIg ko mice was dependent on C3 as infection of C3 ko mice abrogated the difference in bacterial titer in CRIg ko vs. wt mice (FIG. 58E). Interestingly, the circulating levels of bacteria were significantly lower in C3 ko mice as compared to C3 sufficient mice, and likely reflect the increased involvement of C3-independent mechanisms responsible for Listeria clearance in C3 ko mice. The rapid clearance in the absence of C3, however, does not result in efficient pathogen elimination in the long term since C3 deficient mice dye within 2 days following gram-positive bacterial infection (Cunnion et al., *J. Lab. Clin. Med.* 143: 358-365 (2004)). These results strongly indicate that CRIg expressed on liver Kupffer cells plays a critical role in the rapid clearance of complement C3 oposonized pathogen from the circulation.

Example 22

Inhibition of Complement-Mediated Immune Hemolysis with huCRIg molecules

It is well established that rabbit erythrocytes specifically activate the complement alternative pathway, with a resulting lysis of the cells by the C5b-9 complex (Polhill, et al., *J. Immunol.* 121(1), 363-370 (1978)). In particular, rabbit erythrocytes initiate the alternative complement cascade, and the resulting formation of MAC causes lysis of these cells. If a test compound is capable of inhibition of the alternative pathway, then addition of the reagent to rabbit erythrocytes bathed in serum (in the present case serum of cynomolgus monkeys or in human C1q depleted serum) should prevent cellular lysis. This can be assayed by monitoring changes in absorbance of light at 412 nm wavelength caused by the release of hemoglobin from lysed erythrocytes. In the cyno serum experiments, blood was collected from a femoral vein of cynomolgus monkeys. No anticoagulant was used. Samples were allowed to clot at room temperature. The samples were centrifuged, and serum was harvested and stored in a freezer set to maintain −60 to −80° C. Rabbit red blood cells (RRBCs) were washed three-times in GVB ((1× veronal buffer (Biowhittaker), 0.1% gelatin), and resuspended to 1×10⁹/ml in GVB. GVB, huCRIg (short, long, or long ECD) were added, followed by the addition of 10 µl GVB+/EGTA (GVB, 0.1 M EGTA, 0.1 M MgC12). 10 µl cyno or C1q depleted serum (Quidel) was added, followed by the addition of 10 µl RRBCs, and the mixture was mixed by finger flick. Following incubation for 45 min at 37° C., in warm room with shaking, 250 µl GVB/10 mM EDTA were added, and the mixture was centrifuged at 2500 rpm for 5 minutes. 250 µl aliquots were used and read at 412 nm. The results shown in FIGS. 63A and B (cyno serum) and FIGS. 64-66 (human serum) demonstrate that the tested CRIg compounds inhibit complement.hST-L: human CRIg-long hST-S: human CRIg-short
hST-L ECD: human CRIg-long ECD
hPIGR: human polymeric immunoglobulin receptor
fH: complement factor H Example 23

Testing Murine CRIg-Fc Fusion Proteins in a Mouse Model of Choroid Neovascularization Choroid neovascularization (CNV) can be induced experimentally by laser burns in the retina. In the present study, 40 C57BL-6 mice (Charles River Laboratory) were divided into two treatment arms.

Group 1 (control): i.p. injection of 12 mg/kg gp120 mIgG1 on days −1, 1, 3 and 5.

Group 2: i.p. injection of 12 mg/ml murine CRIg (mCRIg) on days −1, 1, 3 and 5.

In each arm, the animals were anesthesized by subcutaneous (s.c.) injection of a mixture of ketamine (25 mg/g) and xylazine (1.28 mg/g). Pupils were dilated using a single drop of 1% tropicamide. The animals were then fixed in a plastic mold. A diode laser (100-µm spot size) was used to generate three lase spots in the eye surrounding the optic nerve, using OcuLight GL Diode Laser (532 nm), a Zeiss 30 W slit lamp and a micro-manipulator. The right eye was lasered with 120 mW, 0.1 seconds, and 100 µm slit size. A bubble formed at the laser spot indicates rupture of the Brach's membrane.

Laser spots were evaluated on day 7 after laser treatment, using confocal microscopy. At this time, animals are anesthesized with isoflurane, and perfused through the heart with 0.5 ml PBS containing 50 mg/ml fluorescein-labeled dextran (Sigma). The eyes were removed and fixed in 1.0% phosphate-buffered formalin, the retinas were discarded, and the remaining eye cup was flat mounted on a slide. Histopathological examination includes immunohistochemical staining of choroid flatmounts for complement fragments and elastin and analysis of the size of the CNV complex by monitoring FITC-dextran-stained vasculature in the eyes by confocal microscopy.

The results are shown in FIGS. 71A and B, where the burn holes in the right eye are scored on a scale of 0-3 and 0-5, respectively.

Example 24

Testing CRIg ECDs and CRIg-Fc Fusion Proteins in Cynomolgus Monkeys Undergoing Laser-Induced Retinal Injury 24 cynomolgus monkeys, either male or female, or 12 males and 12 females are used in this study. The animals are 2 to 7 years old, and weigh 2 to 5 kg.

TABLE 2

Group Designation and Dose Levels

| Group | No. of Animals | Number of Animals Necropsied[a] | | | Dose Level[b] (mg/kg/dose) |
| --- | --- | --- | --- | --- | --- |
| | | Dosing Phase 2 Day 6 | Dosing Phase 1 Day 18 | Dosing Phase 1 Day 32 | |
| 1 (Control)[c] | 12 | 3 | 3 | 6 | 0 |
| 2 (Treated) | 12 | 3 | 3 | 6 | 10 |

[a]The animals scheduled to be euthanized 2 days following laser treatment (Dosing Phase 2) initiates dosing approximately 2 weeks after study start of Dosing Phase 1.
[b]The dose volume is __ mL/kg/dose.
[c]Group 1 receives the vehicle only.

Administration is via intravenous injection through the cephalic vein. Animals are dosed at least once prior to laser treatment, and three-times weekly during the remainder of the study. Doses are based on the most recently recorded body weight, and are in the range of 10-15 mg/kg.

On Day 4, the macula of each eye of all animals undergoes laser treatment by CORL with 532 nm diode green laser burns (OcuLight GL, IRIDEX Corp Inc, Mountain View, Calif.) using a slit lamp delivery system and a Kaufman-Wallow (Ocular Instruments Inc, Bellevue, Wash.) plano fundus contact lens. The laser and supporting equipment are supplied by CORL. The animals are anesthetized with ketamine and xylazine. Nine areas are symmetrically placed in the macula of each eye. The laser parameters include a 75 micron spot size and a 0.1 second duration. The power used is assessed by the ability to produce a blister and a small hemorrhage. Unless hemorrhage is observed with the first laser treatment, a second laser spot is placed adjacent to the first following the same laser procedure (except wattage is adjusted). For areas not adjacent to the fovea the initial power setting is 500 mW; if a second spot is placed, the power is set to 650 mW. For the area adjacent to the fovea the power settings are 400 mW (initial) and 550 mW (second). At the discretion of the retinal surgeon, power settings may be adjusted based on observations at the time of laser.

Clinical Ophthalmic Examinations

Clinical ophthalmic examinations take place for each animal once before initiation of treatment, and on days 8, 15, 22, and 29. The animals are anesthetized with ketamine, and the eyes are dilated with a mydriatic agent. The adnexa and anterior portion of the both eyes is examined using a slitlamp biomicroscope. The ocular fundus of both eyes is examined using an indirect ophthalmoscope. At the discretion of the ophthalmologist, the eyes may be examined using other appropriate instrumentation and photographs may be taken.

Ocular Photographs

Ocular photographs (OP) are taken once on the day of laser treatment (post-laser), on Dosing Phase 1 Days 10, 17, 24, and 3 1, and on Dosing Phase 2 Day 6 (on the day of necropsy). When done concurrently with fluorescein angiography during Dosing Phase 1, OP is done first.

The animals are anesthetized with ketamine and maintained on isoflurane anesthetic when done concomitant with fluorescein angiography and anesthetized with ketamine and xylazine when done alone (i.e., following laser treatment). The eyes are dilated with a mydriatic agent. Color photographs are taken of each eye and include the retina and pertinent ocular abnormalities, stereoscopic photographs of the posterior pole, and nonstereoscopic photographs of two mid-peripheral fields (temporal and nasal).

Fluorescein Angiography

Flurescence angiography is performed once before initiation of treatment for all animals and on Dosing Phase 1 Days 10, 17, 24, and 31 (6, 13, 20, and 27 days postlaser).

Animals are fasted before fluorescein angiography. Animals are anesthetized with ketamine and maintained on isoflurane, and the eyes are dilated with a mydriatic agent. Animals are intubated due to the possibility of emesis following the fluorescein injection. Animals are given an intravenous injection of fluorescein. Photographs are taken at the start and end of the fluorescein injection. Following the fluorescein injection, a rapid series of stereo photographs of the posterior pole is taken of the right eye followed by stereo pairs of the posterior pole of the left eye before 1 minute, and then at each eye at approximately 1 to 2, and 5 minutes. Between approximately 2 and 5 minutes, nonstereoscopic photographs are taken of two mid-peripheral fields (temporal and nasal) of each eye. If fluorescein leakage is observed at the 5-minute time point, a stereo pair of photographs is taken at approximately 10 minutes.

Evaluation of fluorescein angiograms is performed according to the following grading system for evidence of excessive permeability (fluorescein leakage) or any other abnormalities.

| Lesion Grade | Definition |
| --- | --- |
| I | No hyperfluorescence |
| II | Hyperfluorescence without leakage |
| III | Hyperfluorescence early or mid-transit and late leakage |
| IV | Bright hyperfluorescence early or mid-transit and late leakage beyond borders of treated area |

Deposit of Material

The following material has been deposited with the American Type Culture Collection, 10801 University Boulevard, Manassas, Va. 20110-2209, USA (ATCC):

| Designation | ATCC Dep. No. | Deposit Date |
| --- | --- | --- |
| DNA45416-1251 | 209620 | Feb. 5, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC '122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents.

Indeed, various modifications of the invention in addition to those shown and described herein will become apparent to those skilled in the art from the foregoing description and fall within the scope of the appended claims.

What is claimed is:

1. A method for the treatment of an eye condition the pathology of which involves the alternative pathway of complement, comprising administering to a subject in need a therapeutically effective amount of a CRIg polypeptide of SEQ ID NO: 2, 4, 6 or 8, or an extracellular domain thereof.

2. The method of claim 1 wherein the CRIg polypeptide or the extracellular domain thereof is fused to an immunoglobulin sequence.

3. The method of claim 2 wherein the immunoglobulin sequence is an immunoglobulin constant region sequence.

4. The method of claim 3 wherein the immunoglobulin constant region sequence is that of an immunoglobulin heavy chain.

5. The method of claim 4 wherein the immunoglobulin heavy chain constant region sequence is fused to an extracellular region of said CRIg polypeptide of SEQ ID NO: 2, 4, 6, or 8 to produce a CRIg-Ig fusion protein.

6. The method of claim 5 wherein said immunoglobulin constant region sequence is that of an IgG.

7. The method of claim 6 wherein said IgG is IgG-1 or IgG-3.

8. The method of claim 7 wherein the IgG-1 heavy chain constant region sequence comprises at least a hinge, CH2 and CH3 region.

9. The method of claim 7 wherein the IgG-1 heavy chain constant region sequence comprises a hinge, CH1, CH2 and CH3 region.

10. The method of claim 5 wherein the CRIg-Ig fusion protein comprises a linker between the CRIg and the Ig sequences.

11. The method of claim 5 wherein the CRIg-Ig fusion protein is encoded by a nucleic acid selected from the group consisting of SEQ ID NOS: 20, 21, 25, 26, 27, and 28.

12. The method of claim 1 wherein the eye condition is selected from the group consisting of age-related macular degeneration (AMD), choroidal neovascularization (CNV), uveitis, diabetic and other ischemia-related retinopathies, endophthalmitis, diabetic macular edema, pathological myopia, von Hippel-Lindau disease, histoplasmosis of the eye, Central Retinal Vein Occlusion (CRVO), corneal neovascularization, and retinal neovascularization.

13. The method of claim 12 wherein the eye disease is age-related macular degeneration (AMD) or choroidal neovascularization (CNV).

14. The method of claim 13 wherein said method comprises the slowing down of the progression of AMD into CNV.

15. A method of claim 14 wherein said method comprises the slowing down of the progression of AMD into CNV.

16. A method for the delaying or slowing down of the progression of age-related macular degeneration (AMD), comprising administering to subject diagnosed with AMD in at least one eye, an effective amount of a CRIg polypeptide of SEQ ID NO: 2, 4, 6, or 8, or an extracellular domain thereof.

17. The method of claim 16 wherein the extracellular domain of said CRIg polypeptide of SEQ ID NO: 2, 4, 6, or 8 is administered.

18. The method of claim 17 wherein the extracellular domain of said CRIg polypeptide of SEQ ID NO: 4 or 6 is administered.

19. The method of claim 16 wherein said CRIg polypeptide or said extracellular domain thereof is fused to an immunoglobulin sequence to yield a fusion polypeptide.

20. The method of claim 19 wherein the fusion polypeptide comprises the extracellular domain of a polypeptide of SEQ ID NO: 4 or 6 fused to an immunoglobulin heavy chain constant region sequence.

21. The method of claim 20 wherein the fusion polypeptide is selected from the group consisting of fusion polypeptides encoded by the nucleotide sequence of SEQ ID NO: 20, 21, 25, 26, 27, and 28.

22. The method of any one of claim 16 or claim 19, wherein the subject is a human.

23. The method of claim 16 wherein said AMD is category 3 or category 4 dry AMD.

24. The method of claim 23 wherein said subject has been identified to be at risk to develop CNV.

25. The method of claim 24 wherein said subject is genetically at risk of developing CNV.

26. The method of claim 23 wherein said human subject has been diagnosed with AMD in both eyes.

27. The method of claim 26 wherein said human subject has category 3 or category 4 AMD in both eyes.

28. The method of claim 22 wherein said administration slows down the progression of AMD.

29. The method of claim 22 wherein said administration delays the progression of AMD into CNV.

30. The method of claim 22 wherein said administration prevents the progression of AMD into CNV.

31. The method of claim 22 wherein the human subject has been diagnosed with AMD in one eye only.

32. The method of claim 31 wherein said administration delays the development of AMD in the other eye.

33. The method of claim 31 wherein said administration prevents the development of AMD in the other eye.

34. The method of claim 22 wherein said administration is performed by intravitreal injection.

35. The method of claim 22 or claim 31 further comprising the administration of an additional agent for the prevention or treatment of AMD or CNV.

36. The method of claim 35 wherein said additional agent is an anti-VEGF-A antibody.

37. A method for the treatment of dry age-related macular degeneration (AMD), comprising administering to a subject in need a therapeutically effective amount of a CRIg polypeptide of SEQ ID NO: 2, 4, 6 or 8, or an extracellular domain thereof.

38. The method of claim 37 wherein the extracellular domain of said CRIg polypeptide of SEQ ID NO: 2, 4, 6, or 8 is administered.

39. The method of claim 38 wherein the extracellular domain of said CRIg polypeptide of SEQ ID NO: 4 or 6 is administered.

40. The method of claim 37 wherein the CRIg polypeptide or the extracellular domain thereof is fused to an immunoglobulin sequence.

41. The method of claim 40 wherein the immunoglobulin sequence is an immunoglobulin constant region sequence.

42. The method of claim 41 wherein the immunoglobulin constant domain sequence is that of an immunoglobulin heavy chain.

43. The method of claim 42 wherein said immunoglobulin heavy chain constant region sequence is fused to an extracellular domain (ECD) of said CRIg polypeptide of SEQ ID NO: 2, 4, 6, or 8.

44. The method of claim 43 wherein said immunoglobulin constant region sequence is that of an IgG.

45. The method of claim 44 wherein said IgG is IgG-1 or IgG-3.

46. The method of claim 45 wherein the IgG-1 heavy chain constant region sequence comprises at least a hinge, CH2 and CH3 region.

47. The method of claim 45 wherein the IgG-1 heavy chain constant region sequence comprises a hinge, CH1, CH2 and CH3 region.

* * * * *

SEQUENCE LISTING

```
<160> NUMBER OF SEQ ID NOS: 28

<210> SEQ ID NO 1
<211> LENGTH: 2181
<212> TYPE: DNA
<213> ORGANISM: Homo sapiens

<400> SEQUENCE: 1
cccacgcgtc cgcccacgcg tccgcccacg ggtccgccca cgcgtccggg ccaccagaag      60
tttgagcctc tttggtagca ggaggctgga agaaaggaca gaagtagctc tggctgtgat     120
ggggatctta ctgggcctgc tactcctggg gcacctaaca gtggacactt atggccgtcc     180
catcctggaa gtgccagaga gtgtaacagg accttggaaa ggggatgtga atcttccctg     240
cacctatgac cccctgcaag gctacaccca agtcttggtg aagtggctgg tacaacgtgg     300
ctcagaccct gtcaccatct ttctacgtga ctcttctgga gaccatatcc agcaggcaaa     360
gtaccagggc cgcctgcatg tgagccacaa ggttccagga gatgtatccc tccaattgag     420
caccctggag atggatgacc ggagccacta cacgtgtgaa gtcacctggc agactcctga     480
tggcaaccaa gtcgtgagag ataagattac tgagctccgt gtccagaaac tctctgtctc     540
caagcccaca gtgacaactg gcagcggtta tggcttcacg gtgccccagg gaatgaggat     600
tagccttcaa tgccaggctc ggggttctcc tcccatcagt tatatttggt ataagcaaca     660
gactaataac caggaaccca tcaaagtagc aaccctaagt accttactct tcaagcctgc     720
ggtgatagcc gactcaggct cctatttctg cactgccaag ggccaggttg gctctgagca     780
gcacagcgac attgtgaagt tgtggtcaa agactcctca aagctactca agaccaagac     840
tgaggcacct acaaccatga catcccctt gaaagcaaca tctacagtga agcagtcctg     900
ggactggacc actgacatgg atggctacct tggagagacc agtgctgggc caggaaagag     960
cctgcctgtc tttgccatca tcctcatcat ctccttgtgc tgtatggtgg tttttaccat    1020
ggcctatatc atgctctgtc ggaagacatc ccaacaagag catgtctacg aagcagccag    1080
gtaagaaagt ctctcctctt ccatttttga ccccgtccct gccctcaatt ttgattactg    1140
gcaggaaatg tggaggaagg ggggtgtggc acagacccaa tcctaaggcc ggaggccttc    1200
agggtcagga catagctgcc ttccctctct caggcacctt ctgaggttgt tttggccctc    1260
tgaacacaaa ggataattta gatccatctg ccttctgctt ccagaatccc tgggtggtag    1320
gatcctgata attaattggc aagaattgag gcagaagggt gggaaaccag gaccacagcc    1380
ccaagtccct tcttatgggt ggtgggctct tgggccatag ggcacatgcc agagaggcca    1440
acgactctgg agaaaccatg agggtggcca tcttcgcaag tggctgctcc agtgatgagc    1500
caacttccca gaatctgggc aacaactact ctgatgagcc ctgcatagga caggagtacc    1560
agatcatcgc ccagatcaat ggcaactacg cccgcctgct ggacacagtt cctctggatt    1620
```

```
atgagtttct ggccactgag ggcaaaagtg tctgttaaaa atgccccatt aggccaggat    1680
ctgctgacat aattgcctag tcagtccttg ccttctgcat ggccttcttc cctgctacct    1740
ctcttcctgg atagcccaaa gtgtccgcct accaacactg gagccgctgg gagtcactgg    1800
ctttgccctg gaatttgcca gatgcatctc aagtaagcca gctgctggat ttggctctgg    1860
gcccttctag tatctctgcc gggggcttct ggtactcctc tctaaatacc agagggaaga    1920
tgcccatagc actaggactt ggtcatcatg cctacagaca ctattcaact ttggcatctt    1980
gccaccagaa gacccgaggg aggctcagct ctgccagctc agaggaccag ctatatccag    2040
gatcatttct ctttcttcag gccagacag cttttaattg aaattgttat ttcacaggcc    2100
agggttcagt tctgctcctc cactataagt ctaatgttct gactctctcc tggtgctcaa    2160
taaatatcta atcataacag c                                              2181
```

<210> SEQ ID NO 2
<211> LENGTH: 321
<212> TYPE: PRT
<213> ORGANISM: Homo sapiens

<400> SEQUENCE: 2

```
Met Gly Ile Leu Leu Gly Leu Leu Leu Gly His Leu Thr Val Asp
  1               5                  10                  15

Thr Tyr Gly Arg Pro Ile Leu Glu Val Pro Glu Ser Val Thr Gly Pro
                 20                  25                  30

Trp Lys Gly Asp Val Asn Leu Pro Cys Thr Tyr Asp Pro Leu Gln Gly
             35                  40                  45

Tyr Thr Gln Val Leu Val Lys Trp Leu Val Gln Arg Gly Ser Asp Pro
         50                  55                  60

Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
```

```
                275                 280                 285
Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Arg

<210> SEQ ID NO 3
<211> LENGTH: 1372
<212> TYPE: DNA
<213> ORGANISM: Homo sapiens

<400> SEQUENCE: 3
ccaactgcac ctcggttcta tcgataggag gctggaagaa aggacagaag tagctctggc      60
tgtgatgggg atcttactgg gcctgctact cctggggcac ctaacagtgg acacttatgg     120
ccgtcccatc ctggaagtgc cagagagtgt aacaggacct tggaaagggg atgtgaatct     180
tccctgcacc tatgaccccc tgcaaggcta cacccaagtc ttggtgaagt ggctggtaca     240
acgtggctca gaccctgtca ccatctttct acgtgactct tctggagacc atatccagca     300
ggcaaagtac cagggccgcc tgcatgtgag ccacaaggtt ccaggagatg tatccctcca     360
attgagcacc ctggagatgg atgaccggag ccactacacg tgtgaagtca cctggcagac     420
tcctgatggc aaccaagtcg tgagagataa gattactgag ctccgtgtcc agaaactctc     480
tgtctccaag cccacagtga caactggcag cggttatggc ttcacggtgc ccagggaat     540 gaggattagc cttcaatgcc aggctcgggg ttctcctccc atcagttata tttggtataa     600
gcaacagact aataaccagg aacccatcaa agtagcaacc ctaagtacct tactcttcaa     660
gcctgcggtg atagccgact caggctccta tttctgcact gccaagggcc aggttggctc     720
tgagcagcac agcgacattg tgaagtttgt ggtcaaagac tcctcaaagc tactcaagac     780
caagactgag gcacctacaa ccatgacata ccccttgaaa gcaacatcta cagtgaagca     840 gtccctgggac tggaccactg acatggatgg ctaccttgga gagaccagtg ctgggccagg     900
aaagagcctg cctgtctttg ccatcatcct catcatctcc ttgtgctgta tggtggtttt     960
taccatggcc tatatcatgc tctgtcggaa gacatcccaa caagagcatg tctacgaagc    1020
agccagggca catgccagag aggccaacga ctctggagaa accatgaggg tggccatctt    1080
cgcaagtggc tgctccagtg atgagccaac ttcccagaat ctgggcaaca actactctga    1140
tgagccctgc ataggacagg agtaccagat catcgcccag atcaatggca actacgcccg    1200
cctgctggac acagttcctc tggattatga gtttctggcc actgagggca aaagtgtctg    1260
ttaaaaatgc cccattaggc caggatctgc tgacataatc tagagtcgac ctgcagaagc    1320
ttggccgcca tggcccaact tgtttattgc agcttataat ggttacaaat aa           1372

<210> SEQ ID NO 4
<211> LENGTH: 399
<212> TYPE: PRT
<213> ORGANISM: Homo sapiens

<400> SEQUENCE: 4

Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45
```

Tyr Thr Gln Val Leu Val Lys Trp Leu Val Gln Arg Gly Ser Asp Pro
 50                  55                  60

Val Thr Ile Phe Leu Arg Asp Ser Ser Gly Asp His Ile Gln Gln Ala
 65                  70                  75                  80

Lys Tyr Gln Gly Arg Leu His Val Ser His Lys Val Pro Gly Asp Val
                 85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
130                 135                 140

Val Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
            340                 345                 350

Leu Gly Asn Asn Tyr Ser Asp Glu Pro Cys Ile Gly Gln Glu Tyr Gln
        355                 360                 365

Ile Ile Ala Gln Ile Asn Gly Asn Tyr Ala Arg Leu Leu Asp Thr Val
370                 375                 380

Pro Leu Asp Tyr Glu Phe Leu Ala Thr Glu Gly Lys Ser Val Cys
385                 390                 395

<210> SEQ ID NO 5
<211> LENGTH: 1090
<212> TYPE: DNA
<213> ORGANISM: Homo sapiens

<400> SEQUENCE: 5
gtccaactgc acctcggttc tatcgatagg aggctggaag aaaggacaga agtagctctg     60
gctgtgatgg ggatcttact gggcctgcta ctcctggggc acctaacagt ggacacttat    120
ggccgtccca tcctggaagt gccagagagt gtaacaggac cttggaaagg ggatgtgaat    180

```
cttccctgca cctatgaccc cctgcaaggc tacacccaag tcttggtgaa gtggctggta    240
caacgtggct cagaccctgt caccatcttt ctacgtgact cttctggaga ccatatccag    300
caggcaaagt accagggccg cctgcatgtg agccacaagg ttccaggaga tgtatccctc    360
caattgagca ccctggagat ggatgaccgg agccactaca cgtgtgaagt cacctggcag    420
actcctgatg gcaaccaagt cgtgagagat aagattactg agctccgtgt ccagaaacac    480
tcctcaaagc tactcaagac caagactgag gcacctacaa ccatgacata ccccttgaaa    540
gcaacatcta cagtgaagca gtcctgggac tggaccactg acatggatgg ctaccttgga    600
gagaccagtg ctgggccagg aaagagcctg cctgtctttg ccatcatcct catcatctcc    660
ttgtgctgta tggtggtttt taccatggcc tatatcatgc tctgtcggaa gacatcccaa    720
caagagcatg tctacgaagc agccagggca catgccagag aggccaacga ctctggagaa    780
accatgaggg tggccatctt cgcaagtggc tgctccagtg atgagccaac ttcccagaat    840
ctgggcaaca actactctga tgagccctgc ataggacagg agtaccagat catcgcccag    900
atcaatggca actacgcccg cctgctggac acagttcctc tggattatga gtttctggcc    960
actgagggca aaagtgtctg ttaaaaatgc cccattaggc caggatctgc tgacataatc    1020
tagagtcgac ctgcagaagc ttggccgcca tggcccaact tgtttattgc agcttataat    1080
ggttacaata                                                           1090

<210> SEQ ID NO 6
<211> LENGTH: 305
<212> TYPE: PRT
<213> ORGANISM: Homo sapiens

<400> SEQUENCE: 6

Met Gly Ile Leu Leu Gly Leu Leu Leu Gly His Leu Thr Val Asp
 1               5                  10                  15

Thr Tyr Gly Arg Pro Ile Leu Glu Val Pro Glu Ser Val Thr Gly Pro
                20                  25                  30

Trp Lys Gly Asp Val Asn Leu Pro Cys Thr Tyr Asp Pro Leu Gln Gly
            35                  40                  45

Tyr Thr Gln Val Leu Val Lys Trp Leu Val Gln Arg Gly Ser Asp Pro
        50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205
```

```
Tyr Ile Met Leu Cys Arg Lys Thr Ser Gln Gln Glu His Val Tyr Glu
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                    245                 250                 255

Gln Asn Leu Gly Asn Asn Tyr Ser Asp Glu Pro Cys Ile Gly Gln Glu
                260                 265                 270

Tyr Gln Ile Ile Ala Gln Ile Asn Gly Asn Tyr Ala Arg Leu Leu Asp
                275                 280                 285

Thr Val Pro Leu Asp Tyr Glu Phe Leu Ala Thr Glu Gly Lys Ser Val
    290                 295                 300

Cys
305

<210> SEQ ID NO 7
<211> LENGTH: 1590
<212> TYPE: DNA
<213> ORGANISM: Mus musculus

<400> SEQUENCE: 7
gtccaactgc acctcggttc tatcgattcg aattcggcca cactggccgg atcctctaga      60
gatccctcga cctcgaccca cgcgtccgag cagcaagagg atggaaggat gaatagaagt     120
agcttcaaat aggatggaga tctcatcagg cttgctgttc ctgggccacc taatagtgct     180
cacctatggc caccccaccc taaaaacacc tgagagtgtg acaggaccct ggaaaggaga     240
tgtgaagatt cagtgcatct atgatcccct gagaggctac aggcaagttt tggtgaaatg     300
gctggtaaga cacggctctg actccgtcac catcttccta cgtgactcca ctggagacca     360
tatccagcag gcaaagtaca gaggccgcct gaaagtgagc cacaaagttc aggagatgt     420 gtccctccaa ataaataccc tgcagatgga tgacaggaat cactatacat gtgaggtcac     480
ctggcagact cctgatggaa accaagtaat aagagataag atcattgagc tccgtgttcg     540
gaaatataat ccacctagaa tcaatactga agcacctaca accctgcact cctctttgga     600
agcaacaact ataatgagtt caacctctga cttgaccact aatgggactg gaaaacttga     660
ggagaccatt gctggttcag ggaggaacct gccaatcttt gccataatct tcatcatctc     720
cctttgctgc atagtagctg tcaccatacc ttatatcttg ttccgctgca ggacattcca     780
acaagagtat gtctatggag tgagcagggt gtttgccagg aagacaagca actctgaaga     840
aaccacaagg gtgactacca tcgcaactga tgaaccagat tcccaggctc tgattagtga     900
ctactctgat gatccttgcc tcagccagga gtaccaaata accatcagat caacaatgtc     960
tattcctgcc tgctgaacac agtttccaga aactaagaag ttcttgctac tgaagaaaat    1020
aacatctgct aaaatgcccc tactaagtca aggtctactg gcgtaattac ctgttactta    1080
tttactactt gccttcaaca tagctttctc cctggcttcc tttcttctta gacaacctaa    1140
agtatctatc tagtctgcca attctggggc cattgagaaa tcctgggttt ggctaagaat    1200
atactacatg cacctcaaga atctagcttc tgggcttca cccagaacaa tttcttcct    1260 agggccttca caactcttct ccaaacagca gagaaattcc atagcagtag aggttcttta    1320
tcatgcctcc agacagcgtg agtctcagtc ctacaaactc agacaagcac atgggtctag    1380
gattactcct ctttctctag ggccagatga ctttaattg atattactat tgctacatta    1440
tgaatctaat gcacatgtat tcttttgttg ttaataaatg tttaatcatg acatcaaaaa    1500
aaaaaaaaaa aagggcggcc gcgactctag agtcgacctg cagtagggat aacagggtaa    1560
```
taagcttggc cgccatggcc caacttgttt                                    1590

<210> SEQ ID NO 8
<211> LENGTH: 280
<212> TYPE: PRT
<213> ORGANISM: Mus musculus

<400> SEQUENCE: 8

Met Glu Ile Ser Ser Gly Leu Leu Phe Leu Gly His Leu Ile Val Leu
 1               5                  10                  15

Thr Tyr Gly His Pro Thr Leu Lys Thr Pro Glu Ser Val Thr Gly Thr
            20                  25                  30

Trp Lys Gly Asp Val Lys Ile Gln Cys Ile Tyr Asp Pro Leu Arg Gly
        35                  40                  45

Tyr Arg Gln Val Leu Val Lys Trp Leu Val Arg His Gly Ser Asp Ser
    50                  55                  60

Val Thr Ile Phe Leu Arg Asp Ser Thr Gly Asp His Ile Gln Gln Ala
65                  70                  75                  80

Lys Tyr Arg Gly Arg Leu Lys Val Ser His Lys Val Pro Gly Asp Val
                85                  90                  95

Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
        115                 120                 125

Lys Ile Ile Glu Leu Arg Val Arg Lys Tyr Asn Pro Pro Arg Ile Asn
    130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175

Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
        195                 200                 205

Leu Phe Arg Cys Arg Thr Phe Gln Gln Glu Tyr Val Tyr Gly Val Ser
    210                 215                 220

Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
                245                 250                 255

Tyr Ser Asp Asp Pro Cys Leu Ser Gln Glu Tyr Gln Ile Thr Ile Arg
            260                 265                 270

Ser Thr Met Ser Ile Pro Ala Cys
        275                 280

<210> SEQ ID NO 9
<211> LENGTH: 1503
<212> TYPE: DNA
<213> ORGANISM: Homo sapiens

<400> SEQUENCE: 9
gcaggcaaag taccagggcc gcctgcatgt gagccacaag gttccaggag atgtatccct     60
ccaattgagc accctggaga tggatgaccg gagccactac acgtgtgaag tcacctggca    120
gactcctgat ggcaaccaag tcgtgagaga taagattact gagctccgtg tccagaaact    180
ctctgtctcc aagcccacag tgacaactgg cagcggttat ggcttcacgg tgccccaggg    240

-continued

```
aatgaggatt agccttcaat gccagggttc ggggttctcc tcccatcagt tatatttggt    300
ataagcaaca gactaataac cagggaaccc atcaaagtag caaccctaag taccttactc    360
ttcaagcctg cggtgatagc cgactcaggc tcctatttct gcactgccaa gggccaggtt    420
ggctctgagc agcacagcga cattgtgaag tttgtggtca aagactcctc aaagctactc    480
aagaccaaga ctgaggcacc tacaaccatg acatacccct tgaaagcaac atctacagtg    540
aagcagtcct gggactggac cactgacatg gatggctacc ttggagagac cagtgctggg    600
ccaggaaaga gcctgcctgt cttttgccatc atcctcatca tctccttgtg ctgtatggtg    660 gttttttacca tggcctatat catgctctgt cggaagacat cccaacaaga gcatgtctac    720
gaagcagcca gggcacatgc cagagaggcc aacgactctg gagaaaccat gagggtggcc    780
atcttcgcaa gtggctgctc cagtgatgag ccaacttccc agaatctggg gcaacaacta    840
ctctgatgag ccctgcatag gacaggagta ccagatcatc gcccagatca atggcaacta    900
cgcccgcctg ctgacacag ttcctctgga ttatgagttt ctggccactg agggcaaaag    960
tgtctgttaa aaatgcccca ttaggccagg atctgctgac ataattgcct agtcagtcct   1020
tgccttctgc atggccttct tccctgctac ctctcttcct ggatagccca agtgtccgc    1080 ctaccaacac tggagccgct gggagtcact ggctttgccc tggaatttgc cagatgcatc   1140
tcaagtaagc cagctgctgg atttggctct gggcccttct agtatctctg ccggggggctt   1200 ctggtactcc tctctaaata ccagagggaa gatgcccata gcactaggac ttggtcatca   1260
tgcctacaga cactattcaa ctttggcatc ttgccaccag aagacccgag gggaggctca   1320
gctctgccag ctcagaggac cagctatatc caggatcatt tctctttctt cagggccaga   1380
cagcttttaa ttgaaattgt tatttcacag gccagggttc agttctgctc ctccactata   1440
agtctaatgt tctgactctc tcctggtgct caataaatat ctaatcataa cagcaaaaaa   1500
aaa                                                                 1503
```

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 10
tatccctcca attgagcacc ctgg                                           24

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 11
gtcggaagac atcccaacaa g                                              21

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 12
cttcacaatg tcgctgtgct gctc                                           24

```
<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 13
agccaaatcc agcagctggc ttac                                            24

<210> SEQ ID NO 14
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 14
tggatgaccg gagccactac acgtgtgaag tcacctggca gactcctgat                50

<210> SEQ ID NO 15
<211> LENGTH: 7496
<212> TYPE: DNA
<213> ORGANISM: Homo sapiens

<400> SEQUENCE: 15
ttcgagctcg cccgacattg attattgact agttattaat agtaatcaat tacgggtca      60 ttagttcata gcccatatat ggagttccgc gttacataac ttacggtaaa tggcccgcct    120
ggctgaccgc ccaacgaccc ccgcccattg acgtcaataa tgacgtatgt tcccatagta    180
acgccaatag ggactttcca ttgacgtcaa tgggtggagt atttacggta aactgcccac    240
ttggcagtac atcaagtgta tcatatgcca agtacgcccc ctattgacgt caatgacggt    300
aaatggcccg cctggcatta tgcccagtac atgaccttat gggactttcc tacttggcag    360
tacatctacg tattagtcat cgctattacc atggtgatgc ggttttggca gtacatcaat    420
gggcgtggat agcggtttga ctcacgggga tttccaagtc tccaccccat tgacgtcaat    480
gggagtttgt tttggcacca aaatcaacgg gactttccaa aatgtcgtaa caactccgcc    540
ccattgacgc aaatgggcgg taggcgtgta cggtgggagg tctatataag cagagctcgt    600
ttagtgaacc gtcagatcgc ctggagacgc catccacgct gttttgacct ccatagaaga    660
caccgggacc gatccagcct ccgcggccgg gaacggtgca ttggaacgcg gattccccgt    720
gccaagagtg acgtaagtac cgcctataga gtctataggc ccacccccctt ggcttggccc    780 acccccttgg cttcgttaga acgcggctac aattaataca taaccttatg tatcatacac    840
atacgattta ggtgacacta tagaataaca tccactttgc ctttcacatc cactttgcct    900
ttctctccac aggtgtccac tcccaggtcc aactgcacct cggttctatc gattaaacca    960
ccatggggat cttactgggc ctgctactcc tgggcacct aacagtggac acttatggcc   1020
gtcccatcct ggaagtgcca gagagtgtaa caggaccttg gaaagggat gtgaatcttc   1080 cctgcaccta tgaccccctg caaggctaca cccaagtctt ggtgaagtgg ctggtacaac   1140
gtggctcaga ccctgtcacc atctttctac gtgactcttc tggagaccat atccagcagg   1200
caaagtacca gggccgcctg catgtgagcc acaaggttcc aggagatgta tccctccaat   1260
tgagcaccct ggagatggat gaccggagcc actacacgtg taagtcacc tggcagactc   1320 ctgatgcaa ccaagtcgtg agagataaga ttactgagct ccgtgtccag aaactctctg   1380
tctccaagcc cacagtgaca actggcagcg ttatggctt cacggtgccc caggaatga   1440
```

```
ggattagcct tcaatgccag gctcggggtt ctcctcccat cagttatatt tggtataagc    1500
aacagactaa taaccaggaa cccatcaaag tagcaaccct aagtacctta ctcttcaagc    1560
ctgcggtgat agccgactca ggctcctatt tctgcactgc caagggccag gttggctctg    1620
agcagcacag cgacattgtg aagtttgtgg tcaaagactc ctcaaagcta ctcaagacca    1680
agactgaggc acctcaaacc atgacatacc ccttgaaagc aacatctaca gtgaagcagt    1740
cctgggactg gaccactgac atggatggcg ggcgcgccca ggtcaccgac aaagctgcgc    1800
actatactct gtgcccaccg tgcccagcac ctgaactcct gggggaccg tcagtcttcc    1860 tcttccccc aaaacccaag gacaccctca tgatctcccg gacccctgag gtcacatgcg    1920
tggtggtgga cgtgagccac gaagaccctg aggtcaagtt caactggtac gtggacggcg    1980
tggaggtgca taatgccaag acaaagccgc gggaggagca gtacaacagc acgtaccgtg    2040
tggtcagcgt cctcaccgtc ctgcaccagg actggctgaa tggcaaggag tacaagtgca    2100
aggtctccaa caaagccctc ccagccccca tcgagaaaac catctccaaa gccaaagggc    2160
agccccgaga accacaggtg tacaccctgc ccccatcccg ggaagagatg accaagaacc    2220
aggtcagcct gacctgcctg gtcaaaggct tctatcccag cgacatcgcc gtggagtggg    2280
agagcaatgg gcagccggag aacaactaca agaccacgcc tcccgtgctg gactccgacg    2340
gctccttctt cctctacagc aagctcaccg tggacaagag caggtggcag caggggaacg    2400
tcttctcatg ctccgtgatg catgaggctc tgcacaacca ctacacgcag aagagcctct    2460
ccctgtctcc gggtaaatga gtgcgacggc cctagagtcg acctgcagaa gcttctagag    2520
tcgacctgca gaagcttggc cgccatggcc caacttgttt attgcagctt ataatggtta    2580
caaataaagc aatagcatca caaatttcac aaataaagca tttttttcac tgcattctag    2640
ttgtggtttg tccaaactca tcaatgtatc ttatcatgtc tggatcgatc gggaattaat    2700
tcggcgcagc accatggcct gaaataacct ctgaaagagg aacttggtta ggtaccttct    2760
gaggcggaaa gaaccagctg tggaatgtgt gtcagttagg gtgtggaaag tccccaggct    2820
ccccagcagg cagaagtatg caaagcatgc atctcaatta gtcagcaacc aggtgtggaa    2880
agtccccagg ctccccagca ggcagaagta tgcaaagcat gcatctcaat tagtcagcaa    2940
ccatagtccc gcccctaact ccgcccatcc cgcccctaac tccgcccagt tccgcccatt    3000
ctccgcccca tggctgacta atttttttta tttatgcaga ggccgaggcc gcctcggcct    3060
ctgagctatt ccagaagtag tgaggaggct tttttggagg cctaggcttt tgcaaaaagc    3120
tgttaattcg aacacgcaga tgcagtcggg gcggcgcggt cccaggtcca cttcgcatat    3180
taaggtgacg cgtgtggcct cgaacaccga gcgaccctgc agcgacccgc ttaacagcgt    3240
caacagcgtg ccgcagatct gatcaagaga caggatgagg atcgtttcgc atgattgaac    3300
aagatggatt gcacgcaggt tctccggccg cttgggtgga gaggctattc ggctatgact    3360
gggcacaaca gacaatcggc tgctctgatg ccgccgtgtt ccggctgtca gcgcagggc    3420 gcccggttct ttttgtcaag accgacctgt ccggtgccct gaatgaactg caggacgagg    3480
cagcgcggct atcgtggctg gccacgacgg gcgttccttg cgcagctgtg ctcgacgttg    3540
tcactgaagc gggaagggac tggctgctat tgggcgaagt gccggggcag gatctcctgt    3600
catctcacct tgctcctgcc gagaaagtat ccatcatggc tgatgcaatg cggcggctgc    3660
atacgcttga tccggctacc tgcccattcg accaccaagc gaaacatcgc atcgagcgag    3720
cacgtactcg gatggaagcc ggtcttgtcg atcaggatga tctggacgaa gagcatcagg    3780
ggctcgcgcc agccgaactg ttcgccaggc tcaaggcgcg catgcccgac ggcgaggatc    3840
```

```
tcgtcgtgac ccatggcgat gcctgcttgc cgaatatcat ggtggaaaat ggccgctttt    3900
ctggattcat cgactgtggc cggctgggtg tggcggaccg ctatcaggac atagcgttgg    3960
ctacccgtga tattgctgaa gagcttggcg gcgaatgggc tgaccgcttc ctcgtgcttt    4020
acggtatcgc cgctcccgat tcgcagcgca tcgccttcta tcgccttctt gacgagttct    4080
tctgagcggg actctggggt tcgaaatgac cgaccaagcg acgcccaacc tgccatcacg    4140
agatttcgat tccaccgccg ccttctatga aaggttgggc ttcggaatcg ttttccggga    4200
cgccggctgg atgatcctcc agcgcgggga tctcatgctg gagttcttcg cccaccccgg    4260
gagatggggg aggctaactg aaacacggaa ggagacaata ccggaaggaa cccgcgctat    4320
gacggcaata aaaagacaga ataaaacgca cgggtgttgg gtcgtttgtt cataaacgcg    4380
gggttcggtc ccagggctgg cactctgtcg atacccacc gagacccat tggggccaat     4440
acgcccgcgt ttcttccttt tccccacccc aaccccaag ttcgggtgaa ggcccagggc     4500
tcgcagccaa cgtcggggcg gcaagcccgc catagccacg gccccgtgg gttagggacg     4560
gggtccccca tggggaatgg tttatggttc gtgggggtta ttcttttggg cgttgcgtgg    4620
ggtcaggtcc acgactggac tgagcagaca gacccatggt ttttggatgg cctgggcatg    4680
gaccgcatgt actggcgcga cacgaacacc gggcgtctgt ggctgccaaa caccccgac     4740
ccccaaaaac caccgcgcgg atttctggcg ccgccgacg aactaaacct gactacggca     4800
tctctgcccc ttcttcgctg gtacgaggag cgcttttgtt ttgtattggt caccacggcc    4860
gagtttccgc ggaccccgg ccagggcacc tgtcctacga gttgcatgat aaagaagaca     4920
gtcataagtg cggcgacgat agtcatgccc cgcgcccacc ggaaggagct gactgggttg    4980
aaggctctca agggcatcgg tcgagcgcc gcatcaaagc aaccatagta cgcgccctgt     5040
agcggcgcat taagcgcggc gggtgtggtg gttacgcgca gcgtgaccgc tacacttgcc    5100
agcgccctag cgcccgctcc tttcgctttc ttcccttcct ttctcgccac gttcgccggc    5160
tttccccgtc aagctctaaa tcgggggctc cctttagggt tccgatttag tgctttacgg    5220
cacctcgacc ccaaaaaact tgatttgggt gatggttcac gtagtgggcc atcgccctga    5280
tagacggttt ttcgcccttt gacgttggag tccacgttct ttaatagtgg actcttgttc    5340
caaactggaa caacactcaa ccctatctcg ggctattctt ttgatttata agggattttg    5400
ccgatttcgg cctattggtt aaaaaatgag ctgatttaac aaaaatttaa cgcgaatttt    5460
aacaaaatat taacgtttac aattttatgg tgcaggcctc gtgatacgcc tatttttata    5520
ggttaatgtc atgataataa tggtttctta gacgtcaggt ggcactttc ggggaaatgt     5580
gcgcggaacc cctatttgtt tatttttcta aatacattca aatatgtatc cgctcatgag    5640
acaataaccc tgataaatgc ttcaataata ttgaaaaagg aagagtatga gtattcaaca    5700
tttccgtgtc gcccttattc cctttttgc ggcattttgc cttcctgttt ttgctcaccc     5760
agaaacgctg gtgaaagtaa aagatgctga agatcagttg ggtgcacgag tgggttacat    5820
cgaactggat ctcaacagcg gtaagatcct tgagagtttt cgccccgaag aacgttttcc    5880
aatgatgagc acttttaaag ttctgctatg tggcgcggta ttatcccgtg atgacgccgg    5940
gcaagagcaa ctcggtcgcc gcatacacta ttctcagaat gacttggttg agtactcacc    6000
agtcacagaa aagcatctta cggatggcat gacagtaaga gaattatgca gtgctgccat    6060
aaccatgagt gataacactg cggccaactt acttctgaca acgatcggag gaccgaagga    6120
gctaaccgct tttttgcaca acatggggga tcatgtaact cgccttgatc gttgggaacc    6180
ggagctgaat gaagccatac caaacgacga gcgtgacacc acgatgccag cagcaatggc    6240
```

| | |
|---|---|
| aacaacgttg cgcaaactat taactggcga actacttact ctagcttccc ggcaacaatt | 6300 |
| aatagactgg atggaggcgg ataaagttgc aggaccactt ctgcgctcgg cccttccggc | 6360 |
| tggctggttt attgctgata aatctggagc cggtgagcgt gggtctcgcg gtatcattgc | 6420 |
| agcactgggg ccagatggta agccctcccg tatcgtagtt atctacacga cggggagtca | 6480 |
| ggcaactatg gatgaacgaa atagacagat cgctgagata ggtgcctcac tgattaagca | 6540 |
| ttggtaactg tcagaccaag tttactcata tatactttag attgatttaa aacttcattt | 6600 |
| ttaatttaaa aggatctagg tgaagatcct ttttgataat ctcatgacca aaatccctta | 6660 |
| acgtgagttt tcgttccact gagcgtcaga ccccgtagaa aagatcaaag gatcttcttg | 6720 |
| agatcctttt tttctgcgcg taatctgctg cttgcaaaca aaaaaaccac cgctaccagc | 6780 |
| ggtggtttgt ttgccggatc aagagctacc aactctttt ccgaaggtaa ctggcttcag | 6840 |
| cagagcgcag ataccaaata ctgtccttct agtgtagccg tagttaggcc accacttcaa | 6900 |
| gaactctgta gcaccgccta catacctcgc tctgctaatc ctgttaccag tggctgctgc | 6960 |
| cagtggcgat aagtcgtgtc ttaccgggtt ggactcaaga cgatagttac cggataaggc | 7020 |
| gcagcggtcg ggctgaacgg ggggttcgtg cacacagccc agcttggagc gaacgaccta | 7080 |
| caccgaactg agatacctac agcgtgagca ttgagaaagc gccacgcttc ccgaagggag | 7140 |
| aaaggcggac aggtatccgg taagcggcag ggtcggaaca ggagagcgca cgagggagct | 7200 |
| tccaggggga aacgcctggt atctttatag tcctgtcggg tttcgccacc tctgacttga | 7260 |
| gcgtcgattt tgtgatgct cgtcaggggg cggagccta tggaaaaacg ccagctggca | 7320 |
| cgacaggttt cccgactgga agcgggcag tgagcgcaac gcaattaatg tgagttacct | 7380 |
| cactcattag gcaccccagg ctttacactt tatgcttccg gctcgtatgt tgtgtggaat | 7440 |
| tgtgagcgga taacaatttc acacaggaaa cagctatgac catgattacg aattaa | 7496 |

<210> SEQ ID NO 16
<211> LENGTH: 7201
<212> TYPE: DNA
<213> ORGANISM: Homo sapiens

<400> SEQUENCE: 16

| | |
|---|---|
| ttcgagctcg cccgacattg attattgact agttattaat agtaatcaat tacggggtca | 60 |
| ttagttcata gcccatatat ggagttccgc gttacataac ttacggtaaa tggcccgcct | 120 |
| ggctgaccgc ccaacgaccc ccgcccattg acgtcaataa tgacgtatgt tcccatagta | 180 |
| acgccaatag ggactttcca ttgacgtcaa tgggtggagt atttacggta aactgcccac | 240 |
| ttggcagtac atcaagtgta tcatatgcca agtacgcccc ctattgacgt caatgacggt | 300 |
| aaatggcccg cctggcatta tgcccagtac atgaccttat gggactttcc tacttggcag | 360 |
| tacatctacg tattagtcat cgctattacc atggtgatgc ggttttggca gtacatcaat | 420 |
| gggcgtggat agcggtttga ctcacgggga tttccaagtc tccaccccat tgacgtcaat | 480 |
| gggagtttgt tttggcacca aaatcaacgg gactttccaa aatgtcgtaa caactccgcc | 540 |
| ccattgacgc aaatgggcgg taggcgtgta cggtgggagg tctatataag cagagctcgt | 600 |
| ttagtgaacc gtcagatcgc ctggagacgc catccacgct gttttgacct ccatagaaga | 660 |
| caccgggacc gatccagcct ccgcggccgg gaacggtgca ttggaacgcg gattccccgt | 720 |
| gccaagagtg acgtaagtac cgcctataga gtctataggc cccccccctt ggcttggccc | 780 |
| accccccttgg cttcgttaga acgcggctac aattaataca taaccttatg tatcatacac | 840 |
| atacgattta ggtgacacta tagaataaca tccactttgc ctttcacatc cactttgcct | 900 |

```
ttctctccac aggtgtccac tcccaggtcc aactgcacct cggttctatc gatgctctca    960
ataaaccacc atggggatct tactgggcct gctactcctg gggcacctaa cagtggacac   1020
ttatggccgt cccatcctgg aagtgccaga gagtgtaaca ggaccttgga aaggggatgt   1080
gaatcttccc tgcacctatg accccctgca aggctacacc caagtcttgg tgaagtggct   1140
ggtacaacgt ggctcagacc ctgtcaccat ctttctacgt gactcttctg gagaccatat   1200
ccagcaggca aagtaccagg gccgcctgca tgtgagccac aaggttccag agatgtatc    1260 cctccaattg agcaccctgg agatggatga ccggagccac tacacgtgtg aagtcacctg   1320
gcagactcct gatggcaacc aagtcgtgag agataagatt actgagctcc gtgtccagaa   1380
acactcctca aagctactca agaccaagac tgaggcacct acaaccatga catacccctt   1440
gaaagcaaca tctacagtga agcagtcctg ggactggacc actgacatgg atgggggcg    1500 cgcccaggtc accgacaaag ctgcgcacta tactctgtgc ccaccgtgcc cagcacctga   1560
actcctgggg ggaccgtcag tcttcctctt cccccccaaaa cccaaggaca ccctcatgat   1620
ctcccggacc cctgaggtca catgcgtggt ggtggacgtg agccacgaag accctgaggt   1680
caagttcaac tggtacgtgg acggcgtgga ggtgcataat gccaagacaa agccgcggga   1740
ggagcagtac aacagcacgt accgtgtggt cagcgtcctc accgtcctgc accaggactg   1800
gctgaatggc aaggagtaca gtgcaaggt ctccaacaaa gccctcccag cccccatcga    1860
gaaaaccatc tccaaagcca agggcagcc cgagaacca caggtgtaca ccctgccccc    1920
atcccgggaa gagatgacca gaaccaggt cagcctgacc tgcctggtca aaggcttcta   1980
tcccagcgac atcgccgtgg agtgggagag caatgggcag ccggagaaca actacaagac   2040
cacgcctccc gtgctggact ccgacggctc cttcttcctc tacagcaagc tcaccgtgga   2100
caagagcagg tggcagcagg ggaacgtctt ctcatgctcc gtgatgcatg aggctctgca   2160
caaccactac acgcagaaga gcctctcct gtctccgggt aaatgagtgc gacggcccta    2220
gagtcgacct gcagaagctt ctagagtcga cctgcagaag cttggccgcc atggcccaac   2280
ttgtttattg cagcttataa tggttacaaa taaagcaata gcatcacaaa tttcacaaat   2340
aaagcatttt tttcactgca ttctagttgt ggtttgtcca aactcatcaa tgtatcttat   2400
catgtctgga tcgatcggga attaattcgg cgcagcacca tggcctgaaa taacctctga   2460
aagaggaact tggttaggta ccttctgagg cggaaagaac cagctgtgga atgtgtgtca   2520
gttagggtgt ggaaagtccc caggctcccc agcaggcaga agtatgcaaa gcatgcatct   2580
caattagtca gcaaccaggt gtggaaagtc cccaggctcc ccagcaggca agtatgca     2640 aagcatgcat ctcaattagt cagcaaccat agtcccgccc ctaactccgc ccatcccgcc   2700
cctaactccg cccagttccg cccattctcc gccccatggc tgactaattt tttttattta   2760
tgcagaggcc gaggccgcct cggcctctga gctattccag aagtagtgag gaggcttttt   2820
tggaggccta ggcttttgca aaaattcgaa cacgcagatg cagtcggggc ggcgcggtcc   2880
caggtccact tcgcatatta aggtgacgcg tgtggcctcg aacaccgagc gaccctgcag   2940
cgacccgctt aacagcgtca acagcgtgcc gcagatctga tcaagagaca ggatgaggat   3000
cgtttcgcat gattgaacaa gatggattgc acgcaggttc tccggccgct tgggtggaga   3060
ggctattcgg ctatgactgg gcacaacaga caatcggctc tctgatgcc gccgtgttcc     3120 ggctgtcagc gcaggggcgc ccggttcttt ttgtcaagac cgacctgtcc ggtgccctga   3180
atgaactgca ggacgaggca gcgcggctat cgtggctggc cacgacgggc gttccttgcg   3240
cagctgtgct cgacgttgtc actgaagcgg gaagggactg gctgctattg ggcgaagtgc   3300
```

```
cggggcagga tctcctgtca tctcaccttg ctcctgccga gaaagtatcc atcatggctg   3360
atgcaatgcg gcggctgcat acgcttgatc cggctacctg cccattcgac caccaagcga   3420
aacatcgcat cgagcgagca cgtactcgga tggaagccgg tcttgtcgat caggatgatc   3480
tggacgaaga gcatcagggg ctcgcgccag ccgaactgtt cgccaggctc aaggcgcgca   3540
tgcccgacgg cgaggatctc gtcgtgaccc atggcgatgc ctgcttgccg aatatcatgg   3600
tggaaaatgg ccgcttttct ggattcatcg actgtggccg gctgggtgtg gcggaccgct   3660
atcaggacat agcgttggct acccgtgata ttgctgaaga gcttggcggc gaatgggctg   3720
accgcttcct cgtgctttac ggtatcgccg ctcccgattc gcagcgcatc gccttctatc   3780
gccttcttga cgagttcttc tgagcggggac tctggggttc gaaatgaccg accaagcgac   3840
gcccaacctg ccatcacgag atttcgattc caccgccgcc ttctatgaaa ggttgggctt   3900
cggaatcgtt ttccgggacg ccggctggat gatcctccag cgcgggatc tcatgctgga   3960 gttcttcgcc caccccggga gatggggag gctaactgaa acacggaagg agacaatacc   4020
ggaaggaacc cgcgctatga cggcaataaa aagacagaat aaaacgcacg ggtgttgggt   4080
cgtttgttca taaacgcggg gttcggtccc agggctggca ctctgtcgat accccaccga   4140 gacccattg gggccaatac gcccgcgttt cttccttttc cccaccccaa ccccccaagtt   4200 cgggtgaagg cccagggctc gcagccaacg tcggggcggc aagcccgcca tagccacggg   4260
ccccgtgggt tagggacggg gtcccccatg gggaatggtt tatggttcgt ggggggttatt   4320 cttttgggcg ttgcgtgggg tcaggtccac gactggactg agcagacaga cccatggttt   4380
ttggatggcc tgggcatgga ccgcatgtac tggcgcgaca cgaacaccgg gcgtctgtgg   4440
ctgccaaaca cccccgaccc ccaaaaacca ccgcgcggat ttctggcgcc gccggacgaa   4500
ctaaacctga ctacggcatc tctgccccctt cttcgctggt acgaggagcg cttttgtttt   4560
gtattggtca ccacggccga gtttccgcgg ggcacctgtc ctacgagttg catgataaag   4620
aagacagtca taagtgcggc gacgatagtc atgccccgcg cccaccggaa ggagctgact   4680
gggttgaagg ctctcaaggg catcggtcga gcggccgctc aaagcaacca tagtacgcgc   4740
cctgtagcgg cgcattaagc gcggcgggtg tggtggttac gcgcagcgtg accgctacac   4800
ttgccagcgc cctagcgccc gctccttttcg ctttcttccc ttcctttctc gccacgttcg   4860 ccggcttttcc ccgtcaagct ctaaatcggg ggctcccttt agggttccga tttagtgctt   4920
tacggcacct cgaccccaaa aaacttgatt tgggtgatgg ttcacgtagt gggccatcgc   4980
cctgatagac ggttttttcgc cctttgacgt tggagtccac gttctttaat agtggactct   5040
tgttccaaac tggaacaaca ctcaaccctca tctcggcta ttcttttgat ttataaggga   5100
ttttgccgat ttcggcctat tggttaaaaa atgagctgat ttaacaaaaa tttaacgcga   5160
attttaacaa aatattaacg tttacaattt tatggtgcag gcctcgtgat acgcctattt   5220
ttataggtta atgtcatgat aataatggtt tcttagacgt caggtggcac ttttcgggga   5280
aatgtgcgcg gaaccccctat ttgtttattt ttctaaatac attcaaatat gtatccgctc   5340
atgagacaat aaccctgata aatgcttcaa taatattgaa aaaggaagag tatgagtatt   5400
caacatttcc gtgtcgccct tattcccttt tttgcggcat tttgccttcc tgttttgct   5460 cacccagaaa cgctggtgaa agtaaaagat gctgaagatc agttgggtgc acgagtgggt   5520
tacatcgaac tggatctcaa cagcggtaag atccttgaga gttttcgccc cgaagaacgt   5580
tttccaatga tgagcacttt taaagttctg ctatgtggcg cggtattatc ccgtgatgac   5640
gccgggcaag agcaactcgg tcgccgcata cactattctc agaatgactt ggttgagtac   5700
```

| | |
|---|---|
| tcaccagtca cagaaaagca tcttacggat ggcatgacag taagagaatt atgcagtgct | 5760 |
| gccataacca tgagtgataa cactgcggcc aacttacttc tgacaacgat cggaggaccg | 5820 |
| aaggagctaa ccgcttttt gcacaacatg ggggatcatg taactcgcct tgatcgttgg | 5880 |
| gaaccggagc tgaatgaagc cataccaaac gacgagcgtg acaccacgat gccagcagca | 5940 |
| atggcaacaa cgttgcgcaa actattaact ggcgaactac ttactctagc ttcccggcaa | 6000 |
| caattaatag actggatgga ggcggataaa gttgcaggac cacttctgcg ctcggccctt | 6060 |
| ccggctggct ggtttattgc tgataaatct ggagccggtg agcgtgggtc tcgcggtatc | 6120 |
| attgcagcac tggggccaga tggtaagccc tcccgtatcg tagttatcta cacgacgggg | 6180 |
| agtcaggcaa ctatggatga acgaaataga cagatcgctg agataggtgc ctcactgatt | 6240 |
| aagcattggt aactgtcaga ccaagtttac tcatatatac tttagattga tttaaaactt | 6300 |
| cattttaat ttaaaaggat ctaggtgaag atccttttg ataatctcat gaccaaaatc | 6360 |
| ccttaacgtg agttttcgtt ccactgagcg tcagaccccg tagaaaagat caaaggatct | 6420 |
| tcttgagatc ctttttttct gcgcgtaatc tgctgcttgc aaacaaaaaa accaccgcta | 6480 |
| ccagcggtgg tttgtttgcc ggatcaagag ctaccaactc ttttccgaa ggtaactggc | 6540 |
| ttcagcagag cgcagatacc aaatactgtc cttctagtgt agccgtagtt aggccaccac | 6600 |
| ttcaagaact ctgtagcacc gcctacatac ctcgctctgc taatcctgtt accagtggct | 6660 |
| gctgccagtg gcgataagtc gtgtcttacc gggttggact caagacgata gttaccggat | 6720 |
| aaggcgcagc ggtcgggctg aacggggggt tcgtgcacac agcccagctt ggagcgaacg | 6780 |
| acctacaccg aactgagata cctacagcgt gagcattgag aaagcgccac gcttcccgaa | 6840 |
| gggagaaagg cggacaggta tccggtaagc ggcagggtcg gaacaggaga gcgcacgagg | 6900 |
| gagcttccag ggggaaacgc ctggtatctt tatagtcctg tcgggtttcg ccacctctga | 6960 |
| cttgagcgtc gatttttgtg atgctcgtca gggggcgga gcctatggaa aaacgccagc | 7020 |
| tggcacgaca ggtttcccga ctggaaagcg ggcagtgagc gcaacgcaat taatgtgagt | 7080 |
| tacctcactc attaggcacc ccaggcttta cactttatgc ttccggctcg tatgttgtgt | 7140 |
| ggaattgtga gcggataaca atttcacaca ggaaacagct atgaccatga ttacgaatta | 7200 |
| a | 7201 |

<210> SEQ ID NO 17
<211> LENGTH: 5988
<212> TYPE: DNA
<213> ORGANISM: Homo sapiens

<400> SEQUENCE: 17

| | |
|---|---|
| tcgagctcgc ccgacattga ttattgacta gttattaata gtaatcaatt acggggtcat | 60 |
| tagttcatag cccatatatg gagttccgcg ttacataact tacggtaaat ggcccgcctg | 120 |
| gctgaccgcc caacgacccc cgcccattga cgtcaataat gacgtatgtt cccatagtaa | 180 |
| cgccaatagg gactttccat tgacgtcaat gggtggagta tttacggtaa actgcccact | 240 |
| tggcagtaca tcaagtgtat catatgccaa gtacgccccc tattgacgtc aatgacggta | 300 |
| aatggcccgc ctggcattat gcccagtaca tgaccttatg ggactttcct acttggcagt | 360 |
| acatctacgt attagtcatc gctattacca tggtgatgcg gttttggcag tacatcaatg | 420 |
| ggcgtggata gcggtttgac tcacggggat ttccaagtct ccaccccatt gacgtcaatg | 480 |
| ggagtttgtt ttggcaccaa aatcaacggg actttccaaa atgtcgtaac aactccgccc | 540 |
| cattgacgca aatgggcggt aggcgtgtac ggtgggaggt ctatataagc agagctcgtt | 600 |

```
tagtgaaccg tcagatcgcc tggagacgcc atccacgctg ttttgacctc catagaagac    660
accgggaccg atccagcctc cgcggccggg aacggtgcat tggaacgcgg attccccgtg    720
ccaagagtga cgtaagtacc gcctatagag tctataggcc acccccttg gcttggccca    780 ccccttggc ttcgttagaa cgcggctaca attaatacat aaccttatgt atcatacaca    840
tacgatttag gtgacactat agaataacat ccactttgcc tttcacatcc actttgcctt    900
tctctccaca ggtgtccact cccaggtcca actgcacctc ggttctatcg attgaattcc    960
acgcgtccga gcagcaagag gatggaagga tgaatagaag tagcttcaaa taggatggag    1020
atctcatcag gcttgctgtt cctgggccac ctaatagtgc tcacctatgg ccaccccacc    1080
ctaaaaacac ctgagagtgt gacagggacc tggaaaggag atgtgaagat tcagtgcatc    1140
tatgatcccc tgagaggcta caggcaagtt ttggtgaaat ggctggtaag acacggctct    1200
gactccgtca ccatcttcct acgtgactcc actggagacc atatccagca ggcaaagtac    1260
agaggccgcc tgaaagtgag ccacaaagtt ccaggagatg tgtccctcca aataaatacc    1320
ctgcagatgg atgacaggaa tcactataca tgtgaggtca cctggcagac tcctgatgga    1380
aaccaagtaa taagagataa gatcattgag ctccgtgttc ggaaatataa tccacctaga    1440
atcaatactg aagcacctac aaccctgcac tcctctttgg aagcaacaac tataatgagt    1500
tcaacctctg acttgaccac taatgggact ggaaaacttg aggagaccat tgctggttca    1560 ggggggtca ccgacaagaa aattgtgccc agggattgtg gttgtaagcc ttgcatatgt    1620
acagtcccag aagtatcatc tgtcttcatc ttcccccaa agcccaagga tgtgctcacc    1680
attactctga ctcctaaggt cacgtgtgtt gtggtagaca tcagcaagga tgatcccgag    1740
gtccagttca gctggtttgt agatgatgtg gaggtgcaca cagctcagac gcaaccccgg    1800
gaggagcagt tcaacagcac tttccgctca gtcagtgaac ttcccatcat gcaccaggac    1860
tggctcaatg gcaaggagtt caaatgcagg gtcaacagtg cagcttttcc tgcccccatc    1920
gagaaaacca tctccaaaac caaaggcaga ccgaaggctc acaggtgta caccattcca    1980 cctcccaagg agcagatggc caaggataaa gtcagtctga cctgcatgat aacagacttc    2040
ttccctgaag acattactgt ggagtggcag tggaatgggc agccagcgga gaactacaag    2100
aacactcagc ccatcatgga cacagatggc tcttacttcg tctacagcaa gctcaatgtg    2160
cagaagagca actgggaggc aggaaatact ttcacctgct ctgtgttaca tgagggcctg    2220
cacaaccacc atactgagaa gagcctctcc cactctcctg gtaaatgagt cgacctgcag    2280
aagcttggcc gccatggccc aacttgttta ttgcagctta taatggttac aaataaagca    2340
atagcatcac aaatttcaca aataaagcat ttttttcact gcattctagt tgtggtttgt    2400
ccaaactcat caatgtatct tatcatgtct ggatcgggaa ttaattcggc gcagcaccat    2460
ggcctgaaat aacctctgaa agaggaactt ggttaggtac cttctgaggc ggaaagaacc    2520
agctgtggaa tgtgtgtcag ttagggtgtg gaaagtcccc aggctcccca gcaggcagaa    2580
gtatgcaaag catgcatctc aattagtcag caaccaggtg tggaaagtcc caggctcccc    2640
cagcaggcag aagtatgcaa agcatgcatc tcaattagtc agcaaccata gtcccgcccc    2700
taactccgcc catcccgccc ctaactccgc ccagttccgc ccattctccg ccccatggct    2760
gactaatttt ttttatttat gcagaggccg aggccgcctc ggcctctgag ctattccaga    2820
agtagtgagg aggcttttt ggaggcctag gcttttgcaa aaagctgtta acagcttggc    2880
actggccgtc gttttacaac gtcgtgactg ggaaaaccct ggcgttaccc aacttaatcg    2940
ccttgcagca catcccccctt cgccagctg gcgtaatagc gaagaggccc gcaccgatcg    3000
```

```
cccttcccaa cagttgcgca gcctgaatgg cgaatggcgc ctgatgcggt attttctcct   3060
tacgcatctg tgcggtattt cacaccgcat acgtcaaagc aaccatagta cgcgccctgt   3120
agcggcgcat taagcgcggc gggtgtggtg gttacgcgca gcgtgaccgc tacacttgcc   3180
agcgccctag cgcccgctcc tttcgctttc ttcccttcct ttctcgccac gttcgccggc   3240
tttccccgtc aagctctaaa tcggggggctc cctttagggt tccgatttag tgctttacgg   3300
cacctcgacc ccaaaaaact tgatttgggt gatggttcac gtagtgggcc atcgccctga   3360
tagacggttt ttcgcccttt gacgttggag tccacgttct ttaatagtgg actcttgttc   3420
caaactggaa caacactcaa ccctatctcg ggctattctt ttgatttata agggattttg   3480
ccgatttcgg cctattggtt aaaaaatgag ctgatttaac aaaaatttaa cgcgaatttt   3540
aacaaaatat taacgtttac aattttatgg tgcactctca gtacaatctg ctctgatgcc   3600
gcatagttaa gccagccccg acacccgcca cacccgctg acgcgccctg acgggcttgt   3660
ctgctcccgg catccgctta cagacaagct gtgaccgtct ccgggagctg catgtgtcag   3720
aggttttcac cgtcatcacc gaaacgcgcg agacgaaagg gcctcgtgat acgcctattt   3780
ttataggtta atgtcatgat aataatggtt tcttagacgt caggtggcac ttttcgggga   3840
aatgtgcgcg gaacccctat ttgtttattt ttctaaatac attcaaatat gtatccgctc   3900
atgagacaat aaccctgata aatgcttcaa taatattgaa aaaggaagag tatgagtatt   3960
caacatttcc gtgtcgccct tattccctttt tttgcggcat tttgccttcc tgttttgct   4020 cacccagaaa cgctggtgaa agtaaaagat gctgaagatc agttgggtgc acgagtgggt   4080
tacatcgaac tggatctcaa cagcggtaag atccttgaga gttttcgccc cgaagaacgt   4140
tttccaatga tgagcacttt taaagttctg ctatgtggcg cggtattatc ccgtattgac   4200
gccgggcaag agcaactcgg tcgccgcata cactattctc agaatgactt ggttgagtac   4260
tcaccagtca cagaaaagca tcttacggat ggcatgacag taagagaatt atgcagtgct   4320
gccataacca tgagtgataa cactgcggcc aacttacttc tgacaacgat cggaggaccg   4380
aaggagctaa ccgcttttttt gcacaacatg ggggatcatg taactcgcct tgatcgttgg   4440
gaaccggagc tgaatgaagc cataccaaac gacgagcgtg acaccacgat gcctgtagca   4500
atggcaacaa cgttgcgcaa actattaact ggcgaactac ttactctagc ttcccggcaa   4560
caattaatag actggatgga ggcggataaa gttgcaggac cacttctgcg ctcggccctt   4620
ccggctggct ggtttattgc tgataaatct ggagccggtg agcgtgggtc tcgcggtatc   4680
attgcagcac tggggccaga tggtaagccc tcccgtatcg tagttatcta cacgacgggg   4740
agtcaggcaa ctatggatga acgaaataga cagatcgctg agataggtgc ctcactgatt   4800
aagcattggt aactgtcaga ccaagtttac tcatatatac tttagattga tttaaaactt   4860
catttttaat ttaaaaggat ctaggtgaag atccttttttg ataatctcat gaccaaaatc   4920
ccttaacgtg agttttcgtt ccactgagcg tcagacccccg tagaaaagat caaaggatct   4980
tcttgagatc ctttttttct gcgcgtaatc tgctgcttgc aaacaaaaaa accaccgcta   5040
ccagcggtgg tttgtttgcc ggatcaagag ctaccaactc tttttccgaa ggtaactggc   5100
ttcagcagag cgcagatacc aaatactgtt cttctagtgt agccgtagtt aggccaccac   5160
ttcaagaact ctgtagcacc gcctacatac ctcgctctgc taatcctgtt accagtggct   5220
gctgccagtg gcgataagtc gtgtcttacc gggttggact caagacgata gttaccggat   5280
aaggcgcagc ggtcgggctg aacggggggt tcgtgcacac agcccagctt ggagcgaacg   5340
acctacaccg aactgagata cctacagcgt gagctatgag aaagcgccac gcttcccgaa   5400
```

-continued

```
gggagaaagg cggacaggta tccggtaagc ggcagggtcg gaacaggaga gcgcacgagg      5460
gagcttccag ggggaaacgc ctggtatctt tatagtcctg tcgggtttcg ccacctctga      5520
cttgagcgtc gattttttgtg atgctcgtca gggggggcgga gcctatggaa aaacgccagc   5580
aacgcggcct ttttacggtt cctggccttt tgctggcctt ttgctcacat gttctttcct     5640
gcgttatccc ctgattctgt ggataaccgt attaccgcct ttgagtgagc tgataccgct     5700
cgccgcagcc gaacgaccga gcgcagcgag tcagtgagcg aggaagcgga agagcgccca     5760
atacgcaaac cgcctctccc cgcgcgttgg ccgattcatt aatgcagctg gcacgacagg     5820
tttcccgact ggaaagcggg cagtgagcgc aacgcaatta atgtgagtta gctcactcat     5880
taggcacccc aggctttaca ctttatgctt ccggctcgta tgttgtgtgg aattgtgagc     5940
ggataacaat ttcacacagg aaacagctat gacatgatta cgaattaa                  5988
```

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 18

```
tctctgtctc caagcccaca g                                                 21
```

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 19

```
ctttgaggag tctttgacc                                                    19
```

<210> SEQ ID NO 20
<211> LENGTH: 1293
<212> TYPE: DNA
<213> ORGANISM: Artificial Sequence
<220> FEATURE:
<223> OTHER INFORMATION: huCRIg-short-IgG fusion

<400> SEQUENCE: 20

```
acctcggttc tatcgatgct ctcaataaac caccatgggg atcttactgg gcctgctact       60
cctggggcac ctaacagtgg acacttatgg ccgtcccatc ctggaagtgc cagagagtgt      120
aacaggacct tggaaagggg atgtgaatct cccctgcacc tatgaccccc tgcaaggcta     180
cacccaagtc ttggtgaagt ggctggtaca acgtggctca gaccctgtca ccatctttct     240
acgtgactct tctggagacc atatccagca ggcaaagtac cagggccgcc tgcatgtgag     300
ccacaaggtt ccaggagatg tatccctcca attgagcacc ctggagatgg atgaccggag     360
ccactacacg tgtgaagtca cctggcagac tcctgatggc aaccaagtcg tgagagataa     420
gattactgag ctccgtgtcc agaaacactc ctcaaagcta tcaagacca agactgaggc     480 acctacaacc atgacatacc ccttgaaagc aacatctaca gtgaagcagt cctgggactg    540
gaccactgac atggacaaaa ctcacacatg cccaccgtgc ccagcacctg aactcctggg    600
gggaccgtca gtcttcctct tccccccaaa acccaaggac accctcatga tctcccggac    660
ccctgaggtc acatgcgtgg tggtggacgt gagccacgaa gaccctgagg tcaagttcaa   720
ctggtacgtg gacggcgtgg aggtgcataa tgccaagaca aagccgcggg aggagcagta   780
```

```
caacagcacg taccgtgtgg tcagcgtcct caccgtcctg caccaggact ggctgaatgg    840
caaggagtac aagtgcaagg tctccaacaa agccctccca gcccccatcg agaaaaccat    900
ctccaaagcc aaagggcagc ccgagaacc acaggtgtac accctgcccc catcccggga    960
agagatgacc aagaaccagg tcagcctgac ctgcctggtc aaaggcttct atcccagcga   1020
catcgccgtg gagtgggaga gcaatgggca gccggagaac aactacaaga ccacgcctcc   1080
cgtgctggac tccgacggct ccttcttcct ctacagcaag ctcaccgtgg acaagagcag   1140
gtggcagcag gggaacgtct tctcatgctc cgtgatgcat gaggctctgc acaaccacta   1200
cacgcagaag agcctctccc tgtctccggg taaatgagtg cgacggccct agagtcgacc   1260
tgcagaagct tctagagtcg acctgcagaa gct                                1293
```

<210> SEQ ID NO 21
<211> LENGTH: 1556
<212> TYPE: DNA
<213> ORGANISM: Artificial Sequence
<220> FEATURE:
<223> OTHER INFORMATION: huCRIg-long-IgG fusion

<400> SEQUENCE: 21

```
atcgattaaa ccaccatggg gatcttactg ggcctgctac tcctggggca cctaacagtg     60
gacacttatg ccgtcccat cctggaagtg ccagagagtg taacaggacc ttggaagggg    120
gatgtgaatc ttccctgcac ctatgacccc ctgcaaggct acacccaagt cttggtgaag    180
tggctggtac aacgtggctc agaccctgtc accatctttc tacgtgactc ttctggagac    240
catatccagc aggcaaagta ccagggccgc ctgcatgtga gccacaaggt tccaggagat    300
gtatccctcc aattgagcac cctggagatg gatgaccgga gccactacac gtgtgaagtc    360
acctggcaga ctcctgatgg caaccaagtc gtgagagata agattactga gctccgtgtc    420
cagaaactct ctgtctccaa gcccacagtg acaactggca gcggttatgg cttcacggtg    480
ccccagggaa tgaggattag ccttcaatgc caggctcggg gttctcctcc catcagttat    540
atttggtata gcaacagac taataaccag gaacccatca agtagcaac cctaagtacc    600 ttactcttca gcctgcggt gatagccgac tcaggctcct atttctgcac tgccaagggc    660
caggttggct ctgagcagca cagcgacatt gtgaagtttg tggtcaaaga ctcctcaaag    720
ctactcaaga ccaagactga ggcacctaca accatgacat ccccttgaa agcaacatct    780 acagtgaagc agtcctggga ctggaccact gacatggata aaactcacac atgcccaccg    840
tgcccagcac ctgaactcct ggggggaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaagggc agccccgaga accacaggtg   1200
tacaccctgc cccatcccg ggaagagatg accaagaacc aggtcagcct gacctgcctg   1260
gtcaaaggct tctatcccag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggtaaatga   1500
gtgcgacggc cctagagtcg acctgcagaa gcttctagag tcgacctgca gaagct       1556
```

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 22
ccactggtcc cagagaaagt                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 23
cactattagg tggcccagga                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 24
gggaggattg ggaagacaat                                              20

<210> SEQ ID NO 25
<211> LENGTH: 1454
<212> TYPE: DNA
<213> ORGANISM: Artificial Sequence
<220> FEATURE:
<223> OTHER INFORMATION: huCRIg-long-Fc Fusion

<400> SEQUENCE: 25
atcgattaaa ccaccatggg gatcttactg ggcctgctac tcctggggca cctaacagtg    60
gacacttatg gccgtcccat cctggaagtg ccagagagtg taacaggacc ttggaaaggg   120
gatgtgaatc ttccctgcac ctatgacccc ctgcaaggct acacccaagt cttggtgaag   180
tggctggtac aacgtggctc agaccctgtc accatctttc tacgtgactc ttctggagac   240
catatccagc aggcaaagta ccagggccgc ctgcatgtga ccacaaggt tccaggagat   300 gtatccctcc aattgagcac cctggagatg gatgaccgga gccactacac gtgtgaagtc   360
acctggcaga ctcctgatgg caaccaagtc gtgagagata agattactga gctccgtgtc   420
cagaaactct ctgtctccaa gcccacagtg acaactggca gcggttatgg cttcacggtg   480
ccccagggaa tgaggattag ccttcaatgc caggctcggg ttctcctcc catcagttat   540 atttggtata agcaacagac taataaccag gaacccatca agtagcaac cctaagtacc   600 ttactcttca gcctgcggt gatagccgac tcaggctcct atttctgcac tgccaagggc   660
caggttggct ctgagcagca cagcgacatt gtgaagtttg tggtcaaaga ctccgataaa   720
actcacacat gcccaccgtg cccagcacct gaactcctgg gggaccgtc agtcttcctc   780 ttccccccaa acccaaggga caccctcatg atctcccgga cccctgaggt cacatgcgtg   840
gtggtggacg tgagccacga agaccctgag gtcaagttca actggtacgt ggacggcgtg   900
gaggtgcata atgccaagac aaagccgcgg gaggagcagt acaacagcac gtaccgtgtg   960
gtcagcgtcc tcaccgtcct gcaccaggac tggctgaatg gcaaggagta caagtgcaag  1020

```
gtctccaaca aagccctccc agccccatc gagaaaacca tctccaaagc caaagggcag      1080
ccccgagaac cacaggtgta caccctgccc ccatcccggg aagagatgac caagaaccag      1140
gtcagcctga cctgcctggt caaaggcttc tatcccagcg acatcgccgt ggagtgggag      1200
agcaatgggc agccggagaa caactacaag accacgcctc ccgtgctgga ctccgacggc      1260
tccttcttcc tctacagcaa gctcaccgtg gacaagagca ggtggcagca ggggaacgtc      1320
ttctcatgct ccgtgatgca tgaggctctg cacaaccact acacgcagaa gagcctctcc      1380
ctgtctccgg gtaaatgagt gcgacggccc tagagtcgac ctgcagaagc ttctagagtc      1440
gacctgcaga agct                                                        1454
```

<210> SEQ ID NO 26
<211> LENGTH: 1556
<212> TYPE: DNA
<213> ORGANISM: Artificial Sequence
<220> FEATURE:
<223> OTHER INFORMATION: huCRIg-long-Fc Fusion

<400> SEQUENCE: 26

```
atcgattaaa ccaccatggg gatcttactg ggcctgctac tcctggggca cctaacagtg       60
gacacttatg gccgtcccat cctggaagtg ccagagagtg taacaggacc ttggaaaggg      120
gatgtgaatc ttccctgcac ctatgacccc ctgcaaggct acacccaagt cttggtgaag      180
tggctggtac aacgtggctc agaccctgtc accatctttc tacgtgactc ttctggagac      240
catatccagc aggcaaagta ccagggccgc ctgcatgtga ccacaaggt tccaggagat      300 gtatccctcc aattgagcac cctggagatg gatgaccgga ccactacac gtgtgaagtc      360 acctggcaga ctcctgatgg caaccaagtc gtgagagata agattactga gctccgtgtc      420
cagaaactct ctgtctccaa gcccacagtg acaactggca gcggttatgg cttcacggtg      480
ccccagggaa tgaggattag ccttcaatgc caggctcggg ttctcctcc catcagttat      540 atttggtata agcaacagac taataaccag gaacccatca agtagcaac cctaagtacc      600 ttactcttca agcctgcggt gatagccgac tcaggctcct atttctgcac tgccaagggc      660
caggttggct ctgagcagca gcgacatt gtgaagtttg tggtcaaaga ctcctcaaag      720
ctactcaaga ccaagactga ggcacctaca accatgacat ccccttgaa agcaacatct      780 acagtgaagc agtcctggga ctggaccact gacatggata aaactcacac atgcccaccg      840
tgcccagcac ctgaactcct gggggaccg tcagtcttcc tcttcccccc aaaacccaag      900
gacaccctca tgatctcccg gaccctgag gtcacatgcg tggtggtgga cgtgagccac      960
gaagaccctg aggtcaagtt caactggtac gtggacggcg tggaggtgca taatgccaag     1020
acaaagccgc gggaggagca gtacaacagc acgtaccgtg tggtcagcgt cctcaccgtc     1080
ctgcaccagg actggctgaa tggcaaggag tacaagtgca aggtctccaa caaagccctc     1140
ccagccccca tcgagaaaac catctccaaa gccaagggc agccccgaga accacaggtg     1200
tacaccctgc ccccatcccg ggaagagatg accaagaacc aggtcagcct gacctgcctg     1260
gtcaaaggct tctatcccag cgacatcgcc gtggagtggg agagcaatgg gcagccggag     1320
aacaactaca agaccacgcc tcccgtgctg gactccgacg gctccttctt cctctacagc     1380
aagctcaccg tggacaagag caggtggcag caggggaacg tcttctcatg ctccgtgatg     1440
catgaggctc tgcacaacca ctacacgcag aagagcctct ccctgtctcc gggtaaatga     1500
gtgcgacggc cctagagtcg acctgcagaa gcttctagag tcgacctgca gaagct         1556
```

<210> SEQ ID NO 27
<211> LENGTH: 1172
<212> TYPE: DNA
<213> ORGANISM: Artificial Sequence
<220> FEATURE:
<223> OTHER INFORMATION: huCRIg-short-Fc Fusion

<400> SEQUENCE: 27

| | |
|---|---:|
| atcgattaaa ccaccatggg gatcttactg ggcctgctac tcctggggca cctaacagtg | 60 |
| gacacttatg gccgtcccat cctggaagtg ccagagagtg taacaggacc ttggaaaggg | 120 |
| gatgtgaatc ttccctgcac ctatgacccc ctgcaaggct acacccaagt cttggtgaag | 180 |
| tggctggtac aacgtggctc agaccctgtc accatctttc tacgtgactc ttctggagac | 240 |
| catatccagc aggcaaagta ccagggccgc ctgcatgtga gccacaaggt tccaggagat | 300 |
| gtatccctcc aattgagcac cctggagatg gatgaccgga gccactacac gtgtgaagtc | 360 |
| acctggcaga ctcctgatgg caaccaagtc gtgagagata agattactga gctccgtgtc | 420 |
| cagaaacact ccgacaaaac tcacacatgc ccaccgtgcc cagcacctga actcctgggg | 480 |
| ggaccgtcag tcttcctctt ccccccaaaa cccaaggaca ccctcatgat ctcccggacc | 540 |
| cctgaggtca catgcgtggt ggtggacgtg agccacgaag accctgaggt caagttcaac | 600 |
| tggtacgtgg acggcgtgga ggtgcataat gccaagacaa agccgcggga ggagcagtac | 660 |
| aacagcacgt accgtgtggt cagcgtcctc accgtcctgc accaggactg gctgaatggc | 720 |
| aaggagtaca agtgcaaggt ctccaacaaa gccctcccag cccccatcga gaaaaccatc | 780 |
| tccaaagcca aagggcagcc ccgagaacca caggtgtaca ccctgccccc atcccgggaa | 840 |
| gagatgacca agaaccaggt cagcctgacc tgcctggtca aaggcttcta tcccagcgac | 900 |
| atcgccgtgg agtgggagag caatgggcag ccggagaaca actacaagac cacgcctccc | 960 |
| gtgctggact ccgacggctc cttcttcctc tacagcaagc tcaccgtgga caagagcagg | 1020 |
| tggcagcagg ggaacgtctt ctcatgctcc gtgatgcatg aggctctgca caaccactac | 1080 |
| acgcagaaga gcctctccct gtctccgggt aaatgagtgc gacggcccta gagtcgacct | 1140 |
| gcagaagctt ctagagtcga cctgcagaag ct | 1172 |

<210> SEQ ID NO 28
<211> LENGTH: 1293
<212> TYPE: DNA
<213> ORGANISM: Artificial Sequence
<220> FEATURE:
<223> OTHER INFORMATION: huCRIg-short-Fc Fusion

<400> SEQUENCE: 28

| | |
|---|---:|
| acctcggttc tatcgatgct ctcaataaac caccatgggg atcttactgg gcctgctact | 60 |
| cctggggcac ctaacagtgg acacttatgg ccgtcccatc ctggaagtgc cagagagtgt | 120 |
| aacaggacct tggaaagggg atgtgaatct tccctgcacc tatgaccccc tgcaaggcta | 180 |
| cacccaagtc ttggtgaagt ggctggtaca acgtggctca gaccctgtca ccatctttct | 240 |
| acgtgactct tctggagacc atatccagca ggcaaagtac cagggccgcc tgcatgtgag | 300 |
| ccacaaggtt ccaggagatg tatccctcca attgagcacc ctggagatgg atgaccggag | 360 |
| ccactacacg tgtgaagtca cctggcagac tcctgatggc aaccaagtcg tgagagataa | 420 |
| gattactgag ctccgtgtcc agaaacactc tcaaagcta tcaagaccaa agactgaggc | 480 |
| acctacaacc atgacatacc ccttgaaagc aacatctaca gtgaagcagt cctgggactg | 540 |
| gaccactgac atggacaaaa ctcacacatg cccaccgtgc ccagcacctg aactcctggg | 600 |
| gggaccgtca gtcttcctct tccccccaaa acccaaggac accctcatga tctcccggac | 660 |

-continued

```
ccctgaggtc acatgcgtgg tggtggacgt gagccacgaa gaccctgagg tcaagttcaa      720
ctggtacgtg gacggcgtgg aggtgcataa tgccaagaca aagccgcggg aggagcagta      780
caacagcacg taccgtgtgg tcagcgtcct caccgtcctg caccaggact ggctgaatgg      840
caaggagtac aagtgcaagg tctccaacaa agccctccca gccccatcg agaaaaccat       900 ctccaaagcc aagggcagc cccgagaacc acaggtgtac accctgcccc catcccggga       960
agagatgacc aagaaccagg tcagcctgac ctgcctggtc aaaggcttct atcccagcga     1020
catcgccgtg gagtgggaga gcaatgggca gccggagaac aactacaaga ccacgcctcc     1080
cgtgctggac tccgacggct ccttcttcct ctacagcaag ctcaccgtgg acaagagcag     1140
gtggcagcag gggaacgtct tctcatgctc cgtgatgcat gaggctctgc acaaccacta     1200
cacgcagaag agcctctccc tgtctccggg taaatgagtg cgacggccct agagtcgacc     1260
tgcagaagct tctagagtcg acctgcagaa gct                                  1293
```